US007728029B2

(12) United States Patent
Anderson et al.

(10) Patent No.: US 7,728,029 B2
(45) Date of Patent: Jun. 1, 2010

(54) ADAMANTYL-PYRAZOLE CARBOXAMIDES AS INHIBITORS OF 11β-HDROXYSTEROID DEHYDROGENASE

(75) Inventors: Kevin William Anderson, Florham Park, NJ (US); Nader Fotouhi, Basking Ridge, NJ (US); Paul Gillespie, Westfield, NJ (US); Robert Alan Goodnow, Jr., Gillette, NJ (US); Kevin Richard Guertin, Verona, NJ (US); Nancy-Ellen Haynes, Cranford, NJ (US); Michael Paul Myers, Ramsey, NJ (US); Sherrie Lynn Pietranico-Cole, Montclair, NJ (US); Lida Qi, Leonia, NJ (US); Pamela Loreen Rossman, Nutley, NJ (US); Nathan Robert Scott, Livingston, NJ (US); Kshitij Chhabilbhai Thakkar, Clifton, NJ (US); Jefferson Wright Tilley, North Caldwell, NJ (US); Qiang Zhang, Parsippany, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 309 days.

(21) Appl. No.: 11/717,996

(22) Filed: Mar. 14, 2007

(65) Prior Publication Data
US 2007/0225280 A1  Sep. 27, 2007

Related U.S. Application Data

(60) Provisional application No. 60/784,831, filed on Mar. 22, 2006, provisional application No. 60/875,274, filed on Dec. 15, 2006.

(51) Int. Cl.
A61K 31/4155 (2006.01)
A61K 31/415 (2006.01)
A61K 31/454 (2006.01)
A61K 31/5377 (2006.01)
C07D 231/14 (2006.01)
C07D 401/04 (2006.01)
C07D 413/04 (2006.01)
C07D 403/04 (2006.01)

(52) U.S. Cl. ............... 514/406; 514/236.5; 514/254.05; 548/365.4; 548/374.1; 548/365.7; 548/364.1; 546/211; 544/371; 544/140

(58) Field of Classification Search ............... 514/236.5, 514/254.05, 406; 548/365.4, 374.1, 365.7, 548/364.1; 546/211; 544/371, 140
See application file for complete search history.

(56) References Cited

U.S. PATENT DOCUMENTS

| 4,277,418 A | 7/1981 | Ackermann et al. |
| 4,620,865 A | 11/1986 | Beck et al. |
| 4,792,565 A | 12/1988 | Shimotori et al. |
| 5,948,777 A | 9/1999 | Bender et al. |
| 6,096,898 A | 8/2000 | Podhorez et al. |
| 7,345,058 B2 * | 3/2008 | Gillespie et al. ............ 514/314 |
| 2001/0044445 A1 | 11/2001 | Bamaung et al. |
| 2003/0229119 A1 | 12/2003 | Kim et al. |
| 2004/0220170 A1 | 11/2004 | Atkinson et al. |
| 2005/0020564 A1 | 1/2005 | Atkinson et al. |
| 2006/0106052 A1 | 5/2006 | Crooks et al. |
| 2006/0223852 A1 | 10/2006 | Gillespie et al. |

FOREIGN PATENT DOCUMENTS

| DE | 196 15 976 | 4/1996 |
| DE | 198 53 827 | 11/1998 |
| EP | 0 450 566 | 10/1991 |
| EP | 1 067121 | 1/2001 |
| EP | 1 388 535 | 8/2002 |
| WO | WO 86/02641 | 5/1986 |
| WO | WO 97/11690 | 4/1997 |
| WO | WO 99/31976 | 7/1999 |
| WO | WO 99/67235 | 12/1999 |
| WO | WO 00/27394 | 5/2000 |
| WO | WO 01/05769 | 1/2001 |
| WO | WO 01/14339 | 3/2001 |
| WO | WO 01/29007 | 4/2001 |
| WO | WO 01/46172 | 6/2001 |
| WO | WO 02/44133 | 6/2002 |
| WO | WO 02/064545 | 8/2002 |
| WO | WO 02/064546 | 8/2002 |
| WO | WO 02/064565 | 8/2002 |

(Continued)

OTHER PUBLICATIONS

Schafer et al. Drug Discovery Today 2008, 13 (21/22), 913-916.*

(Continued)

Primary Examiner—Rebecca L Anderson
Assistant Examiner—Jason M Nolan
(74) Attorney, Agent, or Firm—George W. Johnston; Dennis P. Tramaloni; Samuel H. Megerditchian

(57) ABSTRACT

Provided herein are compounds of the formula (I):

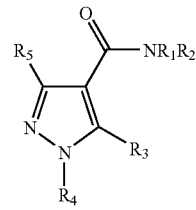

as well as pharmaceutically acceptable salts thereof, wherein the substituents are as those disclosed in the specification. These compounds, and the pharmaceutical compositions containing them, are useful for the treatment of diseases such as, for example, type II diabetes mellitus and metabolic syndrome.

19 Claims, No Drawings

FOREIGN PATENT DOCUMENTS

| | | |
|---|---|---|
| WO | WO 03/028641 | 4/2003 |
| WO | WO 03/037274 | 5/2003 |
| WO | WO 03/051845 | 6/2003 |
| WO | WO 03/070244 | 8/2003 |
| WO | WO 03/093250 A2 | 11/2003 |
| WO | WO 2004/014844 | 2/2004 |
| WO | WO 2004/072034 | 8/2004 |
| WO | WO 2004/089415 | 10/2004 |
| WO | WO 2004/089416 | 10/2004 |
| WO | WO 2004/089470 | 10/2004 |
| WO | WO 2004/089896 A1 | 10/2004 |
| WO | WO 2004/099156 | 11/2004 |
| WO | WO 2005/000793 | 1/2005 |
| WO | WO 2005/009973 | 2/2005 |
| WO | WO 2005/016877 | 2/2005 |
| WO | WO 2005/020897 | 3/2005 |
| WO | WO 2005/048948 | 6/2005 |
| WO | WO 2005/073165 | 8/2005 |
| WO | WO 2005/095357 | 10/2005 |
| WO | WO 2005/110971 | 11/2005 |
| WO | WO 2006/007864 | 1/2006 |
| WO | WO 2006/015860 | 2/2006 |
| WO | WO 2006/031806 | 3/2006 |
| WO | WO 2006/035967 | 4/2006 |
| WO | WO 2006/100502 | 9/2006 |
| WO | WO 2006/106052 A1 | 10/2006 |
| WO | WO 2007/058346 | 5/2007 |

OTHER PUBLICATIONS

Horig et al. Journal of Translational Medicine 2004, 2(44).*
Garg, H.G., *J. Med. Chem.* (1971) 147), 649-650.
Garg, H.G., *J. Med. Chem.* (1979) 22(3), 321-325.
Soliman, R. et al, *J. Med. Chem.* (1983) 26(11) 1659-1663.
Garg, H.G., *J. Med. Chem.* (1968) 11(5), 1103-1104.
Garg, H.G., *J. Med. Chem.* (1968) 11(5) 1104-1105.
Kees,K. et al, *J. Med. Chem*, (1996) 39(20) 3920-3928.
Schroff, J. et al, *J. Med. Chem.* (1981) 24(12) 1521-1525.
R. A. De Fronzo *Drugs* 1999, *58 Suppl. 1*, 29.
S.E. Inzucchi JAMA 2002, 287, 360.
R.C. Turner et al JAMA 1999, 281, 2005.
M. Tadayyon and S.A. Smith Expert Opin. Investig. Drugs 2003, 12, 307.
Advanced Organic Chemistry [J. March, 3$^{rd}$ Edition, John Wiley & Sons, Inc. New York, 1985] on pp. 437-439, and 823-824.
A. Koziara et al Synth. Commun. 1995, 25, 3805-3812.
A.V. Rama Rao et al. Tetrahedron Lett. 1990, 31, 1439-42.
A.X. Wang et al. Bioorg. Med. Chem. Lett 1998, 8, 2787-2792.
B. Mlotkowska and Z. Zwierzak Tetrahedron Lett. 1978, 19, 4731-4734.
B.R. Walker et al. J. Clin. Endocrinol. Metab. 1995, 80, 3155.
Beck, J. et al., J. Heterocycl. Chem. 1987, 24, 693-695.
C.S. Pak et al. Synthesis 1992, 1213-1214.
Comprehensive Organic Transformations: A Guide to Functional Group Preparations [R. C. Larock, VCH Publishers, Inc. New York, 1989] on pp. 1061-1063.
D.E. Seitz et al Tetrahedron Lett. 1995 36, 1413-1416.
E.S. Ford et al. JAMA 2002, 287, 356.
F.B. Dains Chem. 1902, 35, 2496-2500.
F.B. Dains et al. J. Am. Chem. Soc. 1909, 31, 1148-1157.
F.B. Dains et al. J. Am. Chem. Soc. 1916, 38, 1515.
F.B. Dains et al. J. Am. Chem. Soc. 1918, 40, 562-569.
F. Bondavalli et al. J. Med. Chem. 2002, 45, 4875-4887.
G. Giacomelli et al. Eur. J. Org. Chem. 2003, 537-541.
G. Menozzi et al. J. Heterocycl. Chem. 1987, 24, 1669-1676.
H. Emtenas et al. J. Org. Chem. 2001, 26, 6756-6761.
H.H. Wassermann et al. Tetrahedron Lett. 1984, 25, 3743-3746.
H. Masuzaki et al. Science, 2001, 294, 2166.
H. Ohki et al. Biororg. Med. Chem. Lett 2002, 12, 3191-3193.
H.W. Geluk and J.L.M.A. Schlatmann Tetrahedron 1968, 24, 5369-5377.
J. Fugger et al. J. Am. Chem. Soc. 1955, 77, 1843-1848.
J.H. Dewar et al. J. Chem. Soc. 1961, 3254-3260.
J.R. Beck et al. J. Heterocycl. Chem. 1987, 24, 267-270.
J.R. Beck et al. J. Heterocycl. Chem. 1987, 24, 739-740.
J. Svete et al. Synthesis, 1990, 70-72.
J. Svetlik Heterocycles 1984, 22, 2513-2516.
J. Timberlake and J. Stowell, S. Patai Ed., John Wiley & Sons, Ltd. London 1975, 69-107.
J. Viret et al. Tetrahedron 1987, 43, 891-894.
Jirgensons, A., Kauss, V., Kalvinsh, I., Gould, M.R. Synthesis 2000, 12, 1709-1712.
L.A. Paquette and R.F. Doehner, Jr. J. Org. Chem. 1980, 45, 5105-5113.
L. Claisen Liebigs Ann. Chem. 1897, 297, 1-18.
L. Crombie et al. J. Chem Soc. Perkin Trans. I 1979, 464-471.
L. DeLuca et al. J. Comb. Chem. 2003, 5, 465-471.
L.F. Audrieth and L.H. Diamond J. Am. Chem. Soc. 1954, 76, 4869-4871.
M. Kopp et al J Heterocycl. Chem. 2001, 38, 1045-1050.
M.S. Gibson, S. Patai Ed., John Wiley & Sons, Ltd. London 1968, 37-77.
M.S.S. Palanki et al. J. Med. Chem. 2000, 43, 3995-4004.
M. Salas J.J. and Caro adv. Drug React. Tax Rev. 2002, 21, 205-217.
M.T. Herrero et al. Tetrahedron, 58, 8581-8589 2002.
N. Brosse et al. Tetrahedron Lett. 2000, 41, 205-207.
N.I. Ghali et al. J. Org. Chem. 1981, 46, 5413-5414.
N. J. Cusack et al. J. Chem Soc. C 1971, 1501-1507.
N.M. Morton et al. J. Biol. Chem. 2001, 276, 41293.
O.S. Wolfbeis Chem. Ber. 1981, 114, 3471-3484.
Onodera, G. et al. Organic Letters 2005, 18, 4029.
P. Kocienski et al. Tetrahedron Lett. 1988, 29, 4481-4.
P. Seneci et al. Synth. Commun. 1999, 29, 311-341.
R.A.S. Schweizer et al. Mol. Cell. Endocrinol. 2003, 212, 41.
R.C. Andrews et al. J. Clin. Enocrinol. 2003, 212, 41.
R.C. Larock, VCH Publishers, Inc. New York, 1989 on pp. 421-423.
R.C. Larock, VCH Publishers, Inc. New York, 1989 on pp. 685, 694-695, and 768.
Jones, R. G. et al, J. Am. Chem. Soc. 1952 74, 4889-4891.
R. Kuang, et al, Tetrahedron Lett. 2000, 41, 9575-9579.
R. Zupet et al. J. Heterocycl. Chem. 1991, 28, 1731-1740.
S. Diederich et al. Eur. J. Endocrinol. 2000, 142, 200.
S.E. Inzucchi JAMA 2002, 287, 360.
S. Gelin et al. Synthesis 1983, 566-568.
S. Schenone et al. Bioorg. Med. Chem. Lett. 2001, 11, 2529-2531.
S. Zawadzki et al. Synthesis 1987, 485-487.
Meyer, K. G., Synlett 2004, 2355-2356.
T.A. Elmaati et al. Pol. J. Chem. 2002, 76, 945-952.
T.C. Sandeep et al. Proc. Natl. Acad. Sci USA 2004, 101, 6734.
T. Luebbers et al. Bioorg. Med. Chem. Lett. 2000, 10,821-826.
U. Ragnarsson Che. Soc. Rev. 2001, 30, 205-213.
X-J. Wang and K. Grozinger Tetrahedron Lett. 2000, 41, 4713-4716.
Y. Kotolevtsev et al. Proc. Natl. Acad. Sci. USA 1997, 94, 14924.

\* cited by examiner

ADAMANTYL-PYRAZOLE CARBOXAMIDES AS INHIBITORS OF 11β-HDROXYSTEROID DEHYDROGENASE

PRIORITY TO RELATED APPLICATIONS

This application claims the benefit of priority to U.S. Provisional Application Ser. No. 60/784,831, filed Mar. 22, 2006, and U.S. Provisional Application Ser. No. 60/875,274, filed Dec. 15, 2006, which is hereby incorporated by reference in its entirety.

FIELD OF THE INVENTION

The invention relates to inhibitors of 11β-hydroxysteroid dehydrogenase. The inhibitors include, for example, pyrazoles and derivatives thereof and are useful for the treatment of diseases such as type II diabetes mellitus and metabolic syndrome.

All documents cited or relied upon below are expressly incorporated herein by reference.

BACKGROUND OF THE INVENTION

Diabetes mellitus is a serious illness that affects an increasing number of people across the world. Its incidence is escalating along with the increasing trend to obesity in many countries. The serious consequences of the disease include increased risk of stroke, heart disease, kidney damage, blindness, and amputation. Diabetes is characterized by decreased insulin secretion and/or an impaired ability of peripheral tissues to respond to insulin, resulting in increased plasma glucose levels. There are two forms of diabetes: insulin-dependent and non-insulin-dependent, with the great majority of diabetics suffering from the non-insulin-dependent form of the disease, known as type 2 diabetes or non-insulin-dependent diabetes mellitus (NIDDM). Because of the serious consequences, there is an urgent need to control diabetes.

Treatment of NIDDM generally starts with weight loss, a healthy diet and an exercise program. These factors are especially important in addressing the increased cardiovascular risks associated with diabetes, but they are generally ineffective in controlling the disease itself. There are a number of drug treatments available, including insulin, metformin, sulfonylureas, acarbose, and thiazolidinediones. However, each of these treatments has disadvantages, and there is an ongoing need for new drugs to treat diabetes.

Metformin is an effective agent that reduces fasting plasma glucose levels and enhances the insulin sensitivity of peripheral tissue. Metformin has a number of effects in vivo, including an increase in the synthesis of glycogen, the polymeric form in which glucose is stored [R. A. De Fronzo *Drugs* 1999, 58 Suppl. 1, 29]. Metformin also has beneficial effects on lipid profile, with favorable results on cardiovascular health—treatment with metformin leads to reductions in the levels of LDL cholesterol and triglycerides [S. E. Inzucchi *JAMA* 2002, 287, 360]. However, over a period of years, metformin loses its effectiveness [R. C. Turner et al. *JAMA* 1999, 281, 2005] and there is consequently a need for new treatments for diabetes.

Thiazolidinediones are activators of the nuclear receptor peroxisome-proliferator activated receptor-gamma. They are effective in reducing blood glucose levels, and their efficacy has been attributed primarily to decreasing insulin resistance in skeletal muscle [M. Tadayyon and S. A. Smith *Expert Opin. Investig. Drugs* 2003, 12, 307]. One disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [S. E. Inzucchi *JAMA* 2002, 287, 360] and, like metformin, efficacy decreases over time [R. C. Turner et al. *JAMA* 1999, 281, 2005]. A further problem often encountered in patients treated with sulfonylureas is hypoglycemia [M. Salas J. J. and Caro *Adv. Drug React. Tox. Rev.* 2002, 21, 205-217].

Acarbose is an inhibitor of the enzyme alpha-glucosidase, which breaks down disaccharides and complex carbohydrates in the intestine. It has lower efficacy than metformin or the sulfonylureas, and it causes intestinal discomfort and diarrhea which often lead to the discontinuation of its use [S. E. Inzucchi *JAMA* 2002, 287, 360].

The metabolic syndrome is a condition where patients exhibit more than two of the following symptoms: obesity, hypertriglyceridemia, low levels of HDL-cholesterol, high blood pressure, and elevated fasting glucose levels. This syndrome is often a precursor of type 2 diabetes, and has high prevalence in the United States with an estimated prevalence of 24% (E. S. Ford et al. *JAMA* 2002, 287, 356). A therapeutic agent that ameliorates the metabolic syndrome would be useful in potentially slowing or stopping the progression to type 2 diabetes.

In the liver, glucose is produced by two different processes: gluconeogenesis, where new glucose is generated in a series of enzymatic reactions from pyruvate, and glycolysis, where glucose is generated by the breakdown of the polymer glycogen.

Two of the key enzymes in the process of gluconeogenesis are phosphoenolpyruvate carboxykinase (PEPCK) which catalyzes the conversion of oxalacetate to phosphoenolpyruvate, and glucose-6-phosphatase (G6 Pase) which catalyzes the hydrolysis of glucose-6-phosphate to give free glucose. The conversion of oxalacetate to phosphoenolpyruvate, catalyzed by PEPCK, is the rate-limiting step in gluconeogenesis. On fasting, both PEPCK and G6 Pase are upregulated, allowing the rate of gluconeogenesis to increase. The levels of these enzymes are controlled in part by the corticosteroid hormones (cortisol in human and corticosterone in mouse). When the corticosteroid binds to the corticosteroid receptor, a signaling cascade is triggered which results in the upregulation of these enzymes.

The corticosteroid hormones are found in the body along with their oxidized 11-dehydro counterparts (cortisone and II-dehydrocorticosterone in human and mouse, respectively), which do not have activity at the glucocorticoid receptor. The actions of the hormone depend on the local concentration in the tissue where the corticosteroid receptors are expressed. This local concentration can differ from the circulating levels of the hormone in plasma, because of the actions of redox enzymes in the tissues. The enzymes that modify the oxidation state of the hormones are 11beta-hydroxysteroid dehydrogenases forms I and II. Form I (11β-HSD1) is responsible for the reduction of cortisone to cortisol in vivo, while form II (11β-HSD2) is responsible for the oxidation of cortisol to cortisone. The enzymes have low homology and are expressed in different tissues. 11β-HSD1 is highly expressed in a number of tissues including liver, adipose tissue, and brain, while 11β-HSD2 is highly expressed in mineralocorticoid target tissues, such as kidney and colon. 11β-HSD2 prevents the binding of cortisol to the mineralocorticoid receptor, and defects in this enzyme have been found to be associated with the syndrome of apparent mineralocorticoid excess (AME).

Since the binding of the 11β-hydroxysteroids to the corticosteroid receptor leads to upregulation of PEPCK and therefore to increased blood glucose levels, inhibition of 11β-HSD1 is a promising approach for the treatment of diabetes. In addition to the bio-chemical discussion above, there is evidence from transgenic mice, and also from small clinical studies in humans, that confirm the therapeutic potential of the inhibition of 11β-HSD1.

Experiments with transgenic mice indicate that modulation of the activity of 11β-HSD1 could have beneficial therapeutic effects in diabetes and in the metabolic syndrome. For example, when the 11β-HSD1 gene is knocked out in mice, fasting does not lead to the normal increase in levels of G6 Pase and PEPCK, and the animals are not susceptible to stress- or obesity-related hyperglycemia. Moreover, knockout animals which are rendered obese on a high-fat diet have significantly lower fasting glucose levels than weight-matched controls (Y. Kotolevtsev et al. *Proc. Natl. Acad. Sci. USA* 1997, 94, 14924). 11β-HSD1 knockout mice have also been found to have improved lipid profile, insulin sensitivity, and glucose tolerance (N. M. Morton et al. *J. Biol. Chem.* 2001, 276, 41293). The effect of overexpressing the 11β-HSD1 gene in mice has also been studied. These transgenic mice displayed increased 11β-HSD1 activity in adipose tissue and exhibited visceral obesity which is associated with the metabolic syndrome. Levels of the corticosterone were increased in adipose tissue, but not in serum, and the mice had increased levels of obesity, especially when on a high-fat diet. Mice fed on low-fat diets were hyperglycemic and hyperinsulinemic, and also showed glucose intolerance and insulin resistance (H. Masuzaki et al. *Science*, 2001, 294, 2166).

The effects of the non-selective 11β-hydroxysteroid dehydrogenase inhibitor carbenoxolone have been studied in a number of small trials in humans. In one study, carbenoxolone was found to lead to an increase in whole body insulin sensitivity, and this increase was attributed to a decrease in hepatic glucose production (B. R. Walker et al. *J. Clin. Endocrinol. Metab.* 1995, 80, 3155). In another study, decreased glucose production and glycogenolysis in response to glucagon challenge were observed in diabetic but not healthy subjects (R. C. Andrews et al. *J. Clin. Endocrinol. Metab.* 2003, 88, 285). Finally, carbenoxolone was found to improve cognitive function in healthy elderly men and also in type 2 diabetics (T. C. Sandeep et al. *Proc. Natl. Acad. Sci. USA* 2004, 101, 6734).

A number of non-specific inhibitors of 11β-HSD1 and 11β-HSD2 have been identified, including glycyrrhetinic acid, abietic acid, and carbenoxolone. In addition, a number of selective inhibitors of 11β-HSD1 have been found, including chenodeoxycholic acid, flavanone and 2'-hydroxyflavanone (S. Diederich et al. *Eur. J. Endocrinol.* 2000, 142, 200 and R. A. S. Schweizer et al. *Mol. Cell. Endocrinol.* 2003, 212, 41).

A need exists in the art for 11β-HSD1 inhibitors that have efficacy for the treatment of diseases such as type II diabetes mellitus and metabolic syndrome. Further, a need exists in the art for 11β-HSD1 inhibitors having IC50 values less than about 1 µM.

SUMMARY OF THE INVENTION

In one embodiment of the invention, provided is a compound of the formula (I):

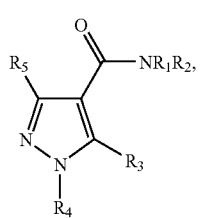

(I)

wherein:

$R_1$ is hydrogen;

$R_2$ is adamantane, unsubstituted or substituted with hydroxy, alkoxy, halogen, amino, loweralkyl-acylamino or loweralkylsulfonylamino;

$R_3$ is lower alkyl, branched or unbranched, halogen, halo-lower alkyl, 3- to 8-membered heteroaryl having 1-3 heteroatoms selected from N, O and S, which may be unsubstituted or substituted with halogen or lower alkyl, —NH$(CH_2)_n$OH, —NH$(CH_2)_n$OCH$_3$, —NHCH(CH$_3$)$_2$, —NH$(CH_2)_n$CH$_3$OH, —NH(CH$_3$)(CH$_2$)$_n$OCH$_3$, —NH(CH$_3$)(CH$_2$)$_n$OH, —NCH$_2$CH(CH$_3$)OH, —NH$(CH_2)_n$O(CH$_2$)$_n$CH$_3$, —N(CH$_2$CH$_3$)$_2$, —(CH$_2$)OH, —(CH$_2$)$_n$O(CH$_2$)$_n$CH$_3$, —(CH$_2$)O(CH$_2$)$_n$-alkyl, —(CH$_2$)O(CH$_2$)$_n$— cycloalkyl, or a 3- to 8-membered monocyclic heterocycle with 1-3 hetero atoms selected from N, O and S, which may be unsubstituted or substituted with lower alkyl, hydroxy, hydroxy phenyl, —(CH$_2$)$_n$-phenyl, —CH$_2$(CH$_2$)$_n$OH or halogen;

$R_4$ is lower alkyl, branched or unbranched, unsubstituted or substituted with hydroxyl, —(CH$_2$)$_m$—(C$_3$-C$_6$)cycloalkyl, unsubstituted or substituted with hydroxy or lower alkyl, halo-alkyl, hydroxyalkyl, —(CH$_2$)$_n$O(CH$_2$)$_n$CH$_3$, —(CH$_2$)$_n$O(CH$_2$)$_p$O(CH$_2$)$_n$CH$_3$, —(CH$_2$)$_n$OC(CH$_3$)$_3$ or —CH(CH$_3$)$_2$(CH$_2$)$_n$OH; saturated heterocyclyl ring containing 4-6 atoms of which 1-2 are selected from N, O or S.

$R_5$ is hydrogen or lower alkyl, unsubstituted or substituted with halogen; and n is 0, 1, 2 or 3;

m is 0, 1 or 2; and p is 1, 2 or 3, and pharmaceutically acceptable salts thereof.

In another embodiment of the present invention, provided is a pharmaceutical composition, comprising a therapeutically effective amount of a compound according to formula I or pharmaceutically acceptable salts thereof, and a pharmaceutically acceptable carrier.

In a further embodiment of the present invention, provided is a method of treating a metabolic disorder, comprising the step of administering a therapeutically effective amount of a compound according to formula I to a patient in need thereof.

DETAILED DESCRIPTION OF THE INVENTION

The present invention pertains to inhibitors of 11β-HSD1. In a preferred embodiment, the invention provides for pharmaceutical compositions comprising pyrazoles of the formula I:

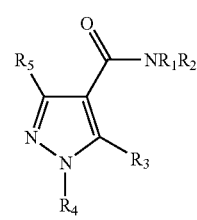

(I)

as well as pharmaceutically acceptable salts thereof, that are useful as inhibitors of 11β-HSD1.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

In this specification the term "aryl" is used to mean a mono- or polycyclic aromatic ring system, in which the rings may be carbocyclic; or in which the rings may contain one or more atoms selected from O, S, and N, typically referred to as a heteroaryl ring. Examples of aryl groups are phenyl, pyridyl, benzimidazolyl, benzofuranyl, benzothiazolyl, benzothiophenyl, cinnolinyl, furyl, imidazo[4,5-c]pyridinyl, imidazolyl, indolyl, isoquinolinyl, isoxazolyl, naphthyl, [1,7] naphthyridinyl, oxadiazolyl, oxazolyl, phthalazinyl, purinyl, pyidazinyl, pyrazolyl, pyrido[2,3-d]pyrimidinyl, pyrimidinyl, pyrimido[4,5-d]pyrimidinyl, pyrrolo[2,3-d]pyrimidinyl, pyrrolyl, quinazolinyl, quinolinyl, quinoxalinyl, tetrazolyl, thiadiazolyl, thiazolyl, thiophenyl, triazolyl, and the like.

As used herein, the term "alkyl" means, for example, a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl(n-butyl, isobutyl, sec-butyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

The term "heterocyclyl" refers to a saturated or partly unsaturated 5- or 6-membered ring which can comprise one, two or three atoms selected from nitrogen, oxygen and/or sulphur. Examples of heterocyclyl rings include piperidinyl, piperazinyl, azepinyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, dihydrofuryl, tetrahydrofuryl, dihydropyranyl, tetrahydropyranyl, and thiomorpholinyl.

As used herein, the term "lower alkyl" means, for example, a branched or unbranched, cyclic or acyclic, saturated or unsaturated (e.g. alkenyl or alkynyl) hydrocarbyl radical wherein said cyclic lower alkyl group is $C_3$, $C_4$, $C_5$, $C_6$, $C_7$, $C_8$, $C_9$ or $C_{10}$, preferably $C_3$, $C_4$, $C_5$, $C_6$ or $C_7$; and wherein said acyclic lower alkyl group is $C_1$, $C_2$, $C_3$, $C_4$, $C_5$, $C_6$ or $C_7$, preferably $C_1$, $C_2$, $C_3$, $C_4$ such as, for example, methyl, ethyl, propyl (n-propyl or isopropyl) or butyl (n-butyl, sec-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cyclo loweralkyl, cyclo loweralkenyl and cyclo loweralkynyl.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, arloxycarbonylamino, aminocarbonyloxy, mono- or di-alkylaminocarbonyloxy, arylaminocarbonyloxy) and ureas (e.g. mono- or di-alkylamino-carbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be, for example, 1 to 3 substitutents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

Compounds of formula I include pharmaceutically acceptable esters thereof. "Pharmaceutically acceptable esters" means that compounds of general formula (I) may be derivatized at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

In more detail, for example, the pharmaceutically usable esters are compounds of formula I, wherein e.g. a hydroxy group can be esterified. Examples of such esters are formate, acetate, propionate, butyrate, isobutyrate, valerate, 2-methylbutyrate, isovalerate and N,N-dimethylaminoacetate.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

General Synthesis of Compounds According to the Invention pound of formula 3 is reacted with a hydrazine to give the compound of formula 4. The ester protective group in the compound of formula 4 is then cleaved and the resulting carboxylic acid is coupled with an amine of formula $HNR_1R_2$ to give the desired compound of formula 1. The reaction of a compound of formula 2 to give a compound of formula 3 can be carried out using conditions that are well known in the art. For example, in the case where X represents dimethylamino, the compound of formula 3 can be prepared by treating a compound of formula 2 with N,N-dimethylformamide dimethyl acetal in an inert solvent such as an aromatic hydrocarbon (for example, toluene) at a temperature between about 50° C. and about 100° C. Examples of conditions for this reaction can be found in the literature, for example, in H. H. Wassermann et al. *Tetrahedron Lett.* 1984, 25, 3743-3746, in S. Gelin et al. *Synthesis* 1983, 566-568, and in J. Svete et al. *Synthesis* 1990, 70-72. In the case where X represents ethoxy, the compound of formula 3 can be prepared by treating a compound of formula 2 with triethylorthoformate in the presence of acetic anhydride at the reflux temperature. Examples of conditions for this reaction can be found in the literature, for example, in L. Claisen *Liebigs Ann. Chem.* 1897, 297, 1-18; in L. Crombie et al. *J. Chem. Soc. Perkin Trans. I* 1979, 464-471; in M. S. S. Palanki et al. *J. Med. Chem.* 2000, 43, 3995-4004; and in M. T. Herrero et al. *Tetrahedron* 2002, 58, 8581-8589.

Another general approach to the synthesis of intermediate 4 is also shown in Scheme 1. In this method as reported (PCT Int. Appl. 2003051820) where X=dimethylamino, commer-

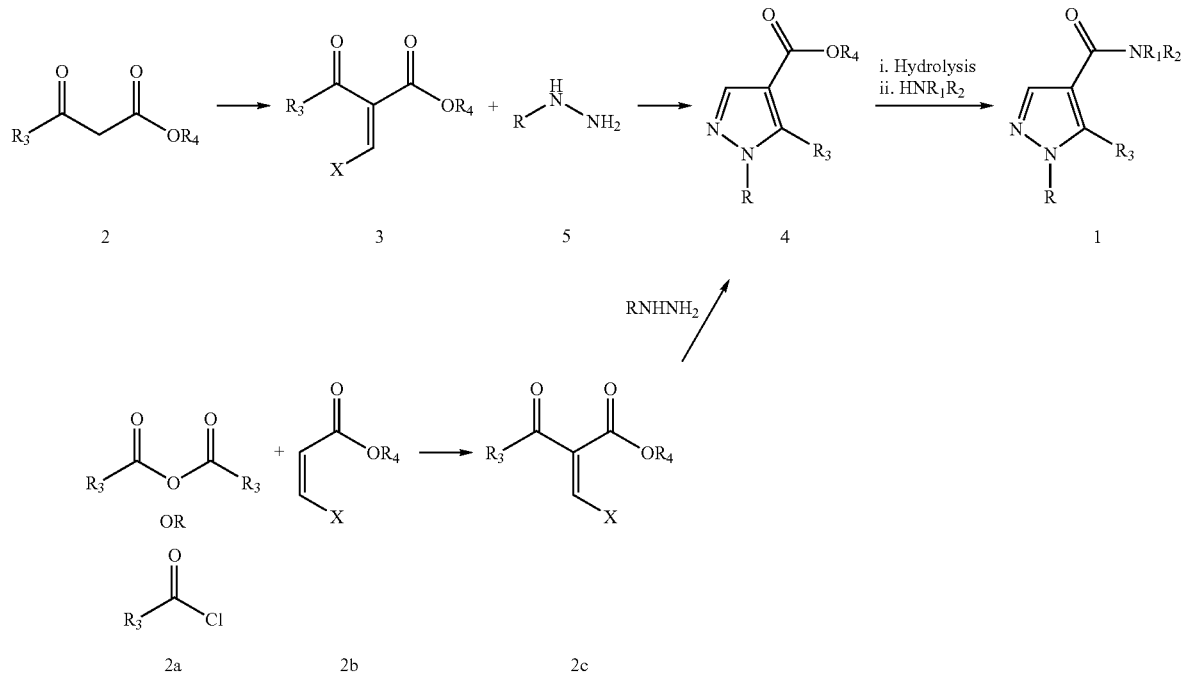

One general approach to the synthesis of compounds of the invention is shown in Scheme 1. According to this process, a β-keto-ester of formula 2 is converted to a compound of formula 3 where X represents dialkylamino (such as dimethylamino) or lower-alkoxy (such as ethoxy) and then the compound is...

cially available 3-dimethylamino-acrylic acid ethyl ester (formula 2b) is treated with trifluoroacetic anhydride in toluene thereby generating an intermediate represented by formula 2c. Treatment of the intermediate of formula 2c with an alkyl hydrazine generates compounds of general formula 4.

The reaction of the compound of formula 3 with a hydrazine can be carried out under a variety of conditions. For example, the compound of formula 3 can be reacted with a hydrazine or the acid addition salt of a hydrazine in an inert solvent such as an alcohol (for example, ethanol). In the case where an acid addition salt of the hydrazine is used, then the reaction is carried out in the additional presence of a base such as a tertiary alkylamine (for example, triethylamine or diisopropylethylamine). The reaction is conveniently carried out at a temperature between about −20° C. and about 80° C. Examples of conditions for this reaction can be found in the literature, for example, in J. R. Beck et al. *J. Heterocycl. Chem.* 1987, 24, 739-740; in G. Menozzi et al. *J. Heterocycl. Chem.* 1987, 24, 1669-1676; in F. R. Busch et al. PCT Int. Appl. WO 2003051845; in J. F. Lambert et al. PCT Int. Appl. WO 2002044133; in H. Shimotori et al. U.S. Pat. No. 4,792,565; and in H. Ohki et al. *Bioorg. Med. Chem. Lett.* 2002, 12, 3191-3193.

The cleavage of a compound of formula 4 to the corresponding carboxylic acid is carried out using reaction conditions that are well known in the field of organic synthesis, many of which are outlined in "Protective Groups in Organic Synthesis" [T. W. Greene and P. G. M. Wuts, 2nd Edition, John Wiley & Sons, N.Y. 1991]. For example, in the case where $R_4$ represents methyl or ethyl, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0° C. and about room temperature, preferably at about room temperature. As another example, in the case where $R_4$ represents a group that can be cleaved under acidic conditions, such as a tert-butyl group, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of an inert organic solvent (such as dichloromethane) and at a temperature between about 0° C. and about room temperature, preferably at about room temperature. As a final (but not limiting) example, in the case where $R_4$ represents a group that can be cleaved by catalytic hydrogenation, and with the further condition that the rest of the molecule is stable to such conditions, the reaction may be carried out by hydrogenation in the presence of a noble metal catalyst such as palladium-on-carbon in the presence of an inert solvent (for example, an alcohol such as ethanol) at about room temperature and under atmospheric pressure.

The coupling of a carboxylic acid of structure 4 where $R_4$ represents hydrogen with an amine of structure $HNR_1R_2$, according to Scheme 1, can be achieved using methods well known to one of ordinary skill in the art. For example, the transformation can be carried out by reaction of a carboxylic acid of structure 4 where $R_4$ represents hydrogen or of an appropriate derivative thereof such as an activated ester, with an amine of structure $HNR_1R_2$ or a corresponding acid addition salt (e.g., the hydrochloride salt) in the presence, if necessary, of a coupling agent, many examples of which are well known per se in peptide chemistry. The reaction is conveniently carried out by treating the carboxylic acid of structure 4 where $R_4$ represents hydrogen with the hydrochloride of the amine of structure $HNR_1R_2$ in the presence of an appropriate base, such as diisopropylethylamine, a coupling agent such as O-(benzotriazol-1-yl)-1,1,3,3-tetramethyluronium hexafluorophosphate or TSTU and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0° C. and about room temperature, preferably at about room temperature. Alternatively, the reaction can be carried out by converting the carboxylic acid of formula 4 where $R_4$ represents hydrogen to an activated ester derivative, such as the N-hydroxysuccinimide ester, and subsequently reacting this with the amine of structure $HNR_1R_2$ or a corresponding acid addition salt. This reaction sequence can be carried out by reacting the carboxylic acid of formula 4 where $R_4$ represents hydrogen with N-hydroxysuccinimide in the presence of a coupling agent such as N,N'-dicyclohexylcarbodiimide in an inert solvent such as tetrahydrofuran at a temperature between about 0° C. and about room temperature. The resulting N-hydroxysuccinimide ester is then treated with the amine of structure $HNR_1R_2$ or a corresponding acid addition salt, in the presence of a base, such as an organic base (e.g., triethylamine or diisopropylethylamine or the like) in a suitable inert solvent such as N,N-dimethylformamide at around room temperature.

The reaction sequence shown in Scheme 1 can also be carried out using solid-phase synthesis, in the case where X represents a polymer-bound amino group. Following this approach, the compound of formula 2 is treated with N-formylimidazole dimethyl acetal and a polymer-bound amine such as an aniline-functionalized cellulose derivative (for example, 4-amino-phenyl-sulfonyl-ethoxy-cellulose, which is available from Ionto-sorb, Usti nad Labem, Czech Republic) in the presence of an acid catalyst such as camphorsulfonic acid in an inert solvent, such as N,N-dimethylformamide at a temperature around 80° C., to give a compound of formula 3 where X represents a polymer-bound aniline. The compound of formula 3 is then converted into the compound of formula 4 by treatment with a hydrazine in an inert solvent such as an alcohol (for example, isopropanol) at a temperature around the boiling point of the solvent. Examples of conditions for this reaction can be found in the literature, for example, in L. De Luca et al. *J. Comb. Chem.* 2003, 5, 465-471.

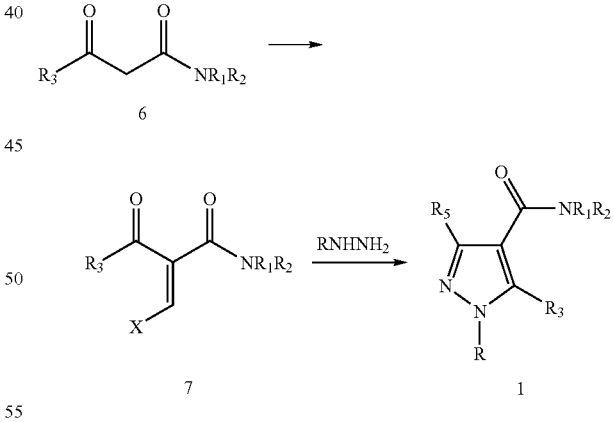

Scheme 2

A pyrazole-4-carboxamide of formula 1 for which $R_5$=hydrogen can be prepared according to Scheme 2, where a β-keto-amide of formula 6 is converted to a compound of formula 7 where X represents dialkylamino (such as dimethylamino) or lower-alkoxy (such as ethoxy) and then the compound of formula 7 reacts with a hydrazine to give the compound of formula 1. The reaction of a compound of formula 6 to give a compound of formula 7 can be carried out using conditions that are well known in the art. For example, in the case where X represents dimethylamino, the compound of formula 7 can be prepared by treating a compound of formula 6 with N,N-dimethylformamide dimethyl acetal in an inert solvent such as an aromatic hydrocarbon (for example, toluene) at a temperature between about 50° C. and about 100° C. Examples of conditions for this reaction can be found in the literature, for example, in R. Zupet et al. *J. Heterocycl. Chem.* 1991, 28, 1731-1740; in D. E. Seitz et al. *Tetrahedron Lett.* 1995, 36, 1413-1416; in A. V. Rama Rao et al. *Tetrahedron Lett.* 1990, 31, 1439-42; and in P. Kocienski et al. *Tetrahedron Lett.* 1988, 29, 4481-4. In the case where X represents ethoxy, the compound of formula 7 can be prepared by treating a compound of formula 6 with triethylorthoformate in the presence of acetic anhydride at the reflux temperature. Examples of conditions for this reaction can be found in the literature, for example, in J. H. Dewar et al. *J. Chem. Soc.* 1961, 3254-3260.

The reaction of the compound of formula 7 with a hydrazine can be carried out under a variety of conditions. For example, the compound of formula 7 can be reacted with a hydrazine or the acid addition salt of a hydrazine in an inert solvent such as an alcohol (for example, ethanol). In the case where an acid addition salt of the hydrazine is used, then the reaction is carried out in the additional presence of a base such as a tertiary alkylamine (for example, triethylamine or diisopropylethylamine). The reaction is conveniently carried out at a temperature between about −20° C. and about 80° C. Examples of conditions for this reaction can be found in the literature, for example, in A. X. Wang et al. *Bioorg. Med. Chem. Lett.* 1998, 8, 2787-2792; in T. A. Elmaati et al. *Pol. J. Chem.* 2002, 76, 945-952 Chemical Abstracts AN 2002:501464; and in G. Giacomelli et al. *Eur. J. Org. Chem.* 2003, 537-541.

The reaction sequence shown in Scheme 2 can also be carried out in the case where X represents an aniline. Thus, a compound of formula 7 can be prepared from a compound of formula 6 by treatment with an N-(alkoxymethylene)-aniline, in the optional presence of an inert solvent such as kerosene, at elevated temperature such as between about 125° C. and about 140° C. Examples of conditions for this reaction can be found in the literature, for example, in F. B. Dains *Chem. Ber.* 1902, 35, 2496-2500; in F. B. Dains et al. *J. Am. Chem. Soc.* 1909, 31, 1148-1157; in F. B. Dains et al. *J. Am. Chem. Soc.* 1918, 40, 562-569; and in O. S. Wolfbeis *Chem. Ber.* 1981, 114, 3471-3484. The compound of formula 7 can then be converted to the compound of formula 1 by treatment with a hydrazine in an inert solvent such as ethanol at a temperature around the reflux temperature of the solvent. Examples of conditions for this reaction can be found in the literature, for example, in F. B. Dains et al. *J. Am. Chem. Soc.* 1909, 31, 1148-1157; in F. B. Dains et al. *J. Am. Chem. Soc.* 1916, 38, 1515; in F. B. Dains et al. *J. Am. Chem. Soc.* 1918, 40, 562-569; and in A. N. Borisevich et al. *Ukrainskii Khimicheskii Zhurnal* 1986, 52, 641-7 Chemical Abstracts AN 1987:458919.

Scheme 3

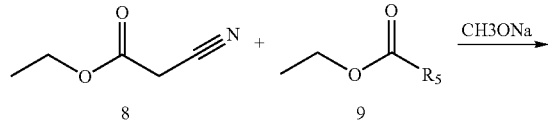

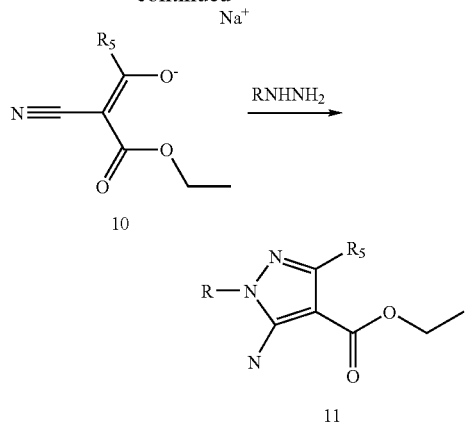

Compounds of the invention in which $R_5$ represents lower alkyl including lower haloalkyl such as trifluoromethyl can be made according to the chemistry shown in Scheme 3. According to this method, as described for the case where $R_5$ represents trifluoromethyl in EP 1067121A2, an alkyl cyanoacetate such as ethyl cyanoacetate is treated with an ester such as ethyl trifluoroaceate in the presence of a base such as sodium ethoxide in ethanol. The resulting sodium salt adduct 10 is then treated with a alkyl hydrazine such as methylhydrazine to effect cyclization to the 5-amino-1-alkylpyrazole 11. The 5-amino group can then be transformed to other groups such as halogen (vide infra).

Scheme 4

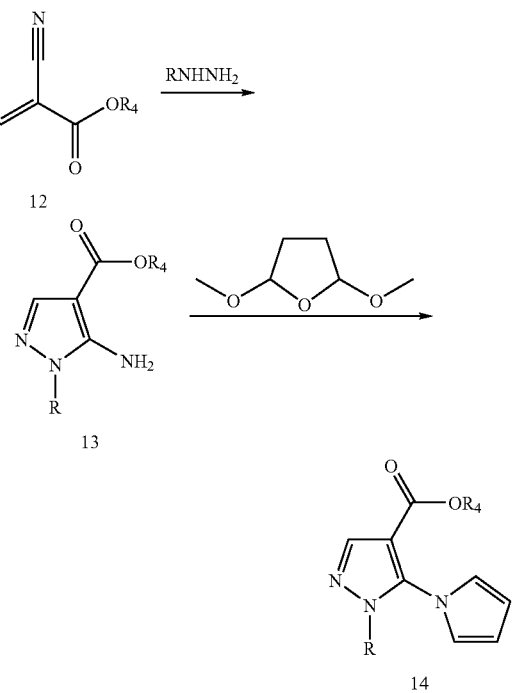

As shown in Scheme 4 a 1-alkyl-5-pyrrolyl-pyrazole-4-carboxylic acid derivative of formula 14 can be prepared starting from a 3-alkoxy-2-cyano-acrylic acid ester of formula 12 by reaction with a hydrazine of formula $RNHNH_2$ to give an intermediate 5-amino-pyrazole of formula 13, which can then be reacted with 2,5-dimethoxy-tetrahydrofuran to give the 5-pyrrolyl-pyrazole of formula 14. This can be converted to a carboxamide of the invention by reactions analogous to those discussed above with reference to Scheme 1. The pyrazole-forming annulation reaction can be conveniently carried out by treating a 3-alkoxy-2-cyano-acrylic acid ester of formula 12 (such as 3-ethoxy-2-cyano-acrylic acid ethyl ester) with a hydrazine of formula $RNHNH_2$ in an inert solvent such as ethanol at the reflux temperature. The subsequent annulation to form the pyrrole ring is conveniently carried out by heating the intermediate 5-amino-pyrazole with 2,5-dimethoxy-tetrahydrofuran in an organic acid such as acetic acid at a temperature of around 100° C. An example of conditions suitable for this process can be found in the literature, for example, in M. Kopp et al. *J. Heterocycl. Chem.* 2001, 38, 1045-1050. Further examples of procedures for the preparation of 5-amino-1-aryl-pyrazole-4-carboxylate esters can be found in J. Svetlik *Heterocycles* 1984, 22, 2513-2516; in J. R. Beck et al. *J. Heterocycl. Chem.* 1987, 24, 267-270; and in T. Luebbers et al. *Bioorg. Med. Chem. Lett.* 2000, 10, 821-826. The carboxylate ester of formula 14 can then be hydrolyzed to the corresponding carboxylic acid and coupled with an amine of formula $HNR_1R_2$ using procedures analogous to those described above for the conversion of a carboxylate ester of formula 4 to a compound of the invention of formula 1.

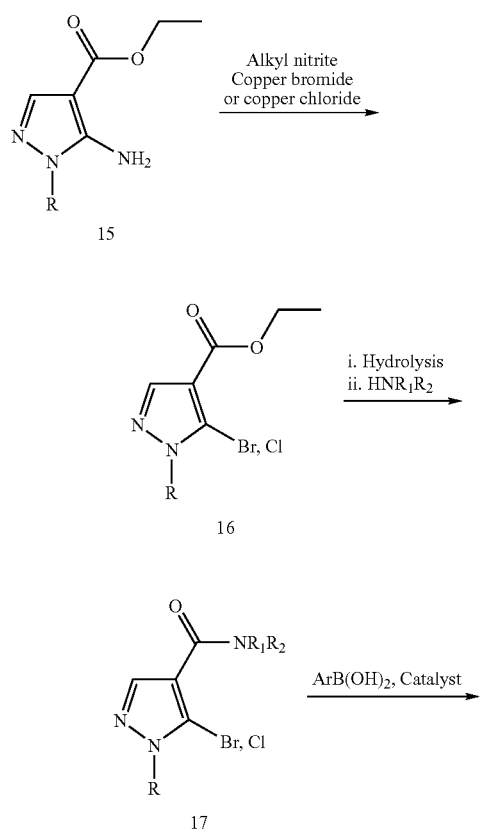

-continued

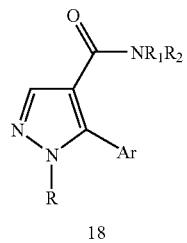

18

As shown in Scheme 5, a 1-alkyl-5-aryl-pyrazole-4-carboxylic acid derivative of formula 18 can be prepared starting from a 5-amino-pyrazole-4-carboxylate ester of formula 15 by diazotization of the amino group in the presence of a halogenating agent such as copper(II) bromide. The reaction is conveniently carried out by treating the compound of formula 15 with an alkyl nitrite such as tert-butyl nitrite or isoamyl nitrite in an inert solvent such as a halogenated hydrocarbon (for example, carbon tetrachloride) at a temperature around 50° C., in the presence of a bromine source such as bromine, copper(II) bromide, dibromomethane, or bromoform. Alternatively, the chlorination of the C-5 position can be effected by substitution of a bromine source with a chloride source such as copper (II) chloride. Conditions appropriate for this reaction can be found in the literature, for example in J. R. Beck and M. P. Lynch U.S. Pat. No. 4,620,865 and in H. Mizukawa JP 2002003410. The conversion of the ester of formula 16 to an amide of formula 17 is analogous to the conversion of a compound of formula 4 to a compound of formula 1 as discussed above, and can be carried out using similar reactions. The conversion of a compound of formula 17 to a compound of the invention of formula 18 can be carried out using a Suzuki reaction with an organoboron intermediate such as an aryl-boronic acid or an ester thereof, a reaction that is well known to one of average skill in the art. For example, the reaction can be conveniently carried out by reacting a compound of formula 17 with an aryl-boronic acid in a convenient inert solvent such as a polar aprotic solvent (e.g., N,N-dimethylformamide) or an ether (e.g., dioxane) or water, in the presence of a catalytic amount of a palladium(0) complex (e.g., tetrakis(triphenylphosphine)palladium(0)) or a compound which can be reduced in situ to give palladium(0) (for example, palladium(II) acetate or bis(triphenylphosphine)-palladium(II) chloride), in the optional additional presence of a catalytic amount of a phosphine ligand, for example tri-o-tolylphosphine or tri-tert-butylphosphine, or alternatively in the presence of a preformed complex of palladium(0) with a phosphine ligand such as bis(tri-cyclohexylphosphine)palladium, and also in the presence of an inorganic base, for example, an alkali metal carbonate, bicarbonate, hydroxide or phosphate (e.g., potassium phosphate or sodium carbonate or sodium hydroxide) at a temperature between about room temperature and about 100° C., and preferably at between about room temperature and about 50° C. Conditions appropriate for this reaction can be seen in the literature, for example in X.-J. Wang and K. Grozinger *Tetrahedron Lett.* 2000, 41, 4713-4716. The starting material of formula 15 can be made from a 3-alkoxy-2-cyano-acrylic acid ester of formula 12 by reaction with an alkyl-hydrazine by reactions analogous to those described above for the preparation of a compound of formula 13. Conditions appropriate for this reaction can be found in the literature, for example in F. Bondavalli et al. *J. Med. Chem.* 2002, 45, 4875-4887; in S. Schenone et al. *Bioorg. Med. Chem. Lett.* 2001, 11, 2529-

2531; in M. Kopp et al. *J. Heterocycl. Chem.* 2001, 38, 1045-1050; and in P. Seneci et al. *Synth. Commun.* 1999, 29, 311-341.

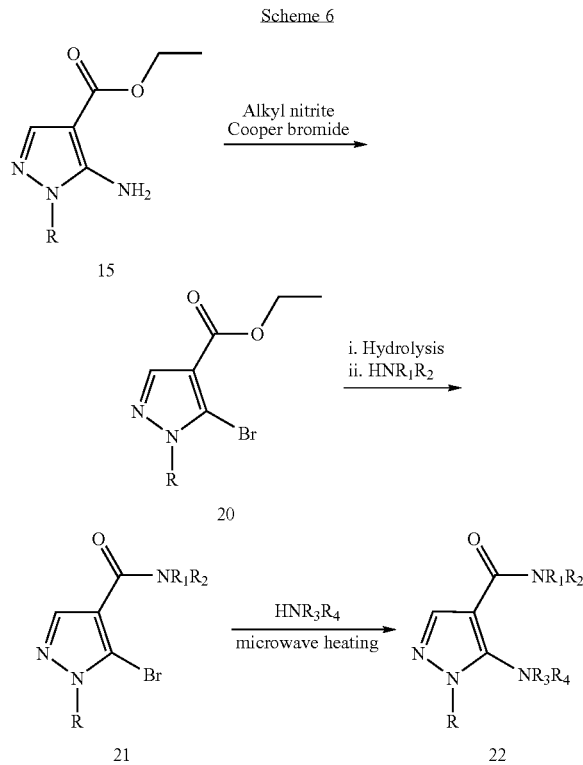

As shown in Scheme 6, it is possible to displace the 5-bromo-pyrazole of structure 21 with amines under microwave heating conditions to generate compounds of general structure 22.

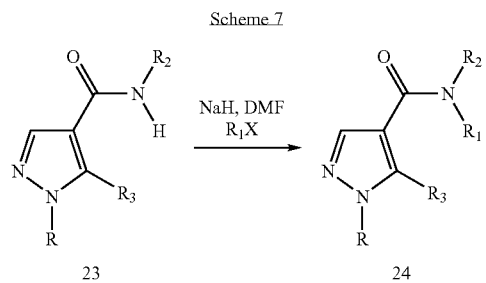

As shown in Scheme 7, a compound of formula 24 in which $R_1$ represents lower alkyl can be prepared from a compound of formula 23 by reaction with a strong base (such as sodium hydride) in an inert solvent (such as dimethylformamide) at room temperature to give the corresponding anion. This is then reacted without isolation with a lower-alkyl halide of formula $R_1X$, again at room temperature, to give the desired compound of formula 24 in which $R_1$ represents lower alkyl.

Methods suitable for the preparation of many β-keto-esters of formula 2 are known in the literature using a variety of synthetic methods. A listing of many of these methods can be found in "Comprehensive Organic Transformations: A Guide to Functional Group Preparations" [R. C. Larock, VCH Publishers, Inc. New York, 1989], for example on pages 685, 694-695, and 768. Additional examples of synthetic methods appropriate for the preparation of many β-keto-esters of formula 2 can be found in "Advanced Organic Chemistry" [J. March, 3$^{rd}$ Edition, John Wiley & Sons, Inc. New York, 1985], on pages 437-439, and 823-824. In addition, more than 100 β-keto-esters of formula 2 are listed as commercially available in the Available Chemicals Directory which is well known to one of skill in the art of organic synthesis.

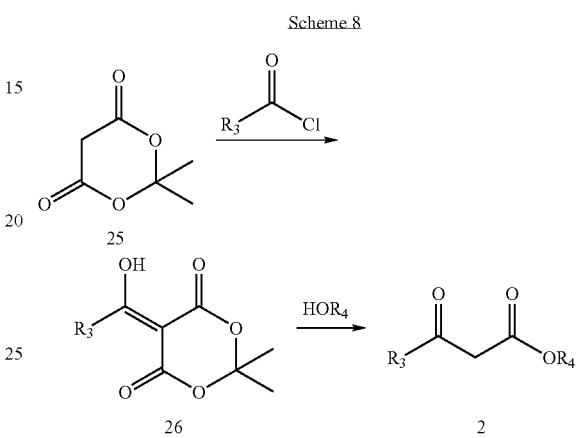

One example of a method to prepare a β-keto-ester of formula 2 is outlined in Scheme 8. Meldrum's acid (25) is treated with an acyl chloride of formula $R_3COCl$ in an anhydrous inert solvent such as a halogenated hydrocarbon (e.g. methylene chloride or dichloroethane). The reaction is carried out in the presence of an anhydrous organic base, such as pyridine, triethylamine, or diisopropylethylamine, at around room temperature. Conditions suitable for this reaction can be found in the literature, for example in H. Emtenäs et al. *J. Org. Chem.* 2001, 26, 6756-6761. The resulting intermediate of formula 26 is then heated with an alcohol of formula $HOR_4$, either using the alcohol as solvent (for example in the case where the alcohol is methanol or ethanol), or in an inert solvent such as benzene (for example in the case where the alcohol is benzyl alcohol or tert-butyl alcohol). The reaction is conveniently carried out at a temperature between about 60° C. and about 80° C. Conditions suitable for this reaction can be found in the literature, for example in Y. Oikawa et al. *J. Org. Chem.* 1978, 43, 2087-2088.

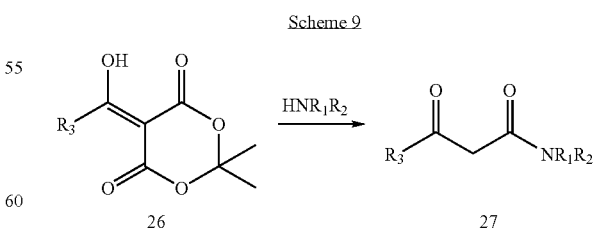

β-Keto-amides of formula 27 can be prepared from the intermediate of formula 26 by treatment with a stoichiometric amount of an amine of formula $HNR_1R_2$ in a suitable inert solvent such as toluene at the refluxing temperature. Conditions suitable for this reaction can be found in the literature, for example in C. S Pak et al. *Synthesis* 1992, 1213-1214.

Sources of Monosubstituted Hydrazines of Formula 5

Many monosubstituted hydrazines of formula 5 can be purchased or prepared using one of a variety of synthetic procedures well known in the field of organic chemistry, as outlined below.

Over a hundred hydrazines some of which may be useful to this invention of formula 5 are commercially available from suppliers such as Aldrich Chemical, Inc., Milwaukee, Wis.; TCI America, Portland, Oreg.; Lancaster Synthesis Ltd, Lancashire, UK; ASDI Inc., Newark, Del.; Ryan Scientific, Isle of Palms, S.C.; Oakwood Products, Inc., West Columbia, S.C.; Alfa Aesar, Ward Hill, Mass. Many other examples can be found by consulting the Available Chemicals Directory (MDL Information Systems, San Leandro, Calif.) or Sci-Finder (Chemical Abstracts Services, Columbus, Ohio).

A variety of methods are known for the preparation of hydrazines and are reviewed in "The Chemistry of the Hydrazo, Azo, and Azoxy Groups. Part 1" [J. Timberlake and J. Stowell; S. Patai Ed.; John Wiley & Sons, Ltd. London 1975, 69-107]. Furthermore, several methods for the preparation of substituted hydrazines are outlined in U. Ragnarsson *Che. Soc. Rev.* 2001, 30, 205-213.

In addition to the procedures outlined in detail below, the following processes have been used to prepare alkyl-hydrazines: the reaction of an aldehyde or ketone with a hydrazide followed by reduction and hydrolysis (CH 307629, Chem. Abs. 51:25623; N. I. Ghali et al. *J Org. Chem.* 1981, 46, 5413-5414); Hofmann reaction of a urea (J. Viret et al. *Tetrahedron* 1987, 43, 891-894); electrophilic amination of an alkyl-amine: (L. F. Audrieth and L. H. Diamond *J. Am. Chem. Soc.* 1954, 76, 4869-4871; A. Koziara et al. *Synth. Commun.* 1995, 25, 3805-3812); Mitsunobu reaction of an alcohol with N-tert-butoxycarbonylaminophthalimide followed by hydrolysis (N. Brosse et al. *Tetrahedron Lett.* 2000, 41, 205-207); conversion of an alkyl-amine to the corresponding N-alkylsydnone followed by hydrolysis (J. Fugger et al. *J. Am. Chem. Soc.* 1955, 77, 1843-1848); reaction of an alkyl bromide with N'-isopropylidene-phosphorohydrazidic acid diethyl ester or diphenylphosphinic hydrazide followed by deprotection (S. Zawadzki et al. *Synthesis* 1987, 485-487; B. Mlotkowska and Z. Zwierzak *Tetrahedron Lett.* 1978, 19, 4731-4734).

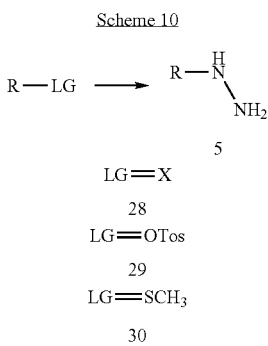

A monosubstituted hydrazine of formula 5 can be prepared by nucleophilic substitution of a compound with a suitable leaving group as shown in Scheme 10. Suitable leaving groups are those compatible with the reaction conditions used to prepare compounds of the invention. Examples of such groups are p-toluenesulfonate (OTos) or halogen groups, including bromide, chloride, and fluoride, preferably bromide and chloride. For example, a compound of structure 5 can be prepared from a compound of structure 28 by treating the halogenated compound of formula 28 with hydrazine hydrate in an alcoholic solvent such as methanol, ethanol, or 1-butanol, at about room temperature, or refluxing temperature of the solvent used.

Alkylhydrazines of formula 5 can be made from the corresponding amine of structure 29 as shown in Scheme 11. The reaction can be carried out by treating the amine of structure 29 with hydroxylamine-O-sulfonic acid in ice-water in the presence of an inorganic base such as potassium hydroxide and water. The synthesis is done at about refluxing temperature. Hydroxylamine-O-sulfonic acid is commercially available.

Alternatively, a compound of structure 5 can be made by adding chloramine to the amine of structure 29 slowly in the presence of potassium hydroxide. The resulting mixture is allowed to stand for a few hours and filtered if it is necessary to free the reaction mixture from precipitated amine hydrochloride and/or ammonium chloride. The alkyl-hydrazine of structure 5 is purified by distillation. Chloramine can be prepared by the reaction of chlorine with ammonia.

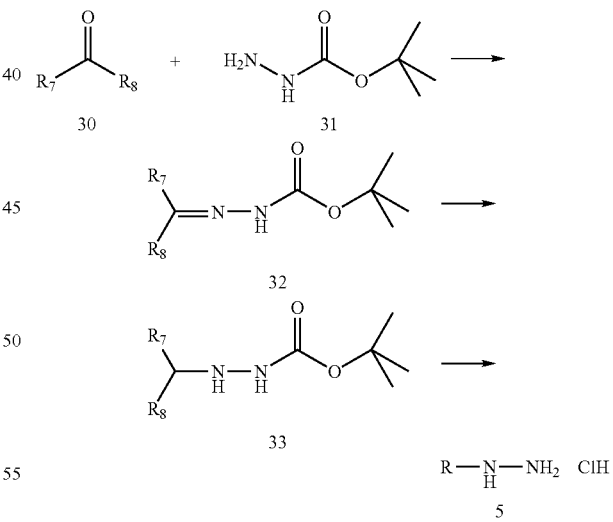

Some alkylhydrazines of structure 5 can also be obtained from a ketone or aldehyde of structure 30, according to Scheme 12, by formation of a tert-butyl alkylidinecarbazate of formula 32, which can be further reduced, and hydrolyzed to give a hydrochloride salt of compound of formula 5. The first reaction can be carried out by treating the carbonyl compound of formula 30 with tert-butyl carbazate of formula 31 in an inert solvent such as hexane, at refluxing temperature for a short period of time. The resulting intermediate 32 can be then reduced by diborane in tetrahydrofuran under anhydrous conditions at about room temperature to give the intermediate carbazate of formula 33. Hydrolysis of the carbazate of structure 33 can be done with a dilute acid, such as hydrochloric acid, at about 100° C. to give the hydrochloride salt of an alkylhydrazine of formula 5. An example of use of this process for the preparation of alkylhydrazines can be found in N. I. Ghali, et. al *J. Org. Chem.* 1981, 46, 5413.

Scheme 13

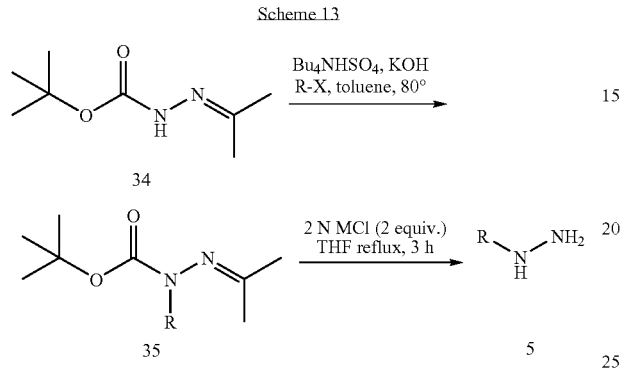

For many alkyl hydrazine derivatives which cannot be obtained commercially, Scheme 13 represents a general procedure which allows for their synthesis. tert-Butyl isopropylidene carbazate is treated under basic alkylation conditions, such as treatment with potassium hydroxide and alkyl halides, in toluene at 80° C. in the presence of a phase transfer catalyst such as tetra-butylammonium bisulfate. After alkylation, the isopropylidene and Boc protecting groups are removed by acid hydrolysis, yielding the desired hydrazine as a hydrochloride salt. The preparation of tert-butyl isopropylidene carbazate as well as its alkylation has been reported in *Synlett* 2004, 2355-2356.

Scheme 14

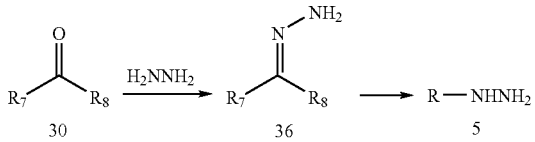

Alternatively, alkylhydrazines of formula 5 can be prepared from a ketone or aldehyde of formula 30, according to Scheme 14, by formation of the intermediate hydrazone of formula 36, followed by a reduction reaction to give the compound of structure 5. It is possible to prepare compounds of the general structure 36 by reacting an aldehyde or ketone (structure 30) with excess hydrazine hydrate in a solvent such as methanol, ethanol, isopropanol, or dioxane at the reflux temperature of the solvent.

The hydrogenation of the intermediate hydrazone of structure 36 can be carried out by using palladium hydroxide or palladium on a carrier (e.g. activated charcoal) as the catalyst, in an alcoholic solvent (e.g. methanol, ethanol) with the presence of acetic acid, at about room temperature under a pressure of 60 p.s.i.

Scheme 15

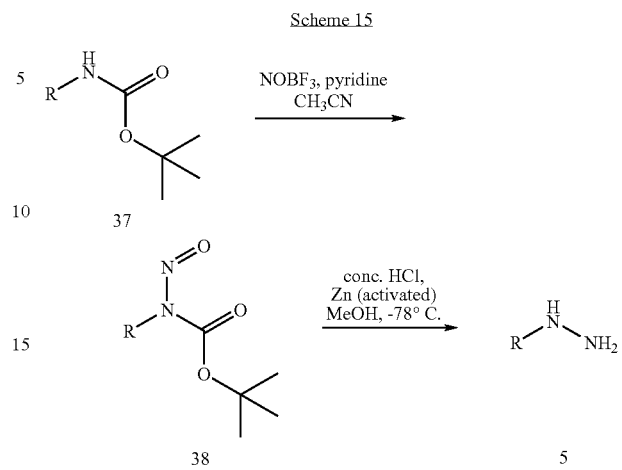

An additional method for the synthesis begins with a Boc-protected amine of formula 37 which is treated with NOBF4 in the presence of pyridine in an aprotic solvent such as acetonitrile to give an N-nitroso-N-Boc-alkyl amine of formula 38. Upon treatment of the N-nitroso-N-Boc-alkyl amine of formula 38 with concentrated HCl and activated zinc powder at a low temperature such as −78° C. in a solvent such as methanol, an alkyl hydrazine of formula 5 is produced (Scheme 15). This method has been reported in the scientific literature (R. Kuang, et al., *Tetrahedron Lett.* 2000, 41, 9575-9579).

Many amines of formula $HNR_1R_2$ are commercially available and known to one skilled in the art. In addition, there are a variety of methods known to one of average skill in the art for the synthesis of amines of formula $HNR_1R_2$. Many of these methods are enumerated in "The Chemistry of the Amino Group" [M. S. Gibson; S. Patai Ed.; John Wiley & Sons, Ltd. London 1968, 37-77], in "Advanced Organic Chemistry" [J. March, 3$^{rd}$ Edition, John Wiley & Sons, Inc. New York, 1985], on pages 1153-1154, and in "Comprehensive Organic Transformations: A Guide to Functional Group Preparations" [R. C. Larock, VCH Publishers, Inc. New York, 1989] on pages 1061-1063. As one example of the preparation of an amine of formula $HNR_1R_2$, a solution of the oxime derived from (1R)-(+)-camphor in an alcohol such as amyl alcohol is treated with sodium added in small pieces over an extended period such as about 4 hours. The reaction is carried out at the reflux temperature of the solvent, and the product is (−)-endobornylamine hydrochloride, a compound of formula $HR_1R_2$ where $R_1$ represents hydrogen and $R_2$ represents the bornyl moiety. Exact conditions for carrying out this reaction can be found in the literature, for example in L. A. Paquette and R. F. Doehner, Jr. *J. Org. Chem.* 1980, 45, 5105-5113. 1-Hydroxyadamantan-4-one reacts with hydroxylamine hydrochloride in refluxing ethanol in the presence of aqueous sodium hydroxide to give 1-hydroxyadamantan-4-one oxime. This is then reduced with lithium aluminum hydride in an inert solvent such as tetrahydrofuran at the reflux temperature to give 4-aminoadamantan-1-ol, which is conveniently isolated and characterized as the hydrochloride salt. Conditions for these reactions can be found in the literature, for example in H. W. Geluk and J. L. M. A. Schlatmann *Tetrahedron* 1968, 24, 5369-5377.

It is also possible to prepare and the cis- and trans-isomers of 4-aminoadamantan-1-ol in a 3-step procedure. First, commercially available 1-hydroxyadamantan-4-one is reacted with (S)-(−)-1-phenylethylamine under reductive amination conditions (sodium triacetoxyborohydride in acetic acid and dichloromethane at room temperature for 12 hours or greater). It is then possible to separate chromatographically the cis- and trans-isomers of the 1-phenylethyl amine reductive amination products. The cis- and trans-isomers of 4-aminoadamantan-1-ol isomers are then obtained under separate hydrogenolysis conditions as shown in Scheme 16 below.

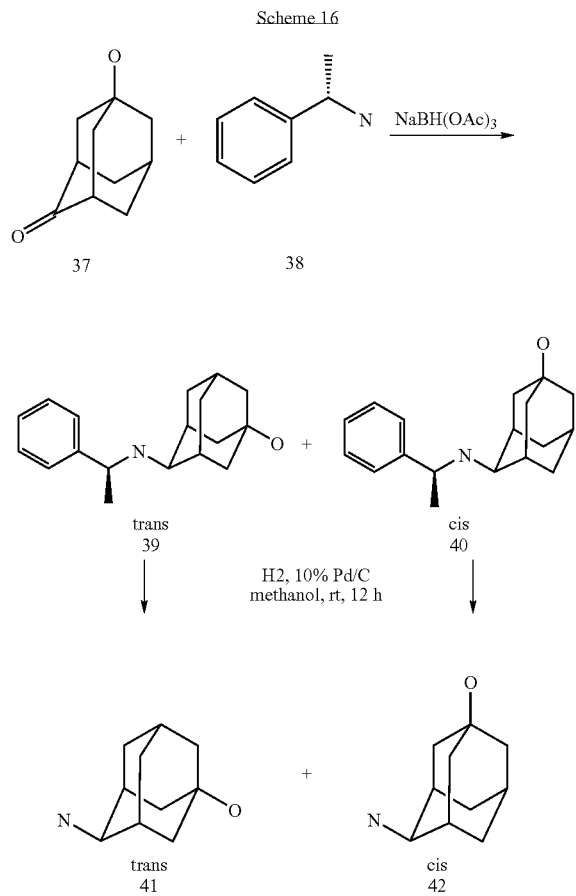

Derivatives of hydroxyadamant-amides can be formed as shown in Scheme 17 below. The tertiary hydroxyl group of 43 can be replaced by fluoro using a suitable reagent such as (diethylamino)sulfur trifluoride (DAST) in a non polar solvent such as methylene chloride. Compound 43 may also be converted to the amine derivative 45 in a two step sequence involving Ritter type reaction with chloroacetonitrile followed by thermolysis with thiourea to provide compound 45. Using similar Ritter reaction conditions, compound 43 may be converted to the N-acetyl derivative 46.

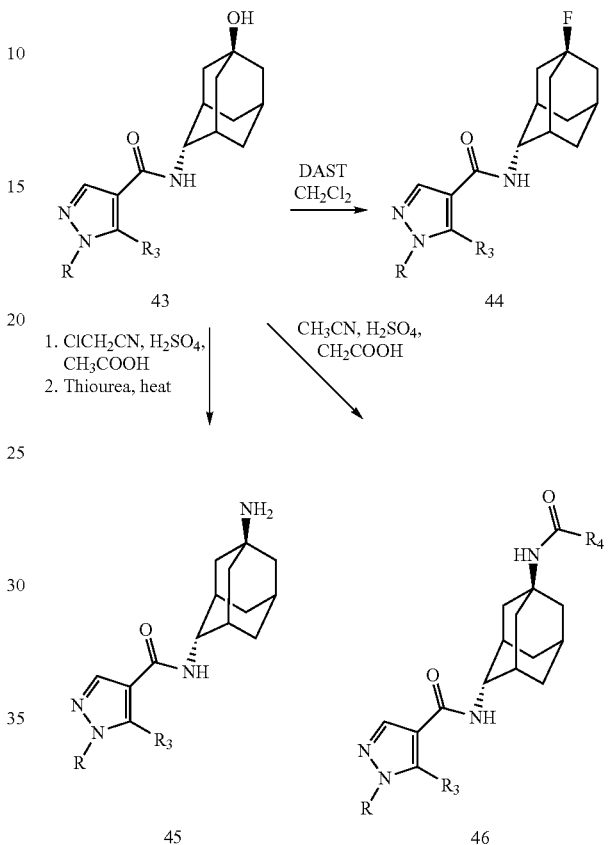

As outlined in Scheme 18, it is possible to prepare intermediate trans-N-(4-amino-adamantan-1-yl)-acetamides (ie 49). Protection of the primary amino group of trans-41 followed by Ritter reaction provides intermediate 48 which is deprotected to provide the trans-N-(4-Amino-adamantan-1-yl)-acetamide 49. Alternatively, compound 49 can be prepared directly from trans-41 (Intermediate 2) by heating with a nitrile in trifluoroacetic acid followed by hydrolysis under basic conditions.

Scheme 18

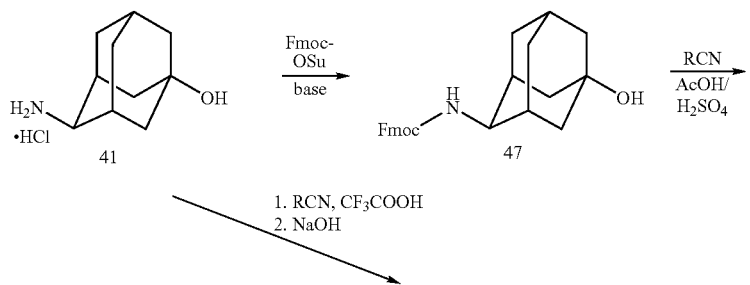

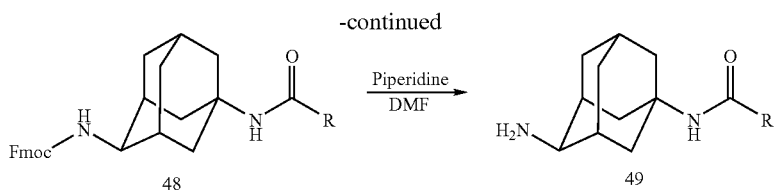

As outlined in Scheme 19, it is also possible to prepare trans-N-(4-aminoadamantan-1-yl)-methanesulfonamides (ie: 53). The FMOC-protected adamantyl alcohol intermediate 47 can be converted to the chloromethylacetamide intermediate 50 using Ritter reaction conditions. Reaction of 50 with thiourea with heating in an alcoholic solvent and acetic acid provides the amine 51. Reaction conditions to carry out the conversion of 47 to 51 can be found in the literature (Jirgensons, A.; Kauss, V.; Kalvinsh, I.; Gould, M. R. *Synthesis* 2000, 12, 1709-1712). Sulfonylation of 51 under basic conditions using a suitable sulfonyl chloride such as methanesulfonylchloride followed by deprotection provides trans-N-(4-amino-adamantan-1-yl)-methanesulfonamides 53.

The trans-N-(4-amino-adamantan-1-yl)-acetamides (ie 49), trans-N-(4-amino-adamantan-1-yl)-methanesulfonamides (ie: 53) or trans-4-amino-adamantan-1-ol (Intermediate-2) can then be coupled to

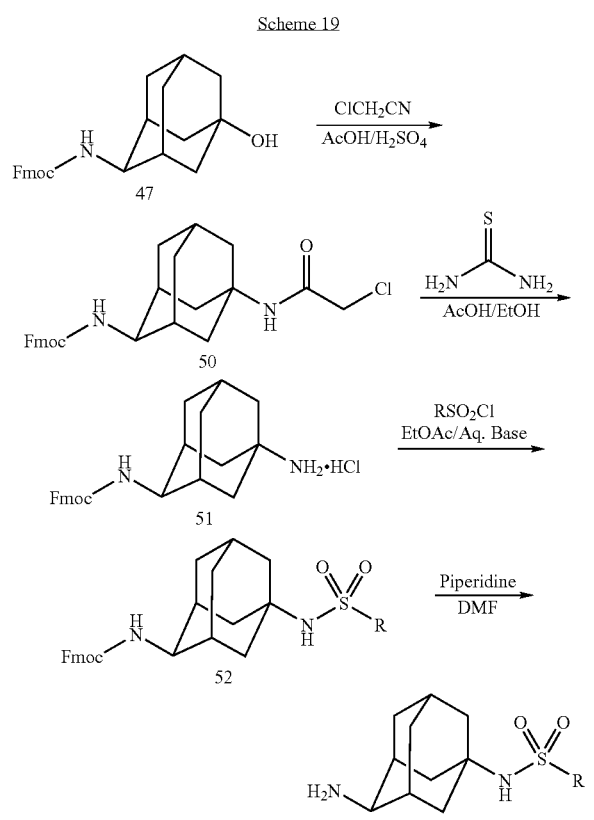

a suitable pyrazole carboxylic acid such as 54 to provide the intermediate adamantly amides 55. Displacement of the chloro group of 55 can be accomplished with a variety of nucleophiles such as pyrazole or substituted pyrazole under basic conditions with heating to provide the product 56.

Scheme 20

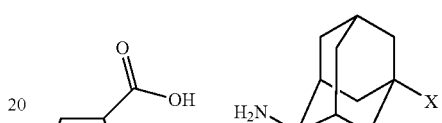

54

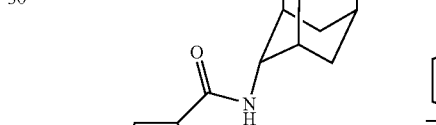

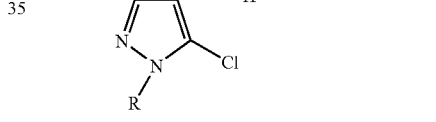

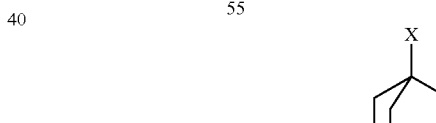

55

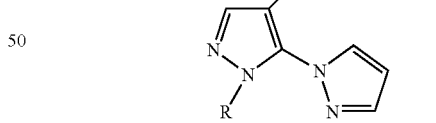

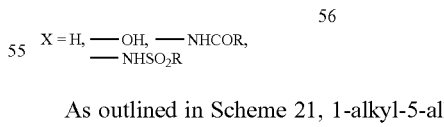

56

X = H, —OH, —NHCOR, —NHSO$_2$R

As outlined in Scheme 21, 1-alkyl-5-alkoxymethyl-pyrazole-4-carboxylic acids 60 can be prepared from a 1-alkyl-5-methyl-pyrazole-4-carboxylic acid ester 57 by bromination with N-bromosuccinimide to provide the intermediate bromomethyl derivative 58. An example of conditions suitable to carry out this bromination reaction can be found in the literature (Beck, J. et al., *J. Heterocycl. Chem.* 1987, 24, 693-695). The displacement of bromine with a suitable alkoxide and concomitant transesterification can be carried out by heating the intermediate 58 in an alcoholic solvent with its corresponding sodium salt. An example of the conditions to carry out this transformation can be found in the literature (Onodera, G. et al. *Organic Letters* 2005, 18, 4029). When not commercially available the sodium alkoxide salts can be easily prepared by treatment of a suitable alcohol with sodium hydride. Hydrolysis of the ester group of 59 provides intermediate acid 60 which may then be coupled to trans-N-(4-Amino-adamantan-1-yl)-acetamides (ie 49), trans-N-(4-amino-adamantan-1-yl)-methanesulfonamides (ie: 53) or trans-4-amino-adamantan-1-ol (Intermediate 2) to provide compounds of structure 61.

As outlined in Scheme 22, isoxazole substituted compounds of structure 65 can be prepared starting from compound 62. Heating compound 62 with a suitable hydrazine 5 followed by hydrolysis of the ester group provides intermediate carboxylic acid 64. Compound 64 may then be coupled to the trans-N-(4-amino-adamantan-1-yl)-acetamides (ie 49), trans-N-(4-amino-adamantan-1-yl)-methanesulfonamides (ie: 53) or trans-4-amino-adamantan-1-ol (Intermediate 2) to provide compounds of structure 65.

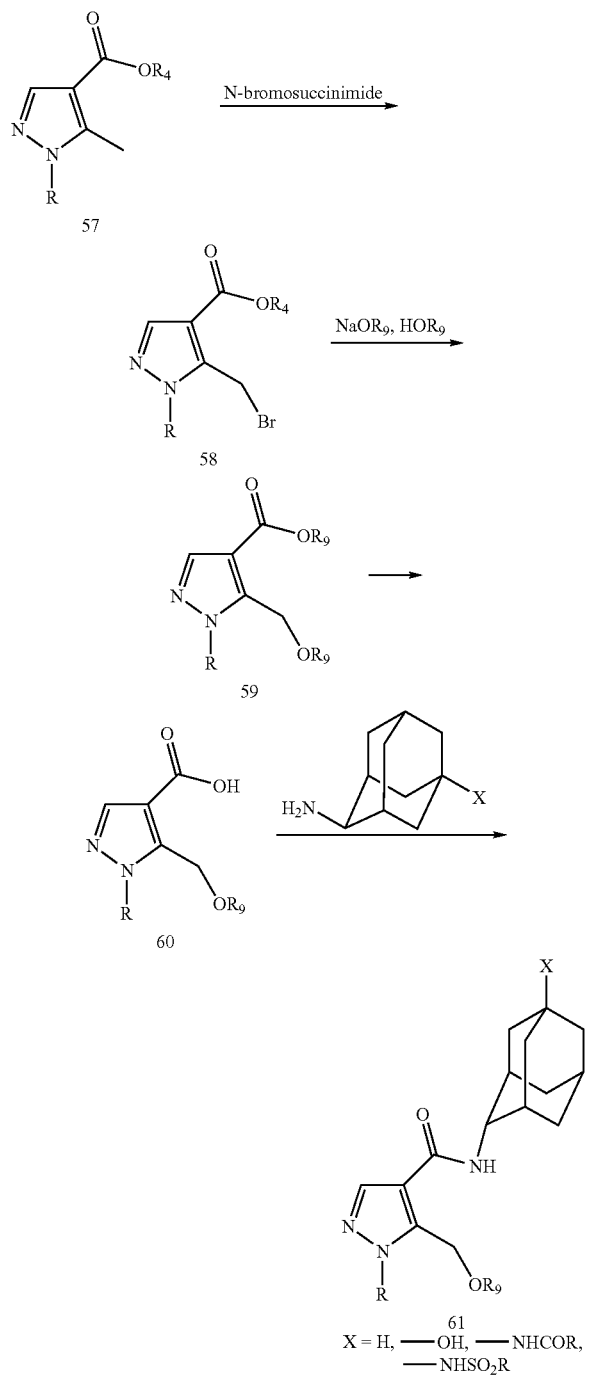

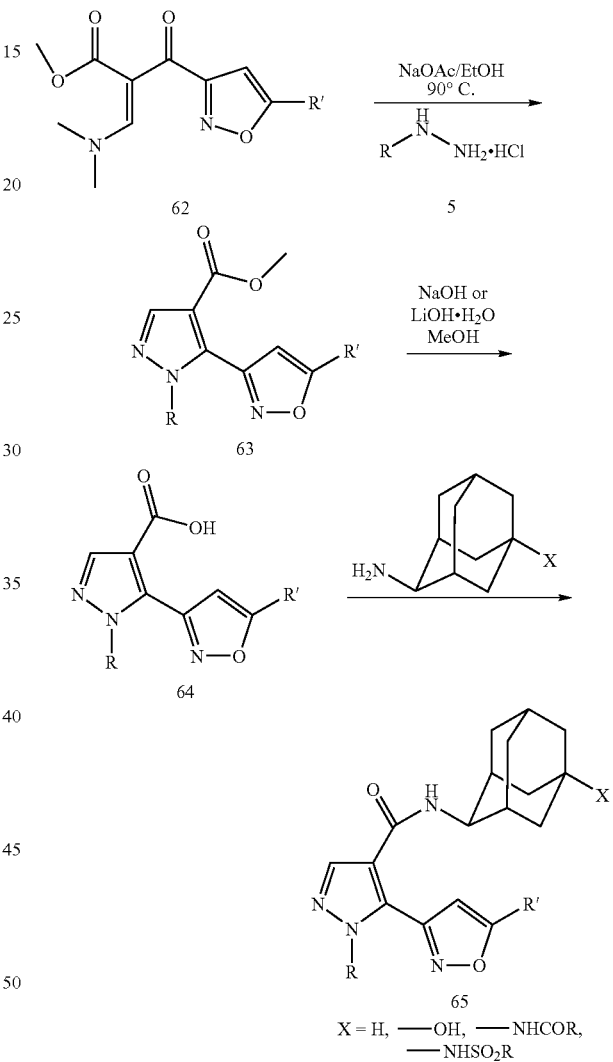

As a final but not limiting example of the synthesis of an amine of formula $HNR_1R_2$, a secondary amine can be prepared by reductive amination, which is well known to one of average skill in the art of organic synthesis, whereby an amine is treated with a ketone to give an imine which is reduced by one of a number of reducing agents. Many examples of conditions that can be used for this reaction are enumerated in "Comprehensive Organic Transformations: A Guide to Functional Group Preparations" [R. C. Larock, VCH Publishers, Inc. New York, 1989] on pages 421-423. For example, the amine and ketone can be treated with a reducing agent such as tetrabutylammonium cyanoborohydride in an inert solvent such as a halogenated hydrocarbon (e.g., dichloromethane) in the presence of methanolic hydrochloric acid at about room temperature.

Starting materials of formula 12 are conveniently prepared by treating a cyanoacetate ester with a trialkyl orthoformate, in the presence of an acid anhydride catalyst such as acetic anhydride, at 80-160° C. Conditions for such a reaction can be found in the literature, for example in R. G. Jones *J. Am. Chem. Soc.* 1952, 74, 4889-4891; in N. J. Cusack et al. *J. Chem. Soc. C* 1971, 1501-1507; and in O. Ackermann et al. U.S. Pat. No. 4,277,418.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose of a compound of the present invention is typically in the range of about 1 to about 1000 mg per day.

The invention will now be further described in the Examples below, which are intended as an illustration only and do not limit the scope of the invention.

EXAMPLES

Reagents were purchased from Aldrich, Sigma, Maybridge, Advanced ChemTech, and Lancaster or other suppliers as indicated below and used without further purification. LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3u 120 Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute.

Super critical fluid chromatography separations were performed using a Mettler-Toledo Minigram system with the following typical conditions: 100 bar, 30° C., 2.0 mL/min eluting a 12 mm AD column with 40% MeOH in super critical fluid $CO_2$. In the case of analytes with basic amino groups, 0.2% isopropyl amine was added to the methanol modifier.

Preparation of Preferred Synthetic Intermediates

Intermediate 1: 4-Amino-adamantan-1-ol (cis/trans mixture)

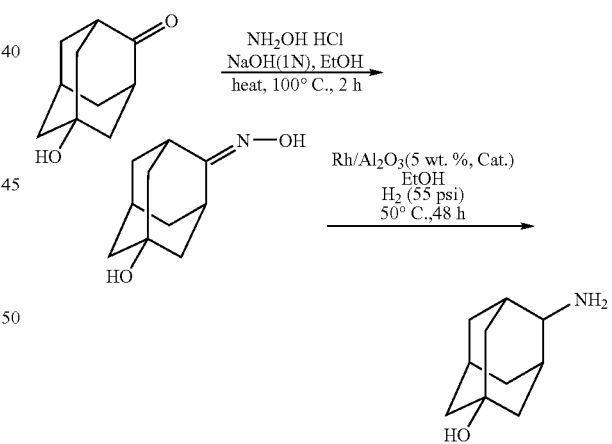

Step 1: 5-Hydroxy-adamantan-2-one oxime

5-Hydroxy-2-admantanone (15 g, 90.2 mmol, CAS #: 20098-14-0, purchased from TCI) was dissolved in EtOH (100 mL) and added to a solution of hydroxylamine hydrochloride (10 g, 143.9 mmol) in 1N NaOH (80 mL). The mixture was heated at 100° C. for 2 hours. The EtOH was evaporated, and water and dichloromethane were added. The resulting mixture was stirred for 10 min and then filtered. The solid was collected. The resulting mixture was separated. The aqueous layer was further extracted twice with dichloromethane. The combined organic phases were concentrated under high vacuum. The resulting residue was combined with the solid from the filtration. Crystallization from EtOAc gave 5-hydroxy-adamantan-2-one oxime (12 g, 73%). Mass spectrum: m/z: 182 (M+1).

Step 2: 4-Amino-adamantan-1-ol

Rh/Al$_2$O$_3$ (2.3 g, 5 wt. %, 1.1 mmol) was added to a mixture of 5-hydroxy-admantane-2-one oxime (10 g, 55 mmol) in EtOH (100 mL) in a Parr hydrogenation bottle. The hydrogenation reaction was performed in a Parr hydrogenation instrument at 55 psi pressure of hydrogen at 50° C. for 48 hours. The disappearance of starting material and generation of the product were detected by LC-MS. The mixture was filtered through celite and concentrated under vacuum to dryness to give 4-amino-adamantan-1-ol (about 9 g, ~98%) which was used for the next step without further purification. Mass spectrum: m/z: 168.1 (M+1).

Intermediate 2: 4-Amino-adamantan-1-ol (trans)

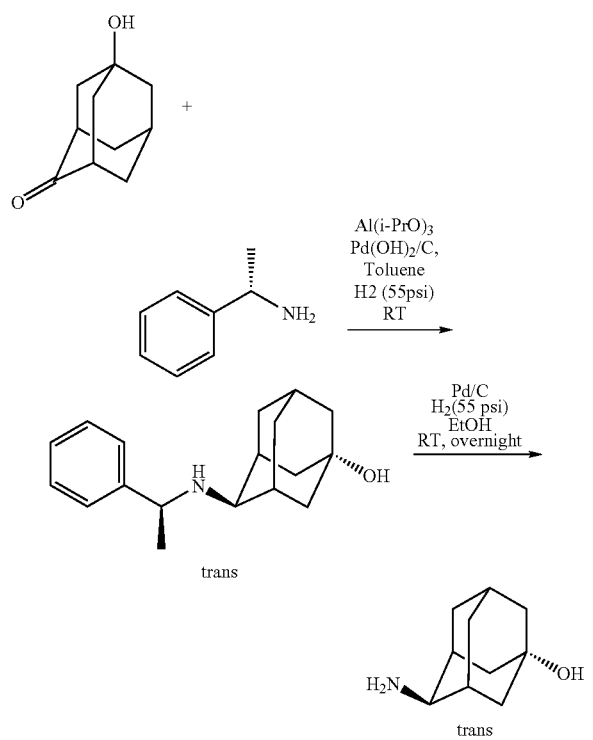

Step 1. 4-(S-1-Phenyl-ethylamino)-adamantan-1-ol

Palladium hydroxide on carbon (2.54 g, 50% water by weight, 20 wt. % Pd dry basis, 4.8 mmol) was added to a Parr bottle (350 mL) under a nitrogen atmosphere. 5-Hydroxy-2-adamantanone (15 g, 90.2 mmol), aluminum isopropoxide (18.43 g, 90.2 mmol), (S)-(−)-1-phenyl-ethylamine (99+%, 99% ee, 10.94 g, 90.3 mmol) and toluene (150 mL) were added sequentially under a nitrogen atmosphere. The mixture was well shaken for a few minutes and then was subjected to hydrogenation with H2 (55 psi) for 5 h at room temperature. 1N NaOH solution (200 mL) was then added and the reaction mixture was mixed well. After filtration through celite and washing with MeOH, the filtrate was concentrated to remove organic solvents. The remaining basic aqueous mixture was extracted with dichloromethane (3×200 mL). The combined organic phases were concentrated under house vacuum and then under high vacuum to give 4-(S-1-phenyl-ethylamino)-adamantan-1-ol (21.65 g, 88%) as an oil. A trans to cis ratio of 100:5 was determined from the crude 1H NMR. Mass spectrum: m/z: 272.2 (M+1).

Step 2. 4-Amino-adamantan-1-ol (trans)

10% Palladium on carbon (1.7 g, 1.6 mmol) was carefully added to a 350 mL Parr bottle. A solution of trans-4-(S-1-phenyl-ethylamino)-adamantan-1-ol (from the above step without further purification, 21.65 g, 79.8 mmol) in ethanol (150 mL) was carefully added into the Parr bottle under an argon atmosphere. The reaction mixture was hydrogenated in the Parr Station with H$_2$ (55 psi) at room temperature overnight. The reaction mixture was filtered through celite under argon, the celite was washed with ethanol, and the combined filtrates were concentrated under high vacuum to give a sticky solid (15 g). Acetonitrile (60 mL) was added and the solution was lyophilized to give trans-4-amino-adamantan-1-ol (13.8 g, quantitative) as a powder. Mass spectrum: m/z: 168.1 (M+1).

A preferred method for the preparation of Intermediate 2 starting from 5-Hydroxy-adamantan-2-one is outlined below.

Step 1: 4-Amino-adamantan-1-ol

5-Hydroxy-adamantan-2-one (15 g, 90.24 mmol, International Specialty) and Pd/C (1.498 g, Degussa 19985880, 5%, 50% water) were added to a Parr reactor, followed by ammonia in methanol solution (7N, 300.4 ml, 2.1 mol). The reactor was pressurized with hydrogen at 200-250 psi for 18 h. The mixture was then filtered over a pad of celite and concentrated in vacuo to give 4-amino-adamantan-1-ol (15.15 g, 4/1=trans/cis by NMR-D$_2$O) as a white solid. This material is used directly without further purification.

Step 2:
trans-4-Amino-adamantan-1-ol-hydrochloride

4-Amino-adamantan-1-ol (15.15 g, 90.58 mmol as a 4/1=trans/cis mixture) was suspended in methanol and cooled to 0° C. Trimethylsilyl chloride (12.16 ml, 95.11 mmol) was added slowly, while maintaining internal temperature below 7° C. The resulting mixture was stirred at 0° C. for 1 h and then was warmed to room temp. and triturated at reflux for 6 h. The suspension was cooled to room temp. and stirred for 13 h. The solid was then filtered and dried at 60° C. in vacuo for 18 h. trans-4-Amino-adamantan-1-ol-hydro chloride (12.7 g) was obtained as a white solid (95.15% pure by gas chromatography, pure trans by NMR-D$_2$O).

Intermediate 3:
1-methyl-5-pyrrol-1-yl-1H-pyrazole-4-carboxylic acid

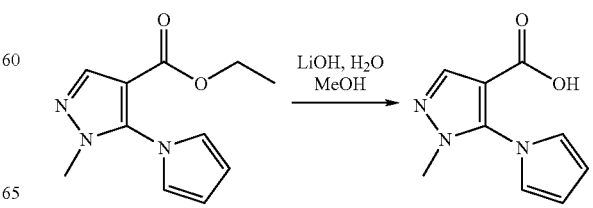

To a solution of 1-methyl-5-pyrrol-1-yl-1H-pyrazole-4-carboxylic acid ethyl ester (20 g, 91.2 mmol; available from Butt Park Ltd., Camelford, Cornwall, UK) in methanol (100 mL) and water (100 mL) was added LiOH (2.4 g, 100 mmol). The reaction mixture was stirred at reflux for 4 hours and then concentrated under reduced pressure to remove the methanol. The residue was diluted with water, acidified to pH 2 with concentrated HCl (9 mL), and extracted with ethyl acetate. The combined extracts were evaporated in vacuo to give 1-methyl-5-pyrrol-1-yl-1H-pyrazole-4-carboxylic acid which was used without further purification.

Intermediate 4: Ethyl 3-N,N-dimethylamino-2-trifluoroacetylacrylate

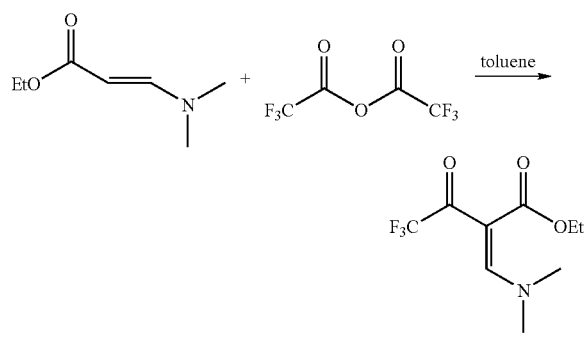

Trifluoroacetic anhydride (10.1 g, 48/1 mmol) was added dropwise in about 20 minutes into a mixture of ethyl N,N-dimethylaminoacrylate (6.9 g, 48.2 mmol) in toluene (10 mL) which was cooled in acetone-ice bath (about −10° C.). The reaction mixture was then allowed to rise back to room temperature and stirred for 1 hour. The reaction mixture was diluted with dichloromethane (100 mL) and water (80 mL). The mixture was stirred for 15 minutes and the organic phase was separated. The aqueous phase was extracted three times with dichloromethane. The combined organic phases were dried under vacuum and purified by silica gel chromatography eluting with a gradient of 0-40% ethyl acetate/hexanes, then 40% ethyl acetate/hexanes to give ethyl 3-N,N-dimethylamino-2-trifluoroacetylacrylate 10.2 g, 89%).

Intermediate 5: Cyclopropylhydrazine hydrochloride

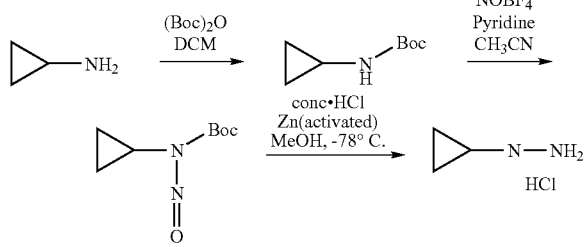

Step 1. N-(tert-Butoxycarbonyl)cyclopropylamine

To a solution of cyclopropylamine (12.4 g, 252.2 mmol) in dichloromethane (50 mL) at 0° C. in an ice-water bath was added a solution of di-tert-butyl dicarbonate (43.7 g, 200 mmol) in dichloromethane (100 mL). The reaction mixture was then allowed to stir at room temperature for 18 hours. The solvent was evaporated under vacuum to give N-(tert-butoxycarbonyl)cyclopropylamine (31 g, 99%).

Step 2. N-Nitroso-N-(tert-butoxycarbonyl)amino-cyclopropane

Nitrosonium tetrafluoroborate (9.32 g, 79.8 mmol) was added carefully in several portions to a cooled (−30° C.) solution of N-(tert-butoxycarbonyl)cyclopropylamine (9.57 g, 60.9 mmol) and anhydrous pyridine (11.7 mL) in dry acetonitrile (150 mL). The solution was stirred at −30° C. for 30 minutes, and then at 0° C. for 2 hours. Ice water and EtOAc were added and the organic phase was separated and washed quickly with 1N HCl to remove pyridine. The organic phase was washed with 1N NaHCO₃ and brine, dried (MgSO4), filtered, and evaporated under high vacuum with a water bath temperature below 40° C. to give N-nitroso-N-(tert-butoxycarbonyl)amino-cyclopropane (12.1 g, quantitative) as an oil.

Step 3. Cyclopropyl hydrazine hydrochloride

N-Nitroso-N-(tert-butoxycarbonyl)amino-cyclopropane (12 g, ~60.9 mmol) was dissolved in MeOH (600 mL) and cooled to −78° C. in an acetone/dry ice bath. At −78° C., conc. HCl (54 mL) was added slowly to the stirred reaction mixture. Then activated zinc (33.7 g, 516 mmol; nanosize activated powder from Aldrich) was slowly added at −78° C. to the stirred reaction mixture. The reaction mixture was stirred at −78° C. for 8 h. Then the reaction mixture was filtered through celite. The filtrate was concentrated under high vacuum with a water bath temperature below 40° C. to give crude cyclopropyl hydrazine hydrochloride as a sticky semi-solid.

Intermediate 6. 1-Cyclopropyl-5-trifluoromethyl-1H-pyrazole-4-carboxylic acid

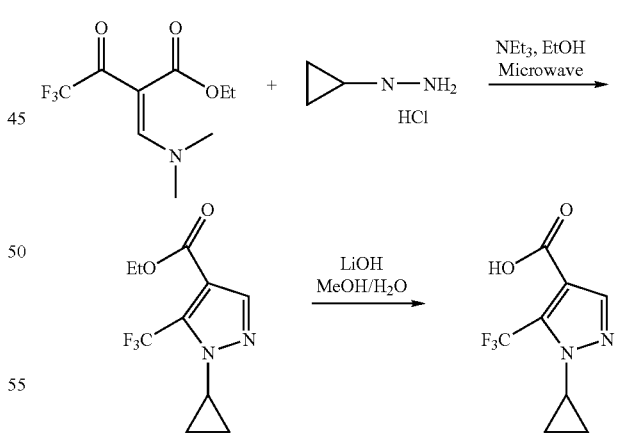

Step 1. 1-Cyclopropyl-5-trifluoromethyl-1H-pyrazole-4-carboxylic acid ethyl ester Triethylamine (2.2 g, 21.7 mmol) and cyclopropyl hydrazine hydrochloride (Intermediate 5 without further purification; 0.8 g, 7.4 mmol) were added sequentially to a solution of ethyl 3-N,N-dimethylamino-2-trifluoroacetylacrylate (Intermediate 4, 1.76 g, 7.4 mmol) in ethanol (12 mL). The resulting suspension was mixed well and divided equally into three 10 mL-size Personal Chemistry microwave process tubes (Biotage AB, Sweden). The tubes were sealed with a septum and submitted to 150 W microwave irradiation using a Personal Chemistry Microwave Synthesis system (Biotage AB, Sweden) at 160° C. for 30 minutes. The reaction mixtures in the three tubes were combined and ethanol was evaporated under reduced pressure. The remaining mixture was partitioned between dichloromethane and water, and the water phase was extracted three times with dichloromethane. The organic phases were combined, concentrated in vacuo, and purified by silica chromatography eluting with a gradient of 0-20% ethyl acetate/hexanes, then 20% ethyl acetate/hexanes to give 1-cyclopropyl-5-trifluoromethyl-1H-pyrazole-4-carboxylic acid ethyl ester (140 mg, 8%). Mass spectrum: m/z: 249.1 (M+1).

Step 2. 1-Cyclopropyl-5-trifluoromethyl-1H-pyrazole-4-carboxylic acid

To a solution of 1-Cyclopropyl-5-trifluoromethyl-1H-pyrazole-4-carboxylic acid ethyl ester (140 mg, 0.56 mmol) in CH₃OH (2 mL) and water (2 mL) was added LiOH (16 mg, 0.67 mmol). The reaction mixture was stirred at reflux overnight, and then the solution was concentrated under reduced pressure to remove the methanol. The residue was diluted with water and the solution was acidified to pH 2 with concentrated HCl. The resulting mixture was then extracted with ethyl acetate three times. The combined organic extracts were concentrated in vacuo to give 1-cyclopropyl-5-trifluoromethyl-1H-pyrazole-4-carboxylic acid (130 mg, quantitative), which was used without further purification.

Intermediate 7: 1-tert-Butyl-5-trifluoromethyl-1H-pyrazole-4-carboxylic acid

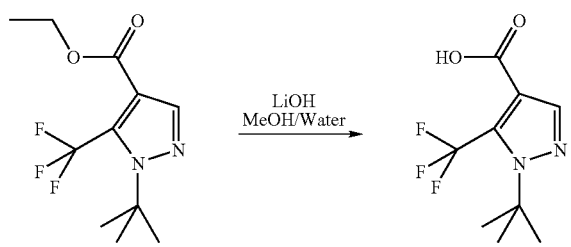

To a solution of 1-tert-butyl-5-trifluoromethyl-1H-pyrazole-4-carboxylic acid ethyl ester (5 g, 21.2 mmol, purchased from Bionet) in CH₃OH (45 mL) and water (45 mL) was added LiOH (0.54 g, 22.5 mmol). The reaction mixture was stirred at reflux for 4 h, and then the solution was concentrated under reduced pressure to remove the methanol. The residue was diluted with water and the solution was acidified to pH 2 with concentrated HCl. The resulting mixture was then extracted with ethyl acetate three times. The combined organic extracts were concentrated in vacuo to give 1-tert-butyl-5-trifluoromethyl-1H-pyrazole-4-carboxylic acid (4.02 g, 80%), which was used without further purification.

Intermediate 8. 2'-Methyl-2'H-[1,3']bipyrazolyl-4'-carboxylic acid

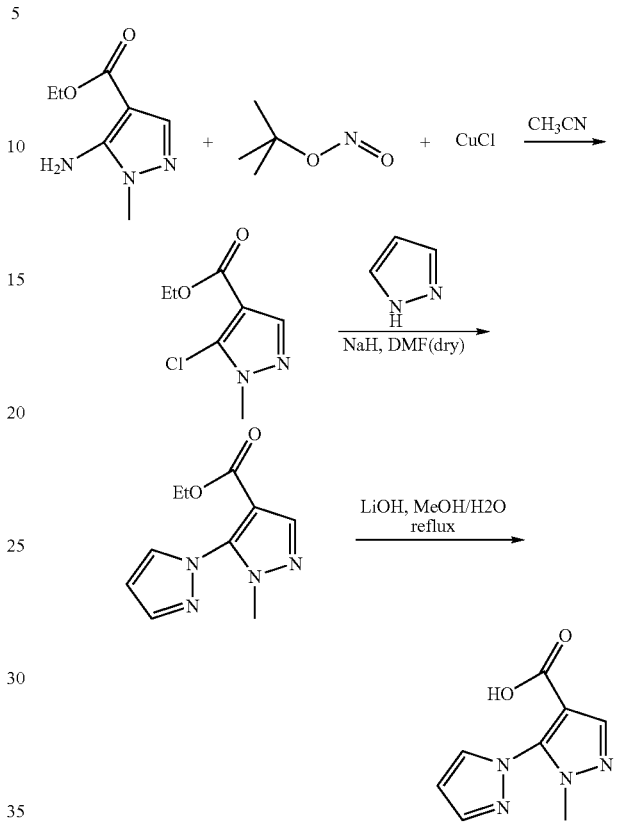

Step 1. 5-Chloro-1-methyl-1H-pyrazole-4-carboxylic acid ethyl ester

To a mixture of t-butyl nitrite (29.5 mL, 248 mmol), cuprous chloride (17.6 g, 177.8 mmol) and anhydrous acetonitrile (490 mL) was added 5-amino-1-methyl-1H-pyrazole-4-carboxylic acid ethyl ester (25 g, 148 mmol) in portions over 30 minutes at 0° C. The reaction mixture was stirred at room temperature for 1 h, then at 65° C. for 1 h. The mixture was then poured into 6N HCl (600 mL) and extracted with dichloromethane. The aqueous phase was extracted three times with dichloromethane. The combined organic phases were concentrated in vacuo, and the crude residue was purified by flash chromatography eluting with a gradient of 0-20% ethyl acetate/hexanes, then 20% ethyl acetate/hexanes to give 5-chloro-1-methyl-1H-pyrazole-4-carboxylic acid ethyl ester (18 g, 64%).

Step 2. 2'-Methyl-2'H-[1,3']bipyrazolyl-4'-carboxylic acid ethyl ester

Sodium hydride (60% in oil; 767 mg, 19 mmol) was added to a solution of pyrazole (1.36 g, 20 mmol) in dry DMF (40 mL) under nitrogen at 0° C. in an ice-water bath and the mixture was heated to 40° C. for 1 h. 5-Chloro-1-methyl-1H-pyrazole-4-carboxylic acid ethyl ester (1.89 g, 10 mmol) was added and the mixture was heated to 100° C. overnight and then cooled. Water and ethyl acetate were added, the organic layer was separated, and the aqueous phase was extracted three times with EtOAc. The combined organic phases were concentrated in vacuo and the residue was purified by flash silica chromatography eluting with a gradient of 0-20% ethyl acetate/hexanes, then 20% ethyl acetate/hexanes to give 2'-methyl-2'H-[1,3']bipyrazolyl-4'-carboxylic acid ethyl ester (0.2 g, 9%).

Step 3. 2'-Methyl-2'H-[1,3']bipyrazolyl-4'-carboxylic acid

To a solution of 2'-methyl-2'H-[1,3']bipyrazolyl-4'-carboxylic acid ethyl ester (340 mg, 1.54 mmol) in CH$_3$OH (5 mL) and water (55 mL) was added LiOH (41 mg, 1.71 mmol). The reaction mixture was stirred at reflux for 4 h, and then the solution was concentrated under reduced pressure to remove the methanol. The residue was diluted with water and the solution was acidified to pH 2 with concentrated HCl. The resulting mixture was then extracted three times with ethyl acetate. The combined organic extracts were concentrated in vacuo to give 2'-methyl-2'H-[1,3']bipyrazolyl-4'-carboxylic acid (300 mg, quantitative), which was used without further purification.

Intermediate 9.
1-tert-Butyl-5-chloro-1H-pyrazole-4-carboxylic acid

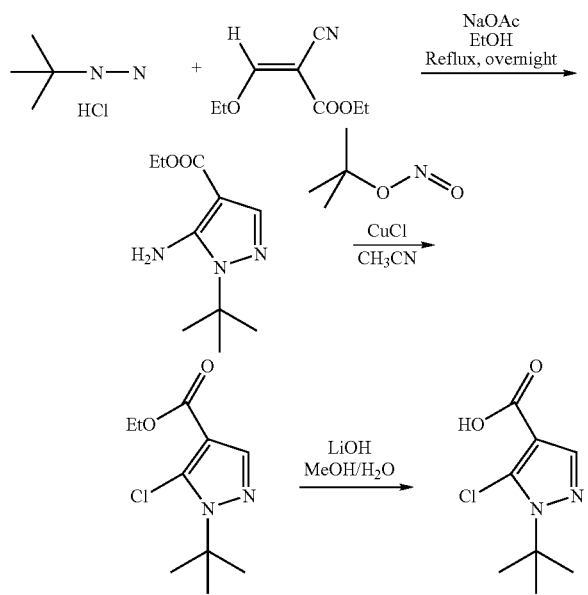

Step 1.
5-Amino-1-tert-butyl-1H-pyrazole-4-carboxylic acid ethyl ester

A solution containing t-butylhydrazine hydrochloride salt (10 g, 80.3 mmol), ethyl (ethoxymethylene)-cyanoacetate (13.6 g, 80.4 mmol), and anhydrous sodium acetate (8.2 g, 100 mmol) in 100 mL ethanol was stirred and refluxed for 16 hours. The solution was poured into ice-water. The separated aqueous phase was extracted three times with dichloromethane. The combined organic phases were washed successively with water and saturated brine solution and dried with sodium sulfate. The solvent was removed in vacuo to give 5-amino-1-tert-butyl-1H-pyrazole-4-carboxylic acid ethyl ester (13 g, 77%).

Step 2.
1-tert-Butyl-5-chloro-1H-pyrazole-4-carboxylic acid ethyl ester

To a mixture of t-butyl nitrite (7.2 mL, 60.5 mmol), cuprous chloride (4.8 g, 48.5 mmol), and anhydrous acetonitrile (120 mL) was added 5-amino-1-tert-butyl-1H-pyrazole-4-carboxylic acid ethyl ester (8.4 g, 39.8 mmol) in portions over 30 minutes at 0° C. The reaction mixture was stirred at room temperature for 1 h, then at 65° C. for 1 h. The mixture was then poured into 6N HCl (120 mL) and extracted with dichloromethane. The aqueous phase was extracted three times with dichloromethane. After the combined organic phases were concentrated in vacuo, the crude residue was purified by flash chromatography eluting with a gradient of 0-20% ethyl acetate/hexanes, then 20% ethyl acetate/hexanes to give 1-tert-butyl-5-chloro-1H-pyrazole-4-carboxylic acid ethyl ester (5.5 g, 39%).

Step 3.
1-tert-Butyl-5-chloro-1H-pyrazole-4-carboxylic acid

To a solution of 1-tert-butyl-5-chloro-1H-pyrazole-4-carboxylic acid ethyl ester (5 g, 21.7 mmol) in methanol (50 mL) and water (50 mL) was added LiOH (0.63 g, 26.3 mmol). The reaction mixture was stirred at reflux overnight and then concentrated under reduced pressure to remove the methanol. The residue was diluted with water, acidified to pH 2 with concentrated HCl (4 mL), and extracted with ethyl acetate. The organic extracts were evaporated in vacuo to give 1-tert-butyl-5-chloro-1H-pyrazole-4-carboxylic acid (4 g, 91%) which was used without further purification.

Preparation of Preferred Compounds of the Invention

Example 1

Methyl-5-pyrrol-1-yl-1H-pyrazole-4-carboxylic acid (5-hydroxy-adamantan-2-yl)-amide Example 1

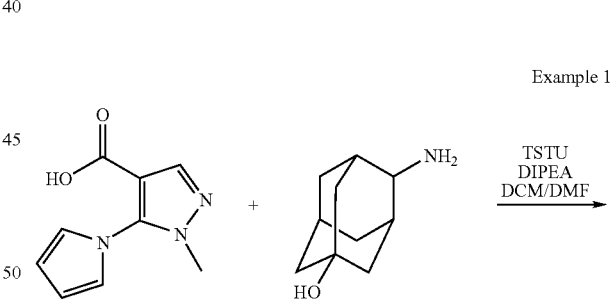

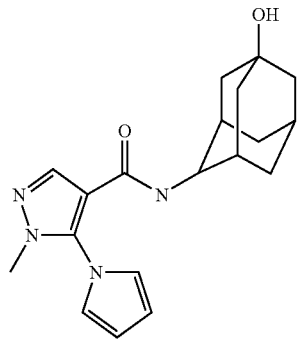

1-Methyl-5-pyrrol-1-yl-1H-pyrazole-4-carboxylic acid (Intermediate 3, 38 mg, 0.2 mmol) was dissolved in a mixture of dry dichloromethane (3.2 mL) and dry DMF (0.8 mL). DIPEA (0.14 mL, 0.8 mmol) and TSTU (72 mg, 0.22 mmol) were added in the above mixture. After the mixture was stirred for 1 h, the appearance of active ester was detected by LC-MS. Then 4-amino-adamantan-1-ol (33 mg, 0.2 mmol) was added. After another 2 hours water was added and the organic layer was separated. The aqueous layer was extracted twice with dichloromethane. The combined organic phases were dried under vacuum and purified by C-18 reversed phase HPLC with a gradient of 10-100% acetonitrile/water to give Example 1: 1-methyl-5-pyrrol-1-yl-1H-pyrazole-4-carboxylic acid (5-hydroxy-adamantan-2-yl)-amide (44 mg, 65%). Mass spectrum: m/z: 341.2 (M+1).

Example 2 trans-1-Methyl-5-pyrrol-1-yl-1H-pyrazole-4-carboxylic acid (5-hydroxy-adamantan-2-yl)-amide

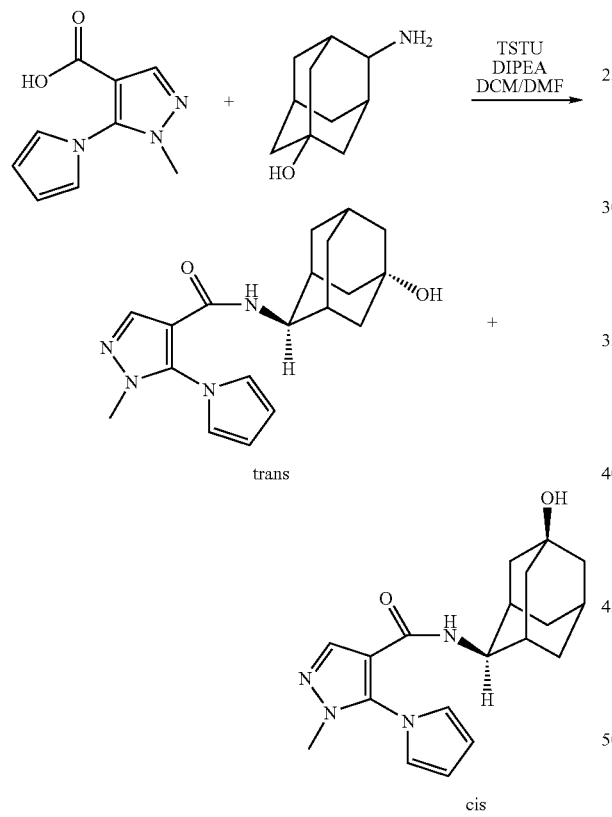

Methyl-5-pyrrol-1-yl-1H-pyrazole-4-carboxylic acid (Intermediate 3, 2.66 g, 13.9 mmol) was dissolved in a mixture of dry dichloromethane (40 mL) and dry DMF (10 mL). DIPEA (14.5 mL, 83.2 mmol) and TSTU (5.02 g, 15.2 mmol) were added in the above mixture. After the mixture was stirred for 1 h, the appearance of active ester were detected by LC-MS. Then 4-amino-adamantan-1-ol (2.32 g, 13.9 mmol) was added. After another 2 hours water was added and the organic layer was separated. The aqueous layer was extracted twice with dichloromethane. The combined organic phases were dried under vacuum and purified by C-18 reversed phase prep-HPLC with a gradient of 25-35%. Example 2, trans-1-methyl-5-pyrrol-1-yl-1H-pyrazole-4-carboxylic acid (5-hydroxyadamantan-2-yl)-amide was isolated as the second peak corresponding to mass spectrum of m/z=341.2 (M+1).

Example 3

2'-Methyl-2'H-[1,3']bipyrazolyl-4'-carboxylic acid adamantan-2-ylamide

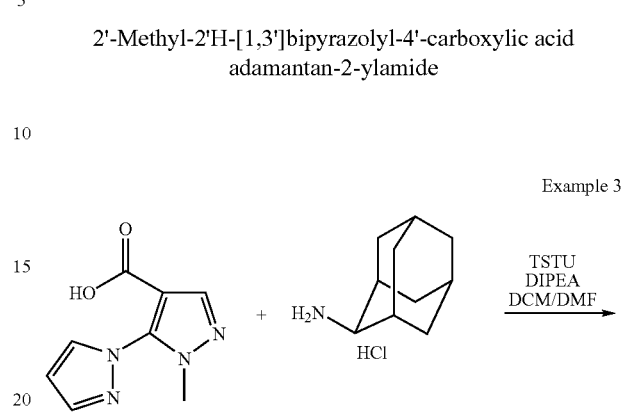

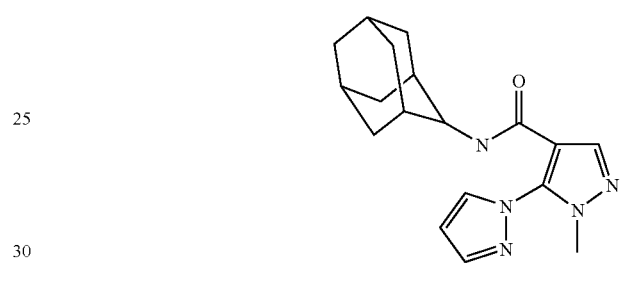

2'-Methyl-2'H-[1,3']bipyrazolyl-4'-carboxylic acid (Intermediate 8, 50 mg, 0.26 mmol) was dissolved in a mixture of dry dichloromethane (3.2 mL) and dry DMF (0.8 mL). DIPEA (0.23 mL, 1.3 mmol) and TSTU (93 mg, 0.28 mmol) were added to the above mixture. After the mixture was stirred for 1 h, the appearance of active ester was detected by LC-MS. Then 2-aminoadamantane hydrochloride (58 mg, 0.31 mmol) was added. After another 2 hours water was added and the organic layer was separated. The aqueous layer was extracted twice with dichloromethane. The combined organic phases were dried under vacuum and purified by C-18 reversed phase prep-HPLC with a gradient of 10-100% acetonitrile/water to give 2'-methyl-2'H-[1,3']bipyrazolyl-4'-carboxylic acid adamantan-2-ylamide (65 mg, 77%). Mass spectrum: m/z: 362.2 (M+1).

Example 4

Methyl-5-trifluoromethyl-1H-pyrazole-4-carboxylic acid adamantan-2-ylamide

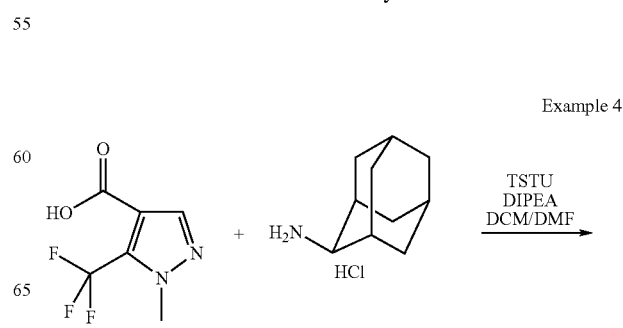

-continued

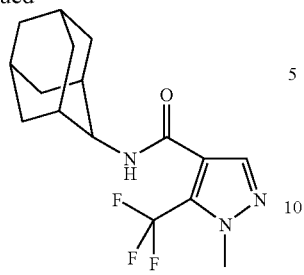

Methyl-5-trifluoromethyl-1H-pyrazole-4-carboxylic acid (77 mg, 0.4 mmol, CAS#: 119083-00-0, purchased from Bionet) was dissolved in a mixture of dry dichloromethane (3.2 mL) and dry DMF (0.8 mL). DIPEA (0.28 mL, 1.6 mmol) and TSTU (145 mg, 0.44 mmol) were added to the above mixture. After the mixture was stirred for 1 h, the appearance of active ester was detected by LC-MS. Then 2-aminoadamantane hydrochloride (75 mg, 0.4 mmol) was added. After another 2 hours water was added and the organic layer was separated. The aqueous layer was extracted twice with dichloromethane. The combined organic phases were dried under vacuum and purified by C-18 reversed phase HPLC with a gradient of 10-100% acetonitrile/water to give 1-methyl-5-trifluoromethyl-1H-pyrazole-4-carboxylic acid adamantan-2-ylamide (85 mg, 65%). Mass spectrum: m/z: 328.2 (M+1).

Example 5

5-Chloro-1-methyl-1H-pyrazole-4-carboxylic acid adamantan-2-ylamide

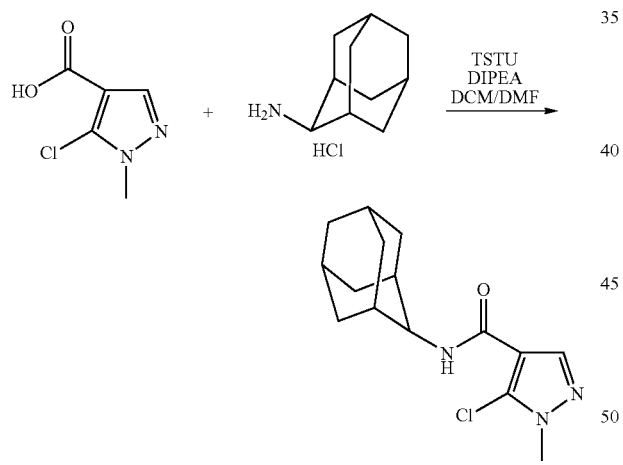

5-Chloro-1-methyl-1H-pyrazole-4-carboxylic acid (64 mg, 0.4 mmol, CAS#: 54367-66-7, purchased from Oakwood) was dissolved in a mixture of dry dichloromethane (3.2 mL) and dry DMF (0.8 mL). DIPEA (0.28 mL, 1.6 mmol) and TSTU (145 mg, 0.44 mmol) were added to the above mixture. After the mixture was stirred for 1 h, the appearance of active ester was detected by LC-MS. Then 2-aminoadamantane hydrochloride (75 mg, 0.4 mmol) was added. After another 2 hours water was added and the organic layer was separated. The aqueous layer was extracted twice with dichloromethane. The combined organic phases were dried under vacuum and purified by C-18 reversed phase HPLC with a gradient of 10-100% acetonitrile/water to give 5-chloro-1-methyl-1H-pyrazole-4-carboxylic acid adamantan-2-ylamide (70 mg, 60%). Mass spectrum: m/z: 294.1 (M+1).

Example 6 tert-Butyl-5-trifluoromethyl-1H-pyrazole-4-carboxylic acid adamantan-2-ylamide

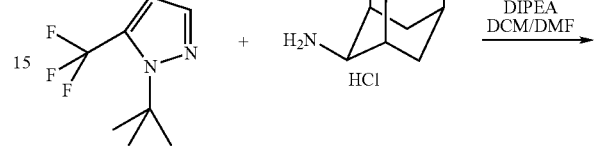

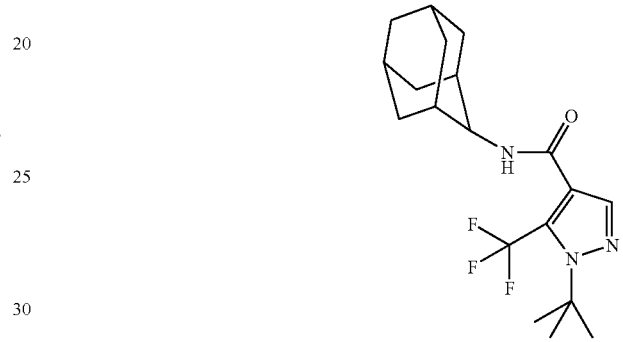

tert-Butyl-5-trifluoromethyl-1H-pyrazole-4-carboxylic acid (Intermediate 7, 61 mg, 0.26 mmol) was dissolved in a mixture of dry dichloromethane (3.2 mL) and dry DMF (0.8 mL). DIPEA (0.23 mL, 1.3 mmol) and TSTU (93 mg, 0.28 mmol) were added to the above mixture. After the mixture was stirred for 1 h, the appearance of active ester was detected by LC-MS. Then 2-aminoadamantane hydrochloride (58 mg, 0.31 mmol) was added. After another 2 hours water was added and the organic layer was separated. The aqueous layer was extracted twice with dichloromethane. The combined organic layers were dried under vacuum and purified by C-18 reversed phase HPLC with a gradient of 10-100% acetonitrile/water to give 1-tert-butyl-5-trifluoromethyl-1H-pyrazole-4-carboxylic acid adamantan-2-ylamide (62 mg, 65%). Mass spectrum: m/z: 370.2 (M+1).

Examples 7 and 8 trans-1-tert-Butyl-5-trifluoromethyl-1H-pyrazole-4-carboxylic acid amide and cis-1-tert-butyl-5-trifluoromethyl-1H-pyrazole-4-carboxylic acid amide

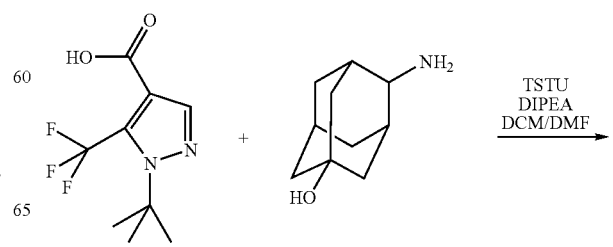

-continued

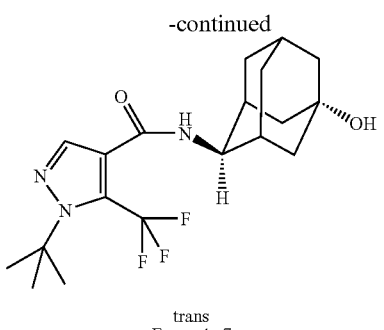

trans
Example 7

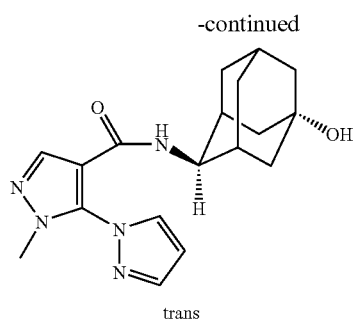

trans

+

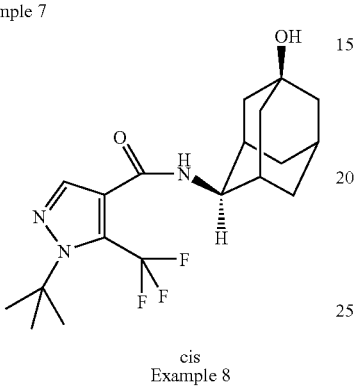

cis
Example 8

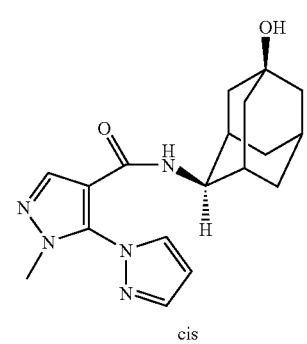

cis tert-Butyl-5-trifluoromethyl-1H-pyrazole-4-carboxylic acid (Intermediate 7, 3.28 g, 13.9 mmol) was dissolved in a mixture of dry dichloromethane (40 mL) and dry DMF (10 mL). DIPEA (14.5 mL, 83.4 mmol) and TSTU (5 g, 16.7 mmol) were added to the above mixture. After the mixture was stirred for 2 h, the appearance of active ester was detected by LC-MS. 4-Amino-adamantan-1-ol (2.32 g, 13.9 mmol) was added. After another 4 hours water was added and the organic layer was separated. The aqueous layer was extracted twice with dichloromethane. The combined organic layers were dried under vacuum and purified by silica chromatography eluting with a gradient of 0-60% ethyl acetate/hexanes, then 60% ethyl acetate/hexanes to give cis-1-tert-butyl-5-trifluoromethyl-1H-pyrazole-4-carboxylic acid (5-hydroxy-adamantan-2-yl)-amide (Example 8, 1.75 g, 33%) and trans-1-tert-butyl-5-trifluoromethyl-1H-pyrazole-4-carboxylic acid (5-hydroxy-adamantan-2-yl)-amide (Example 7, 0.85 g, 16%). The trans isomer eluted after the cis isomer. Both compounds were characterized by mass spectrum: m/z: 386.2 (M+1).

Example 9 trans-2'-Methyl-2'H-[1,3']bipyrazolyl-4'-carboxylic acid (5-hydroxy-adamantan-2-yl)-amide 2'-Methyl-2'H-[1,3']bipyrazolyl-4'-carboxylic acid (Intermediate 8, 296 mg, 1.54 mmol) was dissolved in a mixture of dry dichloromethane (24 mL) and dry DMF (6 mL). DIPEA (1.6 mL, 9.2 mmol) and TSTU (556 mg, 1.68 mmol) were added to the above mixture. After the mixture was stirred for 1 h, the appearance of active ester was detected by LC-MS. 4-Amino-adamantan-1-ol (258 mg, 1.54 mmol) was added. After another 2 hours water was added and the organic layer was separated. The aqueous layer was extracted twice with dichloromethane. The combined organic phases were dried under vacuum and purified by C-18 reversed phase prep-HPLC with a gradient of 15-20% acetonitrile/water to give first cis-2'-methyl-2'H-[1,3']bipyrazolyl-4'-carboxylic acid (5-hydroxyadamantan-2-yl)-amide (100 mg, 19%, Mass spectrum: m/z: 342.2 (M+1)), followed by trans-2'-methyl-2'H-[1,3']bipyrazolyl-4'-carboxylic acid (5-hydroxy-adamantan-2-yl)-amide.

Example 10

5-Chloro-1-methyl-3-trifluoromethyl-1H-pyrazole-4-carboxylic acid adamantan-2-ylamide Example 9

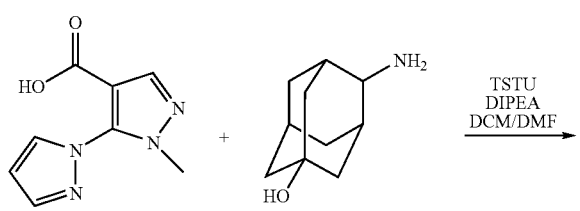

Example 10

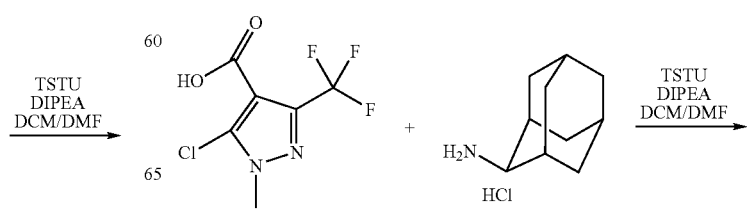

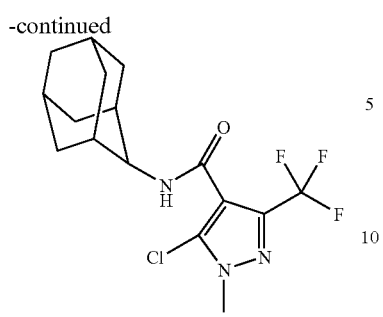

5-Chloro-1-methyl-3-trifluoromethyl-1H-pyrazole-4-carboxylic acid (91 mg, 0.4 mmol, CAS#: 128455-63-0, purchased from Maybridge) was dissolved in a mixture of dry dichloromethane (3.2 mL) and dry DMF (0.8 mL). DIPEA (0.28 mL, 1.6 mmol) and TSTU (145 mg, 0.44 mmol) were added to the above mixture. After the mixture was stirred for 1 h, the appearance of active ester was detected by LC-MS. Then 2-aminoadamantane hydrochloride (75 mg, 0.4 mmol) was added. After another 2 hours water was added and the organic layer was separated. The aqueous layer was extracted twice with dichloromethane. The combined organic phases were dried under vacuum and purified by C-18 reversed phase HPLC with a gradient of 10-100% acetonitrile/water to give 5-chloro-1-methyl-3-trifluoromethyl-1H-pyrazole-4-carboxylic acid adamantan-2-ylamide (55 mg, 38%). Mass spectrum: m/z: 362.1 (M+1).

Example 11

5-Chloro-1,3-dimethyl-1H-pyrazole-4-carboxylic acid adamantan-2-ylamide

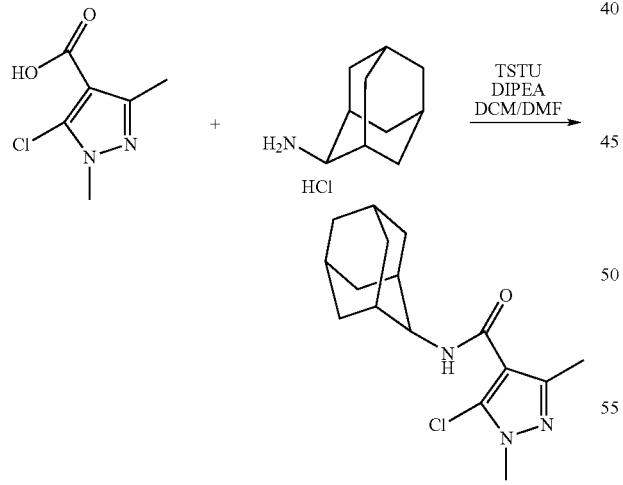

5-Chloro-1,3-dimethyl-1H-pyrazole-4-carboxylic acid (69 mg, 0.4 mmol, CAS#: 27006-82-2, purchased from Maybridge) was dissolved in a mixture of dry dichloromethane (3.2 mL) and dry DMF (0.8 mL). DIPEA (0.28 mL, 1.6 mmol) and TSTU (145 mg, 0.4 mmol) were added to the above mixture. After the mixture was stirred for 1 h, the appearance of active ester was detected by LC-MS. Then 2-aminoadamantane hydrochloride (75 mg, 0.4 mmol) was added. After another 2 hours water was added and the organic layer was separated. The aqueous layer was extracted twice with dichloromethane. The combined organic phases were dried under vacuum and purified by C-18 reversed phase HPLC with a gradient of 10-100% acetonitrile/water to give 5-chloro-1,3-dimethyl-1H-pyrazole-4-carboxylic acid adamantan-2-ylamide (72 mg, 58%). Mass spectrum: m/z: 308.1 (M+1).

Example 12

Cyclopropyl-5-trifluoromethyl-1H-pyrazole-4-carboxylic acid adamantan-2-ylamide

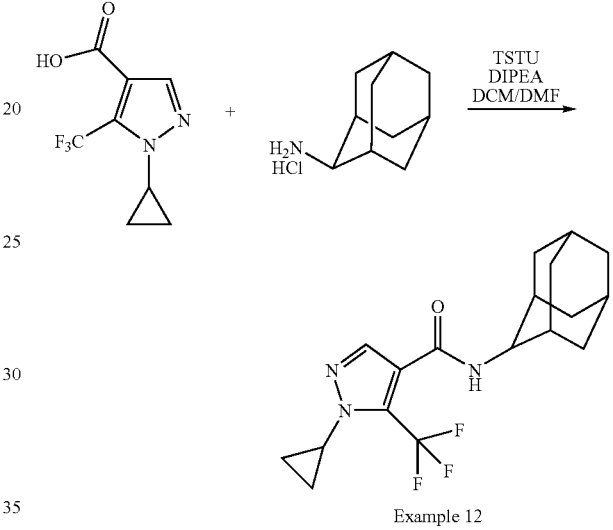

1-Cyclopropyl-5-trifluoromethyl-1H-pyrazole-4-carboxylic acid (Intermediate 6, 20 mg, 0.09 mmol) was dissolved in a mixture of dry dichloromethane (1.6 mL) and dry DMF (0.2 mL). DIPEA (0.1 mL, 0.57 mmol) and TSTU (33 mg, 0.11 mmol) were added to the above mixture. After the mixture was stirred for 1 h, the appearance of active ester was detected by LC-MS. Then 2-aminoadamantane hydrochloride (17 mg, 0.09 mmol) was added. After another 2 hours water was added and the organic layer was separated. The aqueous layer was extracted twice with dichloromethane. The combined organic layers were dried under vacuum and purified by silica chromatography eluting with a gradient of 0-40% ethyl acetate/hexanes, then 40% ethyl acetate/hexanes to give 1-cyclopropyl-5-trifluoromethyl-1H-pyrazole-4-carboxylic acid adamantan-2-ylamide (18 mg, 56%). Mass spectrum: m/z: 354.2 (M+1).

Example 13

Cyclopropyl-5-trifluoromethyl-1H-pyrazole-4-carboxylic acid (5-hydroxy-adamantan-2-yl)-amide

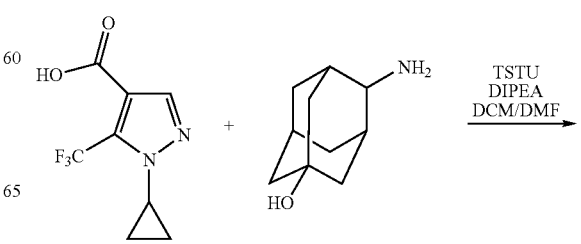

Example 13

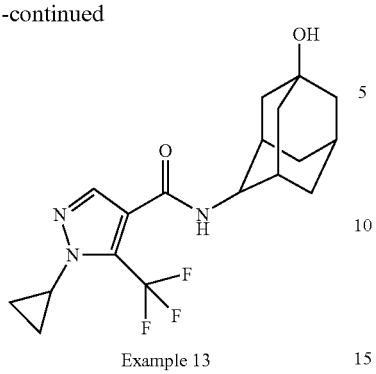

1-Cyclopropyl-5-trifluoromethyl-1H-pyrazole-4-carboxylic acid (Intermediate 6, 100 mg, 0.45 mmol) was dissolved in a mixture of dry dichloromethane (4 mL) and dry DMF (1 mL). DIPEA (0.5 mL, 2.9 mmol) and TSTU (165 mg, 0.5 mmol) were added to the above mixture. After the mixture was stirred for 2 h, the appearance of active ester was detected by LC-MS. Then 4-amino-adamantan-1-ol (77 mg, 0.46 mmol) was added. After another 4 hours water was added and the organic layer was separated. The aqueous layer was extracted twice with dichloromethane. The combined organic layers were dried under vacuum. The crude mixture was purified by C-18 reversed phase preparative-HPLC with a gradient of 10-100% acetonitrile/water to give 1-cyclopropyl-5-trifluoromethyl-1H-pyrazole-4-carboxylic acid (5-hydroxy-adamantan-2-yl)-amide (79 mg, 48%. Mass spectrum: m/z: 370.2 (M+1).

Example 14

Methyl-5-(4-methyl-piperazin-1-yl)-1H-pyrazole-4-carboxylic acid adamantan-2-ylamide

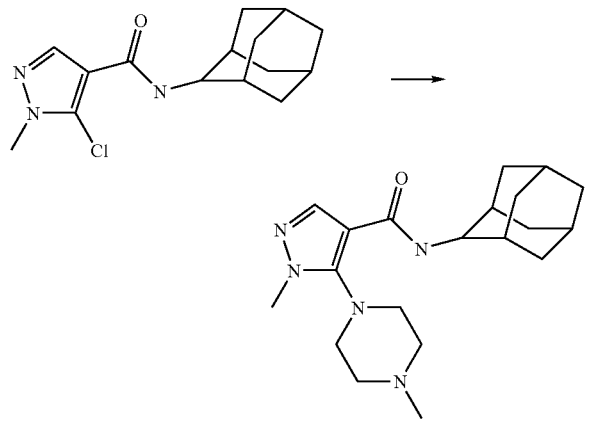

A solution of 5-chloro-1-methyl-1H-pyrazole-4-carboxylic acid adamantan-2-ylamide (Example 5, 59 mg; 0.20 mmol) and 1-methylpiperazine (0.47 mL; 4.2 mmol) in N-methylpyrrolidinone (0.8 mL) was heated to 230° C. in a sealed vial under microwave irradiation for 2 hr. The mixture was allowed to cool to room temperature and the crude product was purified by reverse phase HPLC to provide methyl-5-(4-methyl-piperazin-1-yl)-1H-pyrazole-4-carboxylic acid adamantan-2-ylamide (41 mg, 57%) as an off white solid. ES-HRMS m/e calcd for $C_{20}H_{32}N_5O$ (M+H$^+$) 358.2602, found 358.2597.

Example 15

5-(2-Hydroxy-ethylamino)-1-methyl-1H-pyrazole-4-carboxylic acid adamantan-2-ylamide

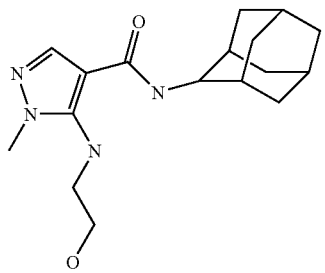

Heating a mixture of 5-chloro-1-methyl-1H-pyrazole-4-carboxylic acid adamantan-2-ylamide (Example 5, 59 mg; 0.20 mmol) and ethanolamine (0.20 mL; 3.3 mmol) under microwave irradiation according to the procedure described in Example 14 Step 2 provided after purification by reverse phase HPLC, 5-(2-hydroxy-ethylamino)-1-methyl-1H-pyrazole-4-carboxylic acid adamantan-2-ylamide (26 mg, 41%) as a white powder. ES-HRMS m/e calcd for $C_{17}H_{27}N_4O_2$ (M+H$^+$) 319.2129, found 319.2127.

Example 16

Methyl-5-[1,2,4]triazol-1-yl-1H-pyrazole-4-carboxylic acid adamantan-2-ylamide

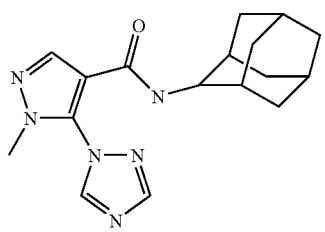

Heating a mixture of 5-chloro-1-methyl-1H-pyrazole-4-carboxylic acid adamantan-2-ylamide (Example 5, 88 mg; 0.30 mmol), triethylamine (0.22 mL; 1.56 mmol) and 1,2,4-triazole (0.21 g; 3.0 mmol) under microwave irradiation for 4 hr according to the procedure described for Example 14 provided after purification by reverse phase HPLC, 1-methyl-5-[1,2,4]triazol-1-yl-1H-pyrazole-4-carboxylic acid adamantan-2-ylamide (11 mg, 11%) as an off-white powder. ES-HRMS m/e calcd for $C_{17}H_{22}N_6O$ (M+H$^+$) 327.1928, found 327.1924.

Example 17

Methyl-5-pyrrolidin-1-yl-1H-pyrazole-4-carboxylic acid adamantan-2-ylamide

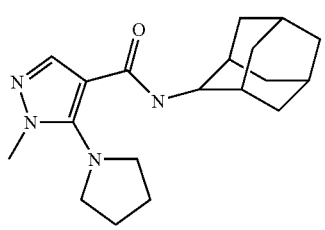

Heating a mixture of 5-chloro-1-methyl-1H-pyrazole-4-carboxylic acid adamantan-2-ylamide (Example 5, 88 mg; 0.30 mmol) and pyrrolidine (0.25 mL; 3.0 mmol) under microwave irradiation according to the procedure described for Example 14 provided after purification by reverse phase HPLC, 1-methyl-5-pyrrolidin-1-yl-1H-pyrazole-4-carboxylic acid adamantan-2-ylamide (60 mg, 61%) as an off-white powder. ES-HRMS m/e calcd for $C_{19}H_{29}N_4O$ (M+H$^+$) 329.2336, found 329.2334.

Example 18

5-(3-Hydroxy-pyrrolidin-1-yl)-1-methyl-1H-pyrazole-4-carboxylic acid adamantan-2-ylamide

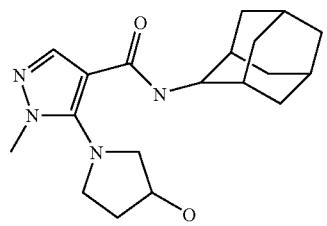

Heating a mixture of 5-chloro-1-methyl-1H-pyrazole-4-carboxylic acid adamantan-2-ylamide (Example 5, 88 mg; 0.30 mmol) and DL-3-pyrrolidinol (0.25 mL; 3.0 mmol) under microwave irradiation according to the procedure described for Example 14 provided after purification by reverse phase HPLC, 5-(3-hydroxy-pyrrolidin-1-yl)-1-methyl-1H-pyrazole-4-carboxylic acid adamantan-2-ylamide (68 mg, 66%) as an off-white powder. ES-HRMS m/e calcd for $C_{19}H_{29}N_4O_2$ (M+H$^+$) 345.2285, found 345.2281.

Example 19

5-(4-Hydroxy-piperidin-1-yl)-1-methyl-1H-pyrazole-4-carboxylic acid adamantan-2-ylamide

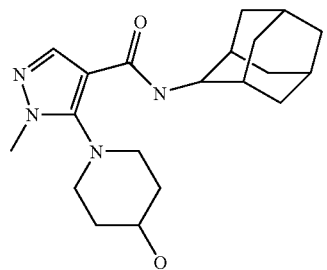

Heating a mixture of 5-chloro-1-methyl-1H-pyrazole-4-carboxylic acid adamantan-2-ylamide (Example 5, 88 mg; 0.30 mmol) and 4-hydroxypiperidine (0.31 mL; 3.0 mmol) under microwave irradiation according to the procedure described for Example 14 provided after purification by reverse phase HPLC, 5-(4-hydroxy-piperidin-1-yl)-1-methyl-1H-pyrazole-4-carboxylic acid adamantan-2-ylamide (87 mg, 81%) as an off-white powder. ES-HRMS m/e calcd for $C_{20}H_{31}N_4O_2$ (M+H$^+$) 359.2442, found 359.2437.

Example 20

5-[(2-Hydroxy-ethyl)-methyl-amino]-1-methyl-1H-pyrazole-4-carboxylic acid adamantan-2-ylamide

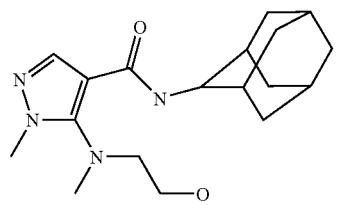

Heating a mixture of 5-chloro-1-methyl-1H-pyrazole-4-carboxylic acid adamantan-2-ylamide (Example 5, 88 mg; 0.30 mmol) and 2-(methylamino)ethanol (0.25 mL; 3.0 mmol) under microwave irradiation according to the procedure described for Example 14 provided after purification by reverse phase HPLC, 5-[(2-hydroxy-ethyl)-methyl-amino]-1-methyl-1H-pyrazole-4-carboxylic acid adamantan-2-ylamide (29 mg, 29%) as an off-white powder. ES-HRMS m/e calcd for $C_{18}H_{29}N_4O_2$ (M+H$^+$) 333.2285, found 333.2282.

Example 21

5-(2-Hydroxy-propylamino)-1-methyl-1H-pyrazole-4-carboxylic acid adamantan-2-ylamide

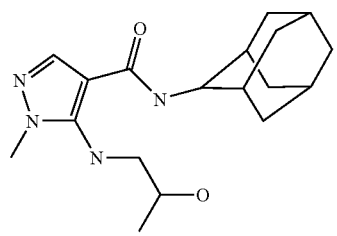

Heating a mixture of 5-chloro-1-methyl-1H-pyrazole-4-carboxylic acid adamantan-2-ylamide (Example 5, 88 mg; 0.30 mmol) and 1-amino-2-propanol (0.25 mL; 3.0 mmol) under microwave irradiation according to the procedure described for Example 14 provided after purification by reverse phase HPLC, 5-(2-hydroxy-propylamino)-1-methyl-1H-pyrazole-4-carboxylic acid adamantan-2-ylamide (65 mg, 65%) as an off-white powder. ES-HRMS m/e calcd for $C_{18}H_{29}N_4O_2$ (M+H$^+$) 333.2285, found 333.2282.

Example 22

Methyl-5-morpholin-4-yl-1H-pyrazole-4-carboxylic acid adamantan-2-ylamide

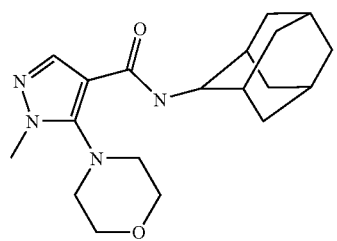

Heating a mixture of 5-chloro-1-methyl-1H-pyrazole-4-carboxylic acid adamantan-2-ylamide (Example 5, 88 mg; 0.30 mmol) and morpholine (0.26 mL; 3.0 mmol) under microwave irradiation for 4 hr according to the procedure described for Example 14 provided after purification by reverse phase HPLC, 1-methyl-5-morpholin-4-yl-1H-pyrazole-4-carboxylic acid adamantan-2-ylamide (76 mg, 74%) as an off-white powder. ES-HRMS m/e calcd for $C_{19}H_{28}N_4O_2$ (M+H$^+$) 345.2285, found 345.2282.

Example 23

5-(2-Methoxy-ethylamino)-1-methyl-1H-pyrazole-4-carboxylic acid adamantan-2-ylamide

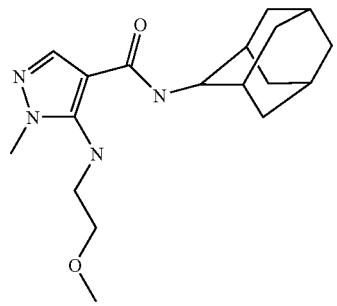

Heating a mixture of 5-chloro-1-methyl-1H-pyrazole-4-carboxylic acid adamantan-2-ylamide (Example 5, 88 mg; 0.30 mmol) and 2-methoxyethylamine (0.26 mL; 3.0 mmol) under microwave irradiation according to the procedure described for Example 14 provided after purification by reverse phase HPLC, 5-(2-methoxy-ethylamino)-1-methyl-1H-pyrazole-4-carboxylic acid adamantan-2-ylamide (65 mg, 65%) as an off-white powder. ES-HRMS m/e calcd for $C_{18}H_{29}N_4O_2$ (M+H$^+$) 333.2285, found 333.2282.

Example 24

5-Isopropylamino-1-methyl-1H-pyrazole-4-carboxylic acid adamantan-2-ylamide

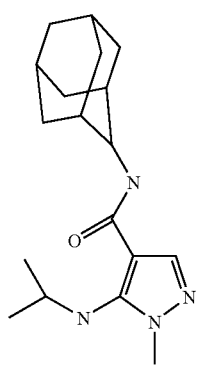

Heating a mixture of 5-chloro-1-methyl-1H-pyrazole-4-carboxylic acid adamantan-2-ylamide (Example 5, 88 mg; 0.30 mmol), triethylamine (0.43 mL; 3.1 mmol) and 2-aminoisobutyric acid (320 mg; 3.1 mmol) under microwave irradiation for 6 hr according to the procedure described for Example 14 provided after purification by reverse phase HPLC, 5-isopropylamino-1-methyl-1H-pyrazole-4-carboxylic acid adamantan-2-ylamide (28 mg, 29%) as an off-white powder. ES-HRMS m/e calcd for $C_{18}H_{29}N_4O$ (M+H$^+$) 317.2336, found 317.2334.

Example 25

Methyl-5-piperidin-1-yl-1H-pyrazole-4-carboxylic acid adamantan-2-ylamide

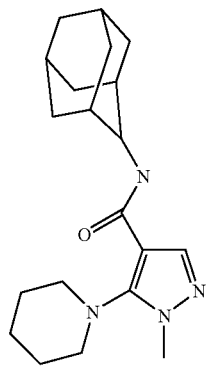

Heating a mixture of 5-chloro-1-methyl-1H-pyrazole-4-carboxylic acid adamantan-2-ylamide (Example 5, 88 mg; 0.30 mmol) and piperidine (0.31 mL; 3.1 mmol) under microwave irradiation according to the procedure described for Example 14 provided after purification by reverse phase HPLC, 1-methyl-5-piperidin-1-yl-1H-pyrazole-4-carboxylic acid adamantan-2-ylamide (52 mg, 51%) as an off-white powder. ES-HRMS m/e calcd for $C_{20}H_{31}N_4O$ (M+H$^+$) 343.2493, found 343.2489.

Example 26

5-(4-Hydroxymethyl-piperidin-1-yl)-1-methyl-1H-pyrazole-4-carboxylic acid adamantan-2-ylamide

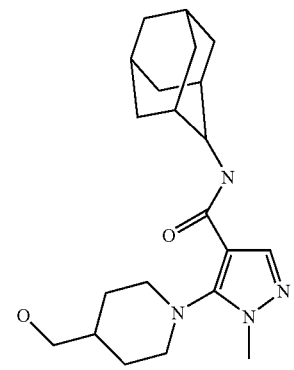

Heating a mixture of 5-chloro-1-methyl-1H-pyrazole-4-carboxylic acid adamantan-2-ylamide (Example 5, 88 mg; 0.30 mmol) and piperidine (0.31 mL; 3.1 mmol) under microwave irradiation according to the procedure described for Example 14 provided after purification by reverse phase HPLC, 5-(4-hydroxymethyl-piperidin-1-yl)-1-methyl-1H-pyrazole-4-carboxylic acid adamantan-2-ylamide (40 mg, 36%) as an off-white powder. ES-HRMS m/e calcd for $C_{21}H_{33}N_4O_2$ (M+H$^+$) 373.2598, found 373.2597.

Example 27

5-(4-Benzyl-piperazin-1-yl)-1-methyl-1H-pyrazole-4-carboxylic acid adamantan-2-ylamide

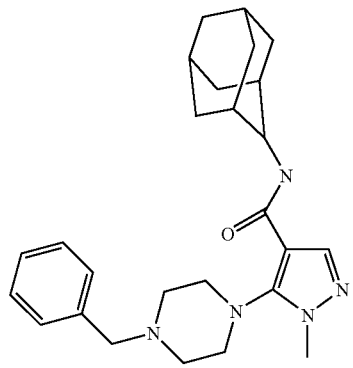

Heating a mixture of 5-chloro-1-methyl-1H-pyrazole-4-carboxylic acid adamantan-2-ylamide (Example 5, 88 mg; 0.30 mmol) and N-benzylpiperazine (0.54 mL; 3.1 mmol) under microwave irradiation according to the procedure described for Example 14 provided after purification by reverse phase HPLC, 5-(4-benzyl-piperazin-1-yl)-1-methyl-1H-pyrazole-4-carboxylic acid adamantan-2-ylamide (50 mg, 38%) as an off-white powder. ES-HRMS m/e calcd for $C_{26}H_{35}N_5O$ (M+H$^+$) 434.2915, found 434.2910.

Example 28

5-(R-3-Hydroxy-pyrrolidin-1-yl)-1-methyl-1H-pyrazole-4-carboxylic acid adamantan-2-ylamide

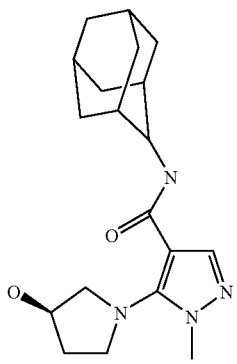

Heating a mixture of 5-chloro-1-methyl-1H-pyrazole-4-carboxylic acid adamantan-2-ylamide (Example 5, 88 mg; 0.30 mmol) and (R)-(+)-3-hydroxypyrrolidine (0.26 mL; 3.1 mmol) under microwave irradiation according to the procedure described for Example 14 provided after purification by reverse phase HPLC, 5-(R-3-hydroxy-pyrrolidin-1-yl)-1-methyl-1H-pyrazole-4-carboxylic acid adamantan-2-ylamide (56 mg, 54%) as an off-white powder. ES-HRMS m/e calcd for $C_{19}H_{29}N_4O_2$ (M+H$^+$) 345.2285, found 345.2283.

Example 29

5-Diethylamino-1-methyl-1H-pyrazole-4-carboxylic acid adamantan-2-ylamide

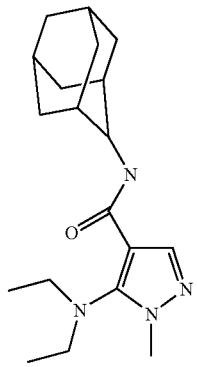

Heating a mixture of 5-chloro-1-methyl-1H-pyrazole-4-carboxylic acid adamantan-2-ylamide (Example 5, 88 mg; 0.30 mmol) and diethylamine (0.32 mL; 3.1 mmol) under microwave irradiation according to the procedure described for Example 14 provided after purification by reverse phase HPLC, 5-diethylamino-1-methyl-1H-pyrazole-4-carboxylic acid adamantan-2-ylamide (16 mg, 16%) as an off-white powder. ES-MS m/e calcd for $C_{19}H_{31}N_4O$ (M+H$^+$) 331, found 331.

Example 30 tert-Butyl-5-pyrrolidin-1-yl-1H-pyrazole-4-carboxylic acid adamantan-2-ylamide

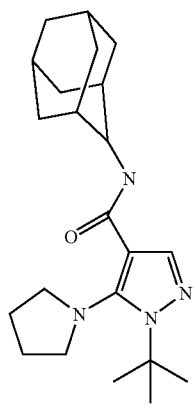

Heating a mixture of 1-tert-butyl-5-chloro-1H-pyrazole-4-carboxylic acid adamantan-2-ylamide (100 mg; 0.30 mmol) and pyrrolidine (0.25 mL; 3.0 mmol) under microwave irradiation according to the procedure described in Example 37, Step 5 provided after purification by reverse phase HPLC, 1-tert-butyl-5-piperidin-1-yl-1H-pyrazole-4-carboxylic acid adamantan-2-ylamide (14 mg, 16%) as an white solid. ES-HRMS m/e calcd for $C_{22}H_{34}N_4O$ (M+H$^+$) 371.2806, found 371.2801.

Example 31

5-[4-(2-Hydroxy-ethyl)-piperazin-1-yl]-1-methyl-1H-pyrazole-4-carboxylic acid adamantanylamide

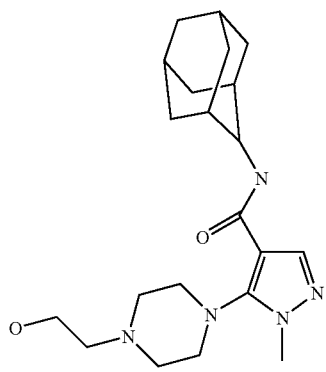

Heating a mixture of 5-chloro-1-methyl-1H-pyrazole-4-carboxylic acid adamantan-2-ylamide (Example 5, 88 mg; 0.30 mmol) and 1-(2-hydroxyethyl)piperazine (0.38 mL; 3.1 mmol) under microwave irradiation according to the procedure described for Example 14 provided after purification by reverse phase HPLC, 5-[4-(2-hydroxy-ethyl)-piperazin-1-yl]-1-methyl-1H-pyrazole-4-carboxylic acid adamantanylamide (71 mg, 61%) as an off-white powder. ES-HRMS m/e calcd for $C_{21}H_{34}N_5O_2$ (M+H$^+$) 388.2707, found 388.2702.

Example 32

5-[(2-Methoxy-ethyl)-methyl-amino]-1-methyl-1H-pyrazole-4-carboxylic acid adamantan-2-ylamide

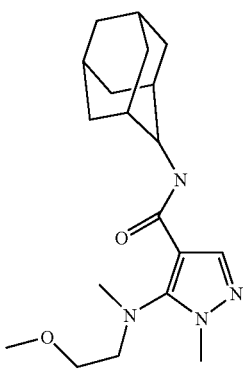

Heating a mixture of 5-chloro-1-methyl-1H-pyrazole-4-carboxylic acid adamantan-2-ylamide (Example 5, 88 mg; 0.30 mmol) and (2-methoxy-ethyl)-methyl-amine (276 mg; 3.1 mmol) under microwave irradiation according to the procedure described for Example 14 provided after purification by reverse phase HPLC, 5-[(2-methoxy-ethyl)-methyl-amino]-1-methyl-1H-pyrazole-4-carboxylic acid adamantan-2-ylamide (61 mg, 59%) as an off-white powder. ES-HRMS m/e calcd for $C_{19}H_{31}N_4O_2$ (M+H$^+$) 347.2442, found 347.2438.

Example 33

2'-tert-Butyl-2'H-[1,3']bipyrazolyl-4'-carboxylic acid adamantan-2-ylamide

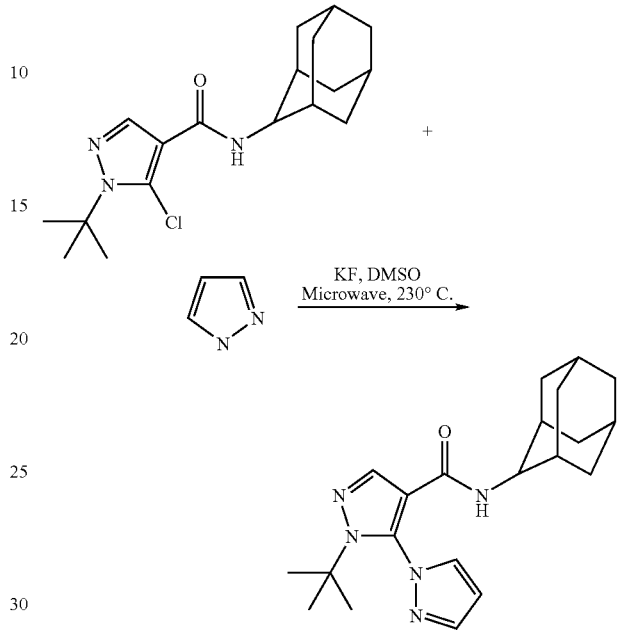

Example 33

In a Personal Chemistry microwave process tube (Biotage AB, Sweden), 1-tert-butyl-5-chloro-1H-pyrazole-4-carboxylic acid adamantan-2-ylamide (Example 36, 100 mg, 0.30 mmol), pyrazole (41 mg, 0.60 mmol), KF (35 mg, 0.60 mmol) and DMSO (2 mL) were well mixed. The tube was sealed with a septum and was submitted to 150 W microwave irradiation using a Personal Chemistry Microwave Synthesis system (Biotage AB, Sweden) at 230° C. for 20 minutes. The reaction mixture was partitioned between ethyl acetate and water and the aqueous phase was extracted three times with ethyl acetate. The organic phases were combined, concentrated in vacuo and purified by C-18 reversed phase prep-HPLC with a gradient of 10-100% acetonitrile/water to give 2'-tert-butyl-2'H-[1,3']bipyrazolyl-4'-carboxylic acid adamantan-2-ylamide (45 mg, 41%). Mass spectrum: m/z: 368.2 (M+1).

Example 34 trans-1-tert-Butyl-5-chloro-1H-pyrazole-4-carboxylic acid (5-hydroxy-adamantan-2-yl)-amide

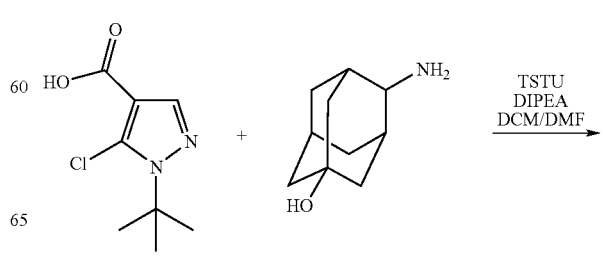

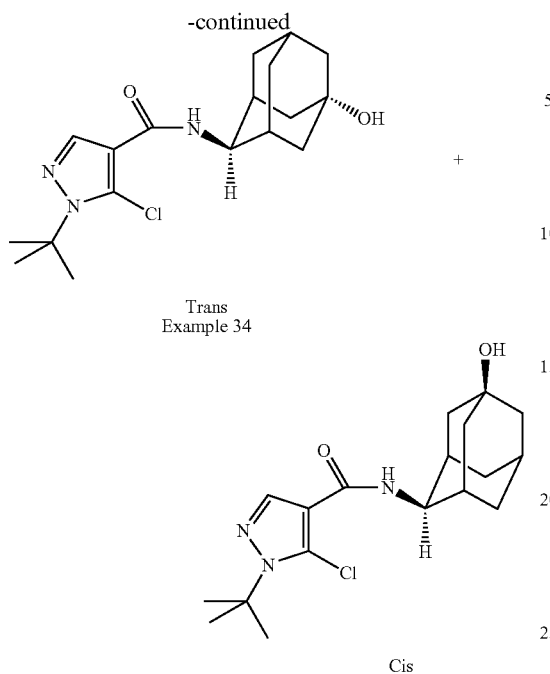

Trans
Example 34

Cis 1-tert-Butyl-5-chloro-1H-pyrazole-4-carboxylic acid (Intermediate 9, 2 g, 9.87 mmol) was dissolved in a mixture of dry dichloromethane (40 mL) and dry DMF (10 mL). DIPEA (10.3 mL, 59.1 mmol) and TSTU (3.6 g, 10.9 mmol) were added to the above mixture. After the mixture was stirred for 2 h, the appearance of active ester was detected by LC-MS. Then 4-Amino-adamantan-1-ol (1.65 g, 9.9 mmol) was added. After another 4 hours water was added and the organic layer was separated. The aqueous layer was extracted twice with dichloromethane. The combined organic phases were dried under vacuum. The crude mixture was first purified by silica chromatography eluting with a gradient of 0-60% ethyl acetate/hexanes, then 60% ethyl acetate/hexanes, and further purified by C-18 reversed phase preparative-HPLC with a gradient of 25-50% acetonitrile/water to give cis-1-tert-butyl-5-chloro-1H-pyrazole-4-carboxylic acid (5-hydroxy-adamantan-2-yl)-amide (Example 34, 900 mg, 26%, Mass spectrum: m/z: 352.2 (M+1)) followed by trans-1-tert-butyl-5-chloro-1H-pyrazole-4-carboxylic acid (5-hydroxy-adamantan-2-yl)-amide (1400 mg, 40%).

Example 35 trans-2'-tert-Butyl-2'H-[1,3']bipyrazolyl-4'-carboxylic acid (5-hydroxy-adamantan-2-yl)-amide

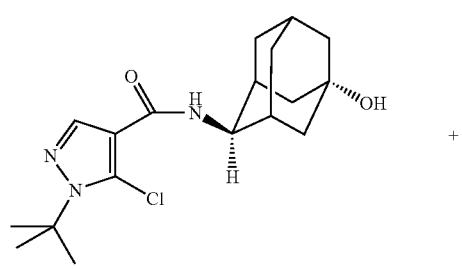

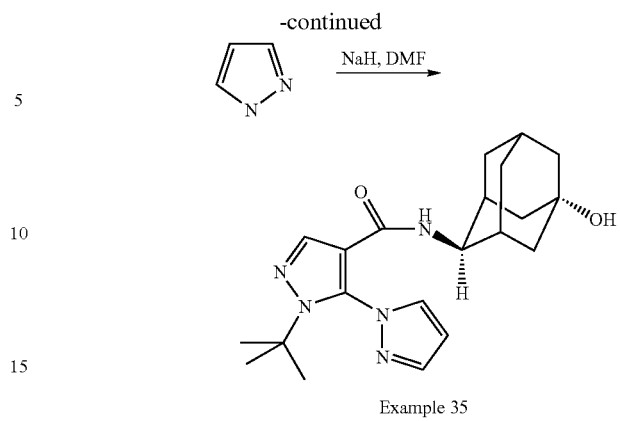

Example 35

Sodium hydride (60% in oil; 420 mg, 10.5 mmol) was added to a solution of pyrazole (714 mg, 10.5 mmol) in dry DMF (140 mL) under nitrogen at 0° C. in an ice-water bath and the mixture was heated to 40° C. for 1 h. trans-5-Chloro-1-tert-butyl-1H-pyrazole-4-carboxylic acid ethyl ester (5-hydroxy-adamantan-2-yl)-amide (Example 34, 1.89 g, 5.4 mmol) was added and the mixture was heated at 110° C. overnight and then cooled. Water and ethyl acetate were added, the organic layer was separated, and the aqueous phase was extracted three times with EtOAc. The combined organic phases were concentrated in vacuo and the residue was purified by C-18 reversed phase preparative-HPLC with a gradient of 10-100% acetonitrile/water to give trans-2'-tert-butyl-2'H-[1,3']bipyrazolyl-4'-carboxylic acid (5-hydroxy-adamantan-2-yl)-amide (500 mg, 24%). Mass spectrum: m/z: 384.2 (M+1).

A preferred method for the preparation of trans-2'-tert-butyl-2'H-[1,3']bipyrazolyl-4'-carboxylic acid (5-hydroxy-adamantan-2-yl)-amide starting from ethyl-3,3-diethoxypropionate is outlined below.

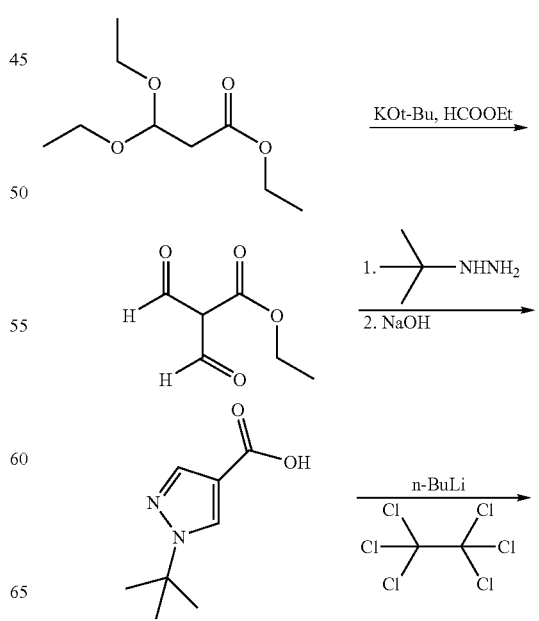

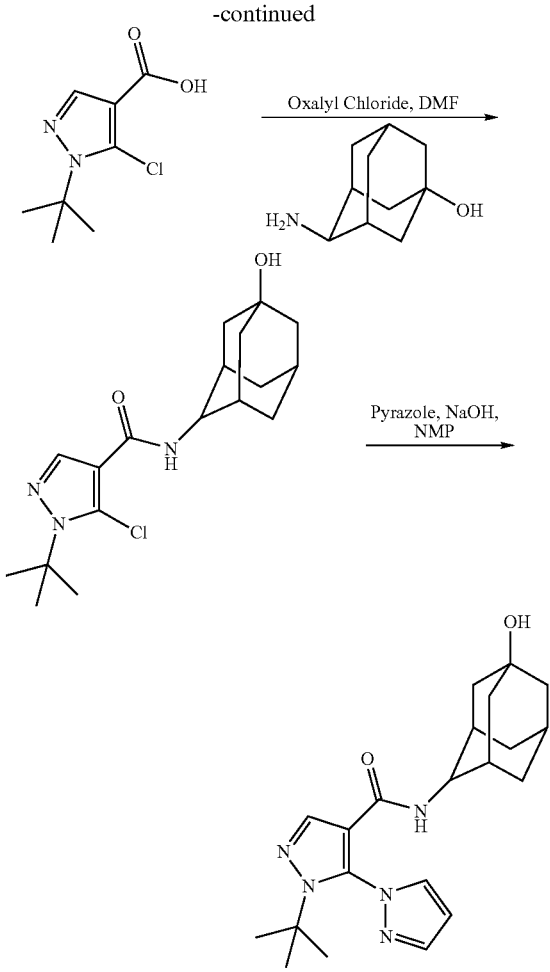

Step 1: 2-Formyl-3-oxo-propionic acid ethyl ester

Ethyl 3,3-diethoxypropionate (100 g, 525.7 mmol) was dissolved in THF (360 ml) at room temp. Ethyl formate (175.1 ml, 2.1 mol) was added at room temp. The solution was cooled in an ice-bath to 0° C. and tBuOK (1M solution in THF, 1,156 ml, 1.156 mol) was added via an addition funnel slowly over 30 min, maintaining internal temperature below 5° C. The color changed instantly from colorless to dark orange. The reaction mixture was allowed to warm up to room temp. and stirred for 2 h. The reaction was allowed to stir at room temp. for 18 h. The reaction mixture was concentrated in vacuo and 1 L of solvent was removed. The remaining brownish solution with white solid in it was cooled in an ice-bath and hydrochloric acid (6N, 200 ml) was added to adjust pH=3, maintaining internal temperature below 20° C. The resulting bright yellow suspension was then warmed up to room temp. and stirred for 1 h. Additional 700 ml solvent was removed in vacuo at room temp. Water (400 ml) was added to dissolve all the white solid and ethyl acetate (500 ml) was added and the mixture transferred to a separatory funnel. The aqueous was extracted once with ethyl acetate (200 ml). The combined organic extracts was washed once with brine (100 ml). After drying over MgSO$_4$ and concentrating in vacuo, 2-formyl-3-oxo-propionic acid ethyl ester (75.85 g) was obtained as yellow oil.

Step 2: 1-tert-Butyl-1H-pyrazole-4-carboxylic acid

Formyl-3-oxo-propionic acid ethyl ester (75.85 g, 525.6 mmol) was dissolved in ethanol (1 L) at room temp. Tert-butylhydrazine hydrochloride (65.5 g, 525.6 mmol) was added at room temp and the reaction temperature gradually increased to 32° C. The flask was then placed in an ice-bath to cool it back to 20° C. It took ca. 1 h for t-butylhydrazine to fully dissolve. The solution was stirred at room temp. for 3 h. The reaction mixture was cooled in an ice-bath. Sodium hydroxide (4N, 152.4 g) was added to neutralize the hydrochloric acid. Most of the ethanol was then removed in vacuo and methanol (300 ml) was added followed by additional sodium hydroxide (4N, 304.8 g, 1.05 mol). The internal temperature gradually rose to 32° C. The reaction flask was then placed in a water bath to cool it back to room temp. and the reaction was allowed to stir at room temp. for 18 h. Methanol (300 ml) was then removed in vacuo with the water bath temperature kept below 30° C. The reaction mixture was then cooled to 0° C. and hydrochloric acid (6N, 190 ml) was added slowly to keep internal temperature below 15° C. The solution was adjusted to pH=2. The resulting suspension was allowed to stir in the ice-bath for 2 h, and the solid was filtered. After drying at 60° C. in vacuo for 2.5 days, 1-tert-butyl-1H-pyrazole-4-carboxylic acid (56.06 g) of off-white solid was collected. The mother liquor was extracted 3 times with dichloromethane (200 ml×3). The combined organic layer was washed once with brine (100 ml) and dried over magnesium sulfate. After concentrating in vacuo and drying, 16.5 g of yellowish solid was collected. The crude material was crystallized in hot iso-propyl acetate (25 ml) and heptane (25 ml). After cooling to room temp, the solid was filtered off and the cake was washed with mixed solvent of isopropyl acetate and heptane (1/1 (v/v, 14 ml) and dried in oven at 60° C. in vacuo for 5 h. A second crop of 1-tert-butyl-1H-pyrazole-4-carboxylic acid (7 g) was collected as a white solid.

Step 3:
1-tert-Butyl-5-chloro-1H-pyrazole-4-carboxylic acid tert-butyl-1H-pyrazole-4-carboxylic acid (5 g, 29.73 mmol) was dissolved in tetrahydrofuran (50 ml) at room temp. In a separate flask was added n-butyllithium (2.5M solution in hexane, 29.73 ml, 74.33 mmol) and was cooled to −15° C. The 1-tert-butyl-1H-pyrazole-4-carboxylic acid solution was added dropwise to the n-Butyllithium solution, maintaining internal temperature below −10° C. The total addition time lasted 30 min. The resulting brownish suspension was stirred and maintained between −10° C. and −15° C. for 40 min. The reaction was then cooled to −15° C. to −20° C. A solution of hexachloroethane (14.08 g, 59.46 mmol) in tetrahydrofuran (50 ml) was added dropwise, maintaining internal temperature below −10° C. The total addition time lasted 20 min. After the addition, the resulting dark brownish solution was stirred at −10° C. to −15° C. for 30 min and was warmed up to room temp. over 1 h. The reaction mixture was then cooled to 15° C. and water (50 ml) was added slowly, maintaining internal temperature below 20° C. 120 ml of organic solvents were distilled under reduced pressure at 25° C. water bath leading to a suspension. Heptane (50 ml) was added leading to a clear brownish biphasic solution. After stirring at room temp. for 15 min, the aqueous layer (pH=11.8) was separated. The organic layer was extracted once with NaOH (1N, 20 ml). The combined aqueous phase was washed with heptane (25 ml) and was cooled in an ice-bath. Hydrochloric acid (6N) was added to adjust pH=2, maintaining internal temperature below 20° C. The suspension was stirred in the ice-bath at 0-5° C. for 1 h and the solid was filtered and washed with water (40 ml). After drying in vacuo at 60° C. for 18 h, 1-tert-butyl-5-chloro-1H-pyrazole-4-carboxylic acid (5.28 g) was obtained as a light yellow solid.

Step 4: trans-1-tert-butyl-5-chloro-1H-pyrazole-4-carboxylic acid (5-hydroxy-adamantan-2-yl)-amide tert-butyl-5-chloro-1H-pyrazole-4-carboxylic acid (5 g, 24.67 mmol) was suspended in toluene (50 ml) at room temp. Dimethylformamide (12 µL) was added and the reaction flask was placed in a water bath. To the suspension was added oxalyl chloride (3.3 ml, 37 mmol) dropwise over 10 min. There was a slight exotherm and the internal temperature rose to 23° C. from 21° C. The suspension was allowed to stir at room temp. for 5 h. Toluene (25 ml) was removed in vacuo at 21° C. bath temperature to remove excess of oxalyl chloride. To the resulting acyl chloride in toluene solution was added tetrahydrofuran (25 ml) to make a clear dark orange solution. In a separate reaction flask was added trans-4-amino-adamantan-1-ol hydrochloride salt (5.28 g, 25.91 mmol, Intermediate 2) and sodium hydroxide solution (1N, 49.34 ml, 49.34 mmol) to give a milky solution. This solution was placed in a water bath. The above acyl chloride solution was added via an addition funnel to the aqueous solution over 20 min, maintaining the internal temperature below 25° C. After the addition, the resulting suspension was allowed to stir at room temp. for 18 h. The solid was filtered off and dried at 60° C. in vacuo for 18 h. trans-1-tert-butyl-5-chloro-1H-pyrazole-4-carboxylic acid (5-hydroxy-adamantan-2-yl)-amide (5.92 g) as a white solid was collected. To the mother liquor was added heptane (50 ml) and the resulting suspension was stirred at room temp. for 1 h. The solid was again filtered off. After drying at 60° C. in vacuo for 18 h., 1.7 g second crop was collected. HPLC purity is 96.92%.

Step 5: trans-2'-tert-Butyl-2'H-[1,3']bipyrazolyl-4'-carboxylic acid (5-hydroxy-adamantan-2-yl)-amide tert-butyl-5-chloro-1H-pyrazole-4-carboxylic acid (5-hydroxy-adamantan-2-yl)-amide (20 g, 56.84 mmol) and pyrazole (7.74 g, 113.7 mmol) were added N-methylpyrrolidinone (400 ml) and stirred at room temp. Sodium hydroxide solution (50%, 18.19 g, 227.4 mmol) was added. The suspension was heated to 120° C. to give a yellowish solution. The reaction was then heated at 120° C. for 10 h. Additional pyrazole (3.87 g, 56.84 mol) and sodium hydroxide solution (50%, 4.55 g, 56.84 mmol) were added. The reaction was allowed to continue at 120° C. for 6 h. The reaction mixture was then cooled in an ice-bath to 5° C. Water (500 ml) and saturated ammonium chloride solution (500 ml) were added while maintaining internal temperature below 20° C. The resulting suspension was stirred in ice-bath for 2 h and then the solid was filtered off and washed with water (300 ml) and dried in oven at 50° C. in vacuo for 18 h. trans-2'-tert-butyl-2'H-[1,3']bipyrazolyl-4'-carboxylic acid (5-hydroxy-adamantan-2-yl)-amide (16.81 g) was obtained as a white solid.

Example 36 tert-Butyl-5-chloro-1H-pyrazole-4-carboxylic acid adamantan-2-ylamide

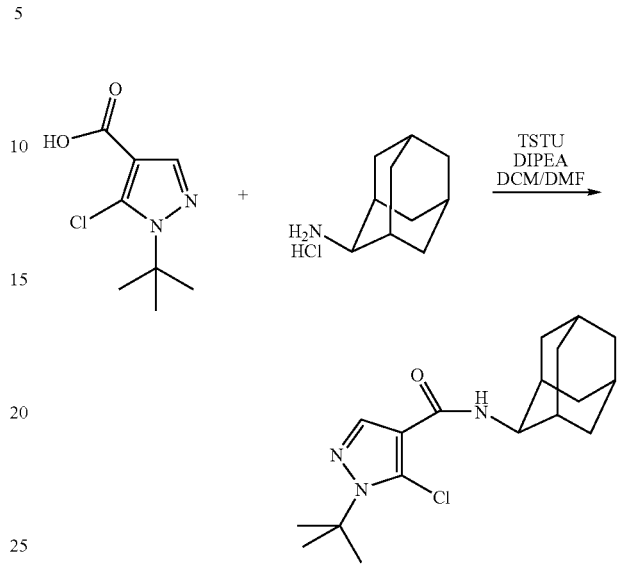

Example 36 tert-Butyl-5-chloro-1H-pyrazole-4-carboxylic acid (Intermediate 9, 0.5 g, 2.47 mmol) was dissolved in a mixture of dry dichloromethane (12 mL) and dry DMF (3 mL). DIPEA (2.6 mL, 14.9 mmol) and TSTU (0.9 g, 2.7 mmol) were added to the above mixture. After the mixture was stirred for 1 h, the appearance of active ester was detected by LC-MS. Then 2-aminoadamantane hydrochloride (0.44 g, 2.34 mmol) was added. After another 2 hours water was added and the organic layer was separated. The aqueous layer was extracted twice with dichloromethane. The combined organic phases were dried under vacuum and purified by C-18 reverse phase pre-parative-HPLC with a gradient of 10-100% acetonitrile/water to give 1-tert-butyl-5-chloro-1H-pyrazole-4-carboxylic acid adamantan-2-ylamide (650 mg, 83%). Mass spectrum: m/z: 336.2 (M+1).

Example 37 tert-Butyl-5-(3-hydroxy-pyrrolidin-1-yl)-1H-pyrazole-4-carboxylic acid adamantan-2-ylamide

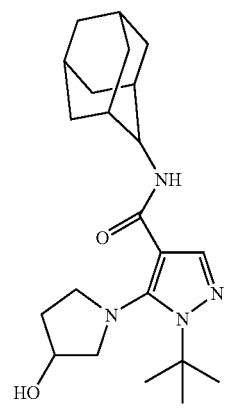

Step 1 to 3:
1-tert-butyl-5-chloro-1H-pyrazole-4-carboxylic acid was prepared according to procedures described previously for Intermediate 9

Step 4: preparation of 1-tert-butyl-5-chloro-1H-pyrazole-4-carboxylic acid adamantan-2-ylamide To a stirred solution of 1-tert-butyl-5-chloro-1H-pyrazole-4-carboxylic acid (3.040 g; 15.0 mmol) in N,N-dimethylformamide/methylene chloride (1:4 ratio, 20 mL) at room temperature was added diisopropylethylamine (21.2 mL; 120.4 mmol). TSTU (5.420 g; 18.0 mmol) was then added. The resulting mixture was allowed to stir at room temp. for 2 hr and then 2-adamantylamine hydrochloride (2.844 g; 15.0 mmol) was added. The mixture was allowed to stir over the weekend at room temperature and then concentrated in vacuo. The residue was partitioned between ethyl acetate and water. The organic layer was washed with brine, dried over sodium sulfate, filtered and concentrated in vacuo. The resulting light yellow gum was triturated with diethyl ether to provide 1-tert-butyl-5-chloro-1H-pyrazole-4-carboxylic acid adamantan-2-ylamide (4.02 g, 80%) as a white powder.

Step 5: preparation of 1-tert-butyl-5-(3-hydroxy-pyrrolidin-1-yl)-1H-pyrazole-4-carboxylic acid adamantan-2-ylamide A mixture of 1-tert-butyl-5-chloro-1H-pyrazole-4-carboxylic acid adamantan-2-ylamide (Example 36, 101 mg; 0.30 mmol) and pyrrolidin-3-ol (+/−) (0.25 mL; 3.0 mmol) in N-methylpyrrolidinone (1 mL) was heated to 250° C. in a sealed vial under microwave irradiation for 4 hr. The mixture was allowed to cool to room temperature and the crude product was purified by reverse phase HPLC to provide 1-tert-butyl-5-(3-hydroxy-pyrrolidin-1-yl)-1H-pyrazole-4-carboxylic acid adamantan-2-ylamide (25 mg, 22%) as an off white solid. ES-HRMS m/e calcd for $C_{22}H_{35}N_4O_2$ (M+H$^+$) 358.2602, found 358.2602.

Example 38 tert-Butyl-5-(4-hydroxy-piperidin-1-yl)-1H-pyrazole-4-carboxylic acid adamantan-2-ylamide

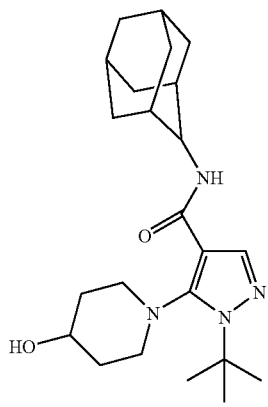

Heating a mixture of 1-tert-butyl-5-chloro-1H-pyrazole-4-carboxylic acid adamantan-2-ylamide (Example 36, 101 mg; 0.30 mmol) and piperidin-4-ol (303 mg; 3.0 mmol) under microwave irradiation according to the procedure described in Example 37, Step 5 provided after purification by reverse phase HPLC, 1-tert-butyl-5-(4-hydroxy-piperidin-1-yl)-1H-pyrazole-4-carboxylic acid adamantan-2-ylamide (14 mg, 12%) as an off-white powder. ES-HRMS m/e calcd for $C_{23}H_{37}N_4O_2$ (M+H$^+$) 357.2649, found 357.2650.

Example 39

5-Azepan-1-yl-1-methyl-1H-pyrazole-4-carboxylic acid adamantan-2-ylamide

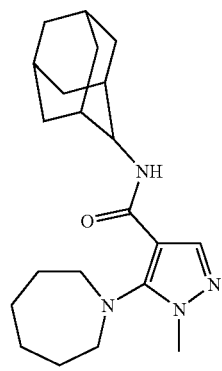

Heating a mixture of 5-chloro-1-methyl-1H-pyrazole-4-carboxylic acid adamantan-2-ylamide (Example 5, 60 mg; 0.20 mmol) and azepane (0.23 mL; 2.0 mmol) to 250° C. under microwave irradiation according to the procedure described in Example 14 provided after purification by reverse phase HPLC, 5-azepan-1-yl-1-methyl-1H-pyrazole-4-carboxylic acid adamantan-2-ylamide (41 mg, 58%) as an off-white powder. ES-HRMS m/e calcd for $C_{21}H_{33}N_4O$ (M+H$^+$) 357.2649, found 357.2644.

Example 40

Methyl-5-thiomorpholin-4-yl-1H-pyrazole-4-carboxylic acid adamantan-2-ylamide

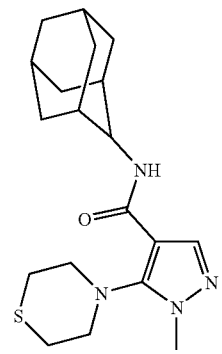

Heating a mixture of 5-chloro-1-methyl-1H-pyrazole-4-carboxylic acid adamantan-2-ylamide (Example 5, 60 mg; 0.20 mmol) and thiomorpholine (0.20 mL; 2.0 mmol) to 250° C. under microwave irradiation according to the procedure described in Example 14 provided after purification by reverse phase HPLC, 1-methyl-5-thiomorpholin-4-yl-1H-pyrazole-4-carboxylic acid adamantan-2-ylamide (15 mg, 21%) as light brown powder. ES-HRMS m/e calcd for $C_{19}H_{29}N_4OS_4$ (M+H⁺) 361.2057, found 361.2053.

Example 41 tert-Butyl-5-piperidin-1-yl-1H-pyrazole-4-carboxylic acid adamantan-2-ylamide

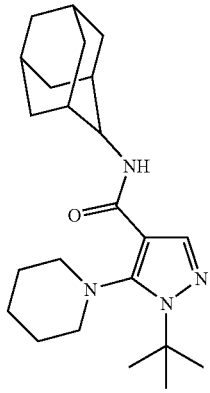

Heating a mixture of 1-tert-butyl-5-chloro-1H-pyrazole-4-carboxylic acid adamantan-2-ylamide (Example 36, 101 mg; 0.30 mmol) and piperidine (0.30 mL; 3.0 mmol) under microwave irradiation according to the procedure described in Example 37, Step 5 provided after purification by reverse phase HPLC, 1-tert-butyl-5-piperidin-1-yl-1H-pyrazole-4-carboxylic acid adamantan-2-ylamide (19 mg, 16%) as an off-white powder. ES-HRMS m/e calcd for $C_{23}H_{37}N_4O$ (M+H⁺) 385.2962, found 385.2958.

Example 42 trans-1-tert-butyl-5-trifluoromethyl-1H-pyrazole-4-carboxylic acid (5-fluoro-adamantan-2-yl)-amide

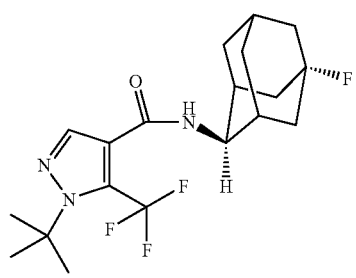

Step 1: preparation of 1-tert-butyl-5-trifluoromethyl-1H-pyrazole-4-carboxylic acid To a stirred mixture of 1-tert-butyl-5-trifluoromethyl-1H-pyrazole-4-carboxylic acid ethyl ester (3.000 g; 11.4 mmol) in methanol/water (1:1 ratio, 50 mL) was added lithium hydroxide (0.383 g; 16.0 mmol) at room temperature. The mixture was heated to reflux for 2 hr, then allowed to cool to room temperature and concentrated to approximately half of the original volume. The resulting mixture was acidified with 1N HCl to ~pH 1 and extracted with methylene chloride. The extracts were dried over sodium sulfate, filtered and concentrated to provide 1-tert-butyl-5-trifluoromethyl-1H-pyrazole-4-carboxylic acid (2.47 g, 92%).

Step 2: preparation of 1-tert-butyl-5-trifluoromethyl-1H-pyrazole-4-carboxylic acid (5-hydroxy-adamantan-2-yl)-amide To a stirred solution of 1-tert-butyl-5-trifluoromethyl-1H-pyrazole-4-carboxylic acid (2.334 g; 9.88 mmol) in N,N-dimethylformamide/methylene chloride (1:4 ratio, 15 mL) at room temperature was added diisopropylethylamine (9.00 mL; 51.13 mmol). TSTU (5.420 g; 18.0 mmol) was then added. The resulting mixture was allowed to stir at room temperature for 2 hr and then 2-adamantylamine (1.654 g; 9.89 mmol) was added. The mixture was allowed to stir over night at room temperature and then concentrated in vacuo. The residue was partitioned between ethyl acetate and water. The organic layer was washed sequentially with 0.5N HCl, saturated sodium bicarbonate then brine, dried over sodium sulfate, filtered and concentrated in vacuo to give the crude product as a light brown solid. Purification by column chromatography (RediSep-120 g silica gel, 10%—100% ethyl acetate/hexanes) provided the desired trans-isomer of 1-tert-butyl-5-trifluoromethyl-1H-pyrazole-4-carboxylic acid (5-hydroxy-adamantan-2-yl)-amide (1.23 g, 32%) as a white solid. by resulting light yellow gum was triturated with diethyl ether to provide 1-tert-butyl-5-chloro-1H-pyrazole-4-carboxylic acid adamantan-2-ylamide (4.02 g, 80%) as a white powder. The cis-isomer was also isolated (1.58 g, 41%).

Step 3: 1-tert-butyl-5-trifluoromethyl-1H-pyrazole-4-carboxylic acid (5-fluoro-adamantan-2-yl)-amide To a stirred solution of trans-1-tert-butyl-5-trifluoromethyl-1H-pyrazole-4-carboxylic acid (5-hydroxy-adamantan-2-yl)-amide (trans-isomer) (60 mg, 0.16 mmol) in dry methylene chloride (2 mL) cooled to 0° C. under nitrogen was added DAST reagent dropwise via syringe. The mixture was then allowed to warm up to room temperature. After 1 hr, the reaction mixture was quenched with saturated sodium bicarbonate solution (0.5 mL). The resulting mixture was diluted with methylene chloride. The organic layer was dried over sodium sulfate, filtered and concentrated to give a crude product. Reverse phase HPLC purification provided trans-1-tert-butyl-5-trifluoromethyl-1H-pyrazole-4-carboxylic acid (5-fluoro-adamantan-2-yl)-amide (28 mg, 45%) as a white solid. ES-HRMS m/e calcd for $C_{19}H_{26}F_4N_3O$ (M+H⁺) 385.2962, found 385.2963

Example 43 trans-N-(4-Amino-adamantan-1-yl)-acetamide

Step 1: trans-(5-hydroxy-adamantan-2-yl)-carbamic acid 9H-fluoren-9-ylmethyl ester To a slurry of 4-amino-adamantanol hydrochloride (Intermediate 2, 26.48 g; 130.0 mmol) in dichloromethane (800 mL) was added triethylamine (92.0 mL; 656.8 mmol). To this mixture was added FMOC-OSu (65.78 g; 195 mmol) portionwise over a 15 minute period. The resulting slurry was stirred under argon at room temperature. After 20 hr., triethylamine (28 m; 199 mmol), FMOC-OSu (21.92 g; 65.0 mmol) and dichloromethane (300 mL) were added. After a further 20 hr., the reaction mixture was cooled to 0° C. and 4N HCL (400 mL0 was slowly added with stirring and allowed to warm to room temperature. The organic phase was separated and washed sequentially with water (300 mL), saturated sodium bicarbonate (300 mL) saturated sodium chloride solution (300 mL). The organic layer was dried over sodium sulfate, filtered and concentrated in vacuo to give 86.8 g of crude product. This material was triturated twice with hexanes (2×300 mL) and the solid material filtered and washed several times with hexanes (total 300 mL) and allowed to air dry to give 40.6 g of trans-(5-hydroxy-adamantan-2-yl)-carbamic acid 9H-fluoren-9-ylmethyl ester as an off white solid.

Step 2: trans-(5-acetylamino-adamantan-2-yl)-carbamic acid 9H-fluoren-9-ylmethyl ester To a stirred slurry of trans-(5-hydroxy-adamantan-2-yl)-carbamic acid 9H-fluoren-9-ylmethyl ester (11.69 g; 30.0 mmol), acetonitrile (23 mL) and glacial acetic acid (30 mL) cooled to 0° C. was added concentrated sulfuric acid (30 mL) slowly over a 20 minute period. The mixture was then allowed to warm up to room temperature and allowed to stir for 30 hr. and then stored in the freezer overnight (20 hr.). The reaction mixture was then poured over crushed ice/water (500 mL) and allowed to warm to room temperature for 2 hr. The resulting mixture was extracted with ethyl acetate. The extract was washed sequentially with water, saturated sodium bicarbonate solution an finally saturated sodium chloride solution. The extract was then dried over sodium sulfate, filtered and concentrated in vacuo to give 10.23 g of trans-(5-acetylamino-adamantan-2-yl)-carbamic acid 9H-fluoren-9-ylmethyl ester as a yellow foam.

Step 3: trans-N-(4-amino-adamantan-1-yl)-acetamide

To a stirred solution of trans-(5-acetylamino-adamantan-2-yl)-carbamic acid 9H-fluoren-9-ylmethyl ester (10.21 g; 23.7 mmol) in dry dimethylformamide (30 mL) was added piperidine (8 mL). After 45 minutes, the reaction mixture was concentrated in vacuo. The resulting residue was suspended in water (100 mL) and allowed to stir at room temperature for 1 hr. The resulting slurry was filtered and the solid material was washed with 100 mL of water. The combined filtrated and washings were transferred to a separatory funnel and washed with diethyl ether. The aqueous phase was then concentrated in vacuo to give a viscous liquid which was lyophilized to give 3.28 g of trans-N-(4-amino-adamantan-1-yl)-acetamide as a pale yellow solid. This material was used without further purification.

A preferred method for the preparation of trans-N-(4-amino-adamantan-1-yl)-acetamide starting from trans-4-amino-adamantan-1-ol-hydrochloride (Intermediate 2) is described below.

Step 1: N-(5-acetylamino-adamantan-2-yl)-2,2,2-trifluoro-acetamide trans-4-amino-adamantan-1-ol-hydrochloride (120 g, 589.1 mmol) was added to a reaction flask followed by acetonitrile (1.5 L) and trifluoroacetic acid (1 L, 12.85 mol). After stirring at room temp. for 6 days, the reaction mixture was concentrated in vacuo. The contents was then taken up into ethyl acetate (4 L), washed sequentially with saturated sodium bicarbonate solution (2×3 L), and water (1×3 L). The organic phase was then separated and filtered through sintered funnel. The filtrate was concentrated in vacuo to give 150 g of solids. This solid was taken up into ethyl acetate (1 L) and stirred for an hour. While concentrating, solvent was exchanged with heptane (1 L) and the resulting suspension was filtered. The solid was washed with a mixed solvent of ethyl acetate-heptane (¼, 500 ml). The solid was then filtered and dried in the oven at 45° C. in vacuo for 18 h to give N-(5-acetylamino-adamantan-2-yl)-2,2,2-trifluoro-acetamide (135 g) as a white solid.

Step 2: N-(4-amino-adamantan-1-yl)-acetamide hydrochloride

N-(5-acetylamino-adamantan-2-yl)-2,2,2-trifluoro-acetamide (135 g, 443.6 mmol) was added to a reaction flask followed by ethanol (2 L) and sodium hydroxide (37 g, 913.8 mmol). The reaction mixture was heated to 50-55° C. and stirred over the weekend. The reaction mixture was then allowed to cool to room temp. and glacial acetic acid (100 ml, 1.748 mol) was added. The resulting mixture was then concentrated in vacuo to give a white solid. The solid was suspended in ether (1 L) and stirred for an hour. The solid was then filtered, washed with ether (200 ml) and dried in the oven at 45° C. for 18 h to give 240 g of solid. The solid was taken in methanol (500 ml). While stirring, hydrochloric acid (4N solution in dioxane, 500 ml) was added followed by dropwise addition of 2 L of ether. The mixture was then concentrated in vacuo to give a white solid. The solid was taken up in methanol (1 L) and stirred for an hour. The solid was filtered and discarded. The filtrate was concentrated in vacuo until it started to crystallize out (ca. 500 mL). The light suspension was transferred to a flask. While stirring, ether (2 L) was added dropwise to give a heavy suspension of white solid. The solid was filtered off and washed with ether. After drying in the oven at 45° C. for 18 h, N-(4-Amino-adamantan-1-yl)-acetamide hydrochloride (96 g) was obtained as a white solid.

Example 44 trans-N-(4-Amino-adamantan-1-yl)-methanesulfonamide

Step 1: trans-[5-(2-Chloro-acetylamino)-adamantan-2-yl]-carbamic acid 9H-fluoren-9-ylmethyl ester To a stirred mixture of trans-(5-hydroxy-adamantan-2-yl)-carbamic acid 9H-fluoren-9-ylmethyl ester (11.69 g; 30.0 mmol), chloroacetonitrile (20 mL) and glacial acetic acid (25 mL) cooled to 0° C. was added concentrated sulfuric acid (25 mL). The resulting mixture was allowed to warm up to room temperature. After 7 hr., the mixture was stored in the freezer at −20° C. overnight and then allowed to warm up to room temperature for 6 hr. The reaction mixture was then poured over crushed ice/water (600 mL) and allowed to warm to room temperature for 3 hr with stirring. The mixture was then extracted with ethyl acetate (550 mL). The extract was sequentially washed with water, saturated sodium bicarbonate and saturated sodium chloride solutions. The organic layer was then dried over sodium sulfate, filtered and concentrated in vacuo to give 6.18 g of Trans-[5-(2-Chloro-acetylamino)-adamantan-2-yl]-carbamic acid 9H-fluoren-9-ylmethyl ester as a yellow foam.

Step 2: trans-(5-Amino-adamantan-2-yl)-carbamic acid 9H-fluoren-9-ylmethyl ester To a stirred solution of Trans-[5-(2-chloro-acetylamino)-adamantan-2-yl]-carbamic acid 9H-fluoren-9-ylmethyl ester (1.017 g; 2.19 mmol) in ethanol (10 mL) was added thiourea (206 mg; 2.67 mmol) followed by glacial acetic acid (2 mL). The resulting solution was heated to 80° C. in a sealed tube 21 hr. and then allowed to stand for 72 hr at room temperature. The mixture was then concentrated to half volume under a stream of dry nitrogen and then suspended in diethyl ether and the solid material filtered off. The solid was washed with diethyl ether to give 1.14 g of trans-(5-amino-adamantan-2-yl)-carbamic acid 9H-fluoren-9-ylmethyl ester as a white solid.

Step 3: trans-(5-Methanesulfonylamino-adamantan-2-yl)-carbamic acid 9H-fluoren-9-yl methyl ester To a stirred solution of trans-(5-amino-adamantan-2-yl)-carbamic acid 9H-fluoren-9-ylmethyl ester (991 mg; 2.33 mmol) in ethyl acetate (100 mL) was added saturated sodium bicarbonate solution (75 mL) followed by water (25 mL). Methanesulfonylchloride (2.0 mL; 25.7 mmol) was then added dropwise over 5 minutes and stirring continued for 1.5 hr. At this point, sodium carbonate (5.83 g) was slowly added to the reaction mixture followed by methanesulfonyl chloride (2.0 mL) and the mixture allowed to stir for 20 hr. at room temperature. The slow addition of sodium carbonate (18.2 g) followed by methanesulfonyl chloride (4.0 mL) was repeated and the mixture was again allowed to stir for 24 hr at room temperature. The organic layer was washed several times with 3N hydrochloric acid solution followed by saturated sodium bicarbonate solution and finally saturated sodium chloride solution. The organic layer was dried over sodium sulfate, filtered and concentrated in vacuo to give 722 mg of crude product as an off-white solid. The crude product was further purified by chromatography (ISCO companion system, RS-40 g silica gel column; eluent: ethyl acetate/hexanes; 0-100% gradient; 40 mL/min. flow rate;) to provide 660 mg of trans-(5-methanesulfonylamino-adamantan-2-yl)-carbamic acid 9H-fluoren-9-yl methyl ester as a white foam.

Step 4: trans-N-(4-Amino-adamantan-1-yl)-methanesulfonamide

To a solution of trans-(5-methanesulfonylamino-adamantan-2-yl)-carbamic acid 9H-fluoren-9-yl methyl ester (1.73 g; 3.71 mmol) in N,N-dimethylformamide (4 mL) was added piperidine (1.0 mL). The mixture became thick after a few minutes and another 4 mL of dimethylfomamide and 1.0 mL of piperidine was added to facilitate stirring. The resulting slurry was stirred at room temperature for 2 hr. and then concentrated in vacuo. The residue was partitioned between diethyl ether and water. The aqueous layer was then concentrated in vacuo with warming and the light yellow oily residue was lyophilized to provide 741 mg of trans-N-(4-amino-adamantan-1-yl)-methanesulfonamide as a pale yellow solid.

Example 45 trans-2'-Methyl-2'H-[1,3']bipyrazolyl-4'-carboxylic acid (5-acetylamino-adamantan-2-yl)-amide

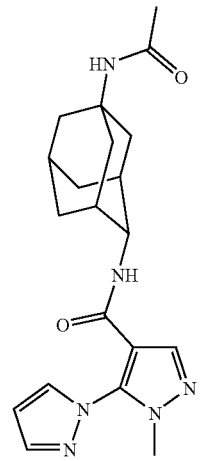

To a stirred solution of trans-2'-methyl-2'H-[1,3']bipyrazolyl-4'-carboxylic acid (5-hydroxy-adamantan-2-yl)-amide (103 mg; 0.30 mmol; prepared in Example 9) in acetonitrile (3 mL) and glacial acetic acid (0.10 mL) cooled to 0° C. was added concentrated sulfuric acid (0.10 mL) dropwise. The ice bath was then removed and the mixture allowed to warm to room temperature. After 4 hr. glacial acetic acid (0.5 mL) and concentrated sulfuric acid (0.50 mL) was added and the mixture allowed to stir for 70 hr at room temperature. The reaction mixture was then concentrated under a stream of dry nitrogen to remove the acetonitrile and then ice (15 mL) was added to the reaction mixture. The mixture was allowed to stir for 1 hr. at room temperature. The mixture was then filtered and the white solid was washed several times with saturated sodium bicarbonate solution followed by water and the solid allowed to air dry overnight to give 93 mg of trans-2'-methyl-2'H-[1,3']bipyrazolyl-4'-carboxylic acid (5-hydroxy-adamantan-2-yl)-amide as a white solid. ES-HRMS m/e calcd for $C_{20}H_{26}N_6O_2Na$ (M+Na$^+$) 405.2009, found 405.2007.

Example 46 trans-1-tert-Butyl-5-chloro-1H-pyrazole-4-carboxylic acid (5-acetylamino-adamantan-2-yl)-amide

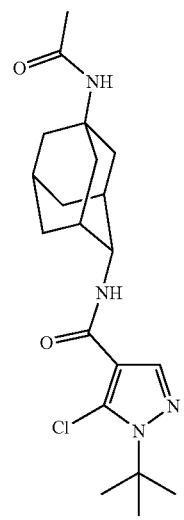

To a solution of 1-tert-butyl-5-chloro-1H-pyrazole-4-carboxylic acid (Intermediate 9; 134 mg; 0.66 mmol) in N,N-dimethylformamide (1.0 mL) was added N,N-diisopropylethylamine (0.63 mL; 3.60 mmol) followed by TSTU (253 mg; 0.84 mmol). After 1 hr., trans-N-(4-amino-adamantan-1-yl)-acetamide (prepared in Example 43; 125 mg; 0.60 mmol) was added and the mixture allowed to stir for 18 hr. at room temperature. The reaction mixture was then concentrated under a stream of dry nitrogen, taken up into ethyl acetate and washed sequentially with 0.5N hydrochloric acid, saturated sodium bicarbonate solution, water and saturated sodium chloride solution. The organic layer was dried (sodium sulfate), filtered and concentrated to give a crude beige solid. The crude product was purified by reverse phase HPLC to provide 104 mg of trans-1-tert-butyl-5-chloro-1H-pyrazole-4-carboxylic acid (5-acetylamino-adamantan-2-yl)-amide as a white solid. ES-HRMS m/e calcd for $C_{20}H_{30}N_4O_2Cl$ (M+H$^+$) 393.2052, found 393.2053.

Example 47 trans-1-tert-Butyl-5-chloro-1H-pyrazole-4-carboxylic acid (5-methanesulfonylamino-adamantan-2-yl)-amide

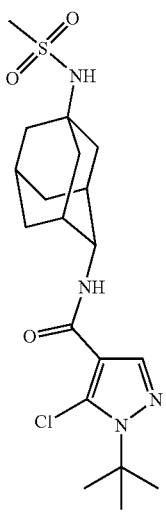

Coupling of 1-tert-butyl-5-chloro-1H-pyrazole-4-carboxylic acid (Intermediate 9; 100 mg; 0.50 mmol) and trans-N-(4-amino-adamantan-1-yl)-methanesulfonamide (Prepared in Example 44; 110 mg; 0.45 mmol) using TSTU according to the procedure described in Example 46 provided after reverse phase HPLC provided 63 mg of trans-1-tert-butyl-5-chloro-1H-pyrazole-4-carboxylic acid (5-methanesulfonylamino-adamantan-2-yl)-amide as a white solid. ES-HRMS m/e calcd for $C_{19}H_{30}N_4O_3ClS$ (M+H$^+$) 429.1722, found 429.1722.

Example 48 trans-1-tert-Butyl-5-trifluoromethyl-1H-pyrazole-4-carboxylic acid (5-acetylamino-adamantan-2-yl)-amide

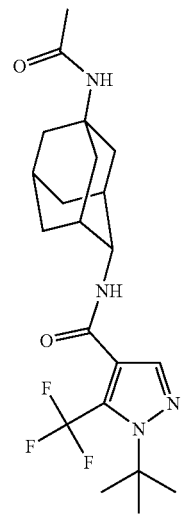

Coupling of 1-tert-butyl-5-trifluoromethyl-1H-pyrazole-4-carboxylic acid (Intermediate 7; 52 mg; 0.26 mmol) and trans-N-(4-amino-adamantan-1-yl)-acetamide (prepared in Example 43; 125 mg; 0.60 mmol) using TSTU according to the procedure described in Example 46 provided after purification by reverse phase HPLC, 43 mg of trans-1-tert-butyl-5-trifluoromethyl-1H-pyrazole-4-carboxylic acid (5-acetylamino-adamantan-2-yl)-amide as a white powder. ES-HRMS m/e calcd for $C_{21}H_{30}N_4O_2F_3$(M+H$^+$) 427.2316, found 427.2314.

Example 49 trans-1-tert-Butyl-5-trifluoromethyl-1H-pyrazole-4-carboxylic acid (5-methanesulfonylamino-adamantan-2-yl)-amide

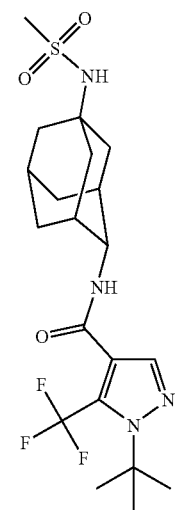

Coupling of 1-tert-butyl-5-trifluoromethyl-1H-pyrazole-4-carboxylic acid (Intermediate 7; 62 mg; 0.22 mmol) and trans-N-(4-amino-adamantan-1-yl)-methanesulfonamide (prepared in Example 44; 61 mg; 0.25 mmol) using TSTU according to the procedure described in Example 46 provided after purification by reverse phase HPLC, 44 mg of trans-1-tert-butyl-5-trifluoromethyl-1H-pyrazole-4-carboxylic acid (5-methanesulfonylamino-adamantan-2-yl)-amide as a white powder. ES-HRMS m/e calcd for $C_{20}H_{30}N_4O_3F_3S$ (M+H$^+$) 463.1985, found 463.1982.

Example 50 trans-2'-tert-Butyl-2'H-[1,3']bipyrazolyl-4'-carboxylic acid (5-acetylamino-adamantan-2-yl)-amide

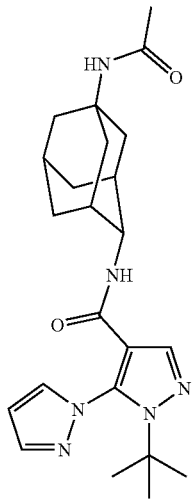

To a stirred suspension of sodium hydride (601 mg; 15.03 mmol) in N,N-dimethylformamide (25.0 mL) under argon at room temperature was added pyrazole (1.255 g; 18.06 mmol). Once the hydrogen evolution ceased, the mixture was warmed to 40° C. in a sealed pressure tube for 1 hr. trans-1-tert-Butyl-5-chloro-1H-pyrazole-4-carboxylic acid (5-acetylamino-adamantan-2-yl)-amide (prepared in Example 46; 589 mg; 1.50 mmol) was added and the resulting mixture heated to 110° C. in the sealed pressure tube for 17 hr. The reaction mixture was then concentrated in vacuo with warming. The residue was suspended in water (50 mL) and acidified to pH=1 with 1N hydrochloric acid and diluted with 100 mL of water. The mixture was then extracted with ethyl acetate. The organic layer was washed with saturated sodium chloride solution, dried over sodium sulfate, filtered and concentrated in vacuo. The residue was triturated with diethyl ether to give 593 mg of trans-2'-tert-butyl-2'H-[1,3']bipyrazolyl-4'-carboxylic acid (5-acetylamino-adamantan-2-yl)-amide as an off white powder. ES-HRMS m/e calcd for $C_{23}H_{33}N_6O_2$ (M+H$^+$) 425.2660, found 425.2660.

Example 51 trans-2'-tert-Butyl-2'H-[1,3']bipyrazolyl-4'-carboxylic acid (5-methanesulfonylamino-adamantan-2-yl)-amide

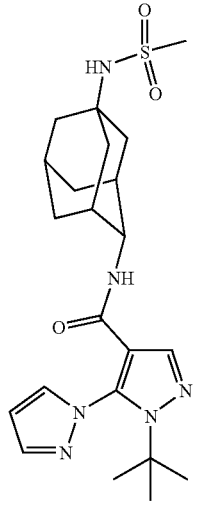

Reaction of trans-1-tert-butyl-5-chloro-1H-pyrazole-4-carboxylic acid (5-methanesulfonylamino-adamantan-2-yl)-amide (prepared in Example 47; 50 mg; 0.12 mmol) with excess pyrazole (102 mg; 1.47 mmol) and sodium hydride (50 mg; 1.24 mmol) using the procedure described in Example 50 and extracting the acidified aqueous mixture with methylene chloride followed by trituration of the crude product with diethyl ether, 51 mg of trans-2'-tert-butyl-2'H-[1,3']bipyrazolyl-4'-carboxylic acid (5-methanesulfonylamino-adamantan-2-yl)-amide as an off-white powder. ES-HRMS m/e calcd for $C_{22}H_{33}N_6O_3S$ (M+H$^+$) 461.2330, found 461.2329.

Example 52 trans-1-Methyl-5-piperidin-1-yl-1H-pyrazole-4-carboxylic acid (5-acetylamino-adamantan-2-yl)-amide

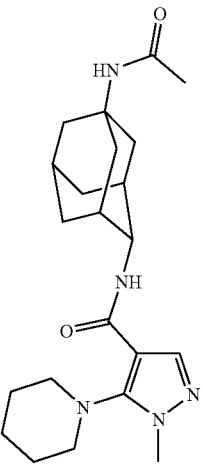

Step 1: trans-5-Chloro-1-methyl-1H-pyrazole-4-carboxylic acid (5-hydroxy-adamantan-2-yl)-amide Coupling of 1-methyl-5-chloro-1H-pyrazole-4-carboxylic acid (CAS# 54367-66-7, purchased from Oakwood; 2.00 g; 12.46 mmol) and trans-4-amino-adamantan-1-ol (Intermediate 2; 2.84 g; 14.00 mmol) using TSTU according to the procedure described in Example 46 provided after trituration of the crude product with diethyl ether, 1.44 g of trans-5-chloro-1-methyl-1H-pyrazole-4-carboxylic acid (5-hydroxy-adamantan-2-yl)-amide as a white solid.

Step 2: trans-1-Methyl-5-piperidin-1-yl-1H-pyrazole-4-carboxylic acid (5-hydroxy-adamantan-2-yl)-amide A mixture of trans-5-chloro-1-methyl-1H-pyrazole-4-carboxylic acid (5-hydroxy-adamantan-2-yl)-amide (500 mg; 1.62 mmol) and piperidine (1.29 mL; 13.0 mmol) in N-methylpyrrolidinone (10 mL) was heated to 250° C. in a sealed pressure tube under microwave irradiation for 3 hr. The mixture was allowed to cool to room temperature and most of the excess piperidine was removed under high vacuo. The resulting solution was purified by reverse phase HPLC to provide 545 mg of trans-1-methyl-5-piperidin-1-yl-1H-pyrazole-4-carboxylic acid (5-hydroxy-adamantan-2-yl)-amide as a white powder.

Step 3: trans-1-Methyl-5-piperidin-1-yl-1H-pyrazole-4-carboxylic acid (5-acetylamino-adamantan-2-yl)-amide To a stirred solution of trans-1-methyl-5-piperidin-1-yl-1H-pyrazole-4-carboxylic acid (5-hydroxy-adamantan-2-yl)-amide (70 mg; 0.20 mmol) in acetonitrile (1.0 mL) and glacial acetic acid (0.20 mL) at room temperature was added concentrated sulfuric acid (0.40 mL) dropwise. After 22 hr., the reaction mixture was neutralized with saturated sodium bicarbonate solution. The mixture was then extracted with ethyl acetate and the extract was dried (sodium sulfate), filtered and concentrated in vacuo. The crude product was purified by reverse phase HPLC to provide 35 mg of trans-1-methyl-5-piperidin-1-yl-1H-pyrazole-4-carboxylic acid (5-acetylamino-adamantan-2-yl)-amide as a white powder. ES-HRMS m/e calcd for $C_{22}H_{34}N_5O_2$ (M+H$^+$) 400.2707, found 400.2708.

Example 53 trans-2'-Methyl-2'H-[1,3']bipyrazolyl-4'-carboxylic acid (5-methanesulfonylamino-adamantan-2-yl)-amide

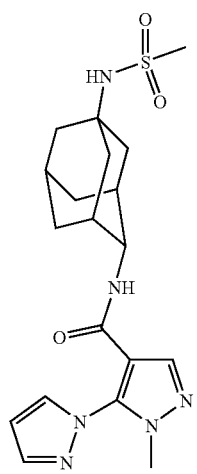

Step 1: trans-5-Chloro-1-methyl-1H-pyrazole-4-carboxylic acid (5-methyl-adamantan-2-yl)-amide Coupling of 1-methyl-5-chloro-1H-pyrazole-4-carboxylic acid (CAS# 54367-66-7, purchased from Oakwood; 80 mg; 0.50 mmol) and trans-N-(4-amino-adamantan-1-yl)-methanesulfonamide (prepared in Example 44; 110 mg; 0.45 mmol) using TSTU according to the procedure described in Example 46 provided after purification of the crude product by reverse phase HPLC, 60 mg of trans-5-chloro-1-methyl-1H-pyrazole-4-carboxylic acid (5-methyl-adamantan-2-yl)-amide as a white solid.

Step 2: trans-2'-Methyl-2'H-[1,3']bipyrazolyl-4'-carboxylic acid (5-methanesulfonylamino-adamantan-2-yl)-amide Reaction of trans-5-chloro-1-methyl-1H-pyrazole-4-carboxylic acid (5-methyl-adamantan-2-yl)-amide (46 mg; 0.12 mmol) with excess pyrazole (71 mg; 1.02 mmol) and sodium hydride (39 mg; 0.97 mmol) using the procedure described in Example 50 and extracting the acidified aqueous mixture with methylene chloride followed by trituration of the crude product with diethyl ether, 43 mg of trans-2'-methyl-2'H-[1,3']bipyrazolyl-4'-carboxylic acid (5-methanesulfonylamino-adamantan-2-yl)-amide as an off-white powder. ES-LRMS m/e calcd for $C_{19}H_{27}N_6O_3S$ (M+H$^+$) 419, found 419.

Example 54 trans-1-tert-Butyl-5-methyl-1H-pyrazole-4-carboxylic acid (5-hydroxy-adamantan-2-yl)-amide

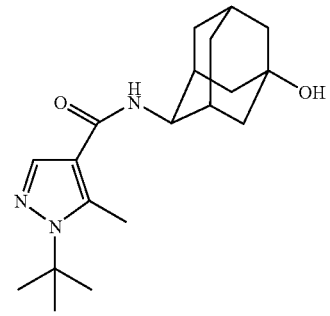

Step 1: 2-dimethylaminomethylene-3-oxo-butyric acid methyl ester

A solution of methyl acetoacetate (5.0 mL, 46.33 mmol) and N,N-dimethylformamide dimethylacetal (6.8 mL, 47.95 mmol) was heated to 80° C. for 2.3 h. At this time, the reaction was cooled to 25° C. and was then concentrated in vacuo to afford 2-dimethylaminomethylene-3-oxo-butyric acid methyl ester (7.43 g, 94%) as a red/black solid. This material was used without further purification.

Step 2: 1-tert-butyl-5-methyl-1H-pyrazole-4-carboxylic acid methyl ester

A solution of 2-dimethylaminomethylene-3-oxo-butyric acid methyl ester (7.43 g, 43.40 mmol) in absolute ethanol (70 mL) was treated with tert-butylhydrazine hydrochloride (5.52 g, 44.29 mmol) and sodium acetate (4.42 g, 53.88 mmol). The resulting mixture was heated to 90° C. for 18 h. At this time, the reaction was cooled to 25° C. The reaction was poured onto ice using dichloromethane to assist the transfer (50 mL). The mixture was transferred to a separatory funnel at which time the layers were shaken and separated. The aqueous layer was further extracted with dichloromethane (1×50 mL). The combined organics were washed with a saturated aqueous sodium bicarbonate solution (1×50 mL), water (1×50 mL) and a saturated aqueous sodium chloride solution (1×50 mL), dried over magnesium sulfate, filtered and concentrated in vacuo. ISCO CombiFlash (120 g column; 0-10% ethyl acetate/hexanes) afforded 1-tert-butyl-5-methyl-1H-pyrazole-4-carboxylic acid methyl ester (6.04 g, 71%) as a yellow oil.

Step 3:
1-tert-butyl-5-methyl-1H-pyrazole-4-carboxylic acid

A solution of 1-tert-butyl-5-methyl-1H-pyrazole-4-carboxylic acid methyl ester (2.0 g, 10.19 mmol) in methanol (6.8 mL) cooled to 0° C. was treated dropwise with a 4N aqueous sodium hydroxide solution (5.1 mL, 20.4 mmol). The reaction was allowed to slowly warm to 25° C. The reaction was stirred at 25° C. overnight. At this time, the reaction was concentrated in vacuo to remove methanol. The residue was diluted with water (25 mL) and was then extracted with ethyl acetate (1×25 mL). The aqueous layer was then acidified to pH=1 with a 3N aqueous hydrochloric acid solution. The resulting precipitate was collected by filtration, washed with water and hexanes, and then dried in vacuo to afford 1-tert-butyl-5-methyl-1H-pyrazole-4-carboxylic acid (1.43 g, 78%) as a white solid.

Step 4: trans-1-tert-butyl-5-methyl-1H-pyrazole-4-carboxylic acid (5-hydroxy-adamantan-2-yl)-amide A solution of 1-tert-butyl-5-methyl-1H-pyrazole-4-carboxylic acid (500 mg, 2.74 mmol), trans-4-amino-adamantan-1-ol hydrochloride (590 mg, 2.89 mmol), 1-hydroxybenzotriazole (450 mg, 3.33 mmol) and O-(benzotriazol-1-yl)-N,N,N',N'-tetramethyluronium hexafluorophosphate (1.25 g, 3.29 mmol) in N,N-dimethylformamide (8.0 mL, 0.34 M) under a nitrogen atmosphere was cooled to 0° C. and was stirred at 0° C. for 35 min. At this time, the reaction was treated dropwise via an additional funnel with N,N-diisopropylethylamine (1.9 mL, 10.90 mmol). The reaction was allowed to gradually warm to 25° C. The reaction was stirred at 25° C. overnight. At this time, the reaction was cooled to 0° C. and was treated dropwise with a 2N aqueous sodium hydroxide solution (4.2 mL, 8.40 mmol). The resulting mixture was allowed to gradually warm to 25° C. over 3 h. At this time, the reaction was treated with dichloromethane (25 mL). The resulting solution was stirred at 25° C. for an additional 1.5 h. At this time, the reaction was partitioned between water (25 mL) and dichloromethane (25 mL). The aqueous layer was further extracted with dichloromethane (1×25 mL). The combined organics were washed with a saturated aqueous sodium chloride solution (1×25 mL), dried over magnesium sulfate, filtered, and concentrated in vacuo. ISCO CombiFlash (40 g column; 50-100% ethyl acetate/hexanes) afforded trans-1-tert-butyl-5-methyl-1H-pyrazole-4-carboxylic acid (5-hydroxy-adamantan-2-yl)-amide (75.3 mg, 8%) as a white solid. ES$^+$-HRMS m/e calcd for $C_{19}H_{29}N_3O_2$ (M+H$^+$) 332.2333, found 332.2333.

In an analogous manner, there were obtained:

From 4-methoxy-3-oxo-butyric acid methyl ester: trans-1-tert-butyl-5-methoxymethyl-1H-pyrazole-4-carboxylic acid (5-hydroxy-adamantan-2-yl)-amide as a light brown solid (494.6 mg, 58.2%). ES$^+$-HRMS m/e calcd for $C_{20}H_{31}N_3O_3$ (M+H$^+$) 362.2438, found 362.2437.

From 4,4,5,5,5-pentafluoro-3-oxo-pentanoic acid methyl ester: trans-1-tert-Butyl-5-pentafluoroethyl-1H-pyrazole-4-carboxylic acid (5-hydroxy-adamantan-2-yl)-amide as a white solid (13.1 mg, 29%). ES$^+$-HRMS m/e calcd for $C_{20}H_{26}F_5N_3O_2$ (M+H$^+$) 436.2018, found 436.2018.

From 5-methoxy-3-oxo-pentanoic acid methyl ester: trans-1-tert-butyl-5-(2-methoxy-ethyl)-1H-pyrazole-4-carboxylic acid (5-hydroxy-adamantan-2-yl)-amide as an off-white solid (389 mg, 47%). ES$^+$-HRMS m/e calcd for $C_{21}H_{33}N_3O_3$ (M+H$^+$) 376.2595, found 376.2595.

From 3-oxo-hexanoic acid methyl ester: trans-1-tert-butyl-5-propyl-1H-pyrazole-4-carboxylic acid (5-hydroxy-adamantan-2-yl)-amide as an off-white solid (698.2 mg, 81.6%). ES$^+$-HRMS m/e calcd for $C_{21}H_{33}N_3O_2$ (M+H$^+$) 360.2646, found 360.2645.

From 3-oxo-pentanoic acid methyl ester: trans-1-tert-butyl-5-ethyl-1H-pyrazole-4-carboxylic acid (5-hydroxy-adamantan-2-yl)-amide as an off-white solid (683.9 mg, 77.9%). ES$^+$-HRMS m/e calcd for $C_{20}H_{31}N_3O_2$ (M+H$^+$) 346.2489, found 346.2490.

From 4-methyl-3-oxo-pentanoic acid methyl ester: trans-1-tert-butyl-5-isopropyl-1H-pyrazole-4-carboxylic acid (5-hydroxy-adamantan-2-yl)-amide as a white solid (94.5 mg, 28%). ES$^+$-HRMS m/e calcd for $C_{21}H_{33}N_3O_2$ (M+H$^+$) 360.2646, found 360.2646.

Example 55 trans-1-tert-Butyl-5-ethoxymethyl-1H-pyrazole-4-carboxylic acid (5-hydroxy-adamantan-2-yl)-amide

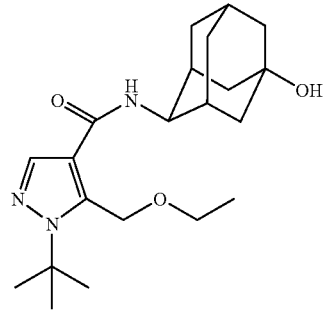

Step 1: 5-bromomethyl-1-tert-butyl-1H-pyrazole-4-carboxylic acid methyl ester

A solution of 1-tert-butyl-5-methyl-1H-pyrazole-4-carboxylic acid methyl ester (3.38 g, 17.22 mmol) (as described in Example 54, Step 2) in carbon tetrachloride (12.2 mL, 1.41M) at 25° C. was treated with N-bromosuccinimide (3.10 g, 17.41 mmol). The reaction flask was fitted with a reflux condenser. The set-up was wrapped with aluminum foil and was then illuminated with a 250 Watt sun lamp for 3 h. At this time, the reaction was filtered and was rinsed with carbon tetrachloride. The filtrate was transferred to a separatory funnel and was washed with water (1×50 mL) and a saturated aqueous sodium chloride solution (1×50 mL). The organics were dried over magnesium sulfate, filtered, rinsed with carbon tetrachloride and concentrated in vacuo to a light yellow oil. ISCO CombiFlash chromatography (120 g, 0-10% ethyl acetate/hexanes) afforded 5-bromomethyl-1-tert-butyl-1H- pyrazole-4-carboxylic acid methyl ester (4.51 g, 95%) as a clear oil. The material was used without further purification.

Step 2: 1-tert-butyl-5-ethoxymethyl-1H-pyrazole-4-carboxylic acid ethyl ester A solution of 5-bromomethyl-1-tert-butyl-1H-pyrazole-4-carboxylic acid methyl ester (220 mg, 0.79 mmol) in ethanol (4.0 mL, 0.2M) was treated with sodium ethoxide (65.4 mg, 0.96 mmol). The reaction mixture was warmed to 90° C. where it was stirred for 2.5 h. At this time, the reaction was concentrated in vacuo. The residue was partitioned between ethyl acetate (75 mL) and water (50 mL). The organics were washed with a saturated aqueous sodium bicarbonate solution (1×50 mL) and a saturated aqueous sodium chloride solution (1×50 mL), dried over magnesium sulfate, filtered and concentrated in vacuo to afford 1-tert-butyl-5-ethoxymethyl-1H-pyrazole-4-carboxylic acid ethyl ester (102.8 mg, 51%) as an orange oil. The material was used without further purification.

Step 3: 1-tert-butyl-5-ethoxymethyl-1H-pyrazole-4-carboxylic acid

A solution of 1-tert-butyl-5-ethoxymethyl-1H-pyrazole-4-carboxylic acid ethyl ester (99.8 mg, 0.39 mmol) in methanol (0.5 mL) and water (0.5 mL) at 25° C. was treated with lithium hydroxide monohydrate (20.2 mg, 0.48 mmol). The reaction mixture was fitted with a reflux condenser and was then heated to 100° C. for 2 h. At this time, the reaction was concentrated in vacuo. The resulting residue was acidified to pH=1 with a 1N aqueous hydrochloric acid solution. A cloudy mixture resulted. The material was brought to a basic pH by treatment with a 1N aqueous sodium hydroxide solution. This solution was extracted with ethyl acetate (1×10 mL). These organics were discarded. The aqueous layer was re-acidified to pH=1 with a 1N aqueous hydrochloric acid solution. This solution was extracted with ethyl acetate (2×10 mL). These organics were dried over magnesium sulfate, filtered and concentrated in vacuo to afford 1-tert-butyl-5-ethoxymethyl-1H-pyrazole-4-carboxylic acid (77.5 mg, 87%) as a yellow solid. The material was used without further purification.

Step 4: trans-1-tert-butyl-5-ethoxymethyl-1H-pyrazole-4-carboxylic acid

A solution of 1-tert-butyl-5-ethoxymethyl-1H-pyrazole-4-carboxylic acid (76.8 mg, 0.33 mmol), trans-4-amino-adamantan-1-ol hydrochloride (71.3 mg, 0.35 mmol), 1-hydroxybenzotriazole (55.8 mg, 0.41 mmol) and O-(benzotriazol-1-yl)-N,N,N',N'-tetramethyluronium hexafluorophosphate (155.1 g, 0.40 mmol) in N,N-dimethylformamide (1.0 mL, 0.34 M) under a nitrogen atmosphere was cooled to 0° C. and was stirred at 0° C. for 35 min. At this time, the reaction was treated dropwise with N,N-diisopropylethylamine (0.23 mL, 1.34 mmol). The reaction was allowed to gradually warm to 25° C. The reaction was stirred at 25° C. overnight. At this time, the reaction was cooled to 0° C. and was treated dropwise with a 2N aqueous sodium hydroxide solution (0.55 mL, 1.1 mmol). The resulting mixture was allowed to gradually warm to 25° C. over 5 h. At this time, the reaction was treated with dichloromethane (5 mL). The resulting solution was stirred at 25° C. for an additional 1.5 h. At this time, the reaction was partitioned between water (25 mL) and dichloromethane (25 mL). The aqueous layer was further extracted with dichloromethane. The combined organics were washed with a saturated aqueous sodium chloride solution (1×25 mL), dried over magnesium sulfate, filtered, and concentrated in vacuo. ISCO CombiFlash (4 g column, 0.5-4% methanol/dichloromethane) afforded trans-1-tert-butyl-5-ethoxymethyl-1H-pyrazole-4-carboxylic acid (5-hydroxy-adamantan-2-yl)-amide (66.2 mg, 52%) as an off-white solid. ES$^+$-HRMS m/e calcd for $C_{21}H_{33}N_3O_3$ (M+H$^+$) 376.2595, found 376.2595.

In an analogous manner, there were obtained:

From 5-bromomethyl-1-tert-butyl-1H-pyrazole-4-carboxylic acid methyl ester and propan-2-ol: trans-1-tert-butyl-5-isopropoxymethyl-1H-pyrazole-4-carboxylic acid (5-hydroxy-adamantan-2-yl)-amide as a white solid (274.7 mg, 68%). ES$^+$-HRMS m/e calcd for $C_{22}H_{35}N_3O_3$ (M+H$^+$) 390.2751, found 390.2751.

From 5-bromomethyl-1-tert-butyl-1H-pyrazole-4-carboxylic acid methyl ester and 2-methyl-propan-1-ol: trans-1-tert-butyl-5-isobutoxymethyl-1H-pyrazole-4-carboxylic acid (5-hydroxy-adamantan-2-yl)-amide as an off-white solid (130.5 mg, 41%). ES$^+$-HRMS m/e calcd for $C_{23}H_{37}N_3O_3$ (M+H$^+$) 404.2908, found 404.2905.

From 5-bromomethyl-1-tert-butyl-1H-pyrazole-4-carboxylic acid methyl ester and cyclopropyl-methanol: trans-1-tert-butyl-5-cyclopropylmethoxymethyl-1H-pyrazole-4-carboxylic acid (5-hydroxy-adamantan-2-yl)-amide as a white solid (153.4 mg, 61%). ES$^+$-HRMS m/e calcd for $C_{23}H_{35}N_3O_3$ (M+H$^+$) 402.2751, found 402.2753.

Example 56 trans-1-tert-Butyl-5-methoxymethyl-1H-pyrazole-4-carboxylic acid (5-acetylamino-adamantan-2-yl)-amide

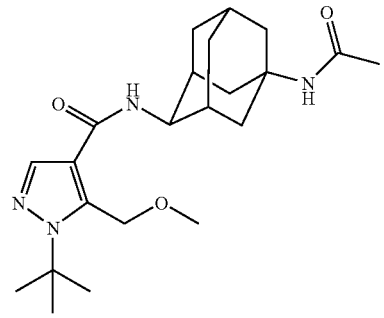

Step 1: 1-tert-butyl-5-methoxymethyl-1H-pyrazole-4-carboxylic acid

A solution of 5-bromomethyl-1-tert-butyl-1H-pyrazole-4-carboxylic acid methyl ester (1.51 g, 5.48 mmol) (as prepared in Example 55, Step 1) in sodium methoxide (23.8 mL, 11.9 mmol, 0.5M solution in methanol) was warmed to 90° C. where it was stirred for 2.5 h. At this time, the reaction was concentrated in vacuo. The resulting white solids were taken up in water (100 mL) and extracted with ethyl acetate (1×150 mL). The organics were then washed with a saturated aqueous sodium bicarbonate solution (1×100 mL), water (1×100 mL) and a saturated aqueous sodium chloride solution (1×100 mL), dried over magnesium sulfate, filtered and concentrated in vacuo. When it was discovered that the product was not in the organic extracts, the aqueous layers were combined and were acidified to pH=1 with concentrated aqueous hydrochloric acid and then were extracted with dichloromethane (1×150 mL). These organics were dried over magnesium sulfate, filtered and concentrated in vacuo to afford 1-tert-butyl-5-methoxymethyl-1H-pyrazole-4-carboxylic acid (1.03 g, 88%) as a white solid. The material was used without further purification.

Step 2: trans-1-tert-butyl-5-methoxymethyl-1H-pyrazole-4-carboxylic acid (5-acetylamino-adamantan-2-yl)-amide A solution of 1-tert-butyl-5-methoxymethyl-1H-pyrazole-4-carboxylic acid (317.9 mg, 1.49 mmol) in dichloromethane (8.5 mL, 0.18 M) was treated with N,N-diisopropylethylamine (1.6 mL, 9.18 mmol) and N,N,N',N'-tetramethyl-O-(N-succinimidyl)uroniumtetrafluoroborate (539.5 mg, 1.79 mmol). The resulting mixture was stirred at 25° C. for 2.6 h. At this time, the reaction was treated with trans-N-(4-amino-adamantan-1-yl)-acetamide hydrochloride (476.8 mg, 1.94 mmol) (as prepared in Example 43). The reaction was stirred at 25° C. overnight. At this time, the reaction was partitioned between water (100 mL) and dichloromethane (100 mL). The aqueous layer was further extracted with dichloromethane (1×100 mL). The combined organics were washed with water (4×100 mL) and a saturated aqueous sodium chloride solution (1×100 mL), dried over magnesium sulfate, filtered, and concentrated in vacuo. ISCO CombiFlash (40 g column, 0.5-5% methanol/dichloromethane) afforded trans-1-tert-butyl-5-methoxymethyl-1H-pyrazole-4-carboxylic acid (5-acetylamino-adamantan-2-yl)-amide (428.7 mg, 71%) as a white solid. ES$^+$-HRMS m/e calcd for $C_{22}H_{34}N_4O_3$ (M+H$^+$) 403.2704, found 403.2706.

Example 57 trans-1-tert-Butyl-5-(5-methyl-isoxazol-3-yl)-1H-pyrazole-4-carboxylic acid (5-acetylamino-adamantan-2-yl)-amide

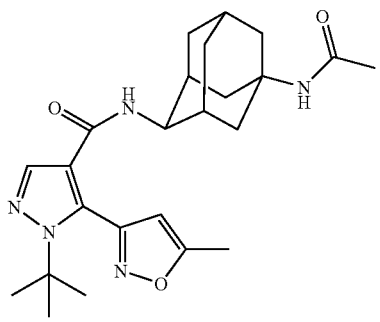

Step 1: 3-dimethylamino-2-(5-methyl-isoxazole-3-carbonyl)-acrylic acid ethyl ester A solution of 5-methyl-isoxazole-3-carboxylic acid (3.5 g, 27.53 mmol) in dichloromethane (27.53 mL, 1.0M) cooled to 0° C. was treated with oxalyl chloride (5.63 mL, 63.33 mmol, 98%) followed by a few drops of N,N-dimethylformamide. The reaction was stirred at 0° C. for 30 min. At this time, it was allowed to gradually warm to 25° C. The reaction was stirred at 25° C. overnight. At this time, the reaction was concentrated in vacuo and then was dried under high vacuum for 1.5 h. The resulting solid was then slurried with toluene (21.2 mL, 1.3M) at 25° C. and then was treated dropwise with a solution of ethyl-(3-dimethylamino)acrylate (3.98 g, 27.81 mmol) in triethylamine (8.02 mL, 57.55 mmol). The resulting black reaction mixture was heated to 120° C. overnight. At this time, the reaction was cooled to 25° C. and then was partitioned between water (150 mL) and dichloromethane (3×100 mL). The combined organics were dried over sodium sulfate, filtered and concentrated in vacuo to afford 3-dimethylamino-2-(5-methyl-isoxazole-3-carbonyl)-acrylic acid ethyl ester (assume quantitative yield, 27.53 mmol) as a black oil. The material was used without further purification.

Step 2: 1-tert-butyl-5-(5-methyl-isoxazol-3-yl)-1H-pyrazole-4-carboxylic acid methyl ester A solution of 3-dimethylamino-2-(5-methyl-isoxazole-3-carbonyl)-acrylic acid ethyl ester (27.53 mmol) in absolute ethanol (41.7 mL) was treated with tert-butylhydrazine hydrochloride (3.57 g, 28.63 mmol) and sodium acetate (2.80 g, 34.13 mmol). The resulting mixture was heated to 90° C. for 18 h. At this time, the reaction was cooled to 25° C. The reaction was diluted with water (200 mL) and was then extracted with dichloromethane (3×150 mL). The combined organics were dried over sodium sulfate, filtered and concentrated in vacuo to afford 1-tert-butyl-5-(5-methyl-isoxazol-3-yl)-1H-pyrazole-4-carboxylic acid methyl ester (7.37 g, 96%) as a black solid. The material was used without further purification.

Step 3: 1-tert-butyl-5-(5-methyl-isoxazol-3-yl)-1H-pyrazole-4-carboxylic acid A solution of 1-tert-butyl-5-(5-methyl-isoxazol-3-yl)-1H-pyrazole-4-carboxylic acid methyl ester (7.37 g, 26.59 mmol) in methanol (17.7 mL, 1.5M) cooled to 0° C. was treated dropwise with a 4N aqueous sodium hydroxide solution (13.3 mL, 53.15 mmol). The reaction was allowed to slowly warm to 25° C. The reaction was stirred at 25° C. over-night. At this time, the reaction was concentrated in vacuo to remove methanol. The residue was diluted with water (150 mL) and was then extracted with dichloromethane (3×150 mL). These organics were discarded. The aqueous layer was then acidified to pH=1 with a 2N aqueous hydrochloric acid solution. This solution was extracted with a 90/10 dichloromethane/methanol solution (3×150 mL). The combined organics were dried over sodium sulfate, filtered and concentrated in vacuo to afford 1-tert-butyl-5-(5-methyl-isoxazol-3-yl)-1H-pyrazole-4-carboxylic acid (5.42 g, 82%) as a brown solid. The material was used without further purification.

Step 4: trans-1-tert-butyl-5-(5-methyl-isoxazol-3-yl)-1H-pyrazole-4-carboxylic acid (5-acetylamino-adamantan-2-yl)-amide A solution of 1-tert-butyl-5-(5-methyl-isoxazol-3-yl)-1H-pyrazole-4-carboxylic acid (350 mg, 1.40 mmol) in dichloromethane (7.8 mL, 0.18 M) was treated with N,N-diisopropylethylamine (1.49 mL, 8.60 mmol) and N,N, N',N'-tetramethyl-O-(N-succinimidyl)uroniumtetrafluoroborate (507.2 mg, 1.68 mmol). The resulting mixture was stirred at 25° C. for 2 h. At this time, the reaction was treated with trans-N-(4-amino-adamantan-1-yl)-acetamide hydrochloride (446.7 mg, 1.82 mmol) (as prepared in Example 43). The reaction was stirred at 25° C. overnight. At this time, the reaction was partitioned between water (150 mL) and dichloromethane (3×100 mL). The combined organics were dried over sodium sulfate, filtered, and concentrated in vacuo.

Biotage chromatography (40M column, 2-4% methanol/dichloromethane) afforded trans-1-tert-butyl-5-(5-methyl-isoxazol-3-yl)-1H-pyrazole-4-carboxylic acid (5-acetylamino-adamantan-2-yl)-amide (330.8 mg, 54%) as an off-white solid. ES$^+$-HRMS m/e calcd for $C_{24}H_{33}N_5O_3$ (M+H$^+$) 440.2656, found 440.2656.

In an analogous manner, there was obtained:

From 1-tert-butyl-5-(5-methyl-isoxazol-3-yl)-1H-pyrazole-4-carboxylic acid and trans-4-amino-adamantan-1-ol: trans-1-tert-butyl-5-(5-methyl-isoxazol-3-yl)-1H-pyrazole-4-carboxylic acid (5-hydroxy-adamantan-2-yl)-amide as an off-white solid (193.4 mg, 60%). ES$^+$-HRMS m/e calcd for $C_{22}H_{30}N_4O_3$ (M+H$^+$) 399.2391, found 399.2387.

Example 58 trans-1-tert-Butyl-5-(5-chloro-isoxazol-3-yl)-1H-pyrazole-4-carboxylic acid (5-hydroxy-adamantan-2-yl)-amide

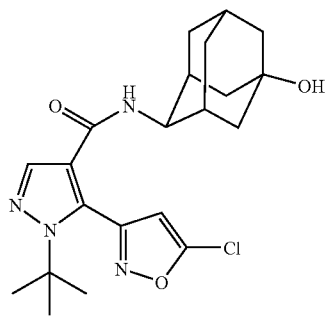

Step 1: 2-(5-chloro-isoxazole-3-carbonyl)-3-dimethylamino-acrylic acid ethyl ester A solution of 5-chloro-isoxazole-3-carboxylic acid (791 mg, 5.43 mmol) (preparation described in WO03093250 A2) in dichloromethane (27.2 mL, 0.2M) cooled to 0° C. was treated with oxalyl chloride (0.71 mL, 8.15 mmol, 98%) followed by a few drops of N,N-dimethylformamide. The reaction was allowed to gradually warm up to 25° C. The reaction was stirred at 25° C. overnight. At this time, the reaction was concentrated in vacuo. The resulting residue was dissolved in dichloromethane and re-concentrated twice to remove residual oxalyl chloride. The residue was then dissolved in dichloromethane (16 mL, 0.34M) and treated dropwise with a solution of ethyl-3-(dimethylamino)acrylate (0.79 g, 5.51 mmol) in triethylamine (1.6 mL, 11.47 mmol). The resulting red/orange reaction solution was heated to 60° C. overnight. At this time, the reaction was cooled to 25° C. and then partitioned between water (50 mL) and dichloromethane (100 mL). The organics were then washed with water (50 mL) and a saturated aqueous sodium chloride solution (50 mL), dried over magnesium sulfate, filtered and concentrated in vacuo. Biotage chromatography (40M column, 50-60% ethyl acetate/hexanes) afforded 2-(5-chloroisoxazole-3-carbonyl)-3-dimethylamino-acrylic acid ethyl ester (300.6 mg, 20%) as a red oil.

Step 2: 1-tert-butyl-5-(5-chloro-isoxazol-3-yl)-1H-pyrazole-4-carboxylic acid ethyl ester A solution of 2-(5-chloro-isoxazole-3-carbonyl)-3-dimethylamino-acrylic acid ethyl ester (294.8 mg, 1.08 mmol) in absolute ethanol (1.4 mL, 0.77M) was treated with tert-butylhydrazine hydrochloride (137.3 mg, 1.10 mmol) and sodium acetate (108.6 mg, 1.32 mmol). The resulting mixture was heated to 90° C. overnight. At this time, the reaction was cooled to 25° C. and was concentrated in vacuo. The reaction was partitioned between water (200 mL) and dichloromethane (2×50 mL). The combined organics were washed with a saturated aqueous sodium chloride solution, dried over magnesium sulfate, filtered and concentrated in vacuo. Biotage chromatography (40S column 60% ethyl acetate/hexanes) followed by ISCO CombiFlash (4 g column 0-20% ethyl acetate/hexanes) afforded 1-tert-butyl-5-(5-chloro-isoxazol-3-yl)-1H-pyrazole-4-carboxylic acid ethyl ester (67.4 g, 21%) as a yellow oil.

Step 3: 1-tert-butyl-5-(5-chloro-isoxazol-3-yl)-1H-pyrazole-4-carboxylic acid

A solution of 1-tert-butyl-5-(5-chloro-isoxazol-3-yl)-1H-pyrazole-4-carboxylic acid ethyl ester (55.3 mg, 0.18 mmol) in absolute ethanol (0.93 mL, 0.2M) was treated with a 2M aqueous lithium hydroxide solution (0.18 mL, 0.37 mmol). The reaction was stirred at 25° C. for 1.5 h and then was heated to 100° C. for 1 h. At this time, the reaction was allowed to cool to 25° C. and was stirred at 25° C. overnight. At this time, the reaction was concentrated in vacuo. The residue was treated with water followed by acidification to pH=1 with a 1N aqueous hydrochloric acid solution. The resulting precipitate that formed was collected by filtration, washed with water and hexanes and dried in vacuo to afford 1-tert-butyl-5-(5-chloro-isoxazol-3-yl)-1H-pyrazole-4-carboxylic acid (38.7 mg, 77%) as an off-white solid.

Step 4: trans-1-tert-butyl-5-(5-chloro-isoxazol-3-yl)-1H-pyrazole-4-carboxylic acid (5-hydroxy-adamantan-2-yl)-amide A solution of 1-tert-butyl-5-(5-chloro-isoxazol-3-yl)-1H-pyrazole-4-carboxylic acid (36.2 mg, 0.13 mmol) in dichloromethane (0.54 mL) and N,N-dimethylformamide (0.13 mL) at 25° C. was treated with N,N-diisopropylethylamine (0.18 mL, 1.03 mmol) and N,N,N',N'-tetramethyl-O-(N-succinimidyl)uroniumtetrafluoroborate (48.3 mg, 0.16 mmol). The resulting mixture was stirred at 25° C. for 6.5 h. At this time, the reaction was treated with trans-4-amino-adamantan-1-ol hydrochloride (Intermediate 2; 35.3 mg, 0.17 mmol). The reaction was stirred at 25° C. overnight. At this time, the reaction was partitioned between water (25 mL) and dichloromethane (3×25 mL). The combined organics were washed with a saturated aqueous sodium chloride solution (1×25 mL), dried over magnesium sulfate, filtered and concentrated in vacuo. ISCO CombiFlash (4 g column, 0-44-100% ethyl acetate/hexanes) afforded trans-1-tert-butyl-5-(5-chloro-isoxazol-3-yl)-1H-pyrazole-4-carboxylic acid (5-hydroxy-adamantan-2-yl)-amide (12.8 mg, 23%) as an off-white solid. ES$^+$-HRMS m/e calcd for $C_{21}H_{27}ClN_4O_3$ (M+H$^+$) 419.1845, found 419.1844.

Example 59 trans-5-Chloro-1-cyclohexyl-1H-pyrazole-4-carboxylic acid (5-hydroxy-adamantan-2-yl)-amide

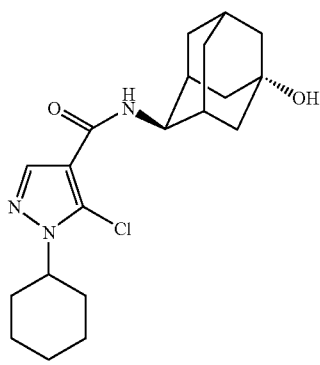

Step 1: 5-Amino-1-cyclohexyl-1H-pyrazole-4-carboxylic acid ethyl ester

Cyclohexylhydrazine hydrochloride (3.057 g, 20.29 mmol, CAS #24214-73-1, purchased from Aldrich) was combined with ethyl (ethoxymethylene)-cyanoacetate (3.390 g, 20.04 mmol) and anhydrous sodium acetate (2.080 g, 25.36 mmol) in 30 mL ethanol. The mixture was heated at 70° C. for 16 hours then cooled to room temperature and concentrated. The residue was partitioned between methylene chloride and water. The separated aqueous phase was extracted with a second portion of methylene chloride. The organic phases were successively washed with water and brine and then combined, dried over sodium sulfate and concentrated in vacuo. The residue was purified by flash chromatography eluting with a gradient of 25-70% ethyl acetate/hexanes to give 5-amino-1-cyclohexyl-1H-pyrazole-4-carboxylic acid ethyl ester (4.42 g, 92%). Mass spectrum: m/z: 238.1 (M+H).

Step 2: 5-Chloro-1-cyclohexyl-1H-pyrazole-4-carboxylic acid ethyl ester

Copper(I) chloride (2.500 g, 25.25 mmol) was suspended in 7.0 mL cold (ice/acetone bath) anhydrous acetonitrile. t-Butyl nitrite (5.75 mL, 90%, 43.56 mmol) was added, followed by a suspension of 5-amino-1-cyclohexyl-1H-pyrazole-4-carboxylic acid ethyl ester (4.408 g, 18.58 mmol) in 27.0 mL acetonitrile. The mixture was stirred at room temperature for 45 minutes and then at 70° C. for 1.25 hour. The mixture was cooled to room temperature, slowly added to 6N HCl (17.5 mL) and then extracted with methylene chloride. The organic phase was washed sequentially with water and brine. The aqueous phases were back extracted with a second portion of methylene chloride. The two organic phases were combined, dried over sodium sulfate and concentrated in vacuo. The crude residue was chromatographed by flash chromatography eluting with a gradient of 10-50% ethyl acetate/hexanes to give 5-chloro-1-cyclohexyl-1H-pyrazole-4-carboxylic acid ethyl ester (1.98 g; 42%). Mass spectrum: m/z: 257.3 (M+H).

Step 3: 5-Chloro-1-cyclohexyl-1H-pyrazole-4-carboxylic acid

5-Chloro-1-cyclohexyl-1H-pyrazole-4-carboxylic acid ethyl ester (1.969 g, 7.67 mmol) was dissolved in methanol (11.5 mL). Lithium hydroxide (0.250 g; 10.44 mmol) and water (11.5 mL) were added. The mixture was heated at 80-85° C. for 1.5 hours, cooled to room temperature and concentrated in vacuo to remove the methanol. The residue was diluted with tetrahydrofuran and concentrated again to ensure complete removal of the methanol. This residue was then diluted with water and acidified with 6N HCl (1.80 mL) to pH 2-2.5. The solid which precipitated out of solution was collected by filtration, washed with water and dried under reduced pressure at 100° C. to give 5-chloro-1-cyclohexyl-1H-pyrazole-4-carboxylic acid (1.676 g, 96%) which was used without further purification. Mass spectrum: m/z: 229.0 (M+H)

Step 4: trans-5-Chloro-1-cyclohexyl-1H-pyrazole-4-carboxylic acid (5-hydroxy-adamantan-2-yl)-amide 5-Chloro-1-cyclohexyl-1H-pyrazole-4-carboxylic acid (0.152 g, 0.66 mmol) was dissolved in a mixture of dry N,N-dimethylformamide (2.6 mL) and dry methylene chloride (0.7 mL). N,N-Diisopropyl-N-ethylamine (0.91 mL, 5.26 mmol) and TSTU (0.238 g, 0.79 mmol) were added to the solution and the solution was stirred under argon for 3.5 hours. At this time, the LC-MS indicated the active ester was formed and trans-4-amino-adamantan-1-ol hydrochloride (0.136 g, 0.67 mmol, Intermediate 2) was added. Stirring continued at room temperature under argon for 44 hours. The reaction mixture was added to water and extracted twice with methylene chloride. The organic phases were combined and washed twice with water and then brine, dried over sodium sulfate and concentrated in vacuo. The crude residue was purified by flash chromatography, eluting with a 60-100% ethyl acetate/hexanes gradient. The product-containing fractions were concentrated in vacuo and the residue was triturated with ethyl acetate-hexanes to yield trans-5-chloro-1-cyclohexyl-1H-pyrazole-4-carboxylic acid (5-hydroxy-adamantan-2-yl)-amide as a white solid (0.179 g, 71%) HR-MS (ES) m/e calculated for $C_{20}H_{28}ClN_3O_2$ (M+H$^+$) 378.1943, Found 378.1943.

Example 60 trans-2'-Cyclohexyl-2'H-[1,3']bipyrazolyl-4'-carboxylic acid (5-hydroxy-adamantan-2-yl)-amide

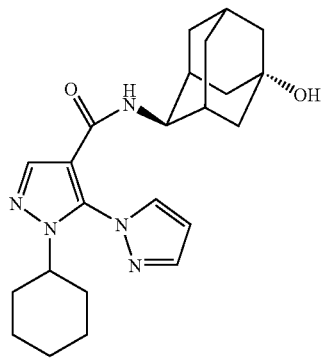

trans-5-Chloro-1-cyclohexyl-1H-pyrazole-4-carboxylic acid (5-hydroxy-adamantan-2-yl)-amide (117 mg, 0.310 mmol, Example 59) and pyrazole (66 mg, 0.969 mmol) were combined in 1-methyl-2-pyrrolidinone (2.1 mL). A 50% aqueous sodium hydroxide (135 mg, 1.688 mmol) was added and the mixture was heated at 120° C. for 10-11 hours. The mixture was cooled in an ice-water bath and water (2.62 mL) and saturated aqueous ammonium chloride solution (2.62 mL) were sequentially added. A clear solution resulted for a brief period of time before the product precipitated out. After stirring in the cold for 1.5 hours, the solid was collected by filtration, washed with water and dried under high vacuum at 100° C. to give trans-2'-cyclohexyl-2'H-[1,3']bipyrazolyl-4'-carboxylic acid (5-hydroxy-adamantan-2-yl)-amide (107.5 mg, 85%). HR-MS(ES) m/e calculated for $C_{23}H_{31}N_5O_2$ (M+H$^+$) 410.2551, Found 410.2550.

Example 61 trans-5-Chloro-1-cyclohexyl-1H-pyrazole-4-carboxylic acid (5-acetylamino-adamantan-2-yl)-amide

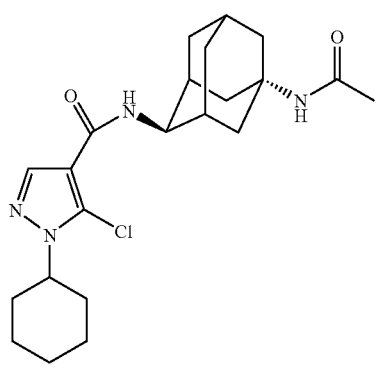

5-Chloro-1-cyclohexyl-1H-pyrazole-4-carboxylic acid (0.213 g, 0.93 mmol, prepared in Example 59, Step 3) was dissolved in a mixture of dry N,N-dimethylformamide (3.6 mL) and dry methylene chloride (0.9 mL). N,N-Diisopropyl-N-ethylamine (1.25 mL, 7.22 mmol) and TSTU (0.334 g, 1.11 mmol) were added and the solution was stirred at room temperature under argon for 3 hours. At this time, the LC-MS indicated the active ester was formed. trans-N-(4-Amino-adamantan-1-yl)acetamide (0.194 g, 0.93 mmol, prepared in Example 43) was added. Stirring continued at room temperature overnight. The reaction mixture was added to water and extracted twice with methylene chloride. Each organic phase was washed with water and brine. The organic phases were combined, dried over sodium sulfate and concentrated in vacuo. The crude residue was purified by flash chromatography eluting with a 0-40% methanol/methylene chloride gradient. The product-containing fractions were concentrated in vacuo. The residue was crystallized with hot ethyl acetate/hexanes and dried under high vacuum at 100° C. to yield trans-5-chloro-1-cyclohexyl-1H-pyrazole-4-carboxylic acid (5-acetylamino-adamantan-2-yl)-amide as a white solid (0.194 g, 50%). HR-MS (ES) m/e calculated for $C_{22}H_{31}ClN_4O_2$ (M+H$^+$) 419.2209, Found 419.2207.

Example 62 trans-2'-Cyclohexyl-2'H-[1,3']bipyrazolyl-4'-carboxylic acid (5-acetylamino-adamantan-2-yl)-amide

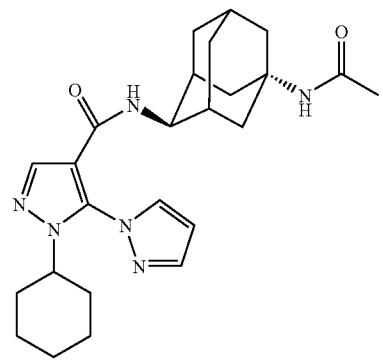

trans-5-Chloro-1-cyclohexyl-1H-pyrazole-4-carboxylic acid (5-acetylamino-adamantan-2-yl)-amide (151.8 mg, 0.362 mmol, Example 61) and pyrazole (77 mg, 1.131 mmol) were combined in 1-methyl-2-pyrrolidinone (2.4 mL). A 50% aqueous sodium hydroxide (158 mg, 1.975 mmol) was added and the mixture was heated at 120° C. for 11 hours. The mixture was cooled in an ice-water bath and water (3.2 mL) and saturated aqueous ammonium chloride (3.2 mL) were added. A clear solution resulted for a brief period of time and then the product precipitated out. The mixture was stirred in the cold for ~2 hours and then the solid was collected by filtration, washed with water and dried under high vacuum at 100° C. to yield trans-2'-cyclohexyl-2'H-[1,3']bipyrazolyl-4'-carboxylic acid (5-acetylamino-adamantan-2-yl)-amide (139.1 mg, 84%). HR-MS (ES) m/e calculated for $C_{25}H_{34}N_6O_2$ (M+H$^+$) 451.2816, Found 451.2816.

Example 63 trans-2'-(Tetrahydro-pyran-4-yl)-2'H-[1,3']bipyrazolyl-4'-carboxylic acid (5-hydroxy-adamantan-2-yl)-amide

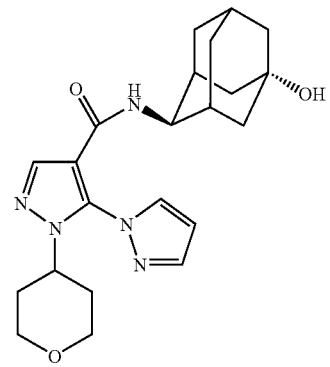

Step 1: N'-(Tetrahydro-pyran-4-ylidene)-hydrazinecarboxylic acid tert-butyl ester Tetrahydro-4H-pyran-4-one (1.002 g, 10.01 mmol, CAS #29943-42-8, purchased from Fluka) was combined with tert-butyl carbazate (1.322 g, 10.00 mmol) in hexanes (10 mL). The mixture was heated in an oil bath at 65-70° C. for 75 minutes. A new precipitate began to precipitate out of solution before the carbazate completely went into solution. The mixture became very thick with the solid precipitate. Diluted with additional hexanes and heated another 15 minutes. The mixture was cooled to room temperature and concentrated in vacuo. Isopropanol was added to the residue and the mixture was stirred vigorously for 5 minutes and then diluted with ether and chilled. The solid was collected by filtration and dried in vacuo to give N'-(tetrahydro-pyran-4-ylidene)-hydrazinecarboxylic acid tert-butyl ester 1.326 g, 62%). A second crop (0.373 g, 17%) was collected from the mother liquor.

Step 2: (Tetrahydro-pyran-4-yl)-hydrazine hydrochloride

N'-(Tetrahydro-pyran-4-ylidene)-hydrazinecarboxylic acid tert-butyl ester (5.210 g, 24.32 mmol) was dissolved in a mixture of dry tetrahydrofuran (22 mL) and dry methanol (30 mL). Sodium cyanoborohydride was added to the solution resulting in effervescence. When the effervescence subsided, the mixture was heated to reflux for 5-10 minutes. After cooling to room temperature 6N HCl (10.5 mL) was slowly added and then the mixture was heated to reflux for 20 minutes. After cooling to room temperature, the solvent was removed in vacuo. The residue was triturated with hot isopropanol and then cooled to room temperature, diluted with ether and chilled. The solid was collected by filtration and was found to be the reduced material but not completely deprotected. The solid was dissolved in the same THF-methanol mixture and treated with 6N HCl (10.5 mL) at reflux for another 1.5 hours. After cooling to room temperature, the reaction mixture was filtered to remove a small amount of insoluble material. The filtrate was then concentrated in vacuo. Isopropanol was added to the residue and solid quickly began to crystallize out of solution. After chilling overnight, ether was added followed by additional chilling. The solid was then collected by filtration, washed with ether and dried in vacuo to give (tetrahydro-pyran-4-yl)-hydrazine hydrochloride (2.22 g, 60%).

Step 3: 5-Amino-1-(tetrahydro-pyran-4-yl)-1H-pyrazole-4-carboxylic acid ethyl ester (Tetrahydro-pyran-4-yl)-hydrazine hydrochloride (1.975 g, 12.94 mmol), ethyl (ethoxymethylene)-cyanoacetate (1.958 g, 11.57 mmol) and sodium acetate (1.370 g; 16.70 mmol) were combined in ethanol (16 mL). The mixture was heated at 80-85° C. for 17 hours. After cooling to room temperature, the reaction was concentrated and the residue was partitioned between methylene chloride and water. The organic phase was separated and washed with water and then brine. Each aqueous phase was back extracted with methylene chloride. The two organic phases were combined, dried over sodium sulfate and concentrated in vacuo. The crude material was purified by flash chromatography eluting with 60-100% ethyl acetate/hexanes to give 5-amino-1-(tetrahydro-pyran-4-yl)-1H-pyrazole-4-carboxylic acid ethyl ester (2.554 g, 92%).

Step 4: 5-Chloro-1-(tetrahydro-pyran-4-yl)-1H-pyrazole-4-carboxylic acid ethyl ester Copper (I) chloride (1.700 g, 17.17 mmol) was suspended in cold (ice-water bath) acetonitrile (5 mL). t-Butyl nitrite (2.35 mL, 90%, 17.80 mmol) was added to the suspension followed by the dropwise addition of a solution of 5-amino-1-(tetrahydro-pyran-4-yl)-1H-pyrazole-4-carboxylic acid ethyl ester (3.157 g, 13.19 mmol) in acetonitrile (19 mL). The cooling bath was removed and the mixture was stirred at room temperature for 1 hour and then at 70° C. for 1 hour. The reaction mixture was cooled to room temperature and added to 6N HCl (12.5 mL). After stirring for 15 minutes the mixture was extracted with methylene chloride. The organic phase was washed sequentially with water and brine. Each aqueous phase was then backwashed with a single portion of methylene chloride. The two organic phases were combined, dried over sodium sulfate and concentrated. Purification by flash chromatography, eluting with a 40-100% EtOAc-hexanes gradient, yielded 5-chloro-1-(tetrahydro-pyran-4-yl)-1H-pyrazole-4-carboxylic acid ethyl ester (2.205 g, 63%). Mass spectrum: m/z: 259.30 (M+H).

Step 5: 5-Chloro-1-(tetrahydro-pyran-4-yl)-1H-pyrazole-4-carboxylic acid

5-Chloro-1-(tetrahydro-pyran-4-yl)-1H-pyrazole-4-carboxylic acid ethyl ester (2.194 g (98%), 8.31 mmol) was dissolved in methanol (12.5 mL). Lithium hydroxide (0.274 g, 11.44 mmol) and water (12.5 mL) were added and the mixture was heated at 80° C. for 1 hour. After cooling to room temperature, the mixture was concentrated to remove the methanol. Tetrahydrofuran was added to the residue and removed in vacuo to ensure complete removal of the methanol. The aqueous residue was treated with 6N HCl (1.88 mL) resulting in the precipitation of a thick milky solid. The solid was collected by filtration, washed with water and dried under high vacuum with heat to give 5-chloro-1-(tetrahydro-pyran-4-yl)-1H-pyrazole-4-carboxylic acid (1.900 g, 99%). Mass spectrum: m/z: 231.30 (M+H).

Step 6: trans-5-Chloro-1-(tetrahydro-pyran-4-yl)-1H-pyrazole-4-carboxylic acid (5-hydroxy-adamantan-2-yl)-amide 5-Chloro-1-(tetrahydro-pyran-4-yl)-1H-pyrazole-4-carboxylic acid (124.5 mg, 0.540 mmol) was dissolved in a mixture of dry N,N-dimethylformamide (2.1 mL) and dry methylene chloride (0.5 mL). N,N-diisopropyl-N-ethylamine (0.75 mL, 4.335 mmol) and TSTU (193.8 mg, 0.644 mmol) were sequentially added to the solution. After 2 hours, the LC-MS indicated the active ester had formed. trans-4-Amino-adamantan-1-ol hydrochloride (113.0 mg, 0.555 mmol, Intermediate 2) was added and the mixture was stirred at room temperature under argon for 45 hours. The reaction mixture was added to water and extracted twice with methylene chloride. The two organic layers were combined and washed twice with water and then once with brine, dried over sodium sulfate and concentrated. Flash chromatography, eluting with a 5-10% methanol-methylene chloride gradient, followed by crystallization from ethyl acetate-hexanes yielded trans-5-chloro-1-(tetrahydro-pyran-4-yl)-1H-pyrazole-4-carboxylic acid (5-hydroxy-adamantan-2-yl)-amide (138 mg (96% pure), 65%). HR-MS (ES) m/e calculated for $C_{19}H_{26}ClN_3O_3$ (M+H$^+$) 380.1736, Found 380.1733.

Step 7: trans-2'-(Tetrahydro-pyran-4-yl)-2'H-[1,3'] bipyrazolyl-4'-carboxylic acid (5-hydroxy-adamantan-2-yl)-amide trans-5-Chloro-1-(tetrahydro-pyran-4-yl)-1H-pyrazole-4-carboxylic acid (5-hydroxy-adamantan-2-yl)-amide (78.3 mg, 96%, 0.198 mmol) was combined with pyrazole (46 mg, 0.676 mmol) and 50% aqueous sodium hydroxide (105.0 mg, 1.313 mmol) in 1-methyl-2-pyrrolidinone. The mixture was heated at 120° C. for 12 hours and then stirred at room temperature for 6 hours. The resulting thick heterogeneous mixture was treated sequentially with water (1.74 mL) and saturated aqueous ammonium chloride (1.74 mL). A clear solution resulted briefly before solid again began to precipitate out of solution. The mixture was stirred in the cold for 2 hours and then filtered, washed with water and dried under high vacuum with heat to give trans-2'-(tetrahydro-pyran-4-yl)-2'H-[1,3']bipyrazolyl-4'-carboxylic acid (5-hydroxy-adamantan-2-yl)-amide (59.3 mg, 73%). HR-MS (ES) m/e calculated for $C_{22}H_{29}N_5O_3$ (M+H$^+$) 412.2343, Found 412.2343.

Example 64 trans-5-Chloro-1-cyclopentyl-1H-pyrazole-4-carboxylic acid (5-hydroxy-adamantan-2-yl)-amide

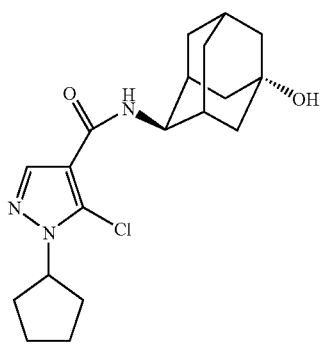

Step 1: N'-Cyclopentyl-hydrazinecarboxylic acid tert-butyl ester

Cyclopentanone (5.000 g, 59.44 mmol; CAS #120-92-3, purchased from Aldrich) was dissolved in hexanes (90 mL). t-Butyl carbazate (7.860 g, 59.47 mmol) was added and the mixture was heated at 65-70° C. for 1 hour. The mixture was cooled and concentrated in vacuo. The residue was taken up in isopropanol (25 mL)-ether (25 mL)-hexanes (50 mL) and chilled. The crystalline material was collected by filtration to give N'-cyclopentyl-hydrazinecarboxylic acid tert-butyl ester (5.51 g; 47%). A second crop (2.62 g, 22%) was collected from the mother liquor.

Step 2: Cyclopentyl-hydrazine hydrochloride

N'-Cyclopentyl-hydrazinecarboxylic acid tert-butyl ester (5.448 g, 27.48 mmol) was dissolved in dry tetrahydrofuran (25 mL) and dry methanol (34 mL). Sodium cyanoborohydride (2.044 g, 32.53 mmol) was added portionwise and then the mixture was refluxed under argon for 10 minutes. After cooling to room temperature, 6N HCl (12 mL) was added and the mixture was refluxed for 1.5 hours. The NMR of an aliquot at this time showed some BOC-protected material to still be present. Additional 6N HCl was added and the mixture was refluxed for another 3 hours and then cooled to room temperature and stirred overnight. The mixture was filtered to remove the insoluble material, concentrated and azeotroped three times with toluene to remove the water. The residue was dissolved in hot isopropanol, cooled to room temperature, diluted with ether and chilled. Filtration yielded cyclopentyl-hydrazine hydrochloride (3.903 g, 103%) which was used without any further purification.

Step 3:
5-Amino-1-cyclopentyl-1H-pyrazole-4-carboxylic acid ethyl ester

Cyclopentyl-hydrazine hydrochloride (1.000 g; 7.32 mmol), ethyl (ethoxymethylene)-cyanoacetate (1.026 g, 6.61 mmol) and anhydrous sodium acetate (0.644 g, 7.85 mmol) were combined in ethanol (10 mL) and heated at 70° C. for 20 hours. After cooling to room temperature, ethanol was removed in vacuo and the residue was partitioned between methylene chloride and water. The organic phase was washed sequentially with water and brine. Each aqueous phase was back extracted with a single portion of methylene chloride. The two organic phases were combined, dried over sodium sulfate and concentrated. Purification by flash chromatography, eluting with 10-40% EtOAc/hexanes yielded 5-amino-1-cyclopentyl-1H-pyrazole-4-carboxylic acid ethyl ester (1.170 g, 73%). Mass spectrum: m/z: 224.1 (M+H).

Step 4:
5-Chloro-1-cyclopentyl-1H-pyrazole-4-carboxylic acid ethyl ester

5-Amino-1-cyclopentyl-1H-pyrazole-4-carboxylic acid ethyl ester (1.164 g, 4.96 mmol) was dissolved in acetonitrile (10.0 mL). Copper (I) chloride (0.722 g, 7.29 mmol) and glacial acetic acid (0.60 mL, 10.48 mmol) were added and the mixture was cooled in an ice-water bath. The first portion of t-butyl nitrite (0.29 mL, 90%, 2.20 mmol) was added. The cooling bath was removed and the mixture was allowed to warm to room temperature. The second portion of t-butyl nitrite (0.58 mL, 4.39 mmol) was added and the mixture was stirred at room temperature for 1 hour. The reaction was quenched with water and diluted with ethyl acetate. After stirring vigorously, the layers were separated. The organic phase was washed with brine, dried over sodium sulfate and concentrated. Purification by flash chromatography, eluting with a 20:80 ethyl acetate-hexane gradient, yielded 5-chloro-1-cyclopentyl-1H-pyrazole-4-carboxylic acid ethyl ester (0.710 g; 61%). Mass spectrum: m/z: 243.1 (M+H).

Step 5:
5-Chloro-1-cyclopentyl-1H-pyrazole-4-carboxylic acid

5-Chloro-1-cyclopentyl-1H-pyrazole-4-carboxylic acid ethyl ester (0.710 g, 2.93 mmol) was dissolved in methanol (4.3 mL). Water (4.3 mL) and lithium hydroxide (0.097 g, 4.05 mmol) were added and the mixture was heated at 80° C. for 2 hours. After cooling to room temperature, methanol was removed in vacuo. Tetrahydrofuran was added to the residue and then removed in vacuo to ensure complete removal of the methanol. The residue was diluted with water and treated with 6N HCl to pH 2-3, resulting in precipitation of a milky solid. The solid was collected, washed with water and dried under house vacuum at 45° C., yielding 5-chloro-1-cyclopentyl-1H-pyrazole-4-carboxylic acid (0.580 g, 91%). This material was used as is without any further purification.

Step 6: trans-5-Chloro-1-cyclopentyl-1H-pyrazole-4-carboxylic acid (5-hydroxy-adamantan-2-yl)-amide 5-Chloro-1-cyclopentyl-1H-pyrazole-4-carboxylic acid (0.225 g, 1.05 mmol) was dissolved in dry N,N-dimethylformamide (4.0 mL) and dry methylene chloride (1.0 mL). N,N-diisopropyl-N-ethylamine (1.45 mL, 8.38 mmol) and TSTU (0.359 g, 1.19 mmol) were sequentially added to the solution and stirring continued at room temperature under argon for 2.5 hours, at which time the reaction to the activated ester was shown to be complete by LC-MS. The trans-4-amino-adamantan-1-ol hydrochloride (0.224 g, 1.10 mmol, Intermediate 2) was added and the mixture was stirred at room temperature under argon overnight. The reaction mixture was added to water and extracted with methylene chloride two times. Each organic phase was washed with water and then brine. The two organic phases were combined, dried over sodium sulfate and concentrated. Purification by flash chromatography (eluting with a 50-100% ethyl acetate-hexanes gradient) followed by crystallization from ethyl acetate-hexanes yielded trans-5-chloro-1-cyclopentyl-1H-pyrazole-4-carboxylic acid (5-hydroxy-adamantan-2-yl)-amide (0.174 g, 46%). HR-MS (ES) m/e calculated for $C_{19}H_{26}ClN_3O_2$ (M+H$^+$) 364.1787, Found 364.1785.

Example 65 trans-2'-Cyclopentyl-2'H-[1,3']bipyrazolyl-4'-carboxylic acid (5-hydroxy-adamantan-2-yl)-amide

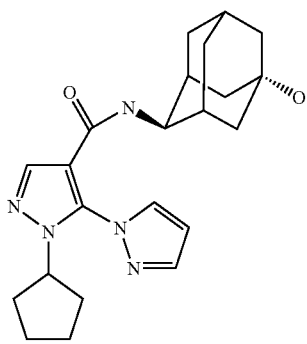

trans-5-Chloro-1-cyclopentyl-1H-pyrazole-4-carboxylic acid (5-hydroxy-adamantan-2-yl)-amide (137 mg, 0.376 mmol, Example 64) was combined with pyrazole (82.8 mg, 1.216 mmol) and 50% aqueous sodium hydroxide (164 mg, 2.050 mmol) in 1-methyl-2-pyrrolidinone (2.5 mL) and heated at 120° C. for 11 hours. The mixture was then cooled to room temperature and stirred for 8 hours. Water (3.0 ml) and saturated aqueous ammonium chloride solution (3.0 mL) were sequentially added. A clear solution was briefly visualized before new solid began to precipitate out of solution. The mixture was stirred in an ice-water bath for 2 hours and then filtered, washed with water and dried under high vacuum at 100° C. to give trans-2'-cyclopentyl-2'H-[1,3']bipyrazolyl-4'-carboxylic acid (5-hydroxy-adamantan-2-yl)-amide (126.5 mg, 84%). HR-MS (ES) m/e calculated for $C_{22}H_{29}N_5O_2$ (M+H$^+$) 418.2213, Found 418.2213

Example 66 trans-2'-Cyclopentyl-2'H-[1,3']bipyrazolyl-4'-carboxylic acid (5-acetylamino-adamantan-2-yl)-amide

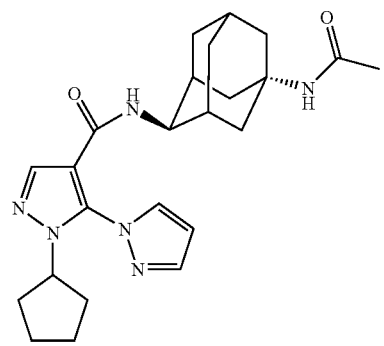

Step 1: trans-5-Chloro-1-cyclopentyl-1H-pyrazole-4-carboxylic acid (5-acetylamino-adamantan-2-yl)-amide 5-Chloro-1-cyclopentyl-1H-pyrazole-4-carboxylic acid (0.334 g, 1.56 mmol, prepared in Example 64, Step 5) was dissolved in dry N,N-dimethylformamide (6.0 mL) and dry methylene chloride (1.5 mL). N,N-diisopropyl-N-ethylamine (2.15 mL, 12.43 mmol) and TSTU (0.563 g, 1.87 mmol) were sequentially added to the solution and stirring continued at room temperature under argon for 3 hours, at which time the reaction to the activated ester was shown to be complete by LC-MS. trans-N-(4-Amino-adamantan-1-yl)-acetamide (0.330 g, 1.58 mmol, prepared in Example 43) was added and the mixture was stirred at room temperature for 22 hours. The reaction mixture was added to water and extracted with methylene chloride two times. The two organic phases were combined, washed twice with water and once with brine, dried over sodium sulfate and concentrated. The crude material was purified by a combination of flash chromatography and crystallization from hot methylene chloride-ether-hexanes yielding trans-5-chloro-1-cyclopentyl-1H-pyrazole-4-carboxylic acid (5-acetylamino-adamantan-2-yl)-amide (0.417 g, 66%). HR-MS (ES) m/e calculated for $C_{21}H_{29}ClN_4O_2$ (M+H$^+$) 405.2052, Found 405.2052.

Step 2: trans-2'-Cyclopentyl-2'H-[1,3']bipyrazolyl-4'-carboxylic acid (5-acetylamino-adamantan-2-yl)-amide trans-5-Chloro-1-cyclopentyl-1H-pyrazole-4-carboxylic acid (5-acetylamino-adamantan-2-yl)-amide (150.0 mg, 0.333 mmol) was combined with pyrazole (69.2 mg, 1.016 mmol) and 50% aqueous sodium hydroxide solution (148 mg, 1.850 mmol) in 1-methyl-2-pyrrolidinone (2.2 mL). The mixture was heated at 120° C. and then cooled to room temperature and stirred for 5 hours. Water (2.8 mL) and saturated aqueous ammonium chloride (2.8 mL) were added to the thick mixture. A clear solution was briefly observed before solid began to precipitate out of solution. The mixture was stirred in the bath for 1.5 hours and then filtered, washed with water and dried under high vacuum at 100° C. The crude solid was recrystallized from methylene chloride-ether-hexanes to give trans-2'-cyclopentyl-2'H-[1,3']bipyrazolyl-4'-carboxylic acid (5-acetylamino-adamantan-2-yl)-amide (103 mg, 71%). HR-MS (ES) m/e calculated for $C_{24}H_{32}N_6O_2$ (M+H$^+$) 437.2660, Found 437.2660.

Example 67 trans-5-Chloro-1-(cis-4-Hydroxy-cyclohexyl)-1H-pyrazole-4-carboxylic acid (5-hydroxy-adamantan-2-yl)-amide

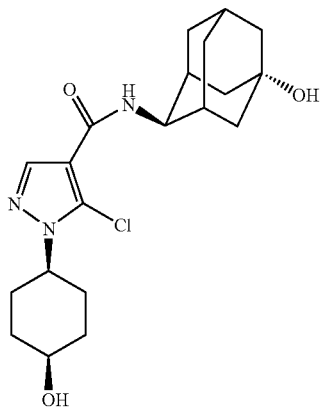

Step 1: N'-[4-(tert-Butyl-dimethyl-silanyloxy)-cyclohexylidene]-hydrazinecarboxylic acid tert-butyl ester tert-Butyldimethylsilyloxy-cyclohexanone (3.146 g, 97%, 13.36 mmol, CAS #55145-45-4, purchased from Aldrich) was dissolved in hexanes (24 mL). tert-Butyl carbazate (1.80 g, 98%, 13.35 mmol) was added and the mixture was heated at 70° C. for 3 hours. Upon cooling to room temperature a white solid precipitated out of solution. The solid was collected by filtration, washed with hexanes and dried to give N'-[4-(tert-butyl-dimethyl-silanyloxy)-cyclohexylidene]-hydrazinecarboxylic acid tert-butyl ester (4.12 g, 90%).

Step 2: 4-Hydrazino-cyclohexanol hydrochloride

N'-[4-(tert-Butyl-dimethyl-silanyloxy)-cyclohexylidene]-hydrazinecarboxylic acid tert-butyl ester (4.103 g, 11.98 mmol) was dissolved in dry tetrahydrofuran (11.5 mL) and dry methanol (15.0 mL). Sodium cyanoborohydride (0.945 g, 14.29 mmol) was added portionwise. When the effervescence subsided the mixture was refluxed for 1.5 hours. At this time a small additional amount of sodium cyanoborohydride (0.047 g, 0.75 mmol) was added and refluxing was continued for another 30 minutes to insure complete reaction. After cooling to room temperature, 6N HCl (10 mL) was added, resulting in precipitation of a white solid. The mixture was heated at 70° C. for 6 hours and then cooled to room temperature and stirred for 12 hours. The reaction mixture was concentrated and azeotroped with toluene to remove nearly all of the water. The residue was then dissolved in hot isopropanol and cooled back down to room temperature. Any insoluble material was removed by filtration. The filtrate was diluted with ether and chilled. The material dropped out of solution as an oil/gum. The mother liquor was removed by decantation. The oil/gum was then washed with ether and dried in vacuo to give 4-hydrazino-cyclohexanol hydrochloride (1.920 g, 96%). A second crop (0.261 g, 13%) was collected from the mother liquor. The yield was greater than theoretical due to the presence of trapped solvent and small impurities. The material was used without any further purification.

Step 3: 5-Amino-1-(4-hydroxy-cyclohexyl)-1H-pyrazole-4-carboxylic acid ethyl ester Hydrazino-cyclohexanol hydrochloride (1.920 g, 9.79 mmol) was dissolved in hot ethanol and then cooled slightly. Ethyl (ethoxymethylene)-cyanoacetate (1.520 g, 8.98 mmol) and anhydrous sodium acetate (2.013 g, 24.54 mmol) were added and the mixture was heated at 70° C. for 15 hours. After cooling to room temperature, the mixture was partitioned between methylene chloride and water. The aqueous phase was washed with a second portion of methylene chloride. The two organic phases were combined, washed with brine, dried over sodium sulfate and concentrated. Flash chromatography, eluting with a 0-20% methanol/ethyl acetate gradient, separated a large portion of the cis-trans mixture of isomers. After chromatography, pure fractions of each isomer were combined and crystallized from EtOAc-hexanes to give 5-amino-1-(cis-4-hydroxy-cyclohexyl)-1H-pyrazole-4-carboxylic acid ethyl ester (0.511 g, 23% (crop 1); 0.121 g, 5% (crop 2)) and 5-amino-1-(trans-4-hydroxy-cyclohexyl)-1H-pyrazole-4-carboxylic acid ethyl ester (0.625 g, 28%).

Step 4: 5-Chloro-1-(cis-4-hydroxy-cyclohexyl)-1H-pyrazole-4-carboxylic acid ethyl ester Copper (I) chloride (126 mg, 1.273 mmol) and t-butyl nitrite (180 µL, 1.364 mmol) were combined in cold (ice-water bath) acetonitrile (2.0 mL). 5-Amino-1-(cis-4-hydroxy-cyclohexyl)-1H-pyrazole-4-carboxylic acid ethyl ester (230 mg, 0.908 mmol) was added portionwise. The cooling bath was removed and the mixture was stirred at room temperature for 30 minutes and then at 70° C. for 30 minutes. After cooling to room temperature, the mixture was treated with 6N HCl (0.9 mL) and extracted with methylene chloride four times. The organic phases were combined, washed with water and brine, dried over sodium sulfate and concentrated in vacuo. Purification by flash chromatography, eluting with 50-100% ethyl acetate/hexanes, gave 5-chloro-1-(cis-4-hydroxy-cyclohexyl)-1H-pyrazole-4-carboxylic acid ethyl ester (137 mg, 55%).

Step 5: 5-Chloro-1-(cis-4-hydroxy-cyclohexyl)-1H-pyrazole-4-carboxylic acid

Chloro-1-(cis-4-hydroxy-cyclohexyl)-1H-pyrazole-4-carboxylic acid ethyl ester (183 mg, 0.631 mmol) was dissolved in methanol (1.2 mL). Lithium hydroxide (20.8 mg, 0.869 mmol) and water (1.2 mL) were added and the mixture was heated at 80° C. for 1 hour. The reaction was concentrated and then concentrated again from tetrahydrofuran to insure complete removal of the methanol. The residue was diluted with water and treated with 6N HCl (160 µL), resulting in precipitation of a solid. The solid was collected by filtration, washed with water and dried under high vacuum at 50° C. to give 5-chloro-1-(cis-4-hydroxy-cyclohexyl)-1H-pyrazole-4-carboxylic acid (140 mg, 91%). Mass spectrum: m/z: 245.0 (M+H).

Step 6: trans-5-Chloro-1-(cis-4-hydroxy-cyclohexyl)-1H-pyrazole-4-carboxylic acid (5-hydroxy-adamantan-2-yl)-amide Chloro-1-(cis-4-hydroxy-cyclohexyl)-1H-pyrazole-4-carboxylic acid (52.4 mg, 0.214 mmol) was dissolved in dry N,N-dimethylformamide (0.8 mL) and dry methylene chloride (0.2 mL). N,N-diisopropyl-N-ethylamine (0.30 mL, 1.734 mmol) and TSTU (73 mg, 0.242 mmol) were sequentially added to the solution and stirring continued at room temperature for 3 hours, at which time the reaction to the activated ester was shown to be complete by LC-MS. trans-4-Amino-adamantan-1-ol hydrochloride (45 mg, 0.221 mmol, Intermediate 2) was added and stirring continued at room temperature, under argon, overnight. The reaction mixture was added to water and extracted two times with methylene chloride. The two organic phases were combined, washed sequentially with water and brine, dried over sodium sulfate and concentrated in vacuo. Purification by flash chromatography (eluting with 0-20% methanol-ethyl acetate), followed by crystallization from hot ethyl acetate-hexanes yielded trans-5-chloro-1-(cis-4-hydroxy-cyclohexyl)-1H-pyrazole-4-carboxylic acid (5-hydroxy-adamantan-2-yl)-amide (42.4 mg, 65%). HR-MS (ES) m/e calculated for $C_{20}H_{28}ClN_3O_3$ (M+H$^+$) 394.1892, Found 394.1894.

Example 68 trans-2'-(cis-4-Hydroxy-cyclohexyl)-2'H-[1,3']bipyrazolyl-4'-carboxylic acid (5-hydroxy-adamantan-2-yl)-amide

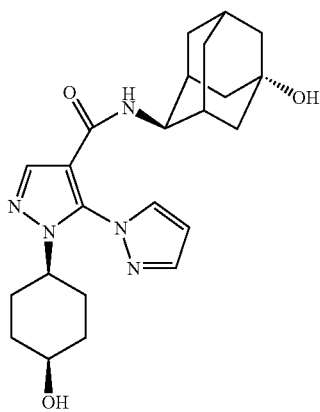

trans-5-Chloro-1-(cis-4-hydroxy-cyclohexyl)-1H-pyrazole-4-carboxylic acid (5-hydroxy-adamantan-2-yl)-amide (143 mg, 97%, 0.352 mmol, Example 67) was combined with pyrazole (75 mg, 1.102 mmol) and 50% aqueous sodium hydroxide (156 mg, 1.950 mmol) in 1-methyl-2-pyrrolidinone (2.4 mL). The mixture was heated at 120° C. for 12 hours and then stirred at room temperature for 5 hours. The mixture was then cooled in an ice-water bath. Water (3.0 mL) and saturated aqueous ammonium chloride (3.0 mL) were sequentially added. The reaction mixture was briefly a clear solution before product precipitated out of solution. After stirring in the cold for 2 hours, the solid was collected by filtration, washed with water and dried under high vacuum at 100° C. to give trans-2'-(cis-4-hydroxy-cyclohexyl)-2'H-[1,3']bipyrazolyl-4'-carboxylic acid (5-hydroxy-adamantan-2-yl)-amide (115 mg, 77%). HR-MS (ES) m/e calculated for $C_{23}H_{31}N_5O_3$ (M+H$^+$) 426.2500, Found 426.2500.

Example 69 trans-1-Cyclopentyl-5-trifluoromethyl-1H-pyrazole-4-carboxylic acid (5-hydroxy-adamantan-2-yl)-amide

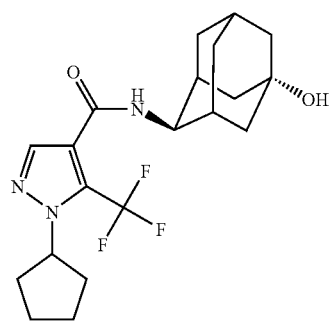

Step 1: 1-Cyclopentyl-5-trifluoromethyl-1H-pyrazole-4-carboxylic acid ethyl ester Cyclopentyl-hydrazine hydrochloride (0.250 g, 1.83 mmol, Example 64, Step 2), 2-dimethylaminomethylene-4,4,4-trifluoro-3-oxo-butyric acid ethyl ester (0.403 g, 1.68 mmol) and anhydrous sodium acetate (0.163 g, 1.99 mmol) were combined in ethanol (2.5 mL) and heated at 70° C. for 17 hours. After cooling to room temperature, the reaction mixture was partitioned between methylene chloride and water. The organic phase was washed with water and brine. Each aqueous phase was back extracted with a second portion of methylene chloride. The two organic phases were combined, dried over sodium sulfate and concentrated in vacuo. Purification by flash chromatography, eluting with a 10-40% ethyl acetate-hexanes gradient, yielded 1-cyclopentyl-5-trifluoromethyl-1H-pyrazole-4-carboxylic acid ethyl ester (0.244 g, 52%). Mass spectrum: m/z: 277.1 (M+H).

Step 2: 1-Cyclopentyl-5-trifluoromethyl-1H-pyrazole-4-carboxylic acid

Cyclopentyl-5-trifluoromethyl-1H-pyrazole-4-carboxylic acid ethyl ester (0.237 g, 0.858 mmol) was dissolved in methanol (2.0 mL). Water (2.0 mL) and lithium hydroxide (0.027 g, 1.127 mmol) were added and the mixture was heated at 80° C. for 2 hours. After cooling to room temperature, the methanol was removed in vacuo. THF was added to the residue and then removed in vacuo to insure complete removal of the methanol. 6N HCl (0.2 mL) was added to the aqueous residue to pH 2-3 resulting in precipitation of a white solid. The solid was collected by filtration, washed with water and dried under high vacuum at 100° C. to give 1-cyclopentyl-5-trifluoromethyl-1H-pyrazole-4-carboxylic acid (0.134 g, 63%).

Step 3: trans-1-Cyclopentyl-5-trifluoromethyl-1H-pyrazole-4-carboxylic acid (5-hydroxy-adamantan-2-yl)-amide Cyclopentyl-5-trifluoromethyl-1H-pyrazole-4-carboxylic acid (125 mg, 0.504 mmol) was dissolved in dry N,N-dimethylformamide (2.0 mL) and dry methylene chloride (0.5 mL). N,N-diisopropyl-N-ethylamine (0.70 mL, 4.046 mmol) and TSTU (181 mg, 0.601 mmole) were sequentially added to the solution and stirring continued at room temperature for 3 hours, at which time the reaction to the activated ester was shown to be complete by LC-MS. trans-4-Amino-adamantan-1-ol hydrochloride (107.8 mg, 0.529 mmol, Intermediate 2) was added and stirring continued at room temperature under argon for 17 hours. The crude reaction mixture was added to water and extracted two times with methylene chloride. Each organic phase was washed sequentially with water and brine. The two organic phases were combined, dried over sodium sulfate and concentrated. Purification by flash chromatography followed by crystallization from ethyl acetate-hexanes yielded trans-1-cyclopentyl-5-trifluoromethyl-1H-pyrazole-4-carboxylic acid (5-hydroxy-adamantan-2-yl)-amide (133 mg, 66%). HR-MS (ES) m/e calculated for $C_{20}H_{26}F_3N_3O_2$ (M+H$^+$) 398.2050, Found 398.2050.

Example 70 trans-1-Cyclohexyl-5-trifluoromethyl-1H-pyrazole-4-carboxylic acid (5-hydroxy-adamantan-2-yl)-amide

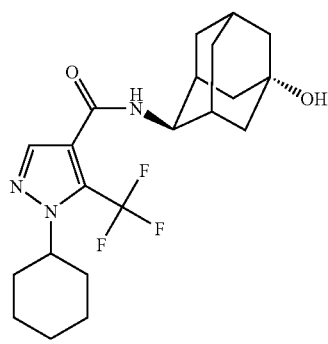

Step 1: 1-Cyclohexyl-5-trifluoromethyl-1H-pyrazole-4-carboxylic acid ethyl ester Cyclohexyl-hydrazine hydrochloride (0.276 g, 1.59 mmol, CAS #24214-73-1, purchased from Aldrich), 2-dimethylaminomethylene-4,4,4-trifluoro-3-oxo-butyric acid ethyl ester (0.459 g, 1.67 mmol) and anhydrous sodium acetate (0.188 g, 2.29 mmol) were combined in ethanol (2.9 mL) and heated at 70° C. for 15 hours. After cooling to room temperature, the reaction mixture was partitioned between methylene chloride and water. The organic phase was washed with water and brine. Each aqueous phase was back extracted with a second portion of methylene chloride. The two organic phases were combined, dried over sodium sulfate and concentrated in vacuo. Purification by flash chromatography, eluting with a 5-40% ethyl acetate-hexanes gradient, yielded 1-cyclohexyl-5-trifluoromethyl-1H-pyrazole-4-carboxylic acid ethyl ester (0.270 g, 55%). Mass spectrum: m/z: 291.3 (M+H).

Step 2: 1-Cyclohexyl-5-trifluoromethyl-1H-pyrazole-4-carboxylic acid

Cyclohexyl-5-trifluoromethyl-1H-pyrazole-4-carboxylic acid ethyl ester (0.265 g, 0.91 mmol) was dissolved in methanol (1.4 mL). Water (1.4 mL) and lithium hydroxide (0.029 g, 1.21 mmol) were added and the mixture was heated at 80° C. for 1.5 hours. After cooling to room temperature, the methanol was removed in vacuo. Tetrahydrofuran was added to the residue and then removed in vacuo to ensure complete removal of the methanol. 6N HCl was added to the aqueous residue to pH 2-3, resulting in precipitation of a solid. The solid was collected by filtration, washed with water and dried under high vacuum at 100° C. to give 1-cyclohexyl-5-trifluoromethyl-1H-pyrazole-4-carboxylic acid (0.206 g, 86%). Mass spectrum: m/z: 263.3 (M+H).

Step 3: trans-1-Cyclohexyl-5-trifluoromethyl-1H-pyrazole-4-carboxylic acid (5-hydroxy-adamantan-2-yl)-amide Cyclohexyl-5-trifluoromethyl-1H-pyrazole-4-carboxylic acid (196 mg, 0.747 mmol) was dissolved in dry N,N-dimethylformamide (2.9 mL) and dry methylene chloride (0.7 mL). N,N-diisopropyl-N-ethylamine (1.00 mL, 5.78 mmol) and TSTU (270 mg, 0.897 mmol) were sequentially added to the solution and stirring continued at room temperature under argon for 3 hours, at which time the reaction to the activated ester was shown to be complete by LC-MS. trans-4-Amino-adamantan-1-ol hydrochloride (160 mg, 0.785 mmol, Intermediate 2) was added and stirring continued at room temperature overnight. The crude reaction mixture was added to water and extracted two times with methylene chloride. Each organic phase was washed sequentially with water and brine. The two organic phases were combined, dried over sodium sulfate and concentrated. Purification by flash chromatography followed by crystallization from ethyl acetate-hexanes yielded trans-1-cyclohexyl-5-trifluoromethyl-1H-pyrazole-4-carboxylic acid (5-hydroxy-adamantan-2-yl)-amide (208 mg, 67%). HR-MS (ES) m/e calculated for $C_{21}H_{28}F_3N_3O_2$ (M+H$^+$) 412.2207, Found 412.2206.

Example 71 trans-1-(cis-4-Hydroxy-cyclohexyl)-5-trifluoromethyl-1H-pyrazole-4-carboxylic acid (5-hydroxy-adamantan-2-yl)-amide

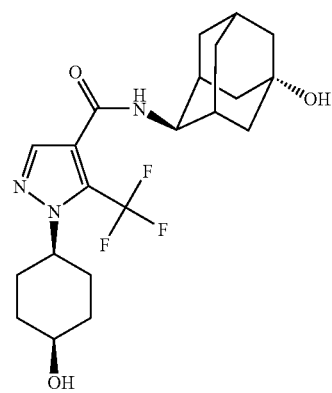

Step 1: 1-(4-Hydroxy-cyclohexyl)-5-trifluoromethyl-1H-pyrazole-4-carboxylic acid ethyl ester 4-Hydrazino-cyclohexanol, hydrochloride (0.255 g, 1.53 mmol, prepared in Example 67, Step 2), 2-dimethylaminomethylene-4,4,4-trifluoro-3-oxo-butyric acid ethyl ester (0.272 g, 1.14 mmol) and anhydrous sodium acetate (0.256 g, 3.12 mmol) were combined in ethanol (2.0 mL) and heated at 70° C. under argon for 14 hours. After cooling to room temperature, the reaction mixture was partitioned between methylene chloride and water. The aqueous phase was washed a second time with methylene chloride. The two organic phases were combined, washed with brine, dried over sodium sulfate and concentrated in vacuo. Purification by flash chromatography (eluting with a 40-100% ethyl acetate-hexanes gradient) successfully separated the cis-trans isomers, yielding cis-1-(4-hydroxy-cyclohexyl)-5-trifluoromethyl-1H-pyrazole-4-carboxylic acid ethyl ester (96.1 mg, 27%) and trans-1-(4-hydroxy-cyclohexyl)-5-trifluoromethyl-1H-pyrazole-4-carboxylic acid ethyl ester (63.5 mg, 18%).

Step 2: cis-1-(4-Hydroxy-cyclohexyl)-5-trifluoromethyl-1H-pyrazole-4-carboxylic acid cis-1-(4-Hydroxy-cyclohexyl)-5-trifluoromethyl-1H-pyrazole-4-carboxylic acid ethyl ester (94.7 mg, 0.309 mmol) was dissolved in methanol (0.5 mL). Lithium hydroxide (10.3 mg, 0.430 mmol) and water (0.5 mL) were added and the mixture was heated at 80° C. for 1 hour. After cooling to room temperature, the methanol was removed in vacuo. Tetrahydrofuran was added and removed in vacuo to insure complete removal of methanol. The residue was diluted with water and acidified with 6N HCl (75 µL; pH 1.5-2). The solid which precipitated out of solution was collected by filtration, washed with water and dried under high vacuum at 50° C. to give cis-1-(4-hydroxy-cyclohexyl)-5-trifluoromethyl-1H-pyrazole-4-carboxylic acid (70 mg; 81%). Mass spectrum: m/z: 279.1 (M+H).

Step 3: trans-1-(cis-4-Hydroxy-cyclohexyl)-5-trifluoromethyl-1H-pyrazole-4-carboxylic acid (5-hydroxy-adamantan-2-yl)-amide cis-1-(4-Hydroxy-cyclohexyl)-5-trifluoromethyl-1H-pyrazole-4-carboxylic acid (67 mg, 0.241 mmol) was dissolved in dry N,N-dimethylformamide (1.0 mL) and dry methylene chloride (0.2 mL). N,N-diisopropyl-N-ethylamine (0.33 mL, 1.907 mmol) and TSTU (82 mg, 0.272 mmol) were sequentially added to the solution and stirring continued at room temperature under argon for 3 hours, at which time the reaction to the activated ester was shown to be complete by LC-MS. trans-4-Amino-adamantan-1-ol hydrochloride (50 mg, 0.245 mmol, Intermediate 2) was added and stirring continued at room temperature under argon overnight. The crude reaction mixture was added to water and extracted two times with methylene chloride. The two organic phases were combined and washed sequentially with water and brine, dried over sodium sulfate and concentrated. Purification by flash chromatography (eluting with a 0-20% methanol-ethyl acetate gradient) followed by crystallization from ethyl acetate-ether yielded trans-1-(cis-4-hydroxy-cyclohexyl)-5-trifluoromethyl-1H-pyrazole-4-carboxylic acid (5-hydroxy-adamantan-2-yl)-amide (44.9 mg, 43%). HR-MS (ES) m/e calculated for $C_{21}H_{28}F_3N_3O_3$ (M+H$^+$) 428.2156, Found 428.2157.

Example 72 trans-1-(trans-4-Hydroxy-cyclohexyl)-5-trifluoromethyl-1H-pyrazole-4-carboxylic acid (5-hydroxy-adamantan-2-yl)-amide

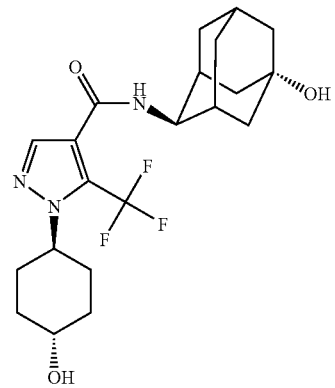

Step 1: trans-1-(4-Hydroxy-cyclohexyl)-5-trifluoromethyl-1H-pyrazole-4-carboxylic acid trans-1-(4-Hydroxy-cyclohexyl)-5-trifluoromethyl-1H-pyrazole-4-carboxylic acid ethyl ester (62.3 mg, 0.203 mmol, prepared in Example 71, Step 1) was dissolved in methanol (0.3 mL). Lithium hydroxide (7.1 mg, 0.297 mmol) and water (0.3 mL) were added and the mixture was heated at 80° C. for 1 hour. After cooling to room temperature, the methanol was removed in vacuo. Tetrahydrofuran was added and removed in vacuo to insure complete removal of methanol. The residue was diluted with water and acidified with 6N HCl. Solid initially precipitated out of solution but quickly went to an oil/gum. The mixture was extracted with methylene chloride two times. The two organic phases were combined, washed with water, dried over sodium sulfate and concentrated to give trans-1-(4-hydroxy-cyclohexyl)-5-trifluoromethyl-1H-pyrazole-4-carboxylic acid (35.8 mg; 63%). Mass spectrum: m/z: 277.1 (M−H).

Step 2: trans-1-(trans-4-Hydroxy-cyclohexyl)-5-trifluoromethyl-1H-pyrazole-4-carboxylic acid (5-hydroxy-adamantan-2-yl)-amide trans-1-(4-Hydroxy-cyclohexyl)-5-trifluoromethyl-1H-pyrazole-4-carboxylic acid (31.6 mg, 0.114 mmol) was dissolved in dry N,N-dimethylformamide (0.5 mL) and dry methylene chloride (0.1 mL). N,N-diisopropyl-N-ethylamine (155 µL, 0.896 mmol) and TSTU (39 mg, 0.130 mmol) were sequentially added to the solution and stirring continued at room temperature under argon for 5 hours. trans-4-Amino-adamantan-1-ol hydrochloride (24 mg, 0.118 mmol, Intermediate 2) was added and stirring continued at room temperature under argon for 23 hours. The crude reaction mixture was added to water and extracted two times with methylene chloride. The two organic phases were combined and washed sequentially with water (3×) and brine, dried over sodium sulfate and concentrated. Purification by flash chromatography, eluting with a 0-20% methanol-ethyl acetate gradient, followed by crystallization from ethyl acetate-ether yielded trans-1-(trans-4-hydroxy-cyclohexyl)-5-trifluoromethyl-1H-pyrazole-4-carboxylic acid (5-hydroxy-adamantan-2-yl)-amide (30.4 mg, 63%). HR-MS (ES) m/e calculated for $C_{21}H_{28}F_3N_3O_3$ (M+H$^+$) 428.2156, Found 428.2156.

Example 73 trans-2'-(2-Methoxyethyl)-2'H-[1,3']bipyrazolyl-4'-carboxylic acid (5-hydroxy-adamantan-2-yl-amide

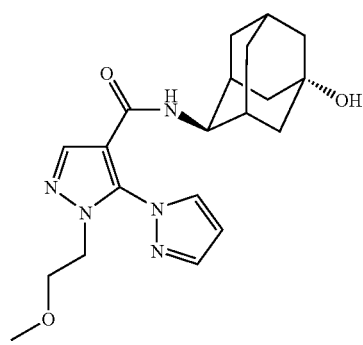

Step 1: Preparation of (2-methoxyethyl)-hydrazine

To a solution of hydrazine monohydrate (22 mL, 453.5 mmol) in ethanol (7 mL) at 0° C. in an ice-water bath was added 1-bromo-2-methoxy ethane (4.0 mL, 42.44 mmol) drop-wise over 20 minutes. The reaction was then allowed to warm to room temperature and stir for 40 minutes and then heated to 45° C. in a preheated oil bath for 12 hours. The reaction was then cooled to room temperature and concentrated to remove the ethanol. The remaining aqueous layer was extracted with methylene chloride (2×100 mL) and diethyl ether (2×100 mL). The organic layers were combined and dried over anhydrous $Na_2SO_4$, filtered and concentrated to provide (2-methoxyethyl)-hydrazine as colorless oil (2.35 g, 61%).

Step 2: Preparation of 5-amino-1-(2-methoxyethyl)-1H-pyrazole-4-carboxylic acid ethyl ester To a solution of (2-methoxyethyl)-hydrazine (2.35 g, 26.07 mmol) in ethanol (40 mL) was added ethyl(ethoxymethylene) cyano acetate (4.40 g, 26.48 mmol). The solution was heated to reflux in a preheated oil bath (90° C.) for 3 h. The reaction was cooled to room temperature and concentrated to remove the ethanol. The residue was dissolved in methylene chloride (~100 mL) and washed with water (10 mL) and brine (10 mL). The organic layer was dried over anhydrous $Na_2SO_4$, filtered and concentrated in vacuo to provide 5-amino-1-(2-methoxyethyl)-1H-pyrazole-4 carboxylic acid ethyl ester (5.3 g, 95%) as a orange oil, which was used without further purification. Mass spectrum: m/z: 214.0 (M+1).

Step 3: Preparation of 5-chloro-1-(2-methoxyethyl)-1H-pyrazole-4-carboxylic acid ethyl ester To a mixture of t-butyl nitrite (5.3 mL, 40.10 mmol), anhydrous cuprous chloride (4.10 g, 41.41 mmol) and anhydrous acetonitrile (100 mL) was added 5-amino-1-(2-methoxyethyl)-1H-pyrazole-4-carboxylic acid ethyl ester (17.8 g, 83.4 mmol) over 10 minutes at 0° C. The reaction mixture was stirred at room temperature for 1 h, then at 60° C. for 2 h and then stirred at room temperature overnight. The mixture was then cooled to room temperature and poured carefully into 6.0 N aqueous HCL (100 mL). The aqueous phase was extracted with methylene chloride (3×300 mL). The combined organic extracts were combined, dried over anhydrous $Na_2SO_4$, filtered and concentrated in vacuo to provide 5-chloro-1-(2-methoxyethyl)-1H-pyrazole-4-carboxylic acid ethyl ester as a orange oil (4.6 g, 80%), which was used without further purification. Mass spectrum: m/z: 233.0 (M+1).

Step 4: Preparation of 5-chloro-1-(2-methoxyethyl)-1H-pyrazole-4-carboxylic acid To a solution of 5-chloro-1-(2-methoxyethyl)-1H-pyrazole-4-carboxylic acid ethyl ester (4.60 g, 19.77 mmol) in methanol (32 mL) and water (32 mL) was added lithium hydroxide (1.10 g, 26.22 mmol). The reaction mixture was stirred at reflux for 3 h, and then the solution was concentrated under reduced pressure to remove the methanol. The residue was then acidified carefully with 6.0 N aqueous HCl. The resulting mixture was extracted with methylene chloride (3×50 mL). The combined organic extracts were dried over anhydrous $Na_2SO_4$, filtered and concentrated in vacuo to provide 5-chloro-1-(2-methoxyethyl)-1H-pyrazole-4-carboxylic acid as a white solid (1.27 g, 31%). Mass spectrum: m/z: 205.3 (M+1).

Step 5: Preparation of trans-5-chloro-1-(2-methoxyethyl)-1H-pyrazole-4-carboxylic acid (5-hydroxy-adamantan-2-yl)-amide 5-Chloro-1-(2-methoxyethyl)-1H-pyrazole-4-carboxylic acid (1.270 g, 6.207 mmol) was dissolved in a mixture of dry methylene chloride (5 mL) and dry N,N-dimethylformamide (6 mL). To the solution was added diisopropylethylamine (9.0 mL, 51.67 mmol) and O-(N-succinimidyl)-1,1,3,3-tetramethyluronium tetrafluoroborate (2.30 g, 7.64 mmol). The solution was allowed to stir at room temperature for 4 h after which an aliquot was analyzed by LC-MS, showing complete conversion to the activated ester. Then trans-4-amino-adamantan-1-ol hydrochloric acid (prepared in Intermediate 2, 1.30 g, 6.382 mmol) was added. The solution was allowed to stir for 24 h, after which the reaction was quenched with water (20 mL). The aqueous layer was extracted with methylene chloride (2×50 mL). The organic extracts were combined, dried over anhydrous $Na_2SO_4$, filtered and concentrated in vacuo to provide the crude material. The crude material was purified by column chromatography on silica gel (eluting with a gradient of ethyl acetate to 10% methanol/ethyl acetate) providing trans-5-chloro-1-(2-methoxyethyl)-1H-pyrazole-4-carboxylic acid (5-hydroxy-adamantan-2-yl)-amide as an off-white solid (0.756 g, 34.5%). ES-HRMS m/e calcd for $C_{17}H_{24}ClN_3O_3$ (M+H$^+$) 353.1579, found 353.1576.

Step 6: Preparation of trans-2'-(2-methoxyethyl)-2'H-[1,3']bipyrazolyl-4'-carboxylic acid (5-acetylamino-adamantan-2-yl-amide To a solution of 5-chloro-1-(2-methoxyethyl)-1H-pyrazole-4-carboxylic acid (5-hydroxy-adamantan-2-yl)-amide (0.177 g, 0.500 mmol) and pyrazole (0.280 g, 4.113 mmol) in dry N,N-dimethylformamide (26 mL) was added 60% sodium hydride (0.160 g, 4 mmol). The solution was heated to 120° C. in a preheated oil bath for 20 h. The solution was cooled to room temperature and quenched with water (1 mL) and aqueous NH$_4$Cl (1 mL). Since no precipitation occurred, the aqueous phase was extracted with methylene chloride (2×50 mL). The organic extracts were combined, dried over anhydrous Na$_2$SO$_4$, filtered and concentrated in vacuo with heating (~100° C.) to remove excess N,N-dimethylformamide. The product was purified by column chromatography on silica gel (eluting with 5% methanol/methylene chloride) to provide trans-2'-(2-methoxyethyl)-2'H-[1,3']bipyrazolyl-4'-carboxylic acid (5-hydroxy-adamantan-2-yl-amide as a white solid (0.125 g, 65%). ES-HRMS m/e calcd for C$_{20}$H$_{27}$N$_5$O$_3$ (M+H$^+$) 408.2006, found 408.2003.

Example 74 trans-1-(2-Methoxyethyl)-5-trifluoromethyl-1H-pyrazole-4-carboxylic acid (5-hydroxy-adamantan-2-yl)-amide

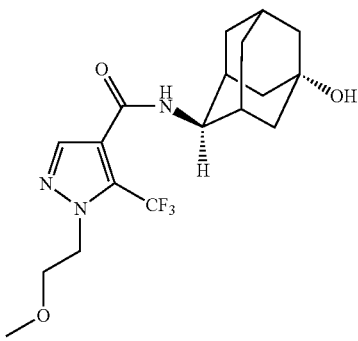

Step 1: Preparation of (2-methoxyethyl)-hydrazine

To a solution of hydrazine monohydrate (22 mL, 453.5 mmol) in ethanol (7 mL) at 0° C. in an ice-water bath was added 1-bromo-2-methoxy ethane (4.0 mL, 42.44 mmol) drop-wise over 20 minutes. The reaction was then allowed to warm to room temperature and stir for 40 minutes and then heated to 45° C. in a preheated oil bath for 12 hours. The reaction was then cooled to room temperature and concentrated to remove the ethanol. The remaining aqueous layer was extracted with methylene chloride (2×100 mL) and diethyl ether (2×100 mL). The organic layers were combined and dried over anhydrous Na$_2$SO$_4$, filtered and concentrated to provide (2-methoxyethyl)-hydrazine as colorless oil (2.35 g, 61%).

Step 2: Preparation of 1-(2-methoxyethyl)-5-trifluoromethyl-1H-pyrazole-4-carboxylic acid ethyl ester To a solution of (2-methoxyethyl)-hydrazine (0.104, 1.15 mmol) in ethanol (2 mL) was added ethyl 3-N,N-dimethylamino-2-trifluoroacetylacrylate (Intermediate 4, 0.261 mg, 1.09 mmol). The resultant solution was micro waved at 160° C. for 0.5 h. The reaction was cooled to room temperature and concentrated to remove the ethanol. The residue was dissolved in methylene chloride (50 mL) and washed with water (20 mL) and brine (10 mL). The organic layer was dried over anhydrous Na$_2$SO$_4$, filtered and concentrated in vacuo to provide 1-(2-methoxyethyl)-5-trifluoromethyl-1H-pyrazole-4-carboxylic acid ethyl ester (296.1 mg, 99%) as an brown oil, which was used without further purification.

Step 3: Preparation of 1-(2-methoxyethyl)-5-trifluoromethyl-1H-pyrazole-4-carboxylic acid To a solution of 1-(2-methoxyethyl)-5-trifluoromethyl-1H-pyrazole-4-carboxylic acid ethyl ester (0.291 g, 1.09 mmol) in methanol (3 mL) and water (3 mL) was added lithium hydroxide (0.072 g, 1.73 mmol). The reaction mixture was stirred at reflux for 2 h, and then the solution was concentrated under reduced pressure to remove the methanol. The residue was then acidified carefully with 6.0 N aqueous HCl. The resulting mixture was extracted with methylene chloride (3×25 mL). The combined organic extracts were dried over anhydrous MgSO$_4$, filtered and concentrated in vacuo to provide 1-(2-methoxyethyl)-5-trifluoromethyl-1H-pyrazole-4-carboxylic acid as a orange oil (0.183 g, 71%), which was used without further purification. Mass spectrum: m/z: 239.0 (M+1).

Step 4: Preparation of trans-1-(2-Methoxyethyl)-5-trifluoromethyl-1H-pyrazole-4-carboxylic acid (5-hydroxy-adamantan-2-yl)-amide 1-(2-Methoxyethyl)-5-trifluoromethyl-1H-pyrazole-4-carboxylic acid (0.180 g, 0.756 mmol) was dissolved in a mixture of dry methylene chloride (4 mL) and dry N,N-dimethylformamide (1 mL). To the solution was added diisopropylethylamine (1.1 mL, 6.31 mmol) and O-(N-succinimidyl)-1,1,3,3-tetramethyluronium tetrafluoroborate (0.280 g, 0.93 mmol). The solution was allowed to stir at room temperature for 3 h after which an aliquot was analyzed by LC-MS, showing complete conversion to the activated ester. Then trans-4-amino-adamantan-1-ol hydrochloric acid (Intermediate 2, 0.160 g, 0.785 mmol) was added. The solution was allowed to stir for 24 h, after which the reaction was quenched with water (20 mL). The aqueous layer was extracted with methylene chloride (2×50 mL). The organic extracts were combined and washed with water (2×20 mL) and brine (20 mL), dried over anhydrous MgSO$_4$, filtered and concentrated in vacuo to provide the crude material as an orange oil. The crude material was purified by column chromatography on silica gel (eluting with a gradient of methylene chloride to 5% to 10% methanol/ethyl acetate) providing trans-1-(2-methoxyethyl)-5-trifluoromethyl-1H-pyrazole-4-carboxylic acid (5-hydroxy-adamantan-2-yl)-amide as a white solid. (0.073 g, 25%). ES-HRMS m/e calcd for C$_{18}$H$_{24}$F$_3$N$_3$O$_3$ (M+H$^+$) 410.1662, found 410.1662.

Example 75 trans-2'-(2-Methoxyethyl)-2'H-[1,3']bipyrazolyl-4'-carboxylic acid (5-acetylamino-adamantan-2-yl-amide

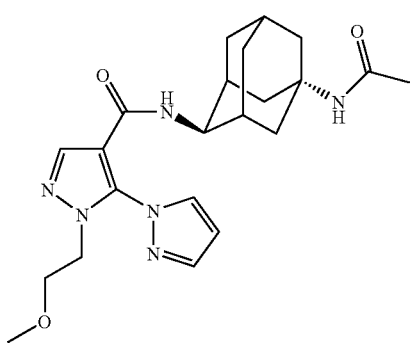

Step 1: (2-Methoxyethyl)-hydrazine

To a solution of hydrazine monohydrate (89.4 mL, 8.00 mol) in ethanol (120 mL) at 0° C. in an ice-water bath was added 1-bromo-2-methoxy ethane (18.8 mL, 0.20 mol) dropwise over 20 minutes. The reaction was then allowed to warm to room temperature and stir for 40 minutes and then heated to 45° C. in a preheated oil bath for 12 hours. The reaction was then cooled to room temperature and concentrated to remove the ethanol. The remaining aqueous layer was extracted with methylene chloride (2×100 mL) and diethyl ether (2×100 mL). The organic layers were combined and dried over anhydrous $Na_2SO_4$, filtered and concentrated to provide (2-methoxyethyl)-hydrazine as a colorless oil (8.0 g, 50%).

Step 2: 5-Amino-1-(2-methoxyethyl)-1H-pyrazole-4-carboxylic acid ethyl ester To a solution of (2-methoxyethyl)-hydrazine (9.0 g, 99.9 mmol) in ethanol (170 mL) was added ethyl(ethoxymethylene)cyano acetate (14.36 g, 84.9 mmol). The solution was heated to reflux in a preheated oil bath (90° C.) for 24 h. The reaction was cooled to room temperature and concentrated to remove the ethanol. The residue was dissolved in methylene chloride (~100 mL) and washed with water (10 mL) and brine (10 mL). The organic layer was dried over anhydrous $Na_2SO_4$, filtered and concentrated in vacuo to provide 5-amino-1-(2-methoxyethyl)-1H-pyrazole-4 carboxylic acid ethyl ester (17.8 g, 98%) as a red oil, which was used without further purification. Mass spectrum: m/z: 214.0 (M+1).

Step 3: 5-Chloro-1-(2-methoxyethyl)-1H-pyrazole-4-carboxylic acid ethyl ester To a mixture of t-butyl nitrite (17.6 mL, 133.4 mmol), anhydrous cuprous chloride (13.55 g, 136.9 mmol) and anhydrous acetonitrile (160 mL) was added 5-amino-1-(2-methoxyethyl)-1H-pyrazole-4-carboxylic acid ethyl ester (17.8 g, 83.4 mmol) over 10 minutes at 0° C. The reaction mixture was stirred at room temperature for 1 h, then at 70° C. for 2 h. The mixture was then cooled to room temperature and poured carefully into 6.0 N aqueous HCL (85 mL). The aqueous phase was extracted with methylene chloride (3×150 mL). The combined organic extracts were combined, dried over anhydrous $Na_2SO_4$, filtered and concentrated in vacuo to provide the crude material as a green oil. The product was purified by column chromatography on silica gel (eluting with ethyl acetate/hexanes, using a gradient of 3:7 to 1:0) to provide 5-chloro-1-(2-methoxyethyl)-1H-pyrazole-4-carboxylic acid ethyl ester as a light yellow oil (8.51 g, 44%). Mass spectrum: m/z: 233.0 (M+1).

Step 4: 5-Chloro-1-(2-methoxyethyl)-1H-pyrazole-4-carboxylic acid

To a solution of 5-chloro-1-(2-methoxyethyl)-1H-pyrazole-4-carboxylic acid ethyl ester (8.51 g, 36.6 mmol) in methanol (37 mL) and water (37 mL) was added lithium hydroxide (1.21 g, 50.4 mmol). The reaction mixture was stirred at reflux for 3 h, and then the solution was concentrated under reduced pressure to remove the methanol. The residue was then acidified carefully with 6.0 N aqueous HCl. The resulting mixture was extracted with methylene chloride (3×50 mL). The combined organic extracts were dried over anhydrous $Na_2SO_4$, filtered and concentrated in vacuo to provide 5-chloro-1-(2-methoxyethyl)-1H-pyrazole-4-carboxylic acid as a white solid (6.93 g, 92%). Mass spectrum: m/z: 205.3 (M+1).

Step 5: trans-5-Chloro-1-(2-methoxyethyl)-1H-pyrazole-4-carboxylic acid (5-acetylamino-adamantan-2-yl)-amide 5-Chloro-1-(2-methoxyethyl)-1H-pyrazole-4-carboxylic acid (178 mg, 0.870 mmol) was dissolved in a mixture of dry methylene chloride (1 mL) and dry N,N-dimethylformamide (3.5 mL). To the solution was added N,N-diisopropylethylamine (1.21 mL, 7.00 mmol) and O-(N-succinimidyl)-1,1,3,3-tetramethyluronium tetrafluoroborate (289 mg, 0.960 mmol). The solution was allowed to stir at room temperature for 4 h after which an aliquot was analyzed by LC-MS, showing complete conversion to the activated ester. Then trans-N-(4-amino-adamantan-1-yl)-acetamide (prepared in Example 43, 200 mg, 0.960 mmol) was added. The solution was allowed to stir for 24 h, after which the reaction was quenched with water (20 mL). The aqueous layer was extracted with methylene chloride (2×50 mL). The organic extracts were combined, dried over anhydrous $Na_2SO_4$, filtered and concentrated in vacuo to provide the crude material. The crude material was purified by column chromatography on silica gel (eluting with a gradient of methylene chloride to 4% methanol/methylene chloride) providing trans-5-chloro-1-(2-methoxyethyl)-1H-pyrazole-4-carboxylic acid (5-acetylamino-adamantan-2-yl)-amide as an off-white solid (174 mg, 50%). ES-HRMS m/e calcd for $C_{19}H_{27}ClN_4O_3$ (M+H$^+$) 395.1842, found 395.1845.

Step 6: trans-2'-(2-Methoxyethyl)-2'H-[1,3']bipyrazolyl-4'-carboxylic acid (5-acetylamino-adamantan-2-yl-amide To a solution of trans-5-chloro-1-(2-methoxyethyl)-1H-pyrazole-4-carboxylic acid (5-acetylamino-adamantan-2-yl)-amide (116 mg, 0.300 mmol) and pyrazole (61 mg, 0.90 mmol) in N-methylpyrolidinone (1.5 mL) was added aqueous sodium hydroxide (0.100 mL, 1.20 mmol, 50% w/w). The solution was heated to 120° C. in a preheated oil bath for 12 h. The solution was cooled to room temperature and quenched with water (1 mL) and aqueous NH$_4$Cl (1 mL). Since no precipitation occurred, the aqueous phase was extracted with methylene chloride (2×50 mL). The organic extracts were combined, dried over anhydrous $Na_2SO_4$, filtered and concentrated in vacuo with heating (~100° C.) to remove excess NMP. The product was purified by column chromatography on silica gel (eluting with 5% methanol/methylene chloride) to provide trans-2'-(2-methoxyethyl)-2'H-[1,3']bipyrazolyl-4'-carboxylic acid (5-acetylamino-adamantan-2-yl-amide as a white solid (77 mg, 60%). In some instances the residual NMP was removed via heating to 100° C. under high vacuum or by dissolving the residue in ethyl acetate, rinsing with water, drying over anhydrous $Na_2SO_4$, filtering and concentrating in vacuo. ES-HRMS m/e calcd for $C_{22}H_{30}N_6O_3$ (M+H$^+$) 427.2452, found 427.2451.

Example 76 trans-2'-[2-(2-Methoxyethoxy)-ethyl]-2'H-[1,3']bipyrazolyl-4'-carboxylic acid (5-hydroxyadamantan-2-yl)-amide

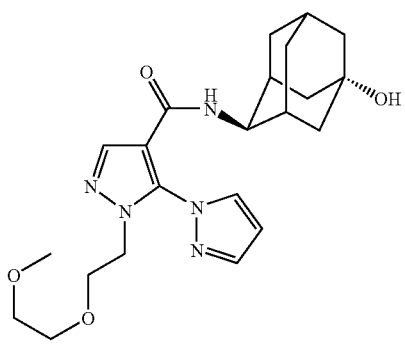

Step 1: [2-(2-Methoxyethoxy)-ethyl]-hydrazine

To a solution of hydrazine monohydrate (44.0 mL, 1.00 mol) in ethanol (75 mL) at 0° C. in an ice-water bath was added 1-(2-bromoethoxy)-2-methoxyethane (13.6 mL, 0.100 mol) drop-wise over 20 minutes. The reaction was then allowed to warm to room temperature and stir for 5 minutes and then heated to 40° C. in a preheated oil bath for 12 hours. The reaction was then cooled to room temperature and concentrated to remove the ethanol. The remaining aqueous layer was extracted with methylene chloride (2×100 mL) and diethyl ether (2×100 mL). The organic layers were combined and dried over anhydrous $Na_2SO_4$, filtered and concentrated to provide [2-(2-methoxyethoxy)-ethyl]-hydrazine as a light yellow oil (10.29 g, 85%).

Step 2: 5-Amino-1-[2-(2-methoxyethoxy)-ethyl]-1H-pyrazole-4-carboxylic acid ethyl ester To a solution of [2-(2-methoxyethoxy)-ethyl]-hydrazine (6.0 g, 44.7 mmol) in ethanol (77 mL) was added ethyl (ethoxymethylene)cyano acetate (6.43 g, 37.99 mmol). The solution was heated to reflux in a preheated oil bath (90° C.) for 24 h. The reaction was cooled to room temperature and concentrated to remove the ethanol. The residue was dissolved in methylene chloride (~100 mL) and washed with water (20 mL) and brine (10 mL). The organic layer was dried over anhydrous $Na_2SO_4$, filtered and concentrated in vacuo to provide 5-amino-1-[2-(2-methoxyethoxy)-ethyl]-1H-pyrazole-4-carboxylic acid ethyl ester (10.38 g, 99%) as an orange oil, which was used without further purification. Mass spectrum: m/z: 258.0 (M+1).

Step 3: 5-Chloro-1-[2-(2-methoxyethoxy)-ethyl]-1H-pyrazole-4-carboxylic acid ethyl ester To a mixture of t-butyl nitrite (8.5 mL, 64.5 mmol), anhydrous cuprous chloride (6.54 g, 66.1 mmol) and anhydrous acetonitrile (80 mL) was added 5-amino-1-[2-(2-methoxyethoxy)-ethyl]-1H-pyrazole-4-carboxylic acid ethyl ester (10.38 g, 40.3 mmol) over 10 minutes at 0° C. The reaction mixture was stirred at room temperature for 1 h, then at 70° C. for 2 h. The mixture was then cooled to room temperature and poured carefully into 6.0 N aqueous HCl (45 mL). The aqueous phase was extracted with methylene chloride (3×150 mL). The combined organic extracts were combined, dried over anhydrous $Na_2SO_4$, filtered and concentrated in vacuo to provide the crude material as an oil. The product was purified by column chromatography on silica gel (eluting with ethyl acetate/hexanes, using a gradient of 1:3 to 1:0) to provide 5-chloro-1-[2-(2-methoxyethoxy)-ethyl]-1H-pyrazole-4-carboxylic acid ethyl ester as a light yellow oil (3.43 g, 30%). Mass spectrum: m/z: 277.0 (M+1).

Step 4: 5-Chloro-1-[2-(2-methoxyethoxy)-ethyl]-1H-pyrazole-4-carboxylic acid To a solution of 5-chloro-1-[2-(2-methoxyethoxy)-ethyl]-1H-pyrazole-4-carboxylic acid ethyl ester (3.43 g, 12.39 mmol) in methanol (12 mL) and water (12 mL) was added lithium hydroxide (415 mg, 17.3 mmol). The reaction mixture was stirred at reflux for 3 h, and then the solution was concentrated under reduced pressure to remove the methanol. The residue was then acidified carefully with 6.0 N aqueous HCl. The resulting mixture was extracted with methylene chloride (3×50 mL). The combined organic extracts were dried over anhydrous $Na_2SO_4$, filtered and concentrated in vacuo to provide 5-chloro-1-[2-(2-methoxyethoxy)-ethyl]-1H-pyrazole-4-carboxylic acid as a white solid (2.65 g, 86%). Mass spectrum: m/z: 249.0 (M+1).

Step 5: trans-5-Chloro-1-[2-(methoxyethoxy)-ethyl]-1H-pyrazole-4-carboxylic acid (5-hydroxy-adamantan-2-yl)-amide 5-Chloro-1-[2-(2-methoxyethoxy)-ethyl]-1H-pyrazole-4-carboxylic acid (497 mg, 2.00 mmol) was dissolved in a mixture of dry methylene chloride (2 mL) and dry N,N-dimethylformamide (8 mL). To the solution was added N,N-diisopropylethylamine (2.8 mL, 16.0 mmol) and O-(N-succinimidyl)-1,1,3,3-tetramethyluronium tetrafluoroborate (722 mg, 2.40 mmol). The solution was allowed to stir at room temperature for 3 h after which an aliquot was analyzed by LC-MS, showing complete conversion to the activated ester. Then trans-4-amino-adamantan-1-ol hydrochloric acid (Intermediate 2, 489 mg, 2.40 mmol) was added. The solution was allowed to stir for 24 h, after which the reaction was quenched with water (20 mL). The aqueous layer was extracted with methylene chloride (2×50 mL). The organic extracts were combined and washed with water (2×20 mL) and brine (20 mL), dried over anhydrous $Na_2SO_4$, filtered and concentrated in vacuo to provide the crude material. The crude material was purified by column chromatography on silica gel (eluting with a gradient of ethyl acetate to 5% and then to 10% methanol/ethyl acetate) providing trans-5-chloro-1-[2-(methoxyethoxy)-ethyl]-1H-pyrazole-4-carboxylic acid (5-hydroxy-adamantan-2-yl)-amide as a white solid (460 mg, 58%). ES-HRMS m/e calcd for $C_{19}H_{28}ClN_3O_4$ (M+H$^+$) 398.1841, found 398.1842.

Step 6: trans-2'-[2-(2-Methoxyethoxy)-ethyl]-2'H-[1,3']bipyrazolyl-4'-carboxylic acid (5-hydroxyadamantan-2-yl)-amide To a solution of 5-chloro-1-[2-(methoxyethoxy)-ethyl]-1H-pyrazole-4-carboxylic acid (5-hydroxy-adamantan-2-yl)-amide (200 mg, 0.500 mmol) and pyrazole (103 mg, 1.5 mmol) in N-methylpyrrolidinone (3 mL) was added aqueous sodium hydroxide (0.200 mL, 3.79 mmol, 50% w/w). The solution was heated to 120° C. in a preheated oil bath for 24 h. The solution was cooled to room temperature and quenched with water (2 mL) and aqueous NH₄Cl (2 mL). Since no precipitation occurred, the aqueous phase was extracted with methylene chloride (2×50 mL). The organic extracts were combined, dried over anhydrous Na₂SO₄, filtered and concentrated in vacuo with heating (~100° C.) to remove excess NMP. The product was purified by column chromatography on silica gel (eluting with 5% methanol/methylene chloride) to provide trans-2'-[2-(2-methoxyethoxy)-ethyl]-2'H-[1,3']bipryazolyl-4'-carboxylic acid (5-hydroxyadamantan-2-yl)-amide as a colorless oil (142 mg, 66%). ES-HRMS m/e calcd for C$_{22}$H$_{31}$N$_5$O$_4$ (M+H⁺) 430.2449, found 430.2449.

Example 77 trans-1-(2-tert-Butoxyethyl)-5-trifluoromethyl-1H-pyrazole-4-carboxylic acid (5-hydroxy-adamantan-2-yl)-amide

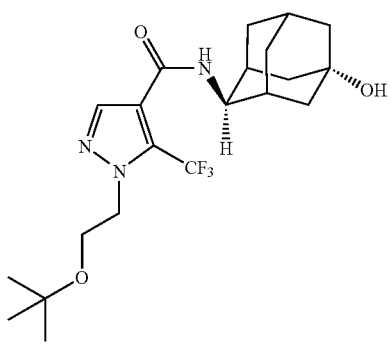

Step 1: 2-(2-Bromoethoxy)-2-methylpropane

To a high pressure flask with stir bar was added 2-bromoethanol (14.1 mL, 200 mmol), methylene chloride (35 mL) and concentrated sulfuric acid (1 mL). The flask was cooled to −78° C. in a dry ice/acetone bath. In a separate flask cooled to −78° C. was condensed 2-methylpropene (~50 mL). The 2-methylpropene was then added to the flask containing 2-bromoethanol. The flask was sealed and stirred at room temperature for 48 h. At this time, the flask was cooled to −78° C. in a dry ice/acetone bath. The flask was opened and carefully poured into a saturated aqueous sodium bicarbonate solution (100 mL). The aqueous layer was extracted with methylene chloride (2×50 mL) and hexanes (1×50 mL). The organic layers were combined, dried over anhydrous sodium sulfate, filtered and concentrated to provide 2-(2-bromoethoxy)-2-methylpropane as a colorless oil (35 g, 97%).

Step 2: (2-tert-Butoxyethyl)-hydrazine

To a solution of hydrazine monohydrate (36.0 mL, 0.750 mol) in ethanol (70 mL) at 0° C. in an ice-water bath was added 2-(2-bromoethoxy)-2-methylpropane (12.1 mL, 0.075 mol) drop-wise over 20 minutes. The reaction was then allowed to warm to room temperature and stir for 5 minutes and then heated to 40° C. in a preheated oil bath for 4 hours. The reaction was then cooled to room temperature and concentrated to remove the ethanol. To the flask was added water (20 mL) and the aqueous layer was extracted with diethyl ether (2×100 mL). The organic layers were combined and dried over anhydrous Na₂SO₄, filtered and concentrated to provide (2-tert-butoxyethyl)-hydrazine as a colorless oil (6.05 g, 61%).

Step 3: 1-(2-tert-Butoxyethyl)-5-trifluoromethyl-1H-pyrazole-4-carboxylic acid ethyl ester To a solution of (2-tert-butoxyethyl)-hydrazine (260 mg, 1.96 mmol) in ethanol (4 mL) was added ethyl 3-N,N-dimethylamino-2-trifluoroacetylacrylate (Intermediate 4, 400 mg, 1.67 mmol). The solution was heated to reflux in a preheated oil bath (90° C.) for 24 h. The reaction was cooled to room temperature and concentrated to remove the ethanol. The residue was dissolved in methylene chloride (50 mL) and washed with water (20 mL) and brine (10 mL). The organic layer was dried over anhydrous Na₂SO₄, filtered and concentrated in vacuo to provide 1-(2-tert-butoxyethyl)-5-trifluoromethyl-1H-pyrazole-4-carboxylic acid ethyl ester (620 mg, >99%) as an orange oil, which was used without further purification. Mass spectrum: m/z: 309.2 (M+1).

Step 4: 1-(2-tert-Butoxyethyl)-5-trifluoromethyl-1H-pyrazole-4-carboxylic acid

To a solution of 1-(2-tert-butoxyethyl)-5-trifluoromethyl-1H-pyrazole-4-carboxylic acid ethyl ester (620 mg, 2.0 mmol) in methanol (2 mL) and water (2 mL) was added lithium hydroxide (67 mg, 2.8 mmol). The reaction mixture was stirred at reflux for 4 h, and then the solution was concentrated under reduced pressure to remove the methanol. The residue was then acidified carefully with 6.0 N aqueous HCl. The resulting mixture was extracted with methylene chloride (2×30 mL). The combined organic extracts were dried over anhydrous Na₂SO₄, filtered and concentrated in vacuo to provide 1-(2-tert-butoxyethyl)-5-trifluoromethyl-1H-pyrazole-4-carboxylic acid as a red oil (425 mg, 75%), which was used without further purification.

Step 5: trans-1-(2-tert-Butoxyethyl)-5-trifluoromethyl-1H-pyrazole-4-carboxylic acid (5-hydroxy-adamantan-2-yl)-amide 1-(2-tert-Butoxyethyl)-5-trifluoromethyl-1H-pyrazole-4-carboxylic acid (425 mg, 1.51 mmol) was dissolved in a mixture of dry methylene chloride (1.5 mL) and dry N,N-dimethylformamide (6 mL). To the solution was added N,N-diisopropylethylamine (2.1 mL, 12.0 mmol) and O-(N-succinimidyl)-1,1,3,3-tetramethyluronium tetrafluoroborate (548 mg, 1.82 mmol). The solution was allowed to stir at room temperature for 3 h after which an aliquot was analyzed by LC-MS, showing complete conversion to the activated ester. Then trans-4-amino-adamantan-1-ol hydrochloride (Intermediate 2, 370 mg, 1.82 mmol) was added. The solution was allowed to stir for 24 h, after which the reaction was quenched with water (20 mL). The aqueous layer was extracted with methylene chloride (2×50 mL). The organic extracts were combined and washed with water (2×20 mL) and brine (20 mL), dried over anhydrous Na₂SO₄, filtered and concentrated in vacuo to provide the crude material. The crude material was purified by column chromatography on silica gel (eluting with a gradient of methylene chloride to 5% to 10% methanol/methylene chloride) providing trans-1-(2-tert-butoxyethyl)-5-trifluoromethyl-1H-pyrazole-4-carboxylic acid (5-hydroxy-adamantan-2-yl)-amide as a white solid. The white solid was recrystallized from hot diethyl ether, methylene chloride and methanol (99/1/0.1) to provide the desired product as a white solid (135 mg, 21%). ES-HRMS m/e calcd for $C_{21}H_{30}F_3N_3O_3$ (M+H$^+$) 430.2312, found 430.2314.

Example 78 trans-2'-(3-Methoxypropyl)-2'H-[1,3']bipyrazolyl-4'-carboxylic acid (5-hydroxy-adamantan-2-yl)-amide

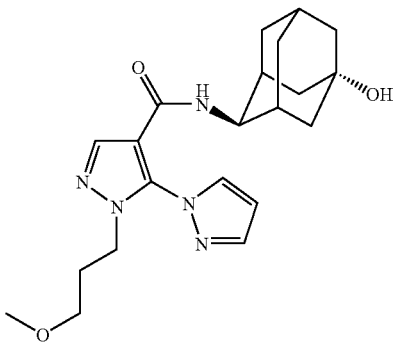

Step 1: Hydrazinecarboxylic acid tert-butyl ester

To a solution of tert-butyl carbazate (10.0 g, 75.6 mmol) in acetone (75 mL, 1.0 mol) was added anhydrous magnesium sulfate (~2.0 g) and 10 drops of glacial acetic acid. The solution was heated to reflux in a preheated oil bath (~85° C.) for 1 h. The solution was cooled to room temperature, filtered and concentrated in vacuo to provide hydrazine-carboxylic acid tert-butyl ester as a white solid (12.0 g, 92%). Mass spectrum: m/z: 173.3 (M+1).

Step 2: N'-Isopropylidene-N-(3-methoxypropyl)-hydrazinecarboxylic acid tert-butyl ester To a solution of hydrazinecarboxylic acid tert-butyl ester (4.67 g, 27.16 mmol) in toluene (90 mL) was added pulverized potassium hydroxide (1.98 g, 35.3 mmol) and tetrabutylammonium hydrogensulfate (904 mg, 2.72 mmol). The solution was heated to 50° C. in a preheated oil bath and 1-bromo-3-methoxypropane (3.67 mL, 32.6 mmol) was added dropwise over 45 minutes. The solution was then heated to 80° C. for 3 h. The solution was cooled to room temperature and washed with water (3×150 mL) until the water layer was neutral. The organic layer was dried over anhydrous magnesium sulfate, filtered and concentrated in vacuo to provide N'-isopropylidene-N-(3-methoxypropyl)-hydrazinecarboxylic acid tert-butyl ester as a viscous oil (6.49 g, 98%), which was used without further purification. Mass spectrum: m/z: 245.4 (M+1).

Step 3: (3-Methoxypropyl)-hydrazine dihydrochloric acid

To a solution of N'-isopropylidene-N-(3-methoxypropyl)-hydrazinecarboxylic acid tert-butyl ester (6.49 g, 26.6 mmol) in tetrahydroufuran (50 mL) was added 2.0N hydrochloric acid (27 mL). The solution was heated to reflux (~80° C.) in a preheated oil bath for 3 h. The solution was cooled to room temperature and concentrated in vacuo to remove the tetrahydrofuran. To the aqueous layer was added toluene (200 mL) and the water was removed via concentrating in vacuo (this was repeated 2 additional times) providing (3-methoxypropyl)-hydrazine dihydrochloric acid (4.65 g, 96%) as a light yellow sticky solid, which was used without further purification.

Step 4: 5-Amino-1-(3-methoxypropyl)-1H-pyrazole-4-carboxylic acid ethyl ester

To a solution of (3-methoxypropyl)-hydrazine dihydrochloric acid (4.5 g, 25.4 mmol) and sodium acetate (4.6 g, 56.0 mmol) in ethanol (38 mL) was added ethyl(ethoxymethylene)cyano acetate (3.89 g, 23.0 mmol). The solution was heated to reflux in a preheated oil bath (90° C.) for 24 h. The reaction was cooled to room temperature and concentrated to remove the ethanol. The residue was dissolved in methylene chloride (~100 mL) and washed with water (30 mL). The organic layer was dried over anhydrous $Na_2SO_4$, filtered and concentrated in vacuo to provide 5-amino-1-(3-methoxypropyl)-1H-pyrazole-4-carboxylic acid ethyl ester (5.01 g, 96%) as a orange oil, which was used without further purification. Mass spectrum: m/z: 228.4 (M+1).

Step 5: 5-Chloro-1-(3-methoxypropyl)-1H-pyrazole-4-carboxylic acid ethyl ester

To a mixture of 5-amino-1-(3-methoxypropyl)-1H-pyrazole-4-carboxylic acid ethyl ester (5.22 g, 23.0 mmol) in dry acetonitrile (46 mL) was added anhydrous cuprous chloride (3.73 g, 37.7 mmol) and acetic acid (2.6 mL, 46.0 mmol). The mixture was cooled to 0° C. in an ice-water bath after which tert-butyl nitrite (4.9 mL, 36.8 mmol) was added over 10 minutes. The solution was allowed to warm to room temperature and stir for 4 h. To the solution was carefully added 6.0N hydrochloric acid (20 mL). The aqueous layer was extracted with methylene chloride (2×100 mL). The organic layers were combined, dried over anhydrous sodium sulfate, filtered and concentrated in vacuo to provide the crude material. The product was purified by column chromatography on silica gel (eluting with ethyl acetate/hexanes, 1:1) to provide 5-chloro-1-(3-methoxypropyl)-1H-pyrazole-4-carboxylic acid ethyl ester (1.71 g, 30%) as an orange oil. Mass spectrum: m/z: 247.3 (M+1).

Step 6: 5-Chloro-1-(3-methoxypropyl)-1H-pyrazole-4-carboxylic acid

To a solution of 5-chloro-1-(3-methoxypropyl)-1H-pyrazole-4-carboxylic acid ethyl ester (1.71 g, 7.0 mmol) in methanol (7 mL) and water (7 mL) was added lithium hydroxide (235 mg, 9.8 mmol). The reaction mixture was stirred at reflux for 3 h, and then the solution was concentrated under reduced pressure to remove the methanol. The residue was then acidified carefully with 6.0 N aqueous HCl. The resulting mixture was extracted with methylene chloride (2×50 mL). The combined organic extracts were dried over anhydrous $Na_2SO_4$, filtered and concentrated in vacuo to provide 5-chloro-1-(3-methoxypropyl)-1H-pyrazole-4-carboxylic acid as an orange solid (1.35 g, 88%). Mass spectrum: m/z: 219.3 (M+1).

Step 7: trans-5-Chloro-1-(3-methoxypropyl)-1H-pyrazole-4-carboxylic acid (5-hydrox-adamantan-2-yl)-amide 5-Chloro-1-(3-methoxypropyl)-1H-pyrazole-4-carboxylic acid (500 mg, 2.29 mmol) was dissolved in a mixture of dry methylene chloride (2.3 mL) and dry N,N-dimethylfor-

113 mamide (9 mL). To the solution was added N,N-diisopropylethylamine (3.2 mL, 18.32 mmol) and O-(N-succinimidyl)-1,1,3,3-tetramethyluronium tetrafluoroborate (827 mg, 2.75 mmol). The solution was allowed to stir at room temperature for 3 h after which an aliquot was analyzed by LC-MS, showing complete conversion to the activated ester. Then trans-4-amino-adamantan-1-ol hydrochloric acid (Intermediate 2, 606 mg, 2.97 mmol) was added. The solution was allowed to stir for 24 h, after which the reaction was quenched with water (20 mL). The aqueous layer was extracted with methylene chloride (2×50 mL). The organic extracts were combined and washed with water (2×20 mL) and brine (20 mL), dried over anhydrous $Na_2SO_4$, filtered and concentrated in vacuo to provide the crude material. The crude material was purified by column chromatography on silica gel (eluting with a gradient of 75% ethyl acetate/hexanes to ethyl acetate) providing trans-5-chloro-1-(3-methoxypropyl)-1H-pyrazole-4-carboxylic acid (5-hydrox-adamantan-2-yl)-amide as a white solid (452 mg, 53%). ES-HRMS m/e calcd for $C_{18}H_{26}ClN_3O_3$ $(M+H^+)$ 368.1736, found 368.1733.

Step 8: trans-2'-(3-Methoxypropyl)-2'H-[1,3']bipyrazolyl-4-'carboxylic acid (5-hydroxy-adamantan-2-yl)-amide To a solution of 5-chloro-1-(3-methoxypropyl)-1H-pyrazole-4-carboxylic acid (5-hydrox-adamantan-2-yl)-amide (200 mg, 0.544 mmol) and pyrazole (74 mg, 1.09 mmol) in N-methylpyrrolidinone (3.5 mL) was added sodium hydroxide (87 mg, 2.18 mmol) and water (0.1 mL). The solution was heated to 120° C. in a preheated oil bath for 16 h. The solution was cooled to room temperature and quenched with water (1 mL) and aqueous $NH_4Cl$ (1 mL). Since no precipitation occurred, the aqueous phase was extracted with methylene chloride (2×50 mL). The organic extracts were combined, dried over anhydrous $Na_2SO_4$, filtered and concentrated in vacuo with heating (~100° C.) to remove excess NMP. The product was purified by column chromatography on silica gel (eluting with 5% methanol/methylene chloride) to provide trans-2'-(3-methoxypropyl)-2'H-[1,3']bipyrazolyl-4-'carboxylic acid (5-hydroxy-adamantan-2-yl)-amide as a white solid (108 mg, 50%). In some instances the residual NMP was removed via heating to 100° C. under high vacuum or by dissolving the residue in ethyl acetate, rinsing with water, drying over anhydrous $Na_2SO_4$, filtering and concentrating in vacuo. ES-HRMS m/e calcd for $C_{21}H_{29}N_5O_3$ $(M+H^+)$ 400.2343, found 400.2342.

Example 79 trans-2'-(3-Methoxypropyl)-2'H-[1,3']bipyrazolyl-4'-carboxylic acid (5-acetylamino-adamantan-2-yl)-amide

114

Step 1: trans-5-Chloro-1-(2-methoxypropyl)-1H-pyrazole-4-carboxylic acid (5-acetylamino-adamantan-2-yl)-amide 5-Chloro-1-(2-methoxypropyl)-1H-pyrazole-4-carboxylic acid (prepared in Example 78, Step 6; 190 mg, 0.872 mmol) was dissolved in a mixture of dry methylene chloride (1 mL) and dry N,N-dimethylformamide (4 mL). To the solution was added diisopropylethylamine (1.4 mL, 8.00 mmol) and O-(N-succinimidyl)-1,1,3,3-tetramethyluronium tetrafluoroborate (290 mg, 0.960 mmol). The solution was allowed to stir at room temperature for 3 h after which an aliquot was analyzed by LC-MS, showing complete conversion to the activated ester. Then trans-N-(4-amino-adamantan-1-yl)-acetamide (prepared in Example 43, 200 mg, 0.960 mmol) was added. The solution was allowed to stir for 24 h, after which the reaction was quenched with water (20 mL). The aqueous layer was extracted with methylene chloride (2×50 mL). The organic extracts were combined, dried over anhydrous $Na_2SO_4$, filtered and concentrated in vacuo to provide the crude material. The crude material was purified by column chromatography on silica gel (eluting with a gradient of methylene chloride to 5% methanol/methylene chloride) providing trans-5-chloro-1-(2-methoxypropyl)-1H-pyrazole-4-carboxylic acid (5-acetylamino-adamantan-2-yl)-amide as a fluffy white solid (200 mg, 56%). ES-HRMS m/e calcd for $C_{20}H_{29}ClN_4O_3$ $(M+H^+)$ 409.2001, found 409.2002.

Step 2: trans-2'-(3-Methoxypropyl)-2'H-[1,3']bipyrazolyl-4'-carboxylic acid (5-acetylamino-adamantan-2-yl)-amide To a solution of 5-chloro-1-(2-methoxypropyl)-1H-pyrazole-4-carboxylic acid (5-acetylamino-adamantan-2-yl)-amide (232 mg, 0.57 mmol) and pyrazole (155 mg, 2.27 mmol) in N-methylpyrrolidinone (2.5 mL) was added aqueous sodium hydroxide (0.300 mL, 5.68 mmol, 50% w/w). The solution was heated to 120° C. in a preheated oil bath for 24 h. The solution was cooled to room temperature and quenched with water (1 mL) and aqueous $NH_4Cl$ (1 mL). Since no precipitation occurred, the aqueous phase was extracted with methylene chloride (2×50 mL). The organic extracts were combined, dried over anhydrous $Na_2SO_4$, filtered and concentrated in vacuo with heating (100° C.) to remove excess NMP. The product was purified by column chromatography on silica gel (eluting with 5% methanol/methylene chloride) to provide trans-2'-(3-methoxypropyl)-2'H-[1,3']bipyrazolyl-4'-carboxylic acid (5-acetylamino-adamantan-2-yl)-amide as a white solid (170 mg, 69%). In some instances the residual NMP was removed via heating to 100° C. under high vacuum or by dissolving the residue in ethyl acetate, rinsing with water, drying over anhydrous $Na_2SO_4$, filtering and concentrating in vacuo. ES-HRMS m/e calcd for $C_{23}H_{32}N_6O_3$ $(M+H^+)$ 441.2609, found 441.2609.

Example 80 trans-1-Cyclopropyl-5-trifluoromethyl-1H-pyrazole-4-carboxylic acid (5-hydroxy-adamantan-2-yl)-amide

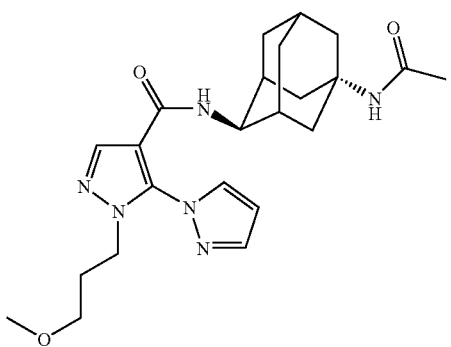

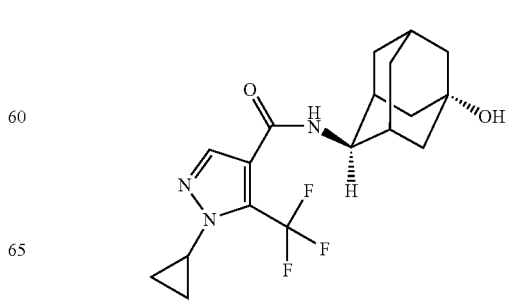

Cyclopropyl-5-trifluoromethyl-1H-pyrazole-4-carboxylic acid (Intermediate 6, 291 mg, 1.33 mmol) was dissolved in a mixture of dry dichloromethane (12 mL) and dry DMF (3 mL), and TSTU (481 mg, 1.6 mmol) was added. Then DIPEA (1.4 mL, 8 mmol) was added to the above mixture. After the mixture was stirred for 2 h, trans-4-amino-adamantan-1-ol (268 mg, 1.6 mmol, Intermediate 2) was added. After stirring overnight, water was added and the organic layer was separated. The aqueous layer was extracted twice with dichloromethane. The combined organic layers were dried under vacuum. The crude mixture was purified by C-18 reverse phase preparative-HPLC with a gradient of 10-100% acetonitrile/water to give trans-1-cyclopropyl-5-trifluoromethyl-1H-pyrazole-4-carboxylic acid (5-hydroxy-adamantan-2-yl)-amide (254 mg, 52%). LRMS m/z calcd for $C_{18}H_{22}F_3N_3O_2$ (M+H) 370.2, found 370.2.

Example 81 trans-5-Chloro 1-cyclopropyl-1H-pyrazole-4-carboxylic acid (5-hydroxy-adamantan-2-yl)-amide

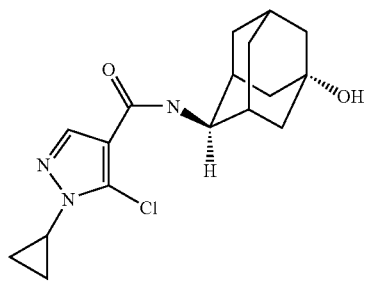

Step 1: Synthesis of a mixture of 5-amino-1-cyclopropyl-1H-pyrazole-4-carboxylic acid ethyl ester and 3-amino-1-cyclopropyl-1H-pyrazole-4-carboxylic acid ethyl ester A mixture containing cyclopropyl hydrazine hydrochloride (Intermediate 5 without further purification; 3.65 g, 33.67 mmol), ethyl(ethoxymethylene)-cyanoacetate (5.69 g, 33.67 mmol), and anhydrous sodium acetate (2.03 g, 33.67 mmol) in 60 mL ethanol was stirred and refluxed overnight. The solution was cooled to room temperature, and water and dichloromethane were added. The separated aqueous phase was extracted three times with dichloromethane. The combined organic phases were washed successively with water and brine solution and dried with sodium sulfate and filtered. The solvent was removed in vacuo, and the crude residue was purified by flash chromatography eluting with a gradient of 0-2% methanol/dichloromethane, to give a mixture of 5-amino-1-cyclopropyl-1H-pyrazole-4-carboxylic acid ethyl ester (eluted first) and 3-amino-1-cyclopropyl-1H-pyrazole-4-carboxylic acid ethyl ester (eluted slightly later) (two isomers: total 2.03 g, 31%), which was used as a mixture without further separation. LRMS m/z calcd for $C_9H_{13}N_3O_2$ (M+H) 196.1, found 196.1.

Step 2: Synthesis of a mixture of 5-chloro-1-cyclopropyl-1H-pyrazole-4-carboxylic acid ethyl ester and 3-Chloro-1-cyclopropyl-1H-pyrazole-4-carboxylic acid ethyl ester To a mixture of t-butyl nitrite (2.03 mL, 15.38 mmol), cuprous chloride (1.52 g, 15.38 mmol), and anhydrous acetonitrile (30 mL) was added the solution of the mixture of 5-amino-1-cyclopropyl-1H-pyrazole-4-carboxylic acid ethyl ester and 3-amino-1-cyclopropyl-1H-pyrazole-4-carboxylic acid ethyl ester (from last step) in anhydrous acetonitrile (20 mL) at 0° C. The reaction mixture was stirred at room temperature for 1 h and then at 60° C. for 2 h. The mixture was cooled to room temperature and poured into 6N HCl (20 mL) and extracted with dichloromethane. The aqueous phase was extracted three times with dichloromethane. After the combined organic phases were concentrated in vacuo, the crude residue was purified by flash chromatography eluting with a gradient of 10-20% ethyl acetate/hexanes, then 20% ethyl acetate/hexanes to give 5-chloro-1-cyclopropyl-1H-pyrazole-4-carboxylic acid ethyl ester (eluted first, 296 mg, 13%) and 3-chloro-1-cyclopropyl-1H-pyrazole-4-carboxylic acid ethyl ester (eluted later, 159 mg, 7%). LRMS m/z calcd for $C_9H_{11}ClN_2O_2$ (M+H) 215.1, found 215.1.

Step 3: Synthesis of 5-chloro-1-cyclopropyl-1H-pyrazole-4-carboxylic acid

To a solution of 5-Chloro-1-cyclopropyl-1H-pyrazole-4-carboxylic acid ethyl ester (296 mg, 1.38 mmol) in methanol (15 mL) and water (15 mL) was added LiOH (40 mg, 1.66 mmol). The reaction mixture was stirred at reflux overnight and then concentrated under reduced pressure to remove the methanol. The residue was diluted with water, acidified to pH=2 with concentrated HCl, and extracted with ethyl acetate. The organic extracts were evaporated in vacuo to give 5-chloro-1-cyclopropyl-1H-pyrazole-4-carboxylic acid (242 mg, 93%) which was used without further purification.

Step 4: Synthesis of trans-5-chloro-1-cyclopropyl-1H-pyrazole-4-carboxylic acid (5-hydroxy-adamantan-2-yl)-amide 5-Chloro-cyclopropyl-1H-pyrazole-4-carboxylic acid (242 mg, 1.3 mmol) was dissolved in a mixture of dry dichloromethane (8 mL) and dry DMF (2 mL), and TSTU (318 mg, 1.56 mmol) was added. DIPEA (1.4 mL, 7.8 mmol) was added next to the above mixture. After the mixture was stirred for 2 h, trans-4-amino-adamantan-1-ol hydrochloride (318 mg, 1.56 mmol, Intermediate 2) was added. After stirring overnight, water was added and the organic layer was separated. The aqueous layer was extracted twice with dichloromethane. The combined organic layers were dried under vacuum. The crude mixture was purified by C-18 reversed phase preparative-HPLC with a gradient of 10-90% acetonitrile/water to give trans-5-Chloro-1-cyclopropyl-1H-pyrazole-4-carboxylic acid (5-hydroxy-adamantan-2-yl)-amide (200 mg, 46%). LRMS m/z calcd for $C_{17}H_{22}ClN_3O_2$ (M+H) 336.1, found 336.1.

Example 82 trans-2'-Cyclopropyl-2'H-[1,3']bipyrazolyl-4'-carboxylic acid (5-hydroxy-adamantan-2-yl)-amide

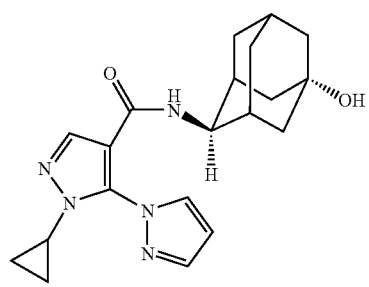

Sodium hydride (60% dispersion in mineral oil; 115 mg, 2.86 mmol) was added to a solution of pyrazole (195 mg, 2.86 mmol) in dry DMF (25 mL) under nitrogen at 0° C. in an ice-water bath and the mixture was heated to 40° C. for 1 h. Trans-5-chloro-1-cyclopropyl-1H-pyrazole-4-carboxylic acid (5-hydroxy-adamantan-2-yl)-amide (120 mg, 0.36 mmol) was added and the mixture was heated at 110° C. for 48 hours and then cooled. After the DMF was evaporated in vacuo, water and ethyl acetate were added. The organic layer was separated, and the aqueous phase was extracted three times with ethyl acetate. The combined organic phases were concentrated in vacuo and the residue was purified by C-18 reverse phase preparative-HPLC with a gradient of 10-60% acetonitrile/water to give trans-2'-Cyclopropyl-2'H-[1,3']bipyrazolyl-4'-carboxylic acid (5-hydroxy-adamantan-2-yl)-amide (126 mg, 95%). LRMS m/z calcd for $C_{20}H_{25}N_5O_2$ (M+H) 368.2, found 368.2.

Example 83 trans-4-Chloro-2'-cyclopropyl-2'H-[1,3']bipyrazolyl-4'-carboxylic acid (5-hydroxy-adamantan-2-yl)-amide

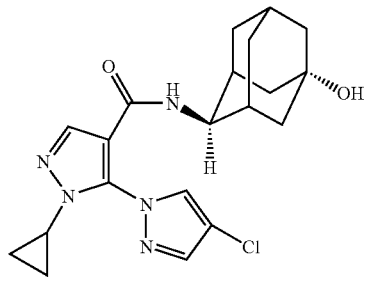

Sodium hydride (60% in oil; 57 mg, 1.43 mmol) was added to a solution of 4-chloro-pyrazole (148 mg, 1.43 mmol) in dry DMF (25 mL) under nitrogen at 0° C. in an ice-water bath and the mixture was heated to 40° C. for 1 h. trans-5-Chloro-1-cyclopropyl-1H-pyrazole-4-carboxylic acid (5-hydroxy-adamantan-2-yl)-amide (60 mg, 0.18 mmol) was added and the mixture was heated at 110° C. overnight and then cooled. After the DMF was evaporated in vacuo, water and dichloromethane were added. The organic layer was separated, and the aqueous phase was extracted three times with dichloromethane. The combined organic phases were concentrated in vacuo and the residue was purified by C-18 reverse phase preparative-HPLC with a gradient of 10-90% acetonitrile/water to give trans-4-chloro-2'-cyclopropyl-2'H-[1,3']bipyrazolyl-4'-carboxylic acid (5-hydroxy-adamantan-2-yl)-amide (56 mg, 77%). LRMS m/z calcd for $C_{20}H_{24}ClN_5O_2$ (M+H) 402.2, found 402.2.

Example 84 trans-1-Cyclopropylmethyl-5-trifluoromethyl-1H-pyrazole-4-carboxylic acid (5-hydroxy-adamantan-2-yl)-amide

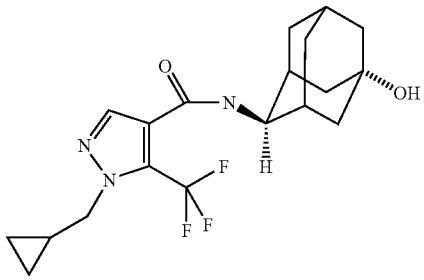

Step 1: Synthesis of Cyclopropylmethyl-hydrazine

Bromomethyl-cyclopropane (7.5 g, 55.6 mmol) was added dropwise to hydrazine hydrate (13.9 g, 277 mmol) at room temperature over 20 minutes with stirring. The stirring was continued at room temperature for 1 hour. Then the mixture was heated to 50° C. and stirred for 1 h. The reaction mixture was cooled to room temperature and was extracted three times with ether. The ether layers were combined and concentrated in vacuo to afford cyclopropylmethyl-hydrazine (3.2 g, 67%) as a colorless oil which was used without further purification.

Step 2: Synthesis of 1-cyclopropylmethyl-5-trifluoromethyl-1H-pyrazole-4-carboxylic acid ethyl ester Triethylamine (0.35 mL, 2.52 mmol) and cyclopropylmethyl-hydrazine (72 mg, 0.84 mmol) were added sequentially to a solution of ethyl 3-N,N-dimethylamino-2-trifluoroacetylacrylate (Intermediate 4, 200 mg, 0.84 mmol) in ethanol (4 mL) in a 10 mL Personal Chemistry Microwave Process Tube (Biotage AB, Sweden). The tube was sealed with a septum and submitted to 150 W microwave irradiation using a Personal Chemistry Microwave Synthesis System (Biotage AB, Sweden) at 160° C. for 30 minutes. The ethanol was evaporated under reduced pressure. The remaining mixture was partitioned between dichloromethane and water, and the water phase was extracted three times with dichloromethane. The organic phases were combined, concentrated in vacuo, and purified by C-18 reverse phase HPLC with a gradient of 10-90% acetonitrile/water to give 1-cyclopropylmethyl-5-trifluoromethyl-1H-pyrazole-4-carboxylic acid ethyl ester (120 mg, 54%). LRMS m/z calcd for $C_{11}H_{14}F_3N_2O_2$ (M+) 263.1, found 263.1.

Step 3: Synthesis of 1-Cyclopropylmethyl-5-trifluoromethyl-1H-pyrazole-4-carboxylic acid To a solution of 1-cyclopropylmethyl-5-trifluoromethyl-1H-pyrazole-4-carboxylic acid ethyl ester (120 mg, 0.46 mmol) in methanol (5 mL) and water (5 mL) was added LiOH (13 mg, 0.54 mmol). The reaction mixture was stirred at reflux overnight, and then the solution was concentrated under reduced pressure to remove the methanol. The residue was diluted with water and the solution was acidified to pH=2 with concentrated HCL. The resulting mixture was then extracted with ethyl acetate three times. The combined organic layers were concentrated in vacuo to give 1-cyclopropylmethyl-5-trifluoromethyl-1H-pyrazole-4-carboxylic acid (100 mg, 93%), which was used without further purification.

Step 4: Synthesis of trans-1-Cyclopropylmethyl-5-trifluoromethyl-1H-pyrazole-4-carboxylic acid (5-hydroxy-adamantan-2-yl)-amide Cyclopropylmethyl-5-trifluoromethyl-1H-pyrazole-4-carboxylic acid (100 mg, 0.43 mmol) was dissolved in a mixture of dry dichloromethane (12 mL) and dry DMF (3 mL), and TSTU (151 mg, 0.52 mmol) was added. Then DIPEA (0.45 mL, 2.58 mmol) was added to the above mixture. After the mixture was stirred for 2 h, trans-4-amino-adamantan-1-ol (87 mg, 0.53 mmol, Intermediate 2) was added. After stirring overnight, water was added and the organic layer was separated. The aqueous layer was extracted twice with dichloromethane. The combined organic layers were dried under vacuum. The crude mixture was purified by C-18 reversed phase prep-HPLC with a gradient of 2-60% acetonitrile/water to give trans-1-cyclopropylmethyl-5-trifluoromethyl-1H-pyrazole-4-carboxylic acid (5-hydroxy-adamantan-2-yl)-amide (26 mg, 16%). LRMS m/z calcd for $C_{19}H_{24}F_3N_3O_2$ (M+H) 384.2, found 384.2.

Example 85 trans-1-(2-Hydroxy-1,1-dimethyl-ethyl)-5-trifluoromethyl-1H-pyrazole-4-carboxylic acid (5-hydroxyadamantan-2-yl)-amide

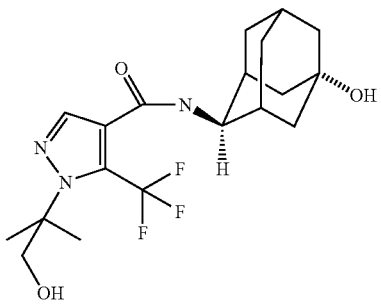

Step 1: Synthesis of N'-(2-hydroxy-1,1-dimethylethyl)-hydrazinecarboxylic acid tertbutyl ester

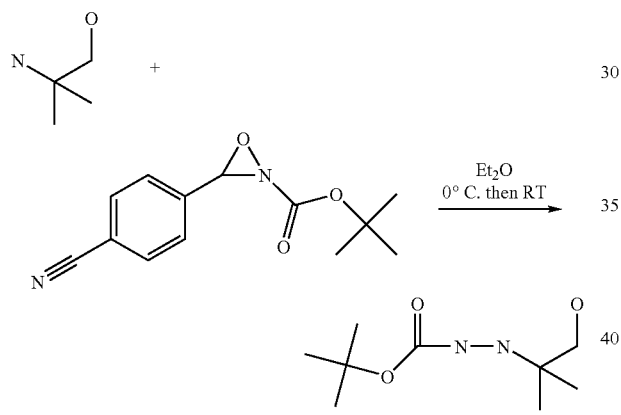

A solution of N-(tert-butoxycarbonyl)-3-(4-cyanophenyl)-oxaziridine (CAS #: 150884-56-3, purchased from Acros, 5.17 g, 21 mmol) in anhydrous diethyl ether (20 mL) was added to a solution of 2-amino-2-methyl-propan-1-ol (1.78 g, 20 mmol) in anhydrous diethyl ether (20 mL) at room temperature. The reaction mixture stirred at room temperature for 2 hours. Diethyl ether was evaporated under reduced pressure and the residue was purified by flash chromatography eluting with a gradient of 3-5% methanol/dichloromethane to give N'-(2-hydroxy-1,1-dimethyl-ethyl)-hydrazinecarboxylic acid tert-butyl ester (1.63 g, 40%) which was used without further purification.

Step 2: Synthesis of 2-hydrazino-2-methyl-propan-1-ol trifluoro-acetic acid salt

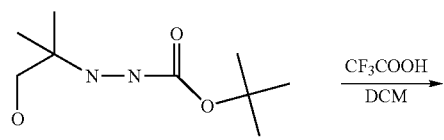

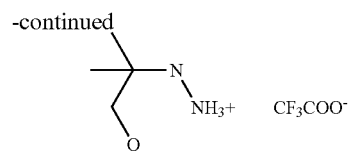

Trifluoroacetic acid (4 mL) was added to a solution of N'-(2-hydroxy-1,1-dimethyl-ethyl)-hydrazinecarboxylic acid tert-butyl ester (490 mg, 2.4 mmol) in dichloromethane (4 mL). The mixture was stirred at room temperature for 1 h. The reaction mixture was concentrated in vacuo to give the trifluoroacetic acid salt of 2-hydrazino-2-methyl-propan-1-ol (520 mg, quantitative) which was used without further purification.

Step 3: Synthesis of 1-(2-hydroxy-1,1-dimethylethyl)-5-trifluoromethyl-1H-pyrazole-4-carboxylic acid ethyl ester

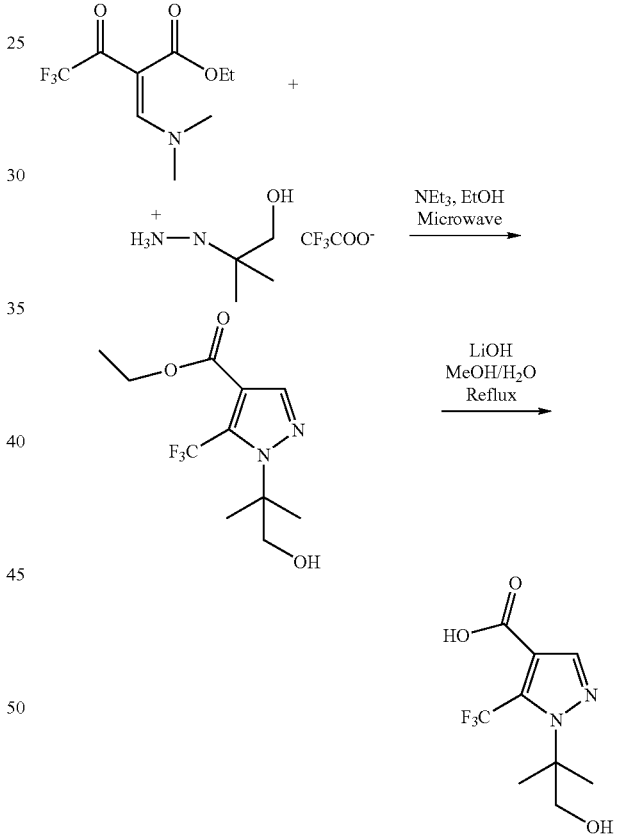

Triethylamine (1.6 mL, 12 mmol) and trifluoroacetic acid salt of 2-hydrazino-2-methyl-propan-1-ol (520 mg, 2.4 mmol) were added sequentially to a solution of ethyl 3-N,N-dimethylamino-2-trifluoroacetylacrylate (Intermediate 4, 574 mg, 2.4 mmol) in ethanol (8 mL) in a 25 mL Personal Chemistry Microwave Process Tube (Biotage AB, Sweden). The tube was sealed with a septum and submitted to 150 W microwave irradiation using a Personal Chemistry Microwave Synthesis System (Biotage AB, Sweden) at 160° C. for 1 hour. The ethanol was evaporated under reduced pressure. The remaining mixture was partitioned between dichloromethane and water, and the water phase was extracted three times with dichloromethane. The organic layers were combined, concentrated in vacuo, and purified by flash chromatography eluting with a gradient of 0-40% ethyl acetate/hexanes, then 40% ethyl acetate/hexanes to give 1-(2-hydroxy-1,1-dimethyl-ethyl)-5-trifluoromethyl-1H-pyrazole-4-carboxylic acid ethyl ester (328 mg, 49%). LRMS m/z calcd for $C_{11}H_{15}F_3N_2O_3$ (M+H) 281.1, found 281.1.

Step 4: Synthesis of 1-(2-Hydroxy-1,1-dimethyl-ethyl)-5-trifluoromethyl-1H-pyrazole-4-carboxylic acid To a solution of 1-(2-hydroxy-1,1-dimethyl-ethyl)-5-trifluoromethyl-1H-pyrazole-4-carboxylic acid ethyl ester (328 mg, 1.17 mmol) in methanol (5 mL) and water (5 mL) was added LiOH (34 mg, 1.4 mmol). The reaction mixture was stirred at reflux overnight, and then the solution was concentrated under reduced pressure to remove the methanol. The residue was diluted with water and the solution was acidified to pH=2 with concentrated HCl. The resulting mixture was then extracted with ethyl acetate three times. The combined organic extracts were concentrated in vacuo to give 1-(2-hydroxy-1,1-dimethyl-ethyl)-5-trifluoromethyl-1H-pyrazole-4-carboxylic acid (280 mg, 95%), which was used without further purification.

Step 5: Synthesis of trans-1-(2-Hydroxy-1,1-dimethyl-ethyl)-5-trifluoromethyl-1H-pyrazole-4-carboxylic acid (5-hydroxy-adamantan-2-yl)-amide 1-(2-Hydroxy-1,1-dimethyl-ethyl)-5-trifluoromethyl-1H-pyrazole-4-carboxylic acid (280 mg, 1.1 mmol) was dissolved in a mixture of dry dichloromethane (12 mL) and dry DMF (3 mL), and TSTU (403 mg, 1.3 mmol) was added. Then DIPEA (1.2 mL, 6.6 mmol) was added to the above mixture. After the mixture was stirred for 2 h, trans-4-amino-adamantan-1-ol (217 mg, 1.3 mmol, Intermediate 2) was added. After stirring overnight, water was added and the organic layer was separated. The aqueous layer was extracted twice with dichloromethane. The combined organic layers were dried under vacuum. The crude mixture was purified by C-18 reverse phase preparative-HPLC with a gradient of 10-40% acetonitrile/water to give trans-1-(2-hydroxy-1,1-dimethyl-ethyl)-5-trifluoromethyl-1H-pyrazole-4-carboxylic acid (5-hydroxy-adamantan-2-yl)-amide (230 mg, 52%). LRMS m/z calcd for $C_{19}H_{26}F_3N_3O_3$ (M+H) 402.2, found 402.2.

Example 86 trans-1-tert-Butyl-5-cyclopropyl-1H-pyrazole-4-carboxylic acid (5-hydroxy-adamantan-2-yl)-amide

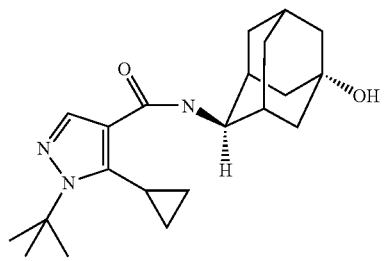

Step 1: Synthesis of 2-cyclopropanecarbonyl-3-dimethylamino-acrylic acid methyl ester

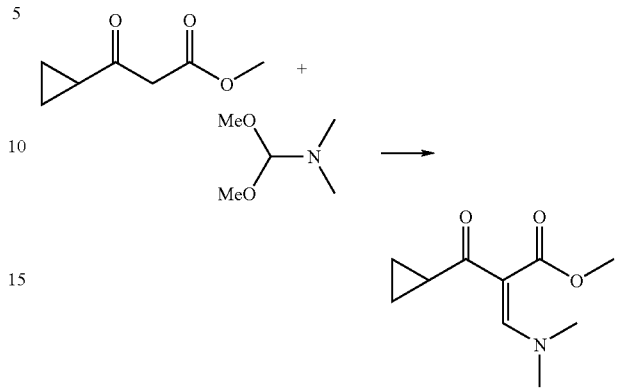

The mixture of 3-cyclopropyl-3-oxo-propionic acid methyl ester (15 g, 106 mmol) and N,N-dimethylformamide dimethylacetal (14.7 mL, 111 mmol) was heated at 75° C. for 2 h.

The crude mixture was concentrated under high vacuum to give crude 2-cyclopropanecarbonyl-3-dimethylamino-acrylic acid methyl ester (20.4 g, 91%) which was used without further purification.

Step 2: Synthesis of 1-tert-Butyl-5-cyclopropyl-1H-pyrazole-4-carboxylic acid methyl ester Triethylamine (4.8 mL, 34.2 mmol) and tert-butyl hydrazine hydrochloride (1.4 g, 11.4 mmol) were added sequentially to a solution of crude 2-cyclopropanecarbonyl-3-dimethylamino-acrylic acid methyl ester (2.4 g, 11.4 mmol) in ethanol (24 mL). The resulting suspension was mixed well and divided equally into two 25 mL Personal Chemistry Microwave Process Tubes (Biotage AB, Sweden). The tubes were sealed with a septum and submitted to 150 W microwave irradiation using a Personal Chemistry Microwave Synthesis System (Biotage AB, Sweden) at 160° C. for 30 minutes. The reaction mixtures in the two tubes were combined and ethanol was evaporated under reduced pressure. The remaining mixture was partitioned between dichloromethane and water, and the water phase was extracted three times with dichloromethane. The organic phases were combined, concentrated in vacuo, and purified by silica chromatography eluting with a gradient of 10-20% ethyl acetate/hexanes, then 20% ethyl acetate/hexanes to give 1-tert-butyl-5-cyclopropyl-1H-pyrazole-4-carboxylic acid methyl ester (921 mg, 36%). LRMS m/z calcd for $C_{12}H_{18}N_2O_2$ (M+H) 223.1, found 223.1.

Step 3: Synthesis of 1-tert-butyl-5-cyclopropyl-1H-pyrazole-4-carboxylic acid

To a solution of 1-tert-butyl-5-cyclopropyl-1H-pyrazole-4-carboxylic acid methyl ester (921 mg, 4.14 mmol) in methanol (15 mL) and water (15 mL) was added LiOH (119 mg, 4.97 mmol). The reaction mixture was stirred at reflux overnight, and then the solution was concentrated under reduced pressure to remove the methanol. The residue was diluted with water and the solution was acidified to pH 2 with concentrated HCl. The resulting mixture was then extracted with ethyl acetate three times. The combined organic extracts were concentrated in vacuo to give 1-tert-butyl-5-cyclopropyl-1H-pyrazole-4-carboxylic acid (789 mg, 92%), which was used without further purification.

Step 4: Synthesis of trans-1-tert-Butyl-5-cyclopropyl-1H-pyrazole-4-carboxylic acid (5-hydroxy-adamantan-2-yl)-amide tert-Butyl-5-cyclopropyl-1H-pyrazole-4-carboxylic acid (200 mg, 0.96 mmol) was dissolved in a mixture of dry dichloromethane (8 mL) and dry DMF (2 mL), and TSTU (349 mg, 1.16 mmol) was added. Then DIPEA (1 mL, 5.76 mmol) was added to the above mixture. After the mixture was stirred for 2 h, trans-4-amino-adamantan-1-ol hydrochloride (236 mg, 1.16 mmol, Intermediate 2) was added. After stirring overnight, water was added and the organic layer was separated. The aqueous layer was extracted twice with dichloromethane. The combined organic layers were dried under vacuum. The crude mixture was purified by C-18 reverse phase prep-HPLC with a gradient of 2-70% acetonitrile/water to give trans-1-tert-butyl-5-cyclopropyl-1H-pyrazole-4-carboxylic acid (trans-5-hydroxy-adamantan-2-yl)-amide (129 mg, 38%). LRMS m/z calcd for $C_{21}H_{31}N_3O_2$ (M+H) 358.3, found 358.2.

Example 87 trans-1-Cyclobutyl-5-trifluoromethyl-1H-pyrazole-4-carboxylic acid (5-hydroxy-adamantan-2-yl)-amide

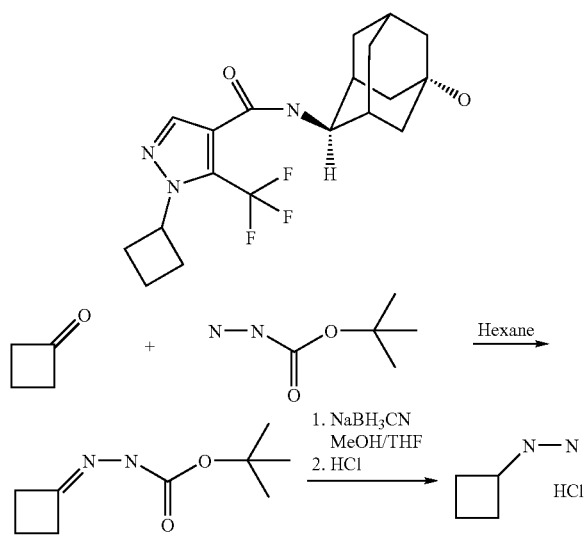

Step 1: Synthesis of N'-cyclobutylidene-hydrazinecarboxylic acid tert-butyl ester The reaction mixture of cyclobutanone (15 g, 214 mmol) and hydrazinecarboxylic acid tert-butyl ester (28.3 g, 214 mmol) in hexane (225 mL) was heated to reflux for 2 hours. After cooling down, a precipitate formed and the solid was filtered under vacuum. Isopropanol (10 mL) and hexane (100 mL) were added to the solid and the mixture was put on the rotary evaporator under vacuum until a slurry was generated. After filtration, the solid was washed with hexane twice and dried in vacuo to afford N'-cyclobutylidene-hydrazinecarboxylic acid tert-butyl ester (32 g, 81%) as white solid which was used without further purification.

Step 2: Synthesis of Cyclobutylhydrazine hydrochloride

To a mixture of N'-cyclobutylidene-hydrazinecarboxylic acid tert-butyl ester (2 g, 10.8 mmol) in anhydrous methanol (12 mL) and anhydrous THF (9 mL) was added sodium cyanoborohydride (860 mg, 13 mmol). The reaction mixture was heated to reflux for 30 minutes and was then cooled to room temperature and stirred for 20 minutes. 6N HCl (4.6 mL) was added dropwise to the reaction mixture. Then the mixture was refluxed for 30 minutes. The mixture was cooled and the salts were removed by filtration. The resulting filtrate was concentrated in vacuo. The residue was slurried with isopropanol and chilled by ice-water bath. Then the hexane was added and the mixture was put on the rotary evaporator under vacuum until a slurry was generated. After filtration and washing with hexane, cyclobutylhydrazine hydrochloride (1.26 g, 95%) was obtained was white solid and was used without further purification.

Step 3: Synthesis of 1-Cyclobutyl-5-trifluoromethyl-1H-pyrazole-4-carboxylic acid ethyl ester

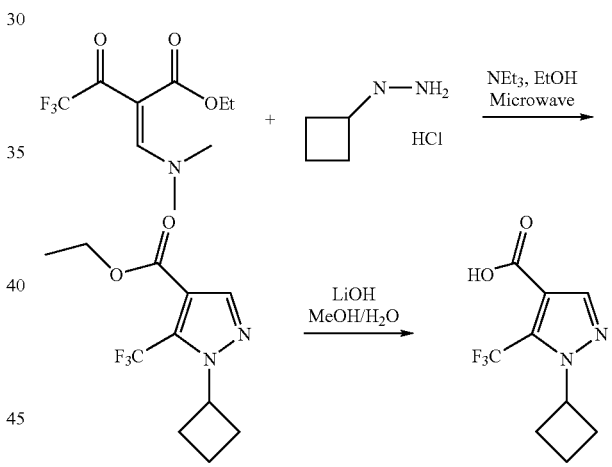

Triethylamine (0.35 mL, 2.52 mmol) and cyclobutylhydrazine hydrochloride (200 mg, 0.84 mmol) were added sequentially to a solution of ethyl 3-N,N-dimethylamino-2-trifluoroacetylacrylate (Intermediate 4, 200 mg, 0.84 mmol) in ethanol (4 mL) in a 10 mL Personal Chemistry Microwave Process Tube (Biotage AB, Sweden). The tube was sealed with a septum and submitted to 150 W microwave irradiation using a Personal Chemistry Microwave Synthesis System (Biotage AB, Sweden) at 160° C. for 30 minutes. The ethanol was evaporated under reduced pressure. The remaining mixture was partitioned between dichloromethane and water, and the water layer was extracted three times with dichloromethane. The organic layers were combined, concentrated in vacuo, and purified by C-18 reverse phase HPLC with a gradient of 40-80% acetonitrile/water to give 1-cyclobutyl-5-trifluoromethyl-1H-pyrazole-4-carboxylic acid ethyl ester (117 mg, 53%). LRMS m/z calcd for $C_{11}H_{14}F_3N_2O_2$ (M+) 263.1, found 263.1.

Step 4: Synthesis of 1-cyclobutyl-5-trifluoromethyl-1H-pyrazole-4-carboxylic acid To a solution of 1-cyclobutyl-5-trifluoromethyl-1H-pyrazole-4-carboxylic acid ethyl ester (117 mg, 0.45 mmol) in methanol (5 mL) and water (5 mL) was added LiOH (13 mg, 0.54 mmol). The reaction mixture was stirred at reflux overnight, and then the solution was concentrated under reduced pressure to remove the methanol. The residue was diluted with water and the solution was acidified to pH=2 with concentrated HCl. The resulting mixture was then extracted with ethyl acetate three times. The combined organic extracts were concentrated in vacuo to give 1-cyclobutyl-5-trifluoromethyl-1H-pyrazole-4-carboxylic acid (93 mg, 89%), which was used without further purification.

Step 5: trans-1-Cyclobutyl-5-trifluoromethyl-1H-pyrazole-4-carboxylic acid (5-hydroxy-adamantan-2-yl)-amide Cyclobutyl-5-trifluoromethyl-1H-pyrazole-4-carboxylic acid (73 mg, 0.31 mmol) was dissolved in a mixture of dry dichloromethane (8 mL) and dry DMF (2 mL), and TSTU (205 mg, 0.68 mmol) was added. Then DIPEA (0.32 mL, 1.86 mmol) was added to the above mixture. After the mixture was stirred for 2 h, trans-4-amino-adamantan-1-ol hydrochloride (77 mg, 0.38 mmol, Intermediate 2) was added. After stirring overnight, water was added and the organic layer was separated. The aqueous layer was extracted twice with dichloromethane. The combined organic layers were concentrated under vacuum. The crude mixture was purified by C-18 reverse phase preparative-HPLC with a gradient of 10-75% acetonitrile/water to give trans-1-Cyclobutyl-5-trifluoromethyl-1H-pyrazole-4-carboxylic acid (5-hydroxy-adamantan-2-yl)-amide (54 mg, 45%). LRMS m/z calcd for $C_{19}H_{24}F_3N_3O_2$ (M+H) 384.2, found 384.2.

Example 88 trans-1-Cyclobutyl-5-trifluoromethyl-1H-pyrazole-4-carboxylic acid (5-acetylamino-adamantan-2-yl)-amide

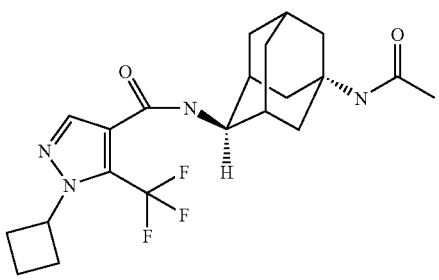

Cyclobutyl-5-trifluoromethyl-1H-pyrazole-4-carboxylic acid (Example 87, Step 4, 100 mg, 0.43 mmol) was dissolved in a mixture of dry dichloromethane (8 mL) and dry DMF (2 mL), and TSTU (285 mg, 0.95 mmol) was added. Then DIPEA (0.45 mL, 2.58 mmol) was added to the above mixture. After the mixture was stirred for 3 h, trans-N-(4-amino-adamantan-1-yl)-acetamide (107 mg, 0.51 mmol prepared in Example 43) was added. After stirring overnight, water was added and the organic layer was separated. The aqueous layer was extracted twice with dichloromethane. The combined organic layers were concentrated under vacuum. The crude mixture was purified by C-18 reverse phase preparative-HPLC with a gradient of 10-90% acetonitrile/water to give trans-1-cyclobutyl-5-trifluoromethyl-1H-pyrazole-4-carboxylic acid (5-acetylamino-adamantan-2-yl)-amide (104 mg, 57%). LRMS m/z calcd for $C_{21}H_{27}F_3N_4O_2$ (M+H) 425.2, found 425.2.

Example 89

Trans-5-Chloro-1-cyclobutyl-1H-pyrazole-4-carboxylic acid (5-acetylamino-adamantan-2-yl)-amide

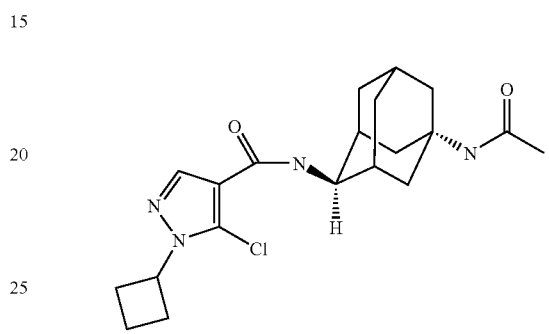

Step 1: Synthesis of cyclobutyl-hydrazine

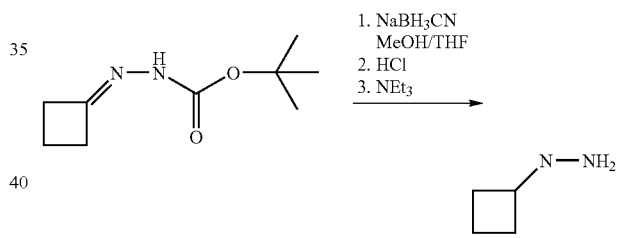

To a mixture of N'-cyclobutylidene-hydrazinecarboxylic acid tert-butyl ester (24 g, 130 mmol) in anhydrous methanol (180 mL) and anhydrous THF (120 mL) was added sodium cyanoborohydride (10.3 g, 156 mmol). The reaction mixture was heated to reflux for 1 hour and was then cooled to room temperature and stirred for 30 minutes. 6N HCl (56 mL) was added dropwise to the reaction mixture. Then the mixture was refluxed for 1 h. The mixture was cooled, and the solids were removed by filtration. The resulting filtrate was concentrated in vacuo. The residue was treated with triethylamine to form a weakly basic mixture and the mixture was diluted water and extracted with ethyl acetate. The separated aqueous layer was extracted three times with ethyl acetate. The combined organic layers were concentrated in vacuo to give crude cyclobutyl-hydrazine (11 g, 98%) as oil which was used without further purification.

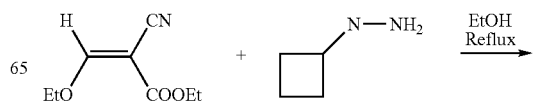

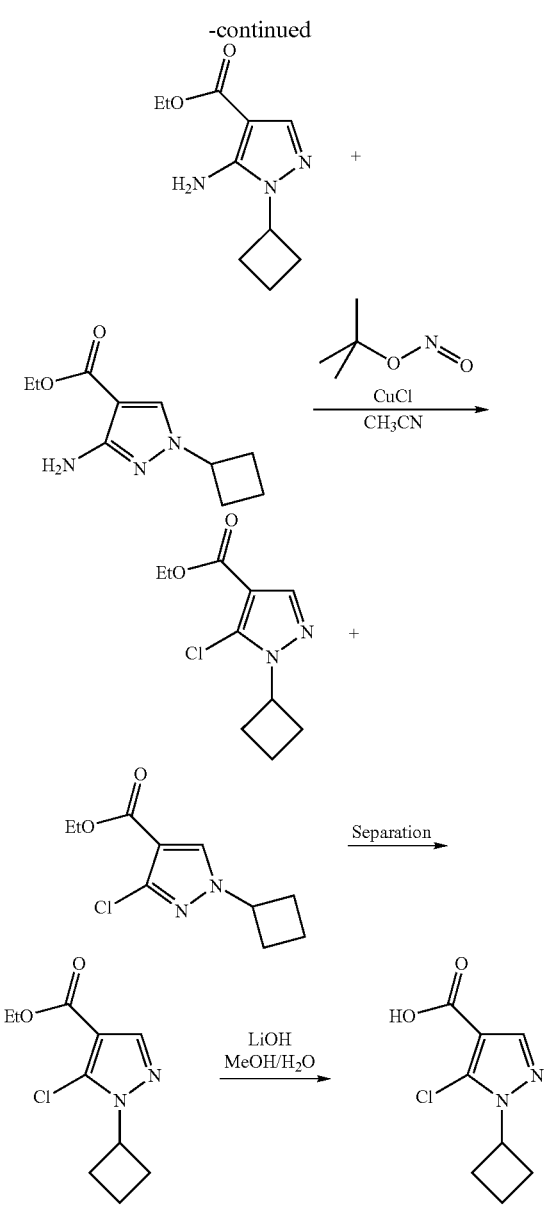

Step 2: Synthesis of a Mixture of 5-amino-1-cyclobutyl-1H-pyrazole-4-carboxylic acid ethyl ester and 3-amino-1-cyclobutyl-1H-pyrazole-4-carboxylic acid ethyl ester A mixture containing crude cyclobutyl-hydrazine (from last step without further purification; 3.5 g, 40.8 mmol) and ethyl(ethoxymethylene)-cyanoacetate (6.9 g, 40.8 mmol) in ethanol (140 mL) was stirred and refluxed overnight. The solution was cooled to room temperature and the mixture was diluted with water and dichloromethane. The separated aqueous layer was extracted three times with dichloromethane. The combined organic layers were washed with water and brine solution and were then dried with sodium sulfate and filtered. The solvent was removed in vacuo, and the crude residue was purified by flash chromatography eluting with a gradient of 0-2% methanol/dichloromethane, to give a mixture of 5-amino-1-cyclobutyl-1H-pyrazole-4-carboxylic acid ethyl ester (eluted first) and 3-amino-1-cyclobutyl-1H-pyrazole-4-carboxylic acid ethyl ester (eluted slightly later) (two isomers: total 5.4 g, 63%), which was used as a mixture without further separation. LRMS m/z calcd for $C_{10}H_{15}N_3O_2$ (M+H) 210.1, found 210.1.

Step 3: Synthesis of 5-chloro-1-cyclobutyl-1H-pyrazole-4-carboxylic acid ethyl ester and 3-chloro-1-cyclobutyl-1H-pyrazole-4-carboxylic acid ethyl ester To a mixture of tert-butyl nitrite (5.1 mL, 38.7 mmol), cuprous chloride (3.8 g, 38.7 mmol), and anhydrous acetonitrile (100 mL) was added a mixture of 5-amino-1-cyclobutyl-1H-pyrazole-4-carboxylic acid ethyl ester and 3-amino-1-cyclobutyl-1H-pyrazole-4-carboxylic acid ethyl ester (from last step without further purification) in anhydrous acetonitrile (50 mL) at 0° C. The reaction mixture was stirred at room temperature for 1 h and then at 60° C. for 2 h. The mixture was cooled to room temperature and then poured into 6N HCl (50 mL) and extracted with dichloromethane. The aqueous layer was extracted three times with dichloromethane. After the combined organic layers were concentrated in vacuo, the crude residue was purified by flash chromatography eluting with a gradient of 10-20% ethyl acetate/hexanes, then 20% ethyl acetate/hexanes. The desired fractions were concentrated in vacuo and dried under vacuum to give 5-chloro-1-cyclobutyl-1H-pyrazole-4-carboxylic acid ethyl ester (eluted first, 610 mg, 10.3%) and 3-chloro-1-cyclobutyl-1H-pyrazole-4-carboxylic acid ethyl ester (eluted later, 147 mg, 2.5%). LRMS m/z calcd for $C_{10}H_{13}ClN_2O_2$ (M+H) 229.1, found 229.1.

Step 4: Synthesis of 5-chloro-1-cyclobutyl-1H-pyrazole-4-carboxylic acid

To a solution of 5-chloro-1-cyclobutyl-1H-pyrazole-4-carboxylic acid ethyl ester (182 mg, 0.79 mmol) in methanol (8 mL) and water (8 mL) was added LiOH (23 mg, 0.96 mmol). The reaction mixture was stirred at reflux for 4 hours and then concentrated under reduced pressure to remove the methanol. The residue was diluted with water, acidified to pH 2 with concentrated HCl and extracted with ethyl acetate. The organic layer was evaporated in vacuo to give 5-chloro-1-cyclobutyl-1H-pyrazole-4-carboxylic acid (148 mg, 94%) which was used without further purification.

Step 5: Synthesis of trans-5-Chloro-1-Cyclobutyl-1H-pyrazole-4-carboxylic acid (5-acetylamino-adamantan-2-yl)-amide 5-Chloro-1-cyclobutyl-1H-pyrazole-4-carboxylic acid (74 mg, 0.37 mmol) was dissolved in a mixture of dry dichloromethane (8 mL) and dry DMF (2 mL), and TSTU (245 mg, 0.81 mmol) was added. Then DIPEA (0.39 mL, 2.22 mmol) was added to the above mixture. After the mixture was stirred for 2.5 h, trans-N-(4-amino-adamantan-1-yl)-acetamide (92 mg, 0.44 mmol, prepared in Example 43) was added. After stirring overnight, water was added and the organic layer was separated. The aqueous layer was extracted twice with dichloromethane. The combined organic layers were concentrated under vacuum. The crude mixture was purified by C-18 reverse phase prepative-HPLC with a gradient of 10-90% acetonitrile/water to give trans-5-chloro-1-cyclobutyl-1H-pyrazole-4-carboxylic acid (5-acetylamino-adamantan-2- yl)-amide (120 mg, 83%). LRMS m/z calcd for $C_{20}H_{27}ClN_4O_2$ (M+H) 391.2, found 391.2.

Example 90 trans-2'-Cyclobutyl-2'H-[1,3']bipyrazolyl-4'-carboxylic acid (5-acetylamino-adamantan-2-yl)-amide

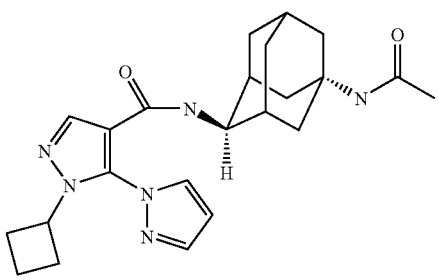

Sodium hydride (60% dispersion in mineral oil; 58 mg, 1.44 mmol) was added to a solution of pyrazole (98 mg, 1.44 mmol) in dry DMF (18 mL) under nitrogen at 0° C. in an ice-water bath and the mixture was heated to 40° C. for 1 h. trans-1-5-Chloro-cyclobutyl-1H-pyrazole-4-carboxylic acid (5-acetylamino-adamantan-2-yl)-amide (70 mg, 0.18 mmol) was added and the mixture was heated at 110° C. for 48 hours and then cooled to room temperature. After the DMF was evaporated in vacuo, water and ethyl acetate were added. The organic layer was separated, and the aqueous layer was extracted three times with ethyl acetate. The combined organic layers were concentrated in vacuo and the residue was purified by C-18 reverse phase preparative-HPLC with a gradient of 10-90% acetonitrile/water. The desired fractions were concentrated under vacuum and dried under vacuum to give trans-2'-cyclobutyl-2'H-[1,3']bipyrazolyl-4'-carboxylic acid (5-acetylamino-adamantan-2-yl)-amide (38 mg, 50%). LRMS m/z calcd for $C_{23}H_{30}N_6O_2$ (M+H) 423.3, found 423.2.

Example 91 trans-2'-tert-Butyl-4-methyl-2'H-[1,3']bipyrazolyl-4'-carboxylic acid (5-hydroxy-adamantan-2-yl)-amide

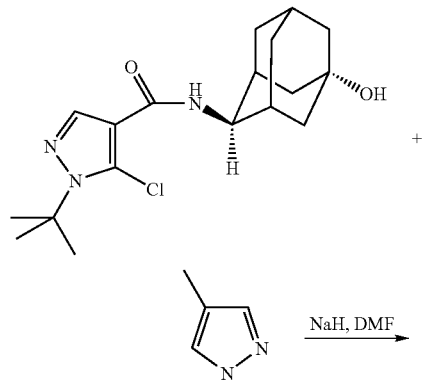

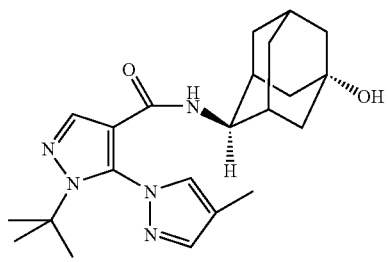

Sodium hydride (60% dispersion in mineral oil; 180 mg, 4.6 mmol) was added slowly to a solution of 4-methylpyrazole (380 ul, 4.6 mmol) in dry DMF (30 mL) at 0° C. in an ice-water bath. The mixture was stirred under argon for 10 minutes and the mixture was then heated to 40° C. for 1.5 hrs. trans-1-tert-Butyl-5-chloro-1H-pyrazole-4-carboxylic acid (5-hydroxy-adamantan-2-yl)-amide (Example 34, 200 mg, 0.57 mmol) was added and the mixture was heated at 110° C. overnight for 3 days and then cooled. The solvent was removed in vacuo. The resulting mixture was diluted with water and extracted with chloroform (2×). The organic layers were combined and washed 3× with water followed by saturated aqueous sodium chloride solution. The organic layer was dried with magnesium sulfate, filtered and concentrated in vacuo. The resulting mixture was purified by column chromatography using silica gel and eluting with 60-70% ethyl acetate in petroleum ether. The desired fractions were concentrated in vacuo to afford trans-2'-tert-butyl-4-methyl-2'H-[1,3']bipyrazolyl-4'-carboxylic acid (5-hydroxy-adamantan-2-yl)-amide as a white solid (53 mg, 23%); ES(+)-HRMS m/z calcd for $C_{22}H_{31}N_5O_2$ (M+H) 398.2551, found 398.2546.

Example 92 trans-2'-tert-Butyl-4-chloro-2'H-[1,3']bipyrazolyl-4'-carboxylic acid (5-hydroxy-adamantan-2-yl)-amide

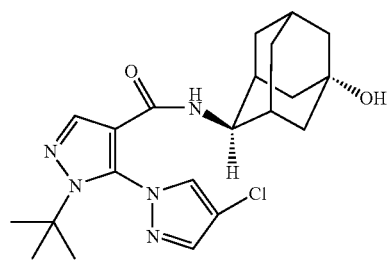

This compound was prepared by a similar method to that described in Example 91 (previous example), except that 4-chloro pyrazole was used in place of 4-methylpyrazole to afford trans-2'-tert-butyl-4-chloro-2'H-[1,3']bipyrazolyl-4'-carboxylic acid (5-hydroxy-adamantan-2-yl)-amide (53%) as an off white solid; LRMS m/z calcd for $C_{21}H_{28}ClN_5O_2$ (M+H) 418.20, found 418.33.

Example 93 trans-4-Bromo-2'-tert-butyl-2'H-[1,3']bipyrazolyl-4'-carboxylic acid (5-hydroxy-adamantan-2-yl)-amide

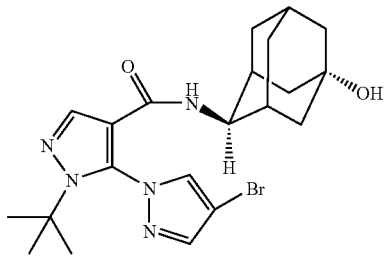

This compound was prepared by a similar method to that described in Example 91, except that 4-bromo pyrazole was used in place of 4-methylpyrazole to afford trans-4-bromo-2'-tert-butyl-2'H-[1,3']bipyrazolyl-4'-carboxylic acid (5-hydroxy-adamantan-2-yl)-amide (23%) as a white solid; ES(+)—HRMS m/z calcd for $C_{21}H_{28}BrN_5O_2$ (M+H) 462.1499, found 462.1497.

Example 94 trans-2'-tert-Butyl-4-chloro-2'H-[1,3']bipyrazolyl-4'-carboxylic acid (5-acetylamino-adamantan-2-yl)-amide

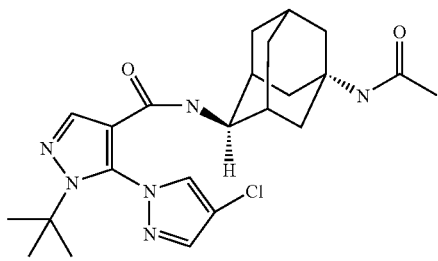

Sodium hydride (60% in oil; 220 mg, 5.5 mmol) was added slowly to a solution of 4-chloro-pyrazole (710 mg, 6.9 mmol) in dry DMF (40 mL) at 0° C. in an ice-water bath. The mixture was stirred under argon for 10 minutes and the mixture was then heated to 40° C. for 2 hrs. trans-1-tert-Butyl-5-chloro-1H-pyrazole-4-carboxylic acid (5-acetylamino-adamantan-2-yl)-amide (270 mg, 0.69 mmol) was added and the mixture was heated at 110° C. overnight for 2 days and then cooled. The solvent was removed in vacuo. The resulting mixture was diluted with water and extracted with ethyl acetate (2×). The organic layers were combined and dried with magnesium sulfate, filtered and concentrated in vacuo. The solid was slurried in ether and filtered and dried under high vacuum to afford trans-2'-tert-butyl-4-chloro-2'H-[1,3']bipyrazolyl-4'-carboxylic acid (5-acetylamino-adamantan-2-yl)-amide as a white solid (237 mg, 74%); ES(+)-HRMS m/z calcd for $C_{23}H_{31}ClN_6O_2$ (M+H) 459.2270, found 459.2268.

Example 95 trans-4-Chloro-2'-cyclobutyl-2'H-[1,3']bipyrazolyl-4'-carboxylic acid (5-acetylamino-adamantan-2-yl)-amide

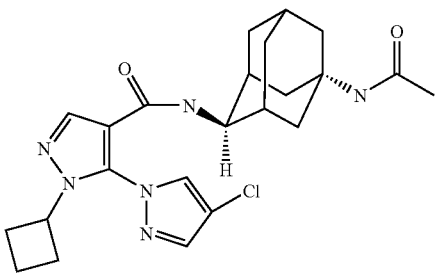

Sodium hydride (60% in oil; 49 mg, 1.23 mmol) was added to a solution of 4-chloro-pyrazole (126 mg, 1.23 mmol) in dry DMF (16 mL) under nitrogen at 0° C. in an ice-water bath and the mixture was heated to 40° C. for 1 h. trans-1-5-Chloro-cyclobutyl-1H-pyrazole-4-carboxylic acid (5-acetylamino-adamantan-2-yl)-amide (60 mg, 0.15 mmol) was added and the mixture was heated at 110° C. for 48 hours and then cooled to room temperature. After the DMF was evaporated in vacuo, water and ethyl acetate were added. The organic layer was separated, and the aqueous layer was extracted three times with ethyl acetate. The combined organic layers were concentrated in vacuo and the residue was purified by C-18 reverse phase preparative-HPLC with a gradient of 10-90% acetonitrile/water. The desired fractions were concentrated under vacuum and dried under vacuum to give trans-4-chloro-2'-cyclobutyl-2'H-[1,3']bipyrazolyl-4'-carboxylic acid (5-acetylamino-adamantan-2-yl)-amide (42 mg, 62%). LRMS m/z calcd for $C_{23}H_{29}ClN_6O_2$ (M+) 456.2, found 456.2.

Example 96 trans-2'-Cyclopropyl-2'H-[1,3']bipyrazolyl-4'-carboxylic acid (5-acetylamino-adamantan-2-yl)-amide

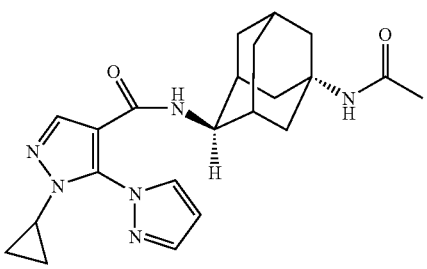

This compound is made in an analogous manner to trans-2'-Cyclopropyl-2'H-[1,3']bipyrazolyl-4'-carboxylic acid (5-hydroxy-adamantan-2-yl)-amide (Example 82) except Intermediate 2 is replaced by trans-N-(4-amino-adamantan-1-yl)-acetamide (prepared in Example 43).

Example 97 trans-4-Chloro-2'-cyclopropyl-2'H-[1,3']bipyrazolyl-4'-carboxylic acid (5-acethylamino-adamantan-2-yl)-amide

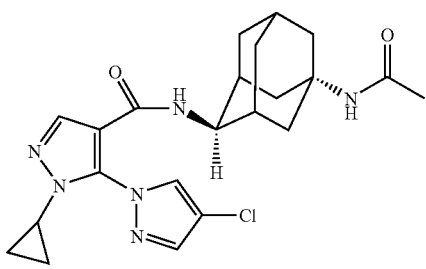

This compound is made in an analogous manner to trans-4-chloro-2'-cyclopropyl-2'H-[1,3']bipyrazolyl-4'-carboxylic acid (5-hydroxy-adamantan-2-yl)-amide (Example 83) except Intermediate 2 is replaced by trans-N-(4-amino-adamantan-1-yl)-acetamide (prepared in Example 43).

Example 98 trans-4-Chloro-2'-(2-methoxy-ethyl)-2'H-[1,3']bipyrazolyl-4'-carboxylic acid (5-acetylamino-adamantan-2-yl)-amide

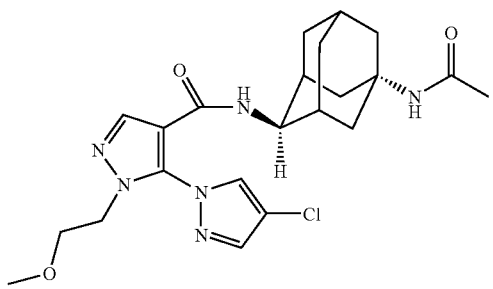

This compound is made in an analogous manner to trans-2'-(2-methoxyethyl)-2'H-[1,3']bipyrazolyl-4'-carboxylic acid (5-acetylamino-adamantan-2-yl-amide (Example 75) except pyrazole is replaced by 4-chloropyrazole.

Example 99

Testing of Compounds of the Invention In Vitro

The in vitro inhibition of 11β-HSD1 by compounds of the present invention were demonstrated by means of the following cellular assay protocols:

Human Hek Assay:

HEK-293 cells stably transfected with full-length human 11betaHSD1 cDNA were propagated and expanded in DMEM high glucose media (Invitrogen Cat# 11995-065), supplemented with 10% FCS (Invitrogen Cat# 10082-147), pen/strep (10 μg/mL), and geneticin (10 μg/mL). One day prior to assay, cells were released from flasks using trypsin/EDTA, centrifuged, and washed with plating media (DMEM high glucose, without phenol red; Invitrogen Cat# 21063-029, supplemented with 2% charcoal stripped FCS; Gemini Cat# A22311P). From a 250,000 cells/mL suspension in plating media, 200 μL of cells were seeded into each well of a 96-well coated plate (BioCoat Cat#356461) and cultured overnight at 37° C. The following day, serially diluted 11betaHSD1 inhibitor compounds dissolved in DMSO were added to plating media supplemented with BSA (2 mg/mL final). The final DMSO concentration was 1%. Media was aspirated from plates, and compounds in media were added to each well. The plates were incubated at 37 degrees C. for 1 hour to allow for cellular uptake of compounds. 10 μL of substrate (cortisone) was then added to each well (100 nM final concentration) and incubated for 1 hour at 37 degrees C. Plates were then transferred to ice and 80 μL of media transferred to a 96-well plate and stored at −30° C.

Quantitation of cortisol in cell media was performed by competitive ELISA using ELISA-Light (Tropix Cat# T10206/EL100S4), anti-cortisol EIA antibody (Assay Designs, Inc. Cat#80-1148), and cortisol-enzyme conjugate (Assay Designs, Inc. Cat# 80-1147). 384-well plates (Falcon Cat#3988) were precoated with anti-mouse IgG (Sigma Cat# M-1397) suspended in 0.9% NaCl (5 mg/mL), 50 μL per well, overnight at 4 degrees C. Plates were washed with PBS, 0.1% Tween-20, then washed with PBS alone. Plates were blocked with Blocking Buffer (Tropix Cat# AI075) for 2 hours at room temperature. The plates were then washed as previously described. Assay samples were thawed, diluted 1:4 in DMEM, 2 mg/mL BSA, 1% DMSO, and 24 μL was transferred to wells of a pre-coated 384-well plate, as well as varying amounts of cortisol standard. To each well, 12 μL of cortisol-conjugate and 12 μL of anti-cortisol EIA antibody were added and incubated 2 hrs at room temperature on a orbital plate shaker. The wells were then emptied by inversion, then washed three times with 100 μL of Wash Buffer (Tropix), and then 2 times with 100 μL of Assay Buffer (Tropix). 60 μL of CDP-STAR (Tropix) was added to each well and incubated 10 minutes at room temperature. Chemiluminescence was measured using a Victor V Reader (Perkin Elmer). Cortisol in each sample was interpolated from a standard curve generated with known amounts of cortisol. $IC_{50}$ values were calculated using the curve fitting software XLFit3 (IDBS).

Human H4IIE Assay:

Cells:

H4IIe cells stably transfected with the human 11-β-HSD1 cDNA (humH4IIe) were maintained in Dulbeccos Modified Essential Medium (DMEM)+10% fetal bovine serum (FBS) containing Penicillin (100 IU/ml) and Streptomycin (100 μg/ml), Geneticin (800 μg/ml) and L-Glutamine (2 mM) at 37° C. in a humidified atmosphere (95% air, 5% $CO_2$).

Preparation of the Cells for Assay:

humH4IIe cells at 80% confluence in a 225 $cm^2$ flask were washed with PBS then detached with warm Trypsin/EDTA. The cells were counted and resuspended in Dulbeccos Modified Essential Medium lacking phenol red (DMEM) containing 2% stripped serum, at a concentration of 100,000 cells per 200 μl, and plated in a 96-well cell culture plate (precoated with Poly-Lysine). The cells were incubated overnight at 37° C. in a humidified atmosphere (95% air, 5% $CO_2$).

Steroid Conversion Assay:

Conversion assays were performed one day after seeding 96-well plates. The media was removed and replaced with 100 ul Dulbeccos Modified Essential Medium without phenol red (DMEM) containing 2 mg/ml Bovine Serum Albumin (BSA)+1% DMSO or test compound dissolved in DMSO.

The cells were incubated with test compound for 60 minutes at 37° C. in a humidified atmosphere (95% air, 5% $CO_2$). After 60 minutes, cortisone was added to 200 nM final, and the cells were incubated for 120 minutes at 37° C. in a humidified atmosphere (95% air, 5% $CO_2$).

The reaction was stopped by transferring 80 μl of media to an empty 96-well plate. Samples were stored at −20° C. until assayed for cortisol concentration using an ELISA method.

The results of the cellular assays giving evidence of the in vitro inhibition of 11β-HSD1 by representative compounds of the present invention are shown in the following Table:

| Example # | Name | humHEK ($IC_{50}$, μM) | HumH4IIe ($IC_{50}$, μM) |
|---|---|---|---|
| 1 | 1-Methyl-5-pyrrol-1-yl-1H-pyrazole-4-carboxylic acid (5-hydroxy-adamantan-2-yl)-amide | 0.0399 | ND |
| 2 | trans-1-Methyl-5-pyrrol-1-yl-1H-pyrazole-4-carboxylic acid (5-hydroxy-adamantan-2-yl)-amide | 0.0222 | ND |
| 5 | 5-Chloro-1-methyl-1H-pyrazole-4-carboxylic acid adamantan-2-ylamide | 0.1888 | ND |
| 6 | 1-tert-Butyl-5-trifluoromethyl-1H-pyrazole-4-carboxylic acid adamantan-2-ylamide | 0.0098 | ND |
| 7 | trans-1-tert-butyl-5-trifluoromethyl-1H-pyrazole-4-carboxylic acid (5-hydroxy-adamantan-2-yl)-amide | 0.6009 | ND |
| 8 | cis-1-tert-butyl-5-trifluoromethyl-1H-pyrazole-4-carboxylic acid (5-hydroxy-adamantan-2-yl)-amide | 0.0202 | ND |
| 9 | trans-2'-Methyl-2'H-[1,3']bipyrazolyl-4'-carboxylic acid (5-hydroxy-adamantan-2-yl)-amide | 0.0386 | ND |
| 12 | 1-Cyclopropyl-5-trifluoromethyl-1H-pyrazole-4-carboxylic acid adamantan-2-ylamide | 0.0222 | ND |
| 14 | 1-Methyl-5-(4-methyl-piperazin-1-yl)-1H-pyrazole-4-carboxylic acid adamantan-2-ylamide | 0.0233 | ND |
| 22 | 1-Methyl-5-morpholin-4-yl-1H-pyrazole-4-carboxylic acid adamantan-2-ylamide | 0.0166 | ND |
| 23 | 5-(2-Methoxy-ethylamino)-1-methyl-1H-pyrazole-4-carboxylic acid adamantan-2-ylamide | 0.0715 | ND |
| 32 | 5-[(2-Methoxy-ethyl)-methyl-amino]-1-methyl-1H-pyrazole-4-carboxylic acid adamantan-2-ylamide | 0.0262 | ND |
| 33 | 2'-tert-Butyl-2'H-[1,3']bipyrazolyl-4'-carboxylic acid adamantan-2-ylamide | 0.0068 | ND |
| 34 | 1-tert-Butyl-5-chloro-1H-pyrazole-4-carboxylic acid (5-hydroxy-adamantan-2-yl)-amide | 0.0192 | 0.0056 |
| 35 | trans-2'-tert-Butyl-2'H-[1,3']bipyrazolyl-4'-carboxylic acid (5-hydroxy-adamantan-2-yl)-amide | 0.020 | 0.0005 |
| 45 | trans-2'-Methyl-2'H-[1,3']bipyrazolyl-4'-carboxylic acid (5-hydroxy-adamantan-2-yl)-amide | 0.0482 | 0.0059 |
| 46 | trans-1-tert-Butyl-5-chloro-1H-pyrazole-4-carboxylic acid (5-acetylamino-adamantan-2-yl)-amide | 0.0662 | 0.0085 |
| 48 | trans-1-tert-Butyl-5-trifluoromethyl-1H-pyrazole-4-carboxylic acid (5-acetylamino-adamantan-2-yl)-amide | 0.0181 | 0.0003 |
| 50 | trans-2'-tert-Butyl-2'H-[1,3']bipyrazolyl-4'-carboxylic acid (5-acetylamino-adamantan-2-yl)-amide | 0.0238 | 0.008 |
| 53 | trans-2'-Methyl-2'H-[1,3']bipyrazolyl-4'-carboxylic acid (5-methanesulfonylamino-adamantan-2-yl)-amide | 0.0769 | 0.006 |
| 73 | trans-5-Chloro-1-(2-methoxyethyl)-1H-pyrazole-4-carboxylic acid (5-hydroxy-adamantan-2-yl)-amide | 0.0229 | 0.0006 |
| 76 | trans-2'-[2-(2-methoxyethoxy)-ethyl]-2'H-[1,3']bipryazolyl-4'-carboxylic acid (5-hydroxyadamantan-2-yl)-amide | ND | 0.0153 |
| 77 | trans-1-(2-tert-Butoxyethyl)-5-trifluoromethyl-1H-pyrazole-4-carboxylic acid (5-hydroxy-adamantan-2-yl)-amide | ND | 0.0046 |

It is to be understood that the invention is not limited to the particular embodiments of the invention described above, as variations of the particular embodiments may be made and still fall within the scope of the appended claims.

What is claimed is:

1. A compound of formula (I):

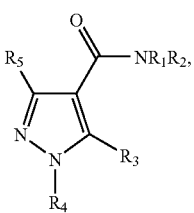

wherein:

$R_1$ is hydrogen;

$R_2$ is adamantane substituted with hydroxy, alkoxy, halogen, amino, loweralkyl-acylamino or loweralkylsulfonylamino;

$R_3$ is lower alkyl, branched or unbranched, halogen, halo-lower alkyl, 3- to 8-membered heteroaryl having 1-3 heteroatoms selected from N, O and S, which may be unsubstituted or substituted with halogen or lower alkyl, —NH(CH$_2$)$_n$OH, —NH(CH$_2$)$_n$OCH$_3$, —NHCH(CH$_3$)$_2$, —NH(CH$_2$)$_n$CH$_3$OH, —NH(CH$_3$)(CH$_2$)$_n$OCH$_3$, —NH(CH$_3$)(CH$_2$)$_n$OH, —NCH$_2$CH(CH$_3$)OH, —NH(CH$_2$)$_n$O(CH$_2$)$_n$CH$_3$, —N(CH$_2$CH$_3$)$_2$, —(CH$_2$)OH, —(CH$_2$)O(CH$_2$)$_n$CH$_3$, —(CH$_2$)O(CH$_2$)$_n$-alkyl, —(CH$_2$)O(CH$_2$)$_n$-cycloalkyl, or a 3- to 8-membered monocyclic heterocycle with 1-3 hetero atoms selected from N, O and S, which may be unsubstituted or substituted with lower alkyl, hydroxy, hydroxy phenyl, —(CH$_2$)$_n$-phenyl, —CH$_2$(CH$_2$)$_n$OH or halogen;

$R_4$ is lower alkyl, branched or unbranched, unsubstituted or substituted with hydroxyl, —(CH$_2$)$_m$—(C$_3$-C$_6$)cycloalkyl, unsubstituted or substituted with hydroxy or lower alkyl, halo-alkyl, hydroxyalkyl, —(CH$_2$)$_n$O(CH$_2$)$_n$CH$_3$, —(CH$_2$)$_n$O(CH$_2$)$_p$O(CH$_2$)$_n$CH$_3$, —(CH$_2$)$_n$OC(CH$_3$)$_3$ or —CH(CH$_3$)$_2$(CH$_2$)$_n$OH;

saturated heterocyclyl ring containing 4-6 atoms of which 1-2 are selected from N, O or S;

$R_5$ is hydrogen or lower alkyl, unsubstituted or substituted with halogen;

n is 0, 1, 2 or 3;

m is 0, 1 or 2; and p is 1, 2 or 3, or a pharmaceutically acceptable salt thereof.

2. The compound according to claim 1, wherein:

$R_2$ is adamantane substituted with hydroxy, halogen, amino, acetylamino or methane sulfonylamino; and $R_3$ is lower alkyl, branched or unbranched, halogen, halo-lower alkyl, 3- to 8-membered heteroaryl having 1-3 heteroatoms selected from N, O and S, which may be unsubstituted or substituted with halogen or lower alkyl, —NH(CH$_2$)$_n$OH, —NH(CH$_2$)$_n$OCH$_3$, —NHCH(CH$_3$)$_2$, —NH(CH$_2$)$_n$CH$_3$OH, —NH(CH$_3$)(CH$_2$)$_n$OCH$_3$, —NH(CH$_3$)(CH$_2$)$_n$OH, —NCH$_2$CH(CH$_3$)OH, —NH(CH$_2$)$_n$O(CH$_2$)$_n$CH$_3$, —N(CH$_2$CH$_3$)$_2$, —(CH$_2$)$_n$OH, —(CH$_2$)nO(CH$_2$)$_n$CH$_3$, or a 3- to 8-membered monocyclic heterocycle with 1-3 hetero atoms selected from N, O and S, which may be unsubstituted or substituted with lower alkyl, hydroxy, hydroxy phenyl, —(CH$_2$)$_n$-phenyl, —(CH$_2$)$_n$OH or halogen.

3. The compound according to claim 1, wherein:

$R_2$ is adamantane substituted with hydroxy, halogen, amino, acetylamino or methane sulfonylamino; and $R_4$ is lower alkyl, branched or unbranched, —(CH$_2$)$_m$—(C$_3$-C$_5$)cycloalkyl, unsubstituted or substituted with hydroxy or lower alkyl, halo-alkyl, hydroxyalkyl, —(CH$_2$)$_n$O(CH$_2$)$_n$CH$_3$, —(CH$_2$)$_n$O(CH$_2$)$_p$O(CH$_2$)$_n$CH$_3$, —(CH$_2$)$_n$OC(CH$_3$)$_3$ or —CH(CH$_3$)$_2$(CH$_2$)$_n$OH.

4. The compound according to claim 1, wherein $R_2$ is trans-hydroxy adamantane.

5. The compound according to claim 1, wherein $R_3$ is a trifluoromethyl group.

6. The compound according to claim 1, wherein $R_3$ is a pyrazole, triazole, piperidine, pyrrolidine, hydroxymethyl piperidine, benzylpiperazine, hydroxypyrrolidine, tert-butyl pyrrolidine, hydroxyethyl piperazine, hydroxypiperidine or thiomorpholine group.

7. The compound according to claim 1, wherein $R_4$ is a cyclopropyl, tert-butyl, —CH(CH$_3$)$_2$CH$_2$OH, methyl, —CF$_3$ or —(CH$_2$)nCF$_3$ group, wherein n is 1 or 2.

8. The compound according to claim 1, wherein $R_5$ is a trifluoromethyl group.

9. The compound according to claim 1, wherein said compound is trans-2'-tert-butyl-2'H-[1,3']bipyrazolyl-4'-carboxylic acid (5-hydroxy-adamantan-2-yl)-amide.

10. The compound according to claim 1, wherein said compound is 1-methyl-5-pyrrol-1-yl-1H-pyrazole-4-carboxylic acid (5-hydroxy-adamantan-2-yl)-amide.

11. The compound according to claim 1, wherein said compound is trans-1-methyl-5-pyrrol-1-yl-1H-pyrazole-4-carboxylic acid (5-hydroxy-adamantan-2-yl)-amide.

12. The compound according to claim 1, wherein said compound is trans-1-tert-butyl-5-trifluoromethyl-1H-pyrazole-4-carboxylic acid (5-hydroxy-adamantan-2-yl)-amide.

13. The compound according to claim 1, wherein said compound is cis-1-tert-butyl-5-trifluoromethyl-1H-pyrazole-4-carboxylic acid (5-hydroxy-adamantan-2-yl)-amide.

14. The compound according to claim 1, wherein said compound is trans-2'-methyl-2'H-[1,3']bipyrazolyl-4'-carboxylic acid (5-hydroxy-adamantan-2-yl)-amide.

15. The compound according to claim 1, wherein said compound is 1-cyclopropyl-5-trifluoromethyl-1H-pyrazole-4-carboxylic acid (5-hydroxy-adamantan-2-yl)-amide.

16. The compound according to claim 1, wherein said compound is 1-tert-butyl-5-chloro-1H-pyrazole-4-carboxylic acid (5-hydroxy-adamantan-2-yl)-amide.

17. The compound according to claim 1, wherein said compound is selected from the group consisting of:

trans-1-tert-Butyl-5-chloro-1H-pyrazole-4-carboxylic acid (5-acetylamino-adamantan-2-yl)-amide;

trans-2'-tert-Butyl-2'H-[1,3']bipyrazolyl-4'-carboxylic acid (5-acetylamino-adamantan-2-yl)-amide;

trans-2'-tert-Butyl-2'H-[1,3']bipyrazolyl-4'-carboxylic acid (5-methanesulfonylamino-adamantan-2-yl)-amide;

trans-1-tert-Butyl-5-ethoxymethyl-1H-pyrazole-4-carboxylic acid (5-hydroxy-adamantan-2-yl)-amide;

trans-1-tert-Butyl-5-methoxymethyl-1H-pyrazole-4-carboxylic acid (5-acetylamino-adamantan-2-yl)-amide;

trans-1-tert-Butyl-5-(5-methyl-isoxazol-3-yl)-1H-pyrazole-4-carboxylic acid (5-acetylamino-adamantan-2-yl)-amide;

trans-1-tert-Butyl-5-(5-chloro-isoxazol-3-yl)-1H-pyrazole-4-carboxylic acid (5-hydroxy-adamantan-2-yl)-amide;

trans-2'-Cyclohexyl-2'H-[1,3']bipyrazolyl-4'-carboxylic acid (5-hydroxy-adamantan-2-yl)-amide;

trans-2'-Cyclohexyl-2'H-[1,3']bipyrazolyl-4'-carboxylic acid (5-acetylamino-adamantan-2-yl)-amide;

trans-2'-(Tetrahydro-pyran-4-yl)-2'H-[1,3']bipyrazolyl-4'-carboxylic acid (5-hydroxy-adamantan-2-yl)-amide;

trans-2'-Cyclopentyl-2'H-[1,3']bipyrazolyl-4'-carboxylic acid (5-hydroxy-adamantan-2-yl)-amide;

trans-2'-Cyclopentyl-2'H-[1,3']bipyrazolyl-4'-carboxylic acid (5-acetyamino-adamantan-2-yl)-amide;

trans-2'-(cis-4-Hydroxy-cyclohexyl)-2'H-[1,3']bipyrazolyl-4'-carboxylic acid (5-hydroxy-adamantan-2-yl)-amide;

trans-1-(cis-4-Hydroxy-cyclohexyl)-5-trifluoromethyl-1H-pyrazole-4-carboxylic acid (5-hydroxy-adamantan-2-yl)-amide;

trans-1-(trans-4-Hydroxy-cyclohexyl)-5-trifluoromethyl-1H-pyrazole-4-carboxylic acid (5-hydroxy-adamantan-2-yl)-amide;
trans-2'-(2-Methoxyethyl)-2'H-[1,3']bipyrazolyl-4'-carboxylic acid (5-hydroxy-adamantan-2-yl-amide;
trans-1-(2-Methoxyethyl)-5-trifluoromethyl-1H-pyrazole-4-carboxylic acid (5-hydroxy-adamantan-2-yl)-amide;
trans-2'-(2-Methoxyethyl)-2'H-[1,3']bipyrazolyl-4'-carboxylic acid (5-acetylamino-adamantan-2-yl-amide;
trans-2'-(3-Methoxypropyl)-2'H-[1,3']bipyrazolyl-4-'carboxylic acid (5-hydroxy-adamantan-2-yl)-amide;
trans-2'-(3-Methoxypropyl)-2'H-[1,3']bipyrazolyl-4'-carboxylic acid (5-acetylamino-adamantan-2-yl)-amide;
trans-1-Cyclopropyl-5-trifluoromethyl-1H-pyrazole-4-carboxylic acid (5-hydroxy-adamantan-2-yl)-amide;
trans-5-Chloro 1-cyclopropyl-1H-pyrazole-4-carboxylic acid (5-hydroxy-adamantan-2-yl)-amide;
trans-2'-Cyclopropyl-2'H-[1,3']bipyrazolyl-4'-carboxylic acid (5-hydroxy-adamantan-2-yl)-amide;
trans-4-Chloro-2'-cyclopropyl-2'H-[1,3']bipyrazolyl-4'-carboxylic acid (5-hydroxy-adamantan-2-yl)-amide;
trans-1-Cyclopropylmethyl-5-trifluoromethyl-1H-pyrazole-4-carboxylic acid (5-hydroxy-adamantan-2-yl)-amide;
trans-1-(2-Hydroxy-1,1-dimethyl-ethyl)-5-trifluoromethyl-1H-pyrazole-4-carboxylic acid (5-hydroxy-adamantan-2-yl)-amide;
trans-1-tert-Butyl-5-cyclopropyl-1H-pyrazole-4-carboxylic acid (5-hydroxy-adamantan-2-yl)-amide;
trans-1-Cyclobutyl-5-trifluoromethyl-1H-pyrazole-4-carboxylic acid (5-hydroxy-adamantan-2-yl)-amide;
trans-1-Cyclobutyl-5-trifluoromethyl-1H-pyrazole-4-carboxylic acid (5-acetylamino-adamantan-2-yl)-amide;
trans-5-Chloro-1-cyclobutyl-1H-pyrazole-4-carboxylic acid (5-acetylamino-adamantan-2-yl)-amide;
trans-2'-Cyclobutyl-2'H-[1,3']bipyrazolyl-4'-carboxylic acid (5-acetylamino-adamantan-2-yl)-amide;
trans-2'-tert-Butyl-4-methyl-2'H-[1,3']bipyrazolyl-4'-carboxylic acid (5-hydroxy-adamantan-2-yl)-amide;
trans-2'-tert-Butyl-4-chloro-2'H-[1,3']bipyrazolyl-4'-carboxylic acid (5-hydroxy-adamantan-2-yl)-amide;
trans-2'-tert-Butyl-4-chloro-2'H-[1,3']bipyrazolyl-4'-carboxylic acid (5-acetylamino-adamantan-2-yl)-amide; and
trans-4-Chloro-2'-cyclobutyl-2'H-[1,3']bipyrazolyl-4'-carboxylic acid (5-acetylamino-adamantan-2-yl)-amide.

18. A pharmaceutical composition, comprising a therapeutically effective amount of a compound according to claim 1 or a pharmaceutically acceptable salt thereof, and a pharmaceutically acceptable carrier.

19. A method of treating diabetes, comprising the step of administering a therapeutically effective amount of a compound according to claim 1 to a patient in need thereof.

* * * * *